(12) United States Patent
Conradie et al.

(10) Patent No.: US 11,268,110 B2
(45) Date of Patent: Mar. 8, 2022

(54) METHODS AND MATERIALS FOR THE ENZYMATIC CONVERSION OF A NON-3-ENAL TO AZELAIC ACID

(71) Applicant: INV Nylon Chemicals Americas, LLC, Wilmington, DE (US)

(72) Inventors: Alex Van Eck Conradie, Eaglescliffe (GB); Adriana L. Botes, Rosedale East (GB); Alexander Brett Foster, Wilton (GB); Changlin Chen, Ingleby Barwick (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 16/656,816

(22) Filed: Oct. 18, 2019

(65) Prior Publication Data
US 2020/0277634 A1  Sep. 3, 2020

Related U.S. Application Data

(63) Continuation of application No. 16/351,324, filed on Mar. 12, 2019, now abandoned, which is a continuation of application No. 15/421,164, filed on Jan. 31, 2017, now abandoned.

(60) Provisional application No. 62/289,877, filed on Feb. 1, 2016.

(51) Int. Cl.
| | | |
|---|---|---|
| *C12P 7/40* | (2006.01) | |
| *C12P 7/04* | (2006.01) | |
| *C12P 7/46* | (2006.01) | |
| *C12P 7/64* | (2006.01) | |
| *C12P 13/00* | (2006.01) | |
| *C12P 7/42* | (2006.01) | |
| *C12P 7/50* | (2006.01) | |
| *C07C 47/21* | (2006.01) | |
| *C07C 59/147* | (2006.01) | |
| *C08G 69/10* | (2006.01) | |
| *C08G 69/26* | (2006.01) | |
| *C12N 9/02* | (2006.01) | |
| *C12N 9/10* | (2006.01) | |
| *C12N 9/80* | (2006.01) | |
| *C12N 9/88* | (2006.01) | |
| *C12N 9/90* | (2006.01) | |
| *C12P 7/24* | (2006.01) | |
| *C12P 17/18* | (2006.01) | |
| *C12P 7/6427* | (2022.01) | |
| *C12P 7/6409* | (2022.01) | |

(52) U.S. Cl.
CPC .............. *C12P 7/40* (2013.01); *C07C 47/21* (2013.01); *C07C 59/147* (2013.01); *C08G 69/10* (2013.01); *C08G 69/26* (2013.01); *C12N 9/001* (2013.01); *C12N 9/0008* (2013.01); *C12N 9/1029* (2013.01); *C12N 9/1096* (2013.01); *C12N 9/80* (2013.01); *C12N 9/88* (2013.01); *C12N 9/90* (2013.01); *C12P 7/04* (2013.01); *C12P 7/24* (2013.01); *C12P 7/42* (2013.01); *C12P 7/46* (2013.01); *C12P 7/50* (2013.01); *C12P 7/6409* (2013.01); *C12P 7/6427* (2013.01); *C12P 13/001* (2013.01); *C12P 17/182* (2013.01); *C12Y 102/99006* (2013.01); *C12Y 103/01031* (2013.01); *C12Y 203/01032* (2013.01); *C12Y 206/01018* (2013.01); *C12Y 305/01* (2013.01); *C12Y 402/99* (2013.01); *C12Y 503/03008* (2013.01)

(58) Field of Classification Search
None
See application file for complete search history.

(56) References Cited

FOREIGN PATENT DOCUMENTS

| | | |
|---|---|---|
| WO | WO 2012/025629 A1 | 3/2012 |
| WO | WO 2014/105797 A2 | 7/2014 |
| WO | WO 2017/136344 A1 | 8/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. CurrOpin Biotechnol. Oct. 2008;19(5):468-74. (Year: 2008).*
Adkins, et al., "Engineering Microbial Chemical Factories to Produce Renewable Biomonomers," *Synthetic Biology Applications in Industrial Microbiology*, vol. 3, Article 313, Aug. 2012, pp. 1-12.
Barker, et al., "Enzymatic Reactions in the Degradation of 5-Aminovalerate by Clostridium Aminovalericum," *The Journal of Biological Chemistry*, vol. 262, No. 19, 1987, pp. 8994-9003.

(Continued)

*Primary Examiner* — Christian L Fronda

(57) ABSTRACT

This document describes biochemical pathways for producing pimeloyl-CoA using a polypeptide having the enzymatic activity of a hydroperoxide lyase to form non-3-enal and 9-oxononanoate from 9-hydroxyperoxyoctadec-10,12-dienoate. Non-3-enal and 9-oxononanoate can be enzymatically converted to pimeloyl-CoA or a salt thereof using one or more polypeptides having the activity of a dehydrogenase, a CoA ligase, an isomerase, a reductase, a thioesterase, a monooxygenase, a hydratase, and/or a thiolase. Pimeloyl-CoA can be enzymatically converted to pimelic acid, 7-aminoheptanoic acid, 7-hydroxyheptanoic acid, heptamethylenediamine, or 1,7-heptanediol, or corresponding salts thereof. This document also describes recombinant microorganisms producing pimeloyl-CoA, as well as pimelic acid, 7-aminoheptanoic acid, 7-hydroxyheptanoic acid, heptamethylenediamine, and 1,7-heptanediol, or corresponding salts thereof.

21 Claims, 32 Drawing Sheets

Specification includes a Sequence Listing.

(56) References Cited

OTHER PUBLICATIONS

Bartsch et al., "Molecular Analysis of Two Genes of the *Escherichia coli* Gab Cluster: Nucleotide Sequence of the Glutamate: Succinic Semialdehyde Transaminase Gene (gabT) and Characterization of the Succinic Semialdehyde Dehydrogenase Gene (gabD)," *Journal of Bacterialogy*, vol. 172, No. 12, Dec. 1990, pp. 7035-7042.
Becker, et al., "Metabolic Flux Engineering of L-Lysine Production in Corynebacterium Glutamicum—Over Expression and Modification of G6P Dehydrogenase," *Journal of Biotechnology*, vol. 132, 2007, pp. 99-109.
Bellmann, et al., "Expression Control and Specificity of the Basic Amino Acid Exporter LysE of Corynebacterium Glutamicum," *Microbiology*, vol. 147, 2001, pp. 1765-1774.
Blombach et al., "Current Knowledge on Isobutanol Production with *Escherichia coli*, Bacillus Subtillis and Corynebacterium Glutamicum," *Bioengineered Bugs*, vol. 2, No. 6, 2011, pp. 346-350.
Bond-Watts, et al., "Biochemical and Structural Characterization of the Trans-Enoyl-CoA Reductase from Treponema Denticola," *Biochemistry*, vol. 51, 2012, pp. 6827-6837.
Brigham, et al., "Engineering Ralstonia Eutropha for Production of Isobutanol from CO2, H2, and O2," *Advanced Biofuels and Bioproducts, Springer New York*, Chapter 39, 2013, pp. 1065-1090.
Bugg, et al., "The Emerging Role for Bacteria in Lignin Degradation and Bio-Product Formation," *Current Opinion in Biotechnology*, vol. 22, 2011, pp. 394-400.
Bunch et al., "The IdhA Gene Encoding the Fermentative Lactate Dehydrogenase of *Escherichia coli*," *Microbiology*, vol. 143, 1997, pp. 187-195.
Cantu, et al., "Thioesterases: A New Perspective Based on their Primary and Tertiary Structures," *Protein Science*, vol. 19, 2010, pp. 1281-1295.
Chan et al., "Production of Succinic Acid from Sucrose and Sugarcane Molasses by Metabolically Engineered *Escherichia coli*," *Bioresource Technology*, vol. 103, 2012, pp. 329-336.
Chatterjee et al., "Mutation of the PtsG Gene Results in Increased Production of Succinate in Fermentation of Glucose by *Escherichia coli*," *Applied and Environmental Microbiology*, vol. 67, No. 1, Jan. 2001, pp. 148-154.
Demain et al., "Manual of Industrial Microbiology and Biotechnology," 2nd Edition, Scale-Up of Microbial Processes, ASM Press, 1999, 5 pages.
Donnelly et al., "A Novel Fermentation Pathway in an *Escherichia coli* Mutant Producing Succinic Acid, Acetic Acid, and Ethanol," *Applied Biochemistry and Biotechnology*, vol. 70-72, 1998, pp. 187-198.
Donoghue et al.,"The Metabolism of Cyclohexanol by Acinetobacter NCIB 9871," *European Journal of Biochemistry*, vol. 60, 1975, pp. 1-7.
Elkins, et al., "Substrate Specificity of the RND-Type Multidrug Efflux Pumps AcrB and AcrD of *Escherichia coli* is Determined Predominately by Two Large Periplasmic Loops," *Journal of Bacteriology*, vol. 184, No. 23, 2002, pp. 6490-6498.
Eriksen et al., "Protein Design for Pathway Engineering," *Journal of Structural Biology*, vol. 185, Issue 2, Feb. 2014, 18 pages.
Geisbrecht et al., "Molecular Characterization of *Saccharomyces cerevisiae* Δ3 and Δ2-Enoyl-CoA Isomerase," *The Journal of Biological Chemistry*, vol. 273, No. 50, Dec. 11, 1998, pp. 795-798.
GenBank Accession No. AAA57874.1, dated Nov. 21, 2011, 2 pages.
GenBank Accession No. AAC83700.1, dated Dec. 8, 1998, 1 page.
GenBank Accession No. AAF64041.1, dated Oct. 3, 2000, 1 page.
GenBank Accession No. AAG08191.1, dated Jan. 31, 2014, 2 pages.
GenBank Accession No. AAN66878.1, dated Mar. 2, 2016, 2 pages.
GenBank Accession No. AAO77182, dated Jan. 31, 2014, 1 page.
GenBank Accession No. AAQ59697.1, dated Jan. 31, 2014, 2 pages.
GenBank Accession No. AAY39893.1, dated Jan. 31, 2014, 2 pages.
GenBank Accession No. ABA81135.1, dated Jul. 20, 2015, 2 pages.
GenBank Accession No. ABG82470.1, dated Mar. 16, 2017, 2 pages.
GenBank Accession No. ABK71854.1, dated Jan. 31, 2014, 2 pages.
GenBank Accession No. ABK75684.1, dated Jan. 31, 2014, 2 pages.
GenBank Accession No. ACC40567.1, dated Jan. 31, 2014, 2 pages.
GenBank Accession No. ADG98140.1, dated Jan. 28, 2014, 2 pages.
GenBank Accession No. AEA39183.1, dated Apr. 4, 2011, 1 page.
GenBank Accession No. AGP69310.1, dated Jan. 30, 2014, 2 pages.
GenBank Accession No. BAG97978.1, dated Dec. 4, 2008, 2 pages.
GenBank Accession No. CAA81612.1, dated Apr. 18, 2005, 2 pages.
GenBank Accession No. CCC78182.1, dated Feb. 27, 2015, 1 page.
GenBank Accession No. EEI82654.1, dated Jun. 14, 2013, 2 pages.
GenBank Accession No. EFV11917.1, dated Sep. 9, 2013, 2 pages.
GenBank Accession No. EIV11143.1, dated Dec. 19, 2014, 2 pages.
Gloerich, et al., "Peroxisomal Trans—2—Enoyl—CoA Reductase is Involved in Phytol Degradation," *FEBS Letters*, vol. 580, 2006, pp. 2092-2096.
Gokarn et al, "Metabolic Analysis of *Escherichia coli* in the Presence and Absence of the Carboxylating Enzyme Phophoenolpyruvate Carboxylase and Pyruvate Carboxylase," *Applied and Environmental Microbiology*, vol. 66, No. 5, May 2000, pp. 1844-1850.
Gokarn et al., "Expression of Pyruvate Carboxylase Enhances Succinate Production in *Escherichia coli* without Affecting Glucose Uptake," *Biotechnology Letters*, vol. 20, No. 8, Aug. 1998, pp. 795-798.
Guerrillot, et al., "Purification and Characterization of Two Aldehyde Dehydrogenases from Pseudomonas Aeruginosa," *European Journal of Biochemistry*, vol. 81, 1977, pp. 185-192.
Hermann, Thomas, "Industrial Production of Amino Acids by Coryneform Bacteria," *Journal of Biotechnology*, vol. 104, 2003, pp. 155-172.
Hong, et al., "Metabolic Flux Distribution in a Metabolically Engineered *Escherichia coli* Strain Producing Succinic Acid," *J. Microbiol. Biotechnol*, vol. 10, No. 4, Feb. 2, 2017, pp. 496-501.
Huhn, et al., "Identification of the Membrane Protein SucE and its Role in Succinate Transport in Corynebacterium Glutamicum," *Applied Microbiology and Biotechnology*, vol. 89, 2011, pp. 327-335.
Inui, et al., "Fatty Acids Synthesis in Mitochrondria of Euglena Gracilis," *European Journal of Biochemistry*, vol. 142, 1984, pp. 121-126.
Iwaki, et al., "Identification of a Transcriptional Activator (ChnR) and A 6-Oxohexanoate Dehydrogenase (ChnE) in the Cyclohexanol Catabolic Pathway in Acinetobacter sp. Strain NCIMB 9871 and Localization of the Genes That Encode Them," *Applied and Environmental Microbiology*, vol. 65, No. 11, 1999, pp. 5158-5162.
Jarboe, Laura R., "YqhD: A Broad-Substrate Range Aldehyde Reductase with Various Applications in Production of Biorenewable Fuels and Chemicals," *Applied Microbiology and Biotechnology*, vol. 89, No. 2, 2011, pp. 249-257.
Jaremko et al., "The Initial Metabolic Conversion of Levulinic Acid in Cupriavidus Necator," *Journal of Biotechnology*, vol. 155, 2011, pp. 293-298.
Kaulmann, et al., "Substrate Spectrum of ω-Transaminase from Chromobacterium Violaceum DSM30191 and its Potential for Biocatalysis," *Enzyme and Microbial Technology*, vol. 41, 2007, pp. 628-637.
Kim, et al., "Effect of Overexpression of Actinobacillus Succinogenes Phosphoenolypyruvate Carboxykinase on Succinate Production in *Escherichia coli*," *Applied and Environmental Microbiology*, vol. 70, No. 2, Feb. 2004, pp. 1238-1241.
Kim, Ki-Han, "Purification and Properties of A Mine α-Ketoglutarate Transaminase from *Escherichia coli*," *Journal of Biological Chemistry*, vol. 239, No. 3, Feb. 1964, pp. 783-786.
Köpke, et al., "2, 3-Butanediol Production by Acetogenic Bacteria, An Alternative Route to Chemical Synthesis, Using Industrial Waste Gas," *Applied and Environmental Microbiology*, vol. 77, No. 15, 2011, pp. 5467-5475.
Larroy, et al., "Characterization of the *Saccharomyces cerevisiae* YMR318C (ADH6) Gene Product as a Broad Specificity NADPH-Dependent Alcohol Dehydrogenase: Relevance in Aldehyde Reduction," *Biochemical Journal*, vol. 361, No. 1, 2002, 163-172.

(56) References Cited

OTHER PUBLICATIONS

Lee et al., "Heterologous Co-Expression of AccA, FabD, and Thioesterase Genes for Improving Long-Chain Fatty Acid Production in Pseudomonas Aeruginosa and *Escherichia coli*," *Applied Biochemistry and Biotechnology*, vol. 167, No. 1, 2012, pp. 24-38.
Lee, et al., "Synthesis of Pure Meso-2, 3-Butanediol from Crude Glycerol Using an Engineered Metabolic Pathway in *Escherichia coli*," *Applied Biochemistry and Biotechnology*, vol. 166, No. 7, 2012, pp. 1801-1813.
Lee, et al.,"Metabolic Engineering of Pentose Phosphate Pathway in Ralstonia Eutropha for Enhanced Biosynthesis of Poly—β—Hydroxybutyrate," *Biotechnology Process*, vol. 19, No. 5, 2003, pp. 1444-1449.
Li, et al., "Cupriavidus Necator JMP134 Rapidly Reduces Furfural With a Zn-Dependent Alcohol Dehydrogenase," *Biodegradation*, vol. 22, No. 6, 2011, pp. 1215-1225.
Lim, et al., "Amplification of the NADPH-Related Genes zwf and gnd for the Oddball Biosynthesis of PHB in an *E. coli* Transformant Harboring a Cloned phbCAB Operon," *Journal of Bioscience and Bioengineering*, vol. 93, No. 6, 2002, pp. 543-549.
Liu, et al.,"Two Novel Metal-Independent Long-Chain Alkyl Alcohol Dehydrogenases from Geobacillus Thermodenitrificans NG80-2," *Microbiology*, vol. 155, No. 6, 2009, pp. 2078-2085.
Lopez-Sánchez, et al., "Tetralin-Induced and ThnR-Regulated Aldehyde Dehydrogenase and β Oxidation Genes in Sphingomonas Macrogolitabida Strain TFA," *Applied and Environmental Microbiology*, vol. 76, No. 1, 2010, pp. 110-118.
Martin, et al., "High-Titer Production of Monomeric Hydroxyvalerates from Levulinic Acid in Pseudomanas Putida," *Journal of Biotechnology*, vol. 139, No. 1, 2009, pp. 61-67.
Mat-Jan et al., "Mutants of *Escherichia coli* Deficient in the Fermentative Lactate Dehydrogenase," *Journal of Bacteriology*, vol. 171, No. 1, Jan. 1989, pp. 342-348.
Meijnen, et al., "Improved p-Hydroxybenzoate Production by Engineered Pseudomonas Putida S12 by Using a Mixed-Substrate Feeding Strategy," *Applied Microbiology and Biotechnology*, vol. 90, No. 3, 2011, pp. 885-893.
Millard et al., "Enhanced Production of Succinic Acid by Overexpression of Phosphoenolypyruvate Carboxylase in *Escherichia coli*," *Applied and Environmental Microbiology*, vol. 62, No. 5, May 1996, pp. 1808-1810.
Naggert, et al., "Cloning, Sequencing, and Characterization of *Escherichia coli* Thioesterase II," *The Journal of Biological Chemistry*, vol. 266, No. 17, 1991, pp. 11044-11050.
Neyfakh, Alexander A., et al., "The Multidrug Efflux Transporter of Bacillus Subtilis is a Structural and Functional Homolog of the *Staphylococcus* NorA Protein," *Antimcrobial Agents and Chemotherapy*, vol. 36, No. 2, 1992, pp. 484-485.
Ng, et al., "Quinolone Resistance Mediated by norA: Physiologic Characterization and Relationship to flqB, A Quinolone Resistance Locus on the *Staphyloccus aureus* Chromosome," *Antimicrobial Agents and Chemotherapy*, vol. 38, No. 6, 1994, pp. 1345-1355.
Nishimaki, et al., "Studies on the Metabolism of Unsaturated Fatty Acids XIV, Purification and Properties of NADPH-Dependent Trans-2-Enoyl-CoA Reductase of *Escherichia coli* K-12," *The Journal of Biochemistry*, vol. 95, No. 5, 1984, pp. 1315-1321.
Ohashi, et al., "Continuous Production of Lactic Acid from Molasses by Perfusion Culture of Lactococcus Lactis Using a Stirred Ceramic Membrane Reactor," *Journal of Bioscience and Bioengineering*, vol. 87, No. 5, 1999, pp. 647-654.
Otte, Konrade B., et al., "Whole-Cell One-Pot Biosynthesis of Azelaic Acid," *ChemCatchem* 2014, 6, 1003-1009, © 2014 Wiley-VCH Verlag GmbH & Co., 8 pages.
Papanikolaou, et al., "Citric Acid Production by Yarrowia Lipolytica Cultivated on Olive-Mill Wastewater-Based Media," *Bioresource Technology*, vol. 99, 2008, pp. 2419-2428.
PCT International Preliminary Report on Patentability issued in PCT/US2017/015842, dated Aug. 7, 2018, 26 pages.
PCT International Search Report issued in PCT/US2017/015842, dated Aug. 10, 2017, 11 pages.
PCT Written Opinion of the International Searching Authority issued in PCT/US2017/015842, dated Aug. 10, 2017, 25 pages.
Perez-Pantoja, et al., "Metabolic Reconstruction of Aromatic Compounds Degradation from the Genome of the Amazing Pollutant-Degrading Bacterium Cupriavidus Necator JMP134," *FEMS Microbiology Reviews*, vol. 32, 2008, pp. 736-794.
Przbylski, et al., "Third-Generation Feed Stocks for the Clean and Sustainable Biotechnological Production of Bulk Chemicals: Synthesis of 2-Hydroxyisobutric Acid," *Energy, Sustainability and Society*, vol. 2, No. 11, 2012, pp. 1-9.
Ramsay, et al., "Use of a Nylon Manufacturing Waste as an Industrial Fermentation Substrate," *Applied and Environmental Microbiology*, vol. 52, No. 1, 1986, pp. 152-156.
Rathnasingh et al., "Development and Evaluation of Efficient Recombinant *Escherichia coli* Strains for the Production of 3-Hydroxypropionic Acid from Glycerol," *Biotechnology and Bioengineering*, vol. 104, No. 4, Nov. 1, 2009, pp. 729-739.
Samsonova, et al., "Molecular Cloning and Characterization of *Escherichia coli* K12 ygjG Gene," *BMC Microbiology*, vol. 3, No. 2, 2003, pp. 1-10.
Satoh, et al., "Enzyme-Catalyzed Poly (3-Hydroxybutyrate) Synthesis from Acetate with CoA Recycling and NADPH Regeneration in Vitro," *Journal of Bioscience and Bioengineering*, vol. 95, No. 4, 2003, pp. 335-341.
Scheller, et al., "Generation of the Soluble and Functional Cytosolic Domain of Microsomal Cytochrome P450 52A3," *Journal of Biological Chemistry*, vol. 269, No. 17, 1994, pp. 12779-12783.
Seedorf, et al., "The Genome of Clostridium Kluyveri, a Strict Anaerobe with Unique Metabolic Features," Proceedings of the National Academy of Sciences, vol. 105, No. 6, 2008, pp. 2128-2133.
Shen, et al., "Driving Forces Enable High-Titer Anaerobic 1-Butanol Synthesis in *Escherichia coli*," *Applied and Environmental Microbiology*, vol. 77, No. 9, 2011, pp. 2905-2915.
Shin et al., "Chemometric Approach to Fatty Acid Profiles in Runner-Type Peanut Cultivars by Principal Component Analysis (PCA)," *Food Chemistry* 119, 2010, pp. 1262-1270.
Stanbury et al., "Principles of Fermentation Technology," $2^{nd}$ edition, *Aeration and Agitation*, 1995, 14 pages.
Stols et al., "Production of Succinic Acid Through Overexpression of NAD(+)—Dependent Malic Enzyme in an *Escherichia coli* Mutant," *Applied and Environmental Microbiology*, vol. 63, No. 7, Jul. 1997, pp. 2695-2701.
Suzuki, et al., "GriC and GriD Constitute a Carboxylic Acid Reductase Involved in Grixazone Biosynthesis in Streptomyces Griseus," *Journal of Antibiotics*, vol. 60, No. 6, 2007, pp. 380-387.
Uniprot Accession No. A5CKE1, dated Jun. 12, 2007, 4 pages.
Uniprot Accession No. A5J295, dated Jun. 26, 2007, 3 pages.
Uniprot Accession No. A6ZR27, dated Apr. 29, 2008, 5 pages.
Uniprot Accession No. A7LCI9, dated Sep. 11, 2007, 4 pages.
Uniprot Accession No. A8SFP6, dated Jan. 15, 2008, 3 pages.
Uniprot Accession No. B0JFD4, dated Mar. 18, 2008, 3 pages.
Uniprot Accession No. B0MC58, dated Apr. 8, 2008, 3 pages.
Uniprot Accession No. B3EY95, dated Oct. 29, 2014, 6 pages.
Uniprot Accession No. B7SB75, dated Feb. 10, 2009, 4 pages.
Uniprot Accession No. B7SB91, dated Feb. 10, 2009, 4 pages.
Uniprot Accession No. C1KH66, dated May 26, 2009, 4 pages.
Uniprot Accession No. C7H5K4, dated Oct. 13, 2009, 3 pages.
Uniprot Accession No. D2WEY6, dated Mar. 2, 2010, 4 pages.
Uniprot Accession No. D2WEY7, dated Mar. 2, 2010, 3 pages.
Uniprot Accession No. D2WEY8, dated Mar. 2, 2010, 3 pages.
Uniprot Accession No. D2WEZ2, dated Mar. 2, 2010, 3 pages.
Uniprot Accession No. D3U658, dated Apr. 20, 2010, 3 pages.
Uniprot Accession No. D4Q8H2, dated Jun. 15, 2010, 3 pages.
Uniprot Accession No. D4Q8S6, dated Jun. 15, 2010, 3 pages.
Uniprot Accession No. I6YCA3, dated Nov. 30, 2016, 6 pages.
Uniprot Accession No. O16025, dated Sep. 19, 2002, 8 pages.
Uniprot Accession No. O18404, dated Feb. 21, 2001, 7 pages.
Uniprot Accession No. O34660, dated Jul. 7, 2009, 5 pages.
Uniprot Accession No. P07308, dated Apr. 1, 1988, 8 pages.
Uniprot Accession No. P12693, dated Oct. 1, 1989, 4 pages.
Uniprot Accession No. P33224, dated Feb. 1, 1994, 6 pages.
Uniprot Accession No. P38137, dated Oct. 1, 1994, 5 pages.

(56) References Cited

OTHER PUBLICATIONS

Uniprot Accession No. P41929, dated Nov. 1, 1995, 4 pages.
Uniprot Accession No. P46368, dated Nov. 1, 1995, 5 pages.
Uniprot Accession No. P94211, dated Jul. 15, 1998, 4 pages.
Uniprot Accession No. Q00594, dated Oct. 1, 1993, 4 pages.
Uniprot Accession No. Q1JUP4, dated Sep. 5, 2012, 5 pages.
Uniprot Accession No. Q2TME9, dated Jan. 24, 2006, 3 pages.
Uniprot Accession No. Q3MSM3, dated Nov. 22, 2005, 6 pages.
Uniprot Accession No. Q3MSM4, dated Nov. 22, 2005, 6 pages.
Uniprot Accession No. Q56YU0, dated Oct. 31, 2006, 6 pages.
Uniprot Accession No. Q5BEJ3, dated Apr. 26, 2005, 4 pages.
Uniprot Accession No. Q6A2H0, dated Sep. 27, 2004, 6 pages.
Uniprot Accession No. Q6A2H1, dated Sep. 27, 2004, 6 pages.
Uniprot Accession No. Q6A2H2, dated Sep. 27, 2004, 6 pages.
Uniprot Accession No. Q6LYX3, dated Jul. 24, 2013, 4 pages.
Uniprot Accession No. Q6NUN0, dated Oct. 2, 2007, 8 pages.
Uniprot Accession No. Q6RET3, dated Mar. 21, 2012, 6 pages.
Uniprot Accession No. Q76C19, dated Jul. 5, 2004, 4 pages.
Uniprot Accession No. Q80XL6, dated Oct. 31, 2006, 7 pages.
Uniprot Accession No. Q840S9, dated Jun. 1, 2003, 3 pages.
Uniprot Accession No. Q8I0W9, dated Mar. 1, 2003, 5 pages.
Uniprot Accession No. Q8PYC8, dated Jul. 24, 2013, 5 pages.
Uniprot Accession No. Q8W2B9, dated Mar. 1, 2002, 3 pages.
Uniprot Accession No. Q97XS9, dated Oct. 1, 2001, 4 pages.
Uniprot Accession No. Q9FAB1, dated Mar. 1, 2001, 3 pages.
Uniprot Accession No. Q9FDS1, dated Oct. 1, 2014, 4 pages.
Uniprot Accession No. Q9FNT6, dated Mar. 1, 2001, 3 pages.
Uniprot Accession No. Q9HZV8, dated Mar. 1, 2001, 4 pages.
Uniprot Accession No. Q9SAK4, dated Oct. 31, 2006, 7 pages.
Uniprot Accession No. Q9UUS2, dated Feb. 11, 2002, 6 pages.
Uniprot Accession No. Q9VBP6, dated May 1, 2000, 5 pages.
Uniprot Accession No. Q9XWZ2, dated Oct. 14, 2015, 7 pages.
Uniprot Accession No. Q9YF45, dated Nov. 1, 1999, 4 pages.
Vemuri et al., "Succinate Production in Dual-Phase *Escherichia coli* Fermentations Depends on the Time of Transition of Aerobic to Anaerobic Conditions," *Journal of Industrial Microbiology & Biotechnology*, vol. 28, 2002, pp. 325-332.
Venkitasubramanian et al., "Aldehyde Oxidoreductase as a Biocatalyst: Reductions of Vanillic Acid," *Enzyme and Microbial Technology*, vol. 42, No. 2, Jan. 2008, pp. 130-137.
Wee, et al., "Biotechnological Production of Lactic Acid and its Recent Applications," *Food Technology and Biotechnology*, vol. 44, No. 2, 2006, pp. 163-172.
Wittek et al., "Arabidopsis Enhanced Disease SUSCEPTIBILITY1 Promotes Systemic Acquired Resistance Via Azelaic Acid and its Precursors 9-oxo Nonanoic Acid," *Journal of Experimental Botany*, vol. 65, No. 20, Aug. 11, 2014, pp. 5919-5931.
Woolridge, et al., "Efflux of the Natural Polyamine Spermidine Facilitated by the Bacillus Subtillis Multidrug Transporter Bit," *Journal of Biological Chemistry*, vol. 272, No. 14, 1997, pp. 8864-8866.
Yang, et al., "Value-Added Uses for Crude Glycerol—A Byproduct of Biodiesel Production," *Biotechnology for Biofuels*, vol. 5, No. 13, 2012, pp. 1-10.
Yonaha, et al., "4-Aminobutyrate: 2-Oxoglutarate Aminotransferase of Streptomyces Griseus," *European Journal of Biochemistry*, vol. 146, 1985, pp. 101-106.
Zhuang, et al., "Divergence of Function in the Hot Dog Fold Enzyme Superfamily: the Bacterial Thioesterase YciA," *Biochemistry*, vol. 47, No. 9, 2008, pp. 2789-2796.

\* cited by examiner

FIG. 8A

| SEQ ID NOs | Organism | GENBANK reference | Amino acid sequence | Gene ID (Description) | Gene sequence |
|---|---|---|---|---|---|
| 1 and 24 | Mycobacterium marinum | ACC40567.1 | MSPITREERLERRIQDLYANDPQFAAAKPATAITAAIERPGLPLPQIIEFTVMTGYADRPAL ACRSVEFVTDAGTGHTLRLLPHFETISYGELWDRISALADVLSTEQTVRPGDRVCLLGF NSVDYATIDMTLARLGAVAVPLQTSAAIFQLQPIVAETQPTMNAASVDALAADATELALS GDITATHVLVFDHHRQVDAHRAAVESAREHLAGSAVVETLAEAIARGDVIRPGASAGSA PGTIDVSIBDSLALLIYTSGSTGAPKGAMYPHRNVATFWRKETWFEGGSYEPSITLNFMP MSHVMGROIEYGTLCNGGTAYFVAKSDLSTLFEDLALVRPTELTFVPRVWDMVFCEF IQSEVDRRLVDSADRVALEAQVKAEIRNDVLGGRYTSALTCSSAPISOEMKANVVEELID MAHLVEGYGSTEAGMILIDGAIRRPAVLDYKLVDVPDIGYFLTERPHPRGELLVKTDSLFP GYYQBAEVTADVFEDADGFYRTGDIMAEVGPEQFVLDRRMNVLKLSCQEFVTVSKLEA VFGDSPLVRQIMYNGNSARAYLLAVPTQEALDAVPVEELKARLGDSLQEVAKAAGLQS YEIPRDFHETTPWTLENGLLTGRKLARPQLKKHYGELLEQIYTDLAHGCQADELRSLRQS GADAFHVLVFCRAAALLGGSASDVQPDAHFTDLGGDSLSALSFTNLLHEIFDEVPVG VVSIPANDLQALAEDYVEAARKPGSSRPTFASVMGASNGCQVPTEVHASGDLSLDKFHDAAATL AEAPRLPAAMTDVRITVLITGATGFLGRYLAESVLHERMDLIVDSKLLCLVRAKSDTEARAR LDKFEDSGQDPELLAHYRALAGDHHLEVLAGDKGFEADLGLDRGTWDVQRIADTVDLAVDPAA LVNHAVPYSOLFGPNALGTAELLIRLALTSSKIKPYSYTSTTGVADCIPPSAFTEDADHRVHSA TRAVDDSYANGYSNSKWAGEVLREAHDLCGLPVAVFRCDMILADTTWAGQLRVPD MFTRMILSLAATGIAPGSFYELAADGARQRAHYDGLPVEFIAEASTLGAAGLRVPD HVMNPYDDGIGLDEFVDWLNESGCPICRIADYGDWLIORFETALRALPDRQRHSSLIPL LHNYRQPERPVRGSIAPTDRFRAAAVQEAKIGPKDIRHPVIGAPIMRKYVSDLRLLGLL | FadD9<br>(fatty-acid-CoA ligase FadD9) | ATGTCGCCAATCACGCGTGAAGAGCGGCTCGAGCGGCGCATCCAGGACCTCTACGCCAAC GACCCGCAGTTCGCCGCCAAGCCGGCCAACACCGCCATCACCGCAGCAATCGAGCGGCCG GGTCTACCGCTACCCCAGATCACCGAGAACGTCATGACCGGATACGCCGATCGGCCGGCT CTCGCTTGCAGCGCTCGGTCGAATTCGTGACCGACGCCGGCACTGGCCACACCACGTTCTGA CTGCTTCCCCACTTCGAAACCATCAGCTACGGCGAGCTTTGGGACCGGATCAGCGCACTG GCCGACGTGCTCAGCGAGCAGACAGGTAAGCCGGCGACCGGTCTGCTTGGGC TTCAACAGCGTCGACTACGCCGACGATCGACATGACGCTGGCCCGGCTGGGCGTGGCC GTACCAGCGGCCACCGCCGGATCTCAGCCTGCAGCCGATCGTGGCCGAAGCCCAG CCCACCATGATGCGGCCAGCGTCGACGCCGCGAAGCGGCGGCCAACGGGCTTGCT GGTCAGCGGGCTACCCGAGTCCTGGTGTTCGACCACCACCGGCAGGTTGACGCCACCGG GCAGGGGTCGAATCCGCCGGGAGCGCTCGAGTCGGCCCTGGTCCGTCGAAACCTGGCC GAGGCATGCGGCGGAGACTGCTCCGCCTACCGATCTACACCTCGGGCAGCACGGGCACC GATGTCGTCGACGACTTCGTCGCCAGCCAACGGTGCGAACTTGCGACTCTGCGGAAGCACGCGG AAGGGCCGGGCTACCGAGCCGTCGATCAGCTGCACTTCATGCCAATGAGCCACGTCATGGGC CGCCAAATCTCGTACGGCACGCTGTGCAATGGCGGCACCGCTACTTCGTGGCGAAAAGC GATCTCTCCACCTTGTTCGAAGACTGGCTGTCGTGCGGGCCCACCGAGCTGACCTTCGTG CCCGCGTGTGGGACATGGTGTTCGCCGTCGAAGCCCAGGTCGAGGGCATGACCAGGCCT GACGGCGTGGGACGGTATACCAGGCACTGAGGAGCCATTCGGCCCCCATCTCGACGAGATGAAG GGGATGATCCTGATGACGGACGCTACTTCCTGACGACGAGCCACACGGGCAGGGCGGGTGATCCGTC GTCAAGAACCGATAGTTGTCGGCCGAGAGCCAGCCGGGAGTTTGCTG ITCGAGCGGCTTCTACCGACGGTCGAGGACCGGCCAGGGCCTGTGAACAG ITCGTGTACCTGACCCGGGCCAACAGTTGTCCGACAGCGCCGGCTGCTTACGCGAGATCATACTAC GTCGCAAACTGCAAGCCGGTGTCTACCTGTTGGCAGCCACTGGCAACAGGAGCGCCTGGAAC GCCGCTGCTCGTGGAGCGCCTAAGGCGCGGCTTGAGCAACTGGCTGTGCGTGCAAGG GCCGGCCTGCAGTCCTACGAGTCCGCCCGCCGACCTTCATCATGCAACAACACCATGG ACGCTGGAGAACGGCCTTCCTGAAGGAGCATCCACCGGCAAGTTGGCCACCAGGACCCGCAGCTGAAAAG CATTACGGCGAGCTTCTGAAGGCAGAGATCTACACGGCCTGGCCACCAGGCCTCGGCTGGAA CTGCGCGTCGACCCGCGACCCGCCGACTGCACTTGAGCTGCGACGTTGAGCATGCCACTTCACCGAT GCCGCGCCGCTGTTGGCCGCCCGCCAGCTGCGCCTGACGCTCAGCCTGAT TTGGGCGGGCTCGACTGCTCGTCGGCGCTGTGTTCAGCGCGCAACCTGCTCGACGATCTTCGAC ATCGAAGCGGGGGCTGGGCTCATGTCATCGCCCGCGAACGACTTTGCAGCCCTGGCCGAC TACGTGCGGGTGGCAGCGCTGCAACGGGTCACCGAGGTCATGCCGAGCACCTTCGCCTGGTCGACGGC GCCTGAATGGGCAGGTCACCGAGGTGCATGCGGAGCCGACCCTGTCCCTGGACAATTCATC GATGCCCGCAACCTGGCGAAGCTCCCGCCCGTCCGCCCACAAGCCCAAGCCCAAGTGCGACC GTCGTGGACCTGGTCACGGGCAAGACGCATTGCTGCCCGCCCTGGTGAATGGGCTGGAG CGGATGGACCTTGGTCGACGGCAAAGACGTTGACAGGCGGGCAACCTTGCGACCCCACTAC GCAACGGCCGCCGGCTTGGAGACACCGCCAGCTGTTCACAGAGGGTGTCTACGACCTTC GGACTGGACCTGGTCGACGGGCTACCAGCAGCTAGCCCATACGCGGCATAGGCTACTGACGAGCA GCGGCCCGGTCGCAACCACGTACTGCCATACAGCGCACTGTTCGGCCACCAAGCCGTGCG ACCGCGAGCTGTGCCGGCTGCGCGACCAGATCCGCTGGCCGTTCACCGAGGCGCCGATCCGG ACAATCGGGTCTGCCGCGCAGCCGGGCATCGGCCGCCCGAAGATCGGGCCCGAAGAAGAG GTCATCACGCACCCCGGCGAGTGCTTCGCCGGCGCATCACCAGCTAGGTACTGCAACCGCAAG TGGGGCGGCGAGTCTGTTGCCGCCGCATGACCTGCCGTGGCCTGCGGTTCCGCGGAC TTCCGCTGCGACATGATCCTGCCGGCTGACAAAAGCCGTCGCCACGGACGCAGCCAAT |

FIG. 8B

| SEQ ID NOs | Organism | GENBANK reference | Amino acid sequence | Gene ID (Description) | Gene sequence |
|---|---|---|---|---|---|
| | | | | | ATGTTCACCCGGATGATCCTCGAGCCTGGCGGCGGCCACCGGTATCGCGCGGGGTTCGTTCTAT GAGCTGCGCGGCGACGGCGCCCGCGACCTGCACTATGACGCTGCTCGCCGTCGAGTTC ATCGCCGAGGCGGATTTCGACTTTGGGTGGCGAGAGCCAGGGATGGTTCCACACGTATCAC GTGATGAACCCCTACGACGACGGCATGGGACTTCGACTACTATGGGAGCTGGCTCAACGAG TCCGGTTGCCCCATCCAGCGCATCCTGACTATGCACGCCTGCTGAGCCGTTCGAAACC GCCACTGCGCCTGCCCGATCGGTCAGCGGGCACAGCCTCACTGCTGCGCTGCTTGCACAAC TAACCCGCTAGCCCGAGCGCTCGCCGTCCGCTGGCCAGGCAGATCCGGACGCTCCCCCATCCAGCCC GCCGCTGCCAAGAGGCCAAGATCCGGCCCGACAAAGACATTCCGCACGTACGCGCCGATC ATCGTGAAGTACCTCGCGCCTACTCGGCTCTCTGA |
| 2 and 25 | Mycobacterium smegmatis | ABK71854.1 | MTSJVHDATRGVTETALDDEQSTRRAELYATDPFAAAAPLTAYVIDAAHNPGLRLAEL LQTLFTCYGDRPALGYHRARELATDEGGRVTVTRLLPRFDTLTYACVWMSRVQAVAAAALRH NFACQPYPCGDAVATHGFASPDVLTLDLVCAVLGLVSVPLQHNAPVSRLAPHLAEVEPRLT VSAEFYLDLAVESVRDVMNVSQLLVVFDNHPEVDDHRDALARAREQLAGKGIAVTTLDAI ADEGAGLPAEPNYTADHDQRLAMRLYTSGSTGAPKGAMVTEAMVARLMTMSFHTGDP TPVRWVNFMAPLNHLSGGRIPSTAVQNGGTSYFVPESDMSTLEEDLALVRPTELGLVPRV ADMLVQHHLATVGRLVTQGADELTAEKQAGAELRQVLGGRVITGFVSTAPLAAEMR AFLDITLGAHIVDQGYGLTETGAVTRDGVIRPPVDYKLDVPELGYFSTDKVPPRGELLV RSQITLPGYYKRPEVTASVFDRDGVLAVPRCFVGNSERSFLLAVVPTPEALEQVDPAALKAALADSLQR VAVANLEAVFSCGAALVRGHFVGNSERSFLLAVVPTPEALEQYDPAALKAALADSLQR TARDAELQSYEVPADFRVETEPFSAANGILSGVCKLLRPNLKDRYGDBRLEQMAYABAAT QANQJRELRRAAATQPVDTLTQAAATHLGTGSEVASDAHFTDLGSEDSLSATLSNLLSD FFGFEVPGTVNPATNLJAQAQHEAQRTAGDRRIPSFTTVHGADATEBRASELTLTKFA DAETLRAAPGLPKVTTEPRTVLLSGAMGWLGRFLTHLQWLERLAPVGGTLTIVRGRDDA AARARLTQAYDTDPELSRREAELADRHLRVVAGDNGDPNLLGITPEIDWMHRLAAEVDLLVV HPAALVNHNVLPYRQLFGPRNVVGTAEVIKLALTERKPVTYLSTYSVAMAGIPDFEEDGDIR TVSPVRPLDGGYANGVGNSKWAGEVILREAHDLLCGLPVATFRSDMHLAHPRYRGGQVAN VPDMFTRLLLSLLTGVAPRSFYKGDGERPRAHYPGLTVDFVAEAVTTLGAQQOREGVVSY DVMANPHDDGSLDVFVDWLJIRAGHPHIDRVDDVDDWVRRFETALTALPEKRRAGQTVLP LLHAFRAPQAPLRGAPEPFTEVFHAAVRTARVGPGDIPHLDEALEDKYIRDLREFGLJ | MSMEG_5739 (putative long-chain fatty-acid–CoA ligase) | ATGACCAGCGJATGTTCACGACGJCCACGAGCACCGCTACCGAAACATCGACGACGAG CAGTCGACCCGCCGCATCGCCGAGCTGTATGCCACCGATCCGAAGTTCGCCGCTCGCCGCCA CCGTTGCCCGCCTGGTCACCGGGTCGACCGGCGCACAAACCGGCTGCGGCTGGCAGAGATCCTG CAGACCCTGTTCACCGGCTACGGTGACCGGCCGGCTAGGATACCGGCCGTTCGAACCTG GCCAGCGAGCTGGCGACCGACGAGGGGGCACCGTAGCGCTGCTGCCGCCGTTCGACCACCTGCTG TACGCCCAGGTGTCGTTCGCGCGTGCAAGGCGGTCGCCGGACCCTCGCCGACAACTCGCG CAGCCGATCTACCCGGCGACGCCTGGCCTGCTGCTGCTTGCCTGCCCTTGCCGAGTCGAGTACGTC AGCTGGATCATGATGCCACCGTCGACGACGACTCGCCTGCCTGTCTCAGCAACGGA CCGGTCAGCCGGCGTGCCCCCGATCCTGCCCGAGGTGAACCCAGTCGAACCTCGCCACCGGACCGTGAGG GCCAATACCTGACCTCCGACATGGATCCCGAATCGTGTCGCCTGCCTCGCGCCGTCCAGGCT GTGTTGACCATCACCCGGAGCGGGACCACGCGGACGCGCTGCGCGTCGGCCTGCCTGCGCGGT GAACACTGCCCGGCCAAGGGCATCGCCCGTCACCCACCGGAGCGATCGCCGACGAGGGC GCCGCCTGCTGCCGGGCCAACCGATCTACACGCGGACCATGATCAGCGCCTGCCGATGATC CTGTACACCTCGGTTCACCGGCGCCACCCAAGGGTGCGATGTACAGGCCAGGCGATGGGTG AGCGCGCGATGTAAACCGACTGCGTTCATCATCACGCACGCGGTCATCAACGGTGAAC TCATGCGCGCTCCAACCGGGCAGTCCGAGCATCCCAAGGGCACCGCCGTGCCGAAGGG GAAACCAGTACTTGCGCGGGCAATCCGGCCATGTCCGACAGTCGCGACATGTGCGAAGGT CGCCGCCCGACCGCGAACTCGGCCTGGTCAGGTCGCAAACGTCAGTGCCGAAGCAG AAGCCCCCCGAGGTCACCGAGGCGTCTTCCACCGGGACGGTCTACACCGGCGGCTACTAC GTCATGGCCCGAGAACCGACCAGCCGACCACTCTGGTGTACGTGACCGGTGCAAACGTCCTC AAACTGTCGAGACGCAGGGCGAGTTCGTGACGGTCGCAACCAGGAGCGCAGTTCTTCGGCCTG GCCGCTGGTGCCGCAGATTCCGCCGATTCCTGTACGGCAACAGCGAGCGCAGTTCTTCGGCCTG GTGGTCCCGGAGCGGCTCGAGCAGTCGAGCGCCACCGACGGCCAATCCTACGACGGTCGGGGTGG GATTTCATGTTCCGACTGCTGAGCCTGGACGGTCCCGCCACCGAAACGGGTGCTCGTGCAGGCCGA AAACTGTCCGGTCCAACCTCCAAAGACCTACTGGCGCCTGGACGCAGATGACGTACGCG GATATCGGGGCCTGAGTCCACCGCCAGGGCAACCCAGTCGCGCAACCTCGCGACATGGCTACGC CGGGGTGATCGACGACCTCACCAGTCTACCTGACCTGCCAGATCTGCCTGCCCGACGACTCTACGG GCATCCGGTCCCAGATTCGTCAGTTGTACGGCAACAGCGAGCGCAGTTCTTCTCTGGCGTCCAG GTGGTCCCCGGAGCGCCAGGGGCTCGAGCAGTCGAGCGCCACCGACGGCCAATCCTACGAGGGTCGCGGTG GATTTCATGTTCCGACTGCTGAGCCTGGACGGCCCCGCCACCGAAACGGGTGCTCGTGCAGGCCGA AAACTGCCGGTCCAACCTCCAAAGACCTACCTGGCGCCTGGACGCAGATGACGTACGCC GATATCGGGGCCTGAGTTCACCGCCAGGGCAACCAGTTGCGCGCAACCCTGGCGCCCCACACAA CCGGTGATCGACGACCTCACCACCCCAGCCTGCTCACCGACTCTCGCGCGGGACGTTGG GCATCCGGTGCCCAGATTTCGTTCAGGTCTGCGCAGCCTCTACGGGCGCGGACACTTCG AACCTGTCGAGCGATTCTTCGGGTTGCAAGCATCCGGGGACCATCCGTGAAACCGGCC ACCAACTCGGCCAACCTGCCCAGCACGCTGCCACCGCACCGCCGGCACCGGGACCTCGCCGAAACCGACACGCAGG CGGAGTTTCACCACTGCACCCTGCACCGGCAGCGACCCCCTGAGCTGCCTCTGAGCCAGGCACC CGGAACAAGTCATCGATCCGACCCGAAACCGTCAGGCGTCCACCGGGGTCTGCCAAGGTCACC ACCGAGCGACGAGCGGTGTTGCTCTCGGCGCCAACGCCCCTGCATCACGATCGTCCTCACG TTGCAGTGGGCCTCGAACGCCGGGCACCCTGCTCGCATCAGATCGTGCTGGGGGC |

FIG. 8C

| SEQ ID NOs | Organism | GENBANK reference | Amino acid sequence | Gene ID (Description) | Gene sequence |
|---|---|---|---|---|---|
| | | | | | CGGGACGACGCCGCGGCCCGGCCGGCACGGCTGACCCAGGCCTTACGACACCGACGATCCCGAGTTG |
| | | | | | TCCGCGCCTTCGCCGGAGCTGCCGGGTGTGGCGGTGGTGCCGGTGACATCGGC |
| | | | | | GACCGAATCTGGGCTCACACCGAGATCTGGCACCGGCCTGCCGCAGGTCGACCTG |
| | | | | | GTGGTGCACGGCAGCGCTGGTCAACCACGTGCTCCTACCGGCAGTGTTCGGCCCC |
| | | | | | AACTGTGGGCACGGCGGCTCGATCGAATGCAAGCTGACCCTCACCGAACGGATCAAGTCCGTC |
| | | | | | ACGTACCTGTCCACCGGCGTCGTCGGCGAGCTGATCGGGATCATCCCCGACTTCGAGGAGCTGGC |
| | | | | | ATCCGGAACCGTGAGCCGCCGGAGGCTGCTCGGCGAGGTGCCTGATGATCCTGTGCGGGCTGCCCGTG |
| | | | | | AGCAAGTGGCCGGCGAGGTCGCAGTGCACGAGCTCTCCACGGCATGCGCCGCCGCCGCCTGCCC |
| | | | | | GCGACAGTGCTTCGACGACTCCTGTTGAGCCGCCTCCGGAGCCGCACTACCCGGCCTGACGGTCGATTC |
| | | | | | CCAGACATGTTACGGCCAGACCGGTGACGGTCCGCAGCACGCGCGAGGGGATACGGTCCTACGAC |
| | | | | | TTCTACATCCGGAAGACGGTGACGGCCGTCACGACGCTCGGCGTGCAGCACGGTCGAGCGGCAGAAC |
| | | | | | GTGATGAACCGCCACGAGCACGACGACGCGGATCTCCGATGTCGTGAACTGGCTGATCGG |
| | | | | | GCGGGCCATCGATCGCGACCGGGTGCAACGAGCCGTGGAGGCGCACTTCGAGGCG |
| | | | | | GCGTTGACCGCGCGTCTCCGGACACGGCTCTGGACACGCTGCGTTCGGCCGGCCGCCGC |
| | | | | | TCGAGGGTCGCGACCTGCAGGGACACGCTTCGGCGGGAGACATCCGCACTCGAGGAGTGTTGCACGG |
| | | | | | GCGGTGGCGCACCGCGAAGTGCCCGGGGAGCTGCCACCGCTCGAAGAGCGCTGATC |
| | | | | | GACAAGTACATACGGATCTGGTGAGTTGGGGTGATCTGA |
| 3 and 26 | Segniliparus rugosus | EFV11917.1 | MGDGEERAKRFFQRKGELSATDPQFAAAAPQPAVVEAVSDPSLSFRRYLDTLMRGSYAE HPALAHRVGAGYETHSYGELWARVGAIAAAWQADGLAPGDFVATVGFTSPDYVAVEIL AAARSGLVSVPLCQAGASLAQLVGILEETEPKVLAASASSLEGAVACAALAAPSYQRLVAFED LRGPDASESAADERRGALADAEEFQLRARAGRAVVVETLADLAARGEALPEAPLFEPAEG EDPLALUYTSGSTGAPKGAMVYSQRLVSCLWGRTFPVVPGMPNISLHYMPLSHSYGRAV LAGALSAGGTAHFTANSDLSTLFEDIALARPFEJALVPRVCEMLPQESQRGCQDVAELRE RVLCGRLLVAVCGSAPLSPEMRAFMEEVLGFPLLDGYGSTEALGVMRRNGIHQRPPVLDY KLVDVPELGVYRTDKPYPRGELCRSTSLJSGYYKRPETTAEVFDAQGYYKTGDVMAEIAP DHLVYVDRSKNMVLKLSQGEFVAVAKLEAGLSYEVPRDFLIETEPPFTTQNGLLSEVGKKLLRPKLK ARVGEALEARYDEAHGQADELRLPDGAGQRPVVETVRAAVASGSEGAEVGFP.A ARYGEALEARVDEAHGQADELRLPDGAGQRPVVETYVRAAVASGSEGAEVGFP.A NFADLGGDSLSALSLAMLLHDVFEVPVRIIGPTASLAGIAKHEAERAGASAPTAASV HGAGATRIHASELTLEKFLPEDLLSAAKGLPAADQVRTVLLTGANGWLGRFLALEQLER LARSEQDDGKLICLVRGKDAAAARRHEETLGTDPALAARFAELAEGRHLEVVPGOVGEP KFGLDDAAMDRLAEEVDVNVHPAALVNHVPVHQLFGPNVVGTAEIRLATANFKPVT YLSTVAVAAGVEPSSFEEDGDIRAVVPERPLGDGYANGYGMSKRMAGEVILREAHELYG LPVAVFRSDMILAHTRYTGQLNVPDQFTRLVLSLLATGIAPKSFYQOGAAGERQRAHY DGIPVDFTAEAITLGAEPSWFDGGAGFRSFDVFNPHHDGVGLDEFVDVLIEAGHPS RIDDHKEWFARFETAVRGLPEACRQHSLLPLLRAYSFPHPFVDGSVVPTGKFQGAVKA AQVGSDHDVPHLGKALIVKYADDLKALGLL | HMPREF9336_ 03251 (thioester reductase domain-containing protein) | ATGGGCGACGGCGAAGAAGCGGGCGAAGCGTTCTTCCAGAGGATCGGGGAGCTGAGCGCG ACGGACCCGCCGAGTTCGCCGCCGCCCTGCCCGGAGCCCCGGTGGTCGAGGCGTGTCGGAC CCCTCGCTCTCGTTCCACCCGCTACTTCGACACACTGATGCGCGGTCGATACGCGGAAC GCGCTCGCCCACCGGGTCGGCGCGGGCTATGAGACGCATCAGCTACGGCGAGCTCTGGGCG CGGGTCGGGGCGATTGCGGCGGCGTGGCAGGCGGACGGGGATGCGCCCGGGCGACTTCGTC GCCACGGTCGGTTTCACCAGCCCGGACTACGTCGCCGTCGAGATCCTGGCGGCCGCGAGGTCG GGCTGGTCGTCGTTGCCGCTGTGCCAGGCGGGTGCTTCGCTGGCGCAGCTCGTCGGGATCCTC GAGGAGACCGAGCCGAAGGTGCTCGCGGCGAGCGCGAGCAGCCTGAGGGCGCCGTTGCC TGCGCCTGGCGCCGCTCCCCAGCCGTGCGGCCGCCGGCCGGATGCCGAGGAGCAGCTG CGCGGAGAGCCGCGGGCCTGTGTCGTGTCAACCCCTGCGCGACTTGGCGCCGAGCGCACAG GCCCTGCCCGAAGCCCCGCTGTTCGAGCCCGCCGAGGGGGAAGAATGTACTGCAGCGCCTGGTG ATCTACACGTCGGGCTCCGGCTCGACCGGGGCGCCCAAGGGCGCGATGGTATGTCAGCCGACTCGCTCGTATAC TCCCAGCCGCTGAGCGATCTCTGGGCAGGCAGCATGCCGAACATCTCGCTGCATTAC ATGCCGCTGAGCCACTTCTACGGGCGTGCCGTGCTCGCCGGCGCTCTCGGCCGGCGGGGG ACCGCCCACTTCACCGCGAACAGCGACCTTTCCACCCTCTTCGAGGACATCGCGCTCGCC CGCCCGTTCTTCCTGCCGGTCTGCGAGATGCTGCCGCAGGAGAGCCAGCGCGGCCAGGACGTCGCG GTCGGCCGGCCTTCCTGTGCGGAGCCTCGGTCAAGGCCGGTAGCTCGCCCCGGGAGAGCCGTTGCC GTGTGGCGCCTCTGCGCTGGACGCTCGGAGATGCGCGCGGCCATGGAGGAGGCTGTACGAG TTCCGCGCTGCCGACCGCTACGGCTGACCCGCAGACTGCCGAACGCTGCGGAGCTCAGCGGAC ATCCAGCCGCCGACGCTCCGGTCATGCGACGAACAGCTGGCGAGATGATGCCGAGAGCTGGGCCTATGC ACGACGAACAAGCCCTACCCGAACGCCGAGTCGGATGCCGCGGTCAGGCCTCAGCCGCTCCGGAAGCAAGCCGTCTCC GGCTACTACAAGCGCCCCGAGATCACCGCGAGGTGTTTCGACGCAGGGCTACAGCGGCTACACAG ACCGGCGACGTGATGGCCGAGATCGCCCCGGACCACCTGGTGTACGTGGACCGGAAGCAAG AACGTCCTTCAAACTCTCCAAGGCGAGTCGCTGCCGTCGCCGAACATCTCGCTGCATTAC GGCGAGCGCCCGCTACGTGAAGCAGATCTTCTGCGCACAGGCACGCTCCGCCTCTCTG CGGCGACGGCCGGGCGGAAACGCGCGAAAGATGCGAAGAGGTGAGAGGACCAAGGGACCGAAGCTGGTCGCGGGCCTCC GTCCCGGCGACTTCTTGATCGGAGACGAGCTGCAAGCTGGTCAAGGCCCGGTACGGACGAGGCGCTACGAGG CGCTACGAGATCGCGGCTGGTCGAAGACCGTCTGCGAGCTGCAGGCGCCCCGGATGCGGGGCGACGGGCGCG GGACAGCGCCCGGTGGTGCTGAGACCGTCGAGACGGTGGAGACGGTGGAGCTGCTCGGCTCCGAG |

FIG. 8D

| SEQ ID NOs | Organism | GENBANK reference | Amino acid sequence | Gene ID (Description) | Gene sequence |
|---|---|---|---|---|---|
| | | | | | GGGCCGGAGGGTCGGCCTCGGAGGCGGCCCTGAGGCGGAAGTTCGGCGGCGACTCGCTCTCCGCG TTGAGCCTTGCGAACTTGCTCGCACGACGTCTTCGCAGTCGAAGTCGAGGTGCCGGTGCCGGATCATC ATCGGCCCGACCCGCTCGCTCGCCGGCGGCCCTCCGTGCACGGCGCGGAGGCGACCTGCGGAGGATCCAGAGGAGCGAGC GAGCTGAACGCTGGAGAATTCTCCTGAAAGACCTTGCTTGCCGTCGCAGGAAGGGCGTTTCG GCCTGCAACGCTGGAGAAGCAGATCCAAAGGGCTCTCGAAGGCGTCTCTTGACGGCGCCAGCGGCTCGGCTGGCCTCGGCGTTTC CTGCGGTTGAACAGATCTGAAAGACGCGGCTCTCGGGACGGCCTCCGCCGACGCGGATCGGCGGTCAGGAGCGCGAGAAGCTTGATC TGCCTAGTCCGGGAAAGGAAAGACGCGGCTCTGGCAGTTCGCTGAACTTGGGCCAGCGGATCGGAAGGGCGGGATGGAAAACCCTTCGGC ACGGACCGTGCGCGAGCCGAAGTTCGGCTTGACGACGCGCATGGACCGGACCGGCTAGGCC GAGGAGGTGGACGTCATCGTCCACCCGGTGGGAACCAGGTCTCGCCGCAGAGGAAGAAGCCGCAGTTGCGTAGCGCCGTGAGGACCCCTCC TCCTTCGAGGGAGGGACGGGACGACGACGCGCGGGGCCGGGCGGGAAACGGCCTTGGGGGAGTCGGGGAGATCGG TACGCGGAACGGCTACCGGCAACAGGAAATCGGCGGGGGGAGTCGTGCTTGCGGCGAACGACGAC GAGCTGGTCGACGGCGCGGGCGGTTGCAGGTTCGCCAGCTTCAACCGACAGCAC TACGACCGGCACAGCTCAACGTCCCGACAGCTCTTAGCGTAGAGTCCTCTTGAGCTTTGCCGG ACCGGGAATCCGCCCAAGTCTTCTTTATCCGGACATTGCGGTCGGCTGGCAAAGCCAGCGGGGCGG CATTACGACGGCATCCCCGGGCTGCCGATCGCCAGCTACAGCTCTGCGACGTGTTCAACCGCACCAC GAGCGGGGTGGGCTTGACGACGGCGAGTTTGGTGAGCTCATCGAAGGCGGCATCGAGCGCACGCGAGCTCTCC AGGATCGAGACCACAAGGAATGCTTCGCCGCGGTTCGAGACGCCTGCGCCGCGCTCCC GAAGCGCAGCGCCAGCATTCGTCATTCCGACCGGGGAGTTCAGGCGGGCGGTCAAAGCCCAGCGGGAG CCCGTGGACGGCAGTGTCATCGCGACAACGTGCGCGACGTGCGTGCGTGATGTGAAAGCGCGAAGCAG GACCTGAAGGCTCTCGGACTCCTGA |
| 4 and 27 | Mycobacterium smegmatis | ABK75684.1 | MTHETREDRAPNRRIDHLFETQPQFAAARPDEAISAAAAQPELRLPAAAVKQILAGSYADRP ALGKRAVEFVTDEEGRTTAKLLPRFDTITYRQLAGRIGQAVTNAWHKHPVNAGDRVAEL GFTSVDYTTIHALLELGAVSVPLQTSAPVAQLQPHVAETEPKVASSVDFLADAVALVES GPAPSRLUVVFDYSHEVDDQREAFEAAKGKLAGTGVVVETTFDALDRGRSLADAPLYVP DEAPRLTLIJYTSGTGTPKGAMYPESKTATMWNQAGSKARWDETLGVMPSITJNFMFP MSHNMGRGHLCSTDASGGTAYFAARSDLSTFHLEDLALVRPFTSJLNFVPRMWDMLFQEYQ SRLDNRRAEGSEDRAEAAVLEEVRTQJLLGGRFVSALTGSAPISAEMKSWVEDLLDMHL LEGVESTEAGAVFIDGCIUQRPPVIDYKLVDVPDLGYFATDRPYPRGELLVKSEQMPPGV YKRPETAEMFDEDGYVRTGDNVAELGPOHLE

FIG. 8E

| SEQ ID NOs | Organism | GENBANK reference | Amino acid sequence | Gene ID (Description) | Gene sequence |
|---|---|---|---|---|---|
| | | | | | GAGGACGGGTACTACCGGCACCGGCGACATCGTCGCCGAGCTCGGGCTCGGACCATTCTGAA TACCTCGACGCCGCCAACAACGTGCTGAAACTGCAGGGCGAATTCTCACGGTCTCC AAGCTGGAAGCGGCGTCCTATCTGTGGCGGTCGCGACAGCCCCTGGTACGCCAGATTACGTCACGTTGG AGCGCCGGTCCTATCTGTGGCGGTCGACAGCCCCTGGTACGCCAGATTACGCTCAGGTTGG GAGGGTGAGAACTCAAGTCGGCATCAGCGACTTCACTCGCAAGGACGGACTGTCACGTTGG GGATTGCAGTCGTATGAGATCCGTCGTGACTTCCTCGTCGAGAACAACCTTTCACGCTG GAGAACTGGCCTCGAAGCAGCTCTACACCGACCCTGGCCAAGCTTGGCGCGGGAAACTGAAGCCGACTAC GGCGAACGCCTCGAACGAGCTCTACACGACCGACGACCGGTCAGTCAACCTCAAACGACGCTGCGC GAGTTGCCGCCCAACGGAGCGCCGAGGCAGCCGACCGGCGAGCGCACCCTGGAGTCCACGCGACCCTCGGC GCACTCTCGGTGCCTCGCTCACCGATCTCGCCGATGCGCATCGCATCCACCGATCTGGGT GGAGATTCGTTCGGCCGTTGAGCTTCTCGAACCTGTCGACGAGATCTTGATGTCGAC GTGCCGGTCGGCGTCATCGTCACCGCCGACCTGGCAGGCGTGCGCGGCCGTCACGTC GAGGCGAACTCGCCGGACAAGCGCCACCATACCGCTGGTGCACGGGCGACGGCGAGGCCC ACCGAAGGTCGCGGCCGGCTGATCTTGCCCTCGGGCACCGAGATCCCGTTCATGGAAGACCCTGTC GCCGGCTCGGGTTCGCCGCTATCTGCGGCCCGATGCGCGAGGATCGGAACCGGTGCATCGCGGTAGATCC ACCGGTTCATCGTCGCCTCCGCCTCGCAGCGAGCAGGACAAGAGGCGGCGTCTGGTGAC TGGCAAGGTCGATCTGCTGCCCCGCCCAGGGAGGACGACGGAGGCGGCGTCTGGTGAC CACCTCGAGGTTGACTGCGTGACCACCACCCGACAGGGCCGATCTCGGCCAGTGGCAACACG CCACCGAGCTCGTCCGACGATGCGGCCGACCCCGACGACCCGACGACGCGACACACG GTCCGTCGGTTACAACCGCTTCGACACCGCGCGACGGCTCAAGGCGACATCAGGCCGACCAGCCCC ATGCGCTGATCGTCGCCGACAGCATCGAGCTCGCCGCACCTGCCCGGCCATCGACAGGCTGC GGCATCCCCGAGGGCGTTCGTCGCAACGCGTTACGGCGACATCCGGCGAGATCCGCCGGACATGCG CGGTGTGCCGAGCAGGAAGCCCTGCACGCGAGCAGGTCGACCTGAGAACCGACCACAGAGCTCGAAG CTCGGGAGCCGCACGAACTACTCGGTCAGCTGAACTCGCCGGACCTGAGCAGGAAGACTCGGGCC CTGAGCCTGGTGGCGACGGCCCCGACTACGGACGCCCCATCTACACGACGGACCTGCTGTCACGAC GCCGATGCCGCCCCGCATCGGAGGGCCCGTCTGCGCCGCCGCCCATCGCAGCCCTGGAGCGCAACTCCGACGCCG CCCGTGTCCGCGAACAGGAGTCATCTACGACCCGACGATCACGACGACCGTCAGGACGACGACCCAAG ATCGCCCCCACAAGGACTGCGGTCGGAGGACACCGTCGGCAATCGGACAGGAAGACCCAAG ATCGCCCCCACAAGGACTGGCTGGGAGAGAACCGCACCCTGGGCCCTCCGGGCTTCAGG AACCTGACGATGCTGCAGATGCTGGATTGCTGTAA |
| 5 and 28 | Mycobacterium massiliense | EIV11143.1 | MTNETNPQQEQLSRRIESLRESDPQFRAAQPDPAWAEQVLRPGLHLSEAIAALMTGVA ERPALGERARELVPDQDGRTTLRLLPREDTTTYGELWSRTTSVAAAWHHEDATHPVKSAG DLVATLGFTSIDYTVLDLAIMILGGVAVPLCITSAPASQWTTILAEAEPNTLAVSIELGAA MESVRATPSIKQLVVFDYTPEVDQDQREAFEAASTQLAGTGIALETLDAVIARGAALPAA PLYAPSAGDDPLALLIYTSGSTGAPKGAMHSERNIVRRMWNHREDVRAAGTENLPMRGLNF MFMSHMGRGTILSTLSGGTGYFAASSDMSTLFEDMELIRPTALALVPRVCDMVFQ RFQTEVDRRLASGDTASAEAVAAEVKADIRDNLFGGRVSAVMAVGSAPLSEELGEFHESC FELNLITDSYGSTEAGMVFRDGIVQRPPVIDYKLVDVPELGYFSTDKPHPRGELLLKTDG MFLGYVKHPEVTASVFDADGFYMTGDIVAELAHDNIEIERRRNVLKLSCGEPVAVATL EAEYANSPVVHQIYVVGSSERSYLLAVVVPTPEAVAAAKGDAAAKTTIADSLQDIAKEI QLQSYEVPRDFHEPQPFTQGNGLLTGIAKLARPNLKAHVGPRLEGMYAEIAEEQCQAAEL RALHGVDPPDKPALEFVLKAAQALLGGVSSAELAADAAHFTDLGGELSLALSFSDLLRDFAV EVPQGVIVSSAANDLGGVAAKFVDEQRHSGGTRPTAETVHGAGHTERAADUTLDKFIDE ATLHAAPSLPKAAAGIPHTVLLTGSNGYLGHYLALEWLLERLDKTDGKLVNVRGKNAEAAY GRLEEAFDTGDTELLAHFRSLADKHEVLAGDIGDPNLGLDACTWQRLADTVDVVHP | lgrD_21 ERS375547_03771 (Probable fatty-acid-CoA ligase FadE) | ATGACCGTGACCAACGAAACAAACCCAGCCAGGAGCAGCTATCCCGCCGTATTGAAAGT CTGCGGAGAACGAATCCGCAGTTCCGGAGCCGGCCCAGCCCGGCCGGTCGCAACAG GTGCTCGCCCGGGCCTGAGCATCTTCTGAAGCGATTCGCGGGGCATTGCGTTGATTGACTGCGGC GAGCGGCCCCGGGCGCTCGGTTTGACACCGACCACCGACCACCATCACCTACGCCAGGATGCCGGCACA ACATGCAGCGTCCCGCTGGCATGAAGCATCCGGTACCACCGGTCAAGGCCGGGGCGATTCTG CTGGGTGCCGTGGCGCGGCTGCCGCATTGACCAGACGACCAGGCCGGCCTTCGCAGTGCATCATGATC CTGGCCGAAGCGGAACCCAACATCGCTGGTAAGCATCGAATTGATCGTCGCCGAATG GAATCTGTGCGGGCCACCGCCTCCATCAGGGCCAGCATCGAAGGAGCCAGCAACACCGCAACTCGCGGCGACCGGATC TACGCACCATGCGGCCGACGATCCGCTGGCGCTACCTGCATCTCACCCTCCGGACCACCACC GGGGCTCATGGCCGCCACCCGACCATGACGACGGCGAAACATCGTGCGCCCTGTGGATTCGCGAG GACGTCATGGCCGCCACCGACCGGAGAACCTGCCTGATGCAGGAGATTCATGCCGATGAGT |

FIG. 8F

| SEQ ID NOs | Organism | GENBANK reference | Amino acid sequence | Gene ID (Description) | Gene sequence |
|---|---|---|---|---|---|
| | | | AALVNHVLPYNQLFGPNVVGTAEIJKLAITTKIKPVTVLSTVAVAAYVQPPTTFDEESDIRLI SAVRPIDDGYANGYGNAKWJGYGNAKVVAGEVLLREAHDLCGLPVJAVFRSDMILAHSRYTGQLNVP DQFTRLJLSLJATGJAPGSFYQAQTTGERPLAHYDGLPGDFTAEAITTLGTQVPEGGSEGFV TYDCVNPHADGISLDNFVDWLIEAGYPLARIDKNYTEWFTRFDTARGLSEKQKQHSLLPL LHAFEQJPSAAAENHGVVPAKRFQHAVQAAGKPVGQDGTDRPHLSRRILVKYAKDLEQ IGLL | | CACATCATGGGACGGCGGCACCCTGACCTCACCCTGTCTACCGCGGCGGAACCGGATACTTC GCCGGCGTCCAGTGACATGTCAACGCTCTCGAGGACATGGAGCTGATCCGCCCGACGGCG CTGGCCTTGGTTCCACGCGTGTGGGACATGGTGTTCCAGGCGATTCCAGACCGAGGTGGAC GGCGTCTGGCGAGCGGGCGACACCGCCAGTGCCGACCGGTGGGGCCGAGGGCTCGCAAGGGC GATATCCGTCGACAACTCTTCGGGTGGACGCGTATCGGCCGGTCAATCGTCGTTCTGCTCCA ITATTCGAGGAGCTGTGGGTGAGTTCGACCTGAATCTGCTTCGCAGCTGAATCTGACCGATGC TACGGCTTCCACCGAGGCTCGGGCATGGTGTTCCGTGACGGCATCGTTCGAACGTCGTCGGTC ATTGACTACAACTGGTTGACGTGCCCGAACTTGGGTCTACTTCTCCACGAACAAGCCGCAC CCGTGCGGTGACGCTGCTGTGGAAGACCGCATGTTCCTCGGTACTACAAACGCCCC GAGGTGACTGCAGTCGTTGTCTGAAAGACGCGGTTTTTACATGAGCCGACATCGTCGCC GAGCTGGCCACGACAACATGGAGATCATGAGATCGAGATTCGATCGCCAACAACGTCTCAAACTCTCG CAGGGAGAGTTTGTCGCCGGTCGACGAGGTCACAGCAGTACGCCAATGCCCTGTGGTG CACCAGATCTACGTCTACGGCGAGCAGCGAACGGTCTACCTGCTAGGCAGTGTGCGG ACGCCGAGGCGTGCGCCGCCGTGGGCGCCCAGGAAGGCGGACTGCCAAGACTCCCGCGAC GACTCCCTGCAGGACATTGCAAAAGAGATCACCGAGCTGCAGTCCTACAAGGTTCCCGCGAC TCATCATCGAAACCGGACGCAGCCATTTCACCGATCTGGGCTGGGTCGGATTCGCTGTCCCTTCG CTGGCCGCGAACCTGAAGGGCGACATATCTTCGGGATCGGGTCGAAGTACCGGTCATCGTCAGTGCCCGAA ATGCGCGAGGACGCGAGGTCTTCGCTCGGCAGCTTCGGCGCGTTGCACGGGACGTGGACACGGGCAAGTCCTGGGGCCCCAACTG GCCCTGGAAACGGTCTTCAAGGGCGGCTCGAGGCTCTCGGCCGGTTCCTGGCCGAACTG GCCGGACGGCGCATCAGGCGGCCATTTCAACGACCGATTGCCTCTACAGCCAGCTGTTCG GATCTGTCGCGGATCATCTTCGGGTCGAAGTACCGGCTCATGTCAGTGCGCCG AACGATCTCGGCGGGACGGTGCAGGGCCTGGGCATACGGAGATCGGGCGGCGGACTGACC CGACCGGCGAGCGTTCATCGACGAGGCCACCTCGATCGGGCATCGGCACACGGACGACATTCGGACGAA GTCACCTACTCGTCACGGAGCTCGGCGCAATCGTCGATCGACGACGCATTGAACGAC GAGTCCGATATCCGGTCAGCGCCCGGTGCGTCCGGCGATCGACGGAGCGTACGCGGAAGCGGC TACGCAACAGCAAGTGGGCGCGAGAGGTACTCGCGGAGACCATGACCTCTGCGGC CTGCCGCTGGGGGTCTTCCGGTCACCGGACCTGATCTGTCGGCCCCACAGCCCGACCGGGCCAG CTCAAGTCCAGAGACGTTCACCGGACACAACACCGGGAAGACCCTCGCGCACTACGACGGA TACCGGGTGACCTCTACCAGCACACCGGAGGGCGATCGGCCTGGAACGCGGGGATACCCAAGGGG AGCGAGGGGTTTCTTGATGGACGTATGACTCGAAGCGATACCCATGCCATGCGCATCGACTGGAC AACTTCGGACTGGTCATCGAAGCGGAAAATACCCCATCGACGCATTCGACAACTACACC GAATGGTTCACCGCCTTCATCGACGACTACGCCACGCATTCGAAACGGCTCGCCCCGAGGGTGC TCCCTATGGCGACGAAGCGGTCGCAGCACGCTGCAGGACCGGGAATCGGTTCGGTGGGCAA GTCCGGGACTACGGACAGGTTCAGCATCGCCGCCACGCCCACCGAAGCGGGCCCCATGGGGATCGATCGAC AACTTCGGACTGGTCATCGAAGCGGAAAATACCCCATCGACGCATTCGACAACTACACC GAATGGTTCACCGCCTTCATCGACGACTACGCCACGCATTCGAAACGGCTCGCCCCGAGGGTGC CTGAACACAGCTCGGACTCCTATGA |
| 6 and 29 | Segniliparus rotundus | ADG98140.1 | MTQSHTQGPQASAAHSRLARRAAELLATDPQAAATLPDPEVVRQATRPGLRLAERVD AILSGYADRPALGQRSFQTVKDPITGRSSVELLPTFDHTYRELRERATAIASDLAHHPQA PAKPGDFLASIGFSVQYVAIDIAGVFAGLTAVPLQTGATLATLTATAETAPTLFAASIEH LPTAVDAVLATPSVRRLLVFDYRAGSDEDREAVEAAKRKJADAGSSVLVDVLDEVYARG KSAPKPLPPATDAGDDSLSLLIYTSGSTGTPKGAMYPERNVAHFWGGVWAAAAFDED | Srot_1679 (thioester reductase domain protein) | ATGACTCAGTCGCACACTCAAGGTCCGCAAGTCTGCCGGCGCAGCCGTCTCGCCGT CGCTGCGCGGAGCTTCTCGGCAGGCAGCGCCCAGGCCCGCCAGGACCCTCCCGACCCGGAG GTCGTGCGGCAGGCGACGCGTCCAGGGCTCGCGGCTGCGCGAGCGGGTCGACGGATCGCTC AGCGGCGTACGGCGACCGCTCGGTGAAGCTCTTCGGGGCAGCGCTCTTTCAGACGGTCAAAGATCCC ATCACGGGACGCGTCCTCGGTGAGTTGCTCCCAGTTCGACACCATCGACCATCAGCCCGGAG |

| SEQ ID NOs | Organism | GENBANK reference | Amino acid sequence | Gene ID (Description) | Gene sequence |
|---|---|---|---|---|---|
| 7 and 30 | Chromobacterium violaceum | AAQ59697.1 | MQKQRTTSQWRELDAAHHLHPFTDTASLNQAGARVMTRGEGVMLWDSEGNKRDGMAGLWCVNVGYGRKDFAEAARRQMEELPFYNTFFKTTHPAVVELSSLLAEVTPAGFDRVFYTNSGSESVDTMIRHMVRRYWDVQGKPEKKTLIGRWNGYHGSTHGASLGGMKYMHEQGDLIPPGMAHIECPWMVYKHGKDMTHPEGVVAARMLEEKLEIGADKYAAFVGEPIQGAGGVIVPPATYWPEIEHICHKYDVLLVADEVICGFGRTGEWFGHQHFGFQPDLFTAANKGLSSGYLPGAVFVGKRVAEGLHAGGDFNHGFTYSGHPVCAAVAHANVAALHDEGIVQRVKDDIGPYMQKRWRETFSIRFHVDDVHGVGMVXIQAFTLVKNLAKRRELPFIFGEHGTLCRDIFFRNNLMRACGDHVSAPPLVMTIRAEVDEMLAVAERCLEEFEQTLKARGLA | CV_2025 (probable aminotransferase) | ATGCAAAAGCAAACGACCAGCCAATGGCGAACTGGATGGCCCATCACTGCATCGTTCACGGATACCGCATGCTGAACCAGGCGGCGTGATGACGCGGAGAGGGCGTCTACCTGTGGGATTCGGAAGGCAACAAGATCATGACGGCATGGCGGACTGTGGTGCGTGAAGTGCGGTTACGGCGGCAAGGACTTTGCGAAGCGCGCTGGCAGATGGAAGAGCTGCCGTTCTACAACACCTTCTTCAAGACCACCCATCCGCCGTGGTGAGCTGTCCAGCCTGCTCGCCGAAGTGACCCCTGCGGGTTCGACCGGTGTTCTATACCAATTCCGGTTCGAATCGGTGACACCATGATCCGCACATGGTGCAGCCTATCAGGAACGGTACCGCCGAATCCAGGGCAAGCCGGAGAAGAAGAGACCCTGATCGGCCGCTGGAACGGCTACCACGGCATCCACGGCGACTTGGTGCCGATTCCGGGATTCGCCAACATGAAGTACATGCACGAGCAGGGCGACGAGTTCGCTCAGCGGCATGGTGGTCTGGAATGGCGCTGGACCTTCAACCGCGCTTCTACTCGGCGAATGCGGCCATCATCCGGGACGGTACCGCAAGGGCCTGTCCCGCCGATCTGCCGATACGAGGGGCGGCCAAGTGGCGCTGGACCTGTTCAACGCCTCCGGTCATGGCCAGCTTGTGACCCCTGCGGCAAGCCGGCGTCTCAGCCAACTGCGCAAGCGCTGTGAGCACCGTTGCGCAGCTGTCGTCCATGGTACCTGCGGAACTTCGGCGATCGAGATCGGCACCATGAAGCCGGAAGTGGACGAGATGCTGGCGGTCGCGGAGCGCTGCCTGGAGGAGTTCGAGCAGACCCTGAAGGCGCGGCTGGCTTAG |
| 8 and 31 | Pseudomonas aeruginosa | AAG08191.1 | MNARLHATSPLGDADLVRADQAHYMHGYHVFDDHRVNGSLNAAGDGAYVYDTAGKRYLDAVGGMVCTNIGLGREEMARTVAEQTIRLLAYSNPFCDMANPRAIELCRKLAELAPGDJDHVFLTTGGSTAVDTAJRLHMHYQNCRGHRAKKHVJTRNAYHGSTFLGMSLGGKSADRPAEFDFLDERHIHLACPYYYRAPEGLGEAEFLDGLVDEFERKILELLGADRVGAFLSEPVFGSGGVIVPPAGYHRRMWELCQRYDVLVSDEVVTSFGRLGHFFASQAVFGVQPDNILTAKGLTSGYQPLGACHSRSRWIEVIAEPDKGRCFSHGFTYSGHPVACAAALKNIEHEREGLLAHADEVGRYFEERLQSLRDLPNVGDVRGMRFMACVEFVADKASKALFPESLNIGEWVHLRAQDKRGLLVRPIVHLNVMSPPLLLTRECVDTVVRVLRESIEETYEDLVRAGHR | PA4805 (probable class III aminotransferase) | ATGAACGCCAAGACTGCACCACGTCACCTCCCCGTCCTGGGACGCCGACCTGTCCGCGGCGACTGTTCCCCACTGTTCGAGACCACCGACACCACCGCGTCAACGGCTGCCCTGCAGGGCCGACTACATGCACGGCATCCAGCCGCGCGGCCGAGCGCTATATCTACGACACCGCCGGAAGCTACTACGACAACATCGGCCCGCCGGCCATGTGGTGCACCAACATGGGCCTGGGCCGCGAGGAAATGGCTCGCACCGTGGCCGAGCAGACCCGCCTGCTCGCCTATTCCAATCCCTTCTGCGACATGGCCAACCCCGCGCCCATCGAACTCTGCCGCAAGCTGGCCGAGCTGGCCCCGGGCGATCTCGATCACGTGTTCCTCACCACCGGCGGTTCCACCGCCGTCGACACCGCCATCCGCCTGCATATGCACTACCAGAATTGCCGCGGACACCGCGCCAAGAAGCACGTCATCACGCGCAATGCCTATCACGGCAGCACCTTCCTCGGCATGAGCCTGGGCGGCAAGAGCGCCGACCGCCCGGCCGAGTTCGACTTCCTCGACGAGCGCCACATCCACCTGGCCTGCCCCTACTACTACCGCGCGCCCGAAGGCCTGGGCGAGGCCGAGTTCCTCGACGGCCTGGTCGACGAGTTCGAAGCGAAGATCCTCGAACTGCTGGGCGCCGACCGCGTTGGCGCCTTCCTGTCCGAGCCGGTGTTCGGTTCGGGCGGCGTGATCGTTCCGCCGGCCGGCTACCACCGCCGGATGTGGGAGCTGTGCCAGCGCTACGACGTGCTGGTCTCCGACGAAGTGGTGACCTCCTTCGGCCGCCTCGGGCATTTCTTCGCCAGCCAGGCGGTCTTCGGCGTGCAGCCCGACAACATCCTCACCGCGAAGGGCCTGACCTCGGGCTACCAGCCGCTCGGCGCGTGCCACAGCCGCAGCCGCTGGATCGAAGTCATCGCCGAGCCGGACAAGGGCCGCTGCTTCAGCCACGGCTTCACCTACTCCGGGCACCCGGTGGCCTGCGCGGCCGCGCTCAAGAACATCGAGCACGAGCGCGAGGGCCTGCTGGCCCACGCCGACGAGGTCGGCCGCTACTTCGAGGAGCGCCTGCAGTCGCTGCGCGACCTGCCCAACGTCGGCGACGTGCGCGGCATGCGCTTCATGGCCTGCGTCGAGTTCGTCGCCGACAAGGCGTCGAAGGCGCTGTTCCCGGAAAGCCTCAACATCGGCGAGTGGGTCCACCTGCGCGCGCAGGACAAGCGCGGCCTGCTGGTGCGGCCGATCGTCCACCTGAACGTGATGTCGCCGCCGCTGCTGCTGACCCGCGAGTGCGTCGACACCGTGGTCCGCGTGCTGCGCGAGTCGATCGAGGAGACCTACGAGGACCTGGTGCGCGCGGGCCACCGCTGA |

FIG. 8I

| SEQ ID NOs | Organism | GENBANK reference | Amino acid sequence | Gene ID (Description) | Gene sequence |
|---|---|---|---|---|---|
| 9 and 32 | Pseudomonas syringae | AAY39833.1 | MSANMPQTLEWQALSSEHHLAPESDYKQLKEKGPRIITRAEGVPLVWDSEGNKILDGKMSGLWCVAIGYGREELADAASKQMRELPYYNLIFQTAHPPVLELAKAISDIAPEGKMNHVFFTGSGSSEGNIDTMLRMVHRHYWALKGQIPNKKTIISRVNGYHGSTVAAGASLGGGMFYKMHECIGEDLPIPGSVVHIPQ2PYVVFGEGSDMTPDEFGSMVAAEQLIKKIHELIGVENVGAFII4EPPIQGAGGVNRPPDSYWPKKEILSRYDHLFAAEDVICGFRGRTSEWFGSDFYGLRPDMMTIAKGLTSGYVPMAGGLIVRDEIVAYLNEGGDRNHGFTYSGHPVAAAVALENRIHLREEKVERVHSEITAPYLQKRLRELSDHPLVGEVRGVGLLGANELVKDOKTTHERYIDKGAGMICKRITHCFDNGLJMRAVGDTMHIAPPLVISEACIJDELVEKARTCLDLTLAVAJCG | Psyr_4866 (Aminotransferase class-III) | CGGAACAGGTCGATACCGGTCGCGGTCCGGTGCTGCGCGAGAGCATCGAGGAAACCGTGGAGGATCTTGTCCGCGCCGGTCACCGGTAA ATGAGTGCCAACAACCCTGAATGCAGGCCCTGAGCAGGCAGGCGAGCATCACCCTGCCGCACCGTTCAGCGACTACAAACAACTGAAGGAGAACAAGGCCGCGCATCATCACCGTCCCTGGGCTCTTTATCTGTGGACAGCCAGGCCGAGGGCAACCAAGATCCTGCATGGCATGTCGGGCCTGTGGAGTGCCATCGGTTATGGCGACGAGGAAGAACTGGCCGACGCAACCAAGCAGATGCGGGAGCTGCCGTACTACAACCTGTTCTTCCAGACGCAGCCCCACCCGCCGGTGCTGGAACTGGCCAAGGCCATCTCCGACATCGCTCCCGAGGGCATGAACAACATGTTCTTCACCGGTCAGGCTCTGAAGGCTCAATGCACAGTATGCCGATGCTCGTCATTATGGCCGTGAAAGGCCAGCCGAACAAGAACATCATCAGCCGCGTCAATGGCTACCACGGCTCGCCACCGCCGTCGTCTGGTGCCATGCGAGCCTTACGGTTCCGGGAAAGCCGGCGACATGACCGGACGAGAACTCGGATCGCAGTTCATGGCGCCCGCAGCAACTCAGGGCGCTGGCGTGATTGTCCGCCCTGATCCTTACTTCTGGCCCATCCCGCCCGGTCTTCAGGTGGCCAGCAATCAGTGACATCCTTGATCACGAGCGCCTGAGCGAATTGGCGGAGAGGAGCGGCAACTGTAGGAGCGCCCCTGCTCGCGCCGAGAAGCAAGCCCACGGATACAAGATGCGGAGAATCCAGGGGGTAGAAGGCTGTGCGGCAAAACCGGTAGCCTGGTTTTTCGCGGCCTGTCAGTAGTGGGTGAGCCGCTGCGGTGACAGCGCCGAAAGGCGCGATCAATGAGCGCCCAACCTGCTGCGGCCGCCCCCTGAGCGATGAAGGTCTGATATTCCAGGAACGTGCTGAGGGGCTGATCGGTCCGAGTTGGCAGGCGAAGCTGTGCCAGTCAGCGACGCACGGCGGCCACGCATGCGGATCGCCCGGGATGAAGAAATGGGAAGCTCGGCAAGTCGCGCCAGCCGGTCAGCTGACTCATGCCGAGGGCATCTATTGCGCAGGTGGCATGCCGGATCGCGTGCAGAGATCGTCGATGCCATGGCGCATCAGGCGATGGTGCTGCCTACGCCTGGTGTCGCTGATTATGCGACGAAGCGCGTCAACGGCCACTACCGGGAGAAGATCAACCTGGAAGCTGCGTGCCGGGGATCGCATTCAACCGCCAGCCCGATCTTTTCCACCCAGCTGGAGAAGAGATCGAACGGCGGGAATCGTGCGACGGCGTACGCAAGGCTGACGGTGCGAGCCGGGTGGGACCCGGTGCTGGACGACGGGCTACGGGCTGACGGTGCTGCGATCGCCGAGCAGCGACCTGCGGCTGCCGGTATCCTGGAAGCGATCCGCACGCTTCCTTCACCCAAGGCCTTCACCCTGAAGATCGACGAGCCCGCCGCCGTCGAGCCAGCACGCGGACGTGCTGCGGCTGCACGAGAGATCGCAGCAGACGCGTCAAGCCCGGCCGCCAAACGGCTCCAACCTGCGACGAGCGAGAGCCTGGCCGCCGCCGCAGGAATGGCGCAGACGACGCTGGAAAGATCCGCCGCAGACGTATGGGGAAGACGCGAGGTGTCGGTCAGCCTTGGGTGGCGTGCATGGCGGATCATGCTGCGGCAGGAGCAGGCTCCGAAGTGCGAGCGCCGCCACCGGGTCTGA |
| 10 and 33 | Rhodobacter sphaeroides | ABA81135.1 | MTRNDATNAAGAVGAAMRDHILLPAQEMAKLGKSAQPVLTHAEFGIYVHTEDGRRLIDGPAGMWCAQVGYGRREIVDAMAHQAMVLPYYASPIWYMATSPAARLAEKIATLTFGOLNRIFFTTGGSTAVIDSALRFSEFYNINVLGRPQKKRIIVRYDGYHGSTALTAACTGHTGNWPNFDIAQDRISFLSSPNPRHAGNRSDEAFLDDLVQEFFEDRESLGPDTIAAFLAEPILASGGVIIPPAGYNHARFKAICEKHDILYISDEVVTGFGRCGEWFASEKVFGIVPPDHTFAKCVTSGYVPLSGGLAISEAVLARISGENAKGSWFTNGYTYSNQPVACAAALANHELMEREGIVDQAREMADYFAAALASLRDLPGVAETRSVGLVGCVQCLLDPTRADGTAEDKAFTLKIDERCFELGILVRPLGDLCVISPPLIHSRAQDEMVAIMRQATEVSAAHGLIAKEPAAV | RSP_3534 (adenosylmethionine-8-amino-7-oxononanoate aminotransferase) | GCGCACGTGTCTGCGATCTGACCGTGGCCTGTGCAGGCTGA GACGGGGAATGAGACCGCGACGAATGCTGCCGAGCGGTGGGGCGGCGAATGCGGGCAGTGCGACTATCCTTGCTGCAGCAAGGAAATTGGCGAAGCTGCGGCCAAGTCGCGCCAGCCGGTCATTGACGCCATGCCGAGGGCATCTATGCCAAGGGCATCTATTGTCGCCAGGTGGCTACGCCCGCAGCGAGAATCGTGATGCCATGGCGCATCAGGCGATGGTGCTGCCTACGCCTGGTGTCGCTGATTATGCGACGAAGCGCGTCAACGGCCACTACCGGGAGAAGATCAACCTGGAAGCTGCGTGCCGGGGATCGCATTCAACCGCCAGCCCGATCTTTTCCACCCAGCTGGAGAAGAGATCGAACGGCGGGAATCGTGCGACGGCGTACGCAAGGCTGACGGTGCTGCGATCGCCGAGCAGCGACCTGCGGCTGCCGGTATCCTGGAAGCGATCCGCACGCTTCCTTCACCCAAGGCCTTCACCCTGAAGATCGACGAGCCCGCCGCCGTCGAGCCAGCACGCGGACGTGCTGCGGCTGCACGAGAGATCGCAGCAGACGCGTCAAGCCCGGCCGCCAAACGGCTCCAACCTGCGACGAGCGAGAGCCTGGCCGCCGCCGCAGGAATGGCGCAGACGACGCTGGAAAGATCCGCCGCAGACGTATGGGGAAGACGCGAGGTGTCGGTCAGCCTTGGGTGGCGTGCATGGCGGATCATGCTGCGGCAGGAGCAGGCTCCGAAGTGCGAGCGCCGCCACCGGGTCTGA |

FIG. 8J

| SEQ ID NOs | Organism | GENBANK reference | Amino acid sequence | Gene ID (Description) | Gene sequence |
|---|---|---|---|---|---|
| 11, 34, and 48 | Escherichia coli | AAA57874.1 | MNRLPSSASALACSAHALNUEKRTLDHEEMKALNREVIEYFKEHVNPGFLEYRKSVTAG GDYGAVEWQAGSLNTLVDTCGEFIDCLSGGFGIFNVGHRNPVVSAVQNQLAKQPL HSQELLDPLRAMLAKTLAALTPGKILKYSFFCNSGTESVEAALKLAKAYQSPRGKFTHATS GAFHGKSLGALSATAKSTFRKPFMPLLPGFRHVPFGNIEAMRTALNECKKTGDDVAAVI LEPIQGEGGVILPPPGYLTAVRKLCDEFGALMILDEVQTGMGRTGKMFACEHENVQPD ILCLAKALGGGVMPGATIATEVFSVLFDNPFLHTTFGGNPLACAAALATNVLLEQN LPAQAEQKGDLMLLDGFRQLAREYPDLVQEARGKGMLMAIEFVDNEIGYNFASEMFR QRVLVAGTILNNAKTIRREPPLTLTIEQCELVKKAARKALAAMRVSVEEA<br><br>MITEFVFIPIFAIAAGVAQSLQYLMRYHVREPPEHLNRLPSSASALACSAHALNLREKRTL DHEEMKALNREVIEYFKEHVNPGFLEYRKSVTAGGDYGAVEWQAGSLNTLVDTCGGE FIDCLSGGFGIFNVGHRNPVVSAVQNQLAKQPLHSQELLDPLRAMLAKTLAALTPGSKL KYSFFCNSGTESVEAALKLAKAYQSPRGKFTHATSGAFHGKSLGALSATAKSTFRKPFM PLLPGFRHVPFGNIEAMRTALNECKKTGDDVAAVILEPIQGEGGVILPQGEGGVLPPPGYLTAVRKLC DEFGALMILDEVQTGMGRTGKMFACEHENVCQPDILCLAKALGLGGVMPGATI ATEEVFSVLFDNPFLHTTFGGNPLACAAALATNVLLEQNLPAQAEQKGDMLLDGFR QLAREYPDLVQEARGKGMLMAIEFVDNIGYNFASEMFRQRVLVAGTILNNAKTRRIEP PLTLTIEQCELVKKAARKALAAMRVSVEEA | yjiG AC45_0438 (putrescine aminotransferase) | TTGAACACAGGTTACCTTTGGAGCGCATCGGCCTTTAGGCTGCAGCCCCACGCGCCTGAATCTC ATTGAGGAAGCGAACCTGCATCCGATCATGAGGAAGCACTTAACCGAGAGGTGATTGAA TACTTCAAAGAAGACATGTCAATCCTGCGGGGTTTTAGAGTAGTCGCAAATCGTTACCGCCGGC GGGCAGGATTACGGGACGCGTAGAGTGCAAGGGGAAGTTTAAATACGCTCTTCGACACCCAG CCAGTTGTGGATTTCCCGCTACAGAATCACTTGCGAGAAACAACCTCTGCAACAGCCAAGGAG CTGCTTCGATCCGTTACGGCGGATGTTGGCGAAAACCCTTCGTCCGGCTAACGGCCTGGAGCG CTGAAATACGACTCTTCTGTTCTGTAATAGCGGCACGAGGTCCGTGTGAAGCAGCGCCTGAAGCTG GCGAAGGTTACCAGTCACCGGCGCTGTCGGCGCAAGTTTACTTTATTGCGCAGCCCGGCGTTC CACGGCTAAATTACTTGGCCCGGCCCTTTTTATGCTGCCCGGCTGCATGGTGATGTTGATGATC TGGAGTGCACCCGATCCGCGAGATGCAGCCGAAGATGCCAAAAACCGGTGATGTATGCGTGCGCCCGGTCGCGCAGGTCGCGACCGGATTT CAGGGTCGATGTTGCCGTAATTCTGCCACTGAACAAAACGGGCATGGGCGCACG TGGGATGAGTTGGCGCACTGATATATCTGATGAAGTACAAACGGCATGCAACGCGCTGTTGCCAAA GGCAAGATGTTGCCCTGTCGACAACATGAAGGCCGACCATGGCCACTGAAAGAGGTGTTTCA GTTCGTCGAGCTGGCGGGCCGTGGTAGCGCCGTGAACCCATGACACCGTAAACACAGCCCGGCTGGAGGCTGAG GGCGCGCTTCTTGAGCGGCTGGAATCCGCGGACCACCGCTCAGGCTGAG CAAAAGGCGATAGTGTGGTAAAGGATGGTTGAATGGCGGATTGAGTTGTTGATAAGCGAAATC GTAACGGAAGCGCGTGGTAAAGGATGGTTTGAGTTGGTTGATAACGAAATC GGCTATAACTGCCGGAGAGTCCGCAGGGCGTACTGGCTCCGGAACGCCCAAT AACGCCAAAATGATCCGCGTTAACGGCGCGTAAGGTCGAGTAAGGTCGAAGAACGCTGAA GTGATCAAAGGCCTAGGCCTGAGGTCCCGCATGAGGAGTAACGGTCTGAAAAGCGTAA | 
| 12 and 35 | Vibrio fluvialis | AEA39183.1 | MNKPQSWEARAETYSLYGFFTDMPSLHDRKGTVVVHHGEGPYIVDVNGRRYLDANSGL WNMVAGFDHHKGLJDAAKAQYERPGYHAAFFGRMSDQTVMLSEKLVEVSPFDSGRVF YTNSGSEANDTMVKMLVFELHAAEGKPQKRKLTRWNAAYHGVTAVSASMTGKPVNSV FGLRLPGFVHLTCPHYWRYGEEGETEEQFVARLARELEETQREGAETHAGRFAEPVMG AGGVIPPAKGYFQAILPLRLRKYDRPVISDEVGCGFGRTGNTWGCVTYDPTPDANSSKNLTA GFPPMGAVILGPELSKRLETAIEAEEFPHGFTASGHPVGCAALKAIDVVMNEGLAEMV RRLAPREFERLKHIAERPNNGEVRGIGFMWALEAVKDKASKTPFDGNLSVSERIANTCTD LGLICRPLGQSVVLCPPFILTEAQMDEMFDKLEKALDKVFAEVA | pyruvate transaminase | ATGAACAAACCGCAAAGCTGGGAAGCCTGGGAAGCCATCGAGACCTATTCGCTCTATGGTTTCACC GACATCGCCTCGCTCGCTCATGCAGGCGCACGGTCGTGACCCATGGCGAGGGACCCTAT ATCGTCGATGTAACGCGCCGCGGTTATCTGAGACGCCCAACCGGAACATGGTC GCGGGCTTTGACCACCAAGGGCGTGATGACGCCAAGGCCAATACGAGCGTTTTCC GGTTATCAGCGCTTTTCGGCCGCATGTCGCATCAGACGGTAATGCTGCGGAAAAGCTG GTGAAGCTGCGCCCTTGATCAGCCGGGGGCTGTTTCATCAACCGGGGCAGGAAGCTGCGGAGGCG AATGACACCATGGTCAAGATGCTATGGTTCCTGCGTGCAGCGCCAGGCGAGGGCAAACCGCAAAAG CGAAGATCCTGACCGCTGAAGGCTATCACGGCGTGACCGCCGTGAGCGCCAGCATG ACCGGCAAGCCGGTAATTACCTGCGGCCCTGCGCGCGTGCCGCGGTTGTTGCGATATTGCAGTACTGGGCGTAGACTGGGAGGCGGCACCAGATT TGCCCGGCATTACTGGCGGTACGAGGAAGAGACGGAAGCAGTTCGGTCGGCGGCCG CCTCGGATATGCCTGCGCCGATCAGCGGGGCGCTTGCCCCGGACACCAAGGGCGGTGTTCCAG GTGATTGGCCAATCCTCCGAGAAATATGACTCGGTCGATGGAGTATCTCGGACCGAGGTGATCGC GGTTTACGGCGCGCCAATACCAGAGAATCTACAGCGGGGTGCGCGGATCGCTTTACACCGATGA ATCATCGCGGTCGGCGAGGGCGATGCTTTCCCATTGCCGCATGGCGGATCCCCCATGGCC TTTACCGCCTCATACGCCTGGGCGTGGCTGCTTCTCATGAACGCGAATTCCCCGCAGCTCC AGAATATGCGCGAGCGCCGGCGAACCATCGGGTGAATATCGGCCATCGGCCTCATGGGGCG GAGCCGATGCCAATACGCTACGGATCCGTGACCGAGGCCAGATGAGATGTTCGATAA CTGAAAAAGCCCTGATAAGGTCTTTGCCGAAGGTTCGTGA | 
| 13 and 36 | Cucumis sativus | AAF64041.1 | MASSSPELPLKPGPGFPRPLGPKDRYDYFQCGRDEFFRSRTKYNSTVFHANMPPG PFISSDSRVVVLLDALSFPLFDTTVKEKRNILDGTYMPSLSFTCGSRTCAYLDPSETEHTVL KRIFLSFLASHHDRFIPLFRSSLSEMFVKLEDKLADRKNKIADFNSSDDAVSFDYVFRLFSDG TPDSTLAADGRPGWFDLMLGLQAPLASIGILPKIFSVFEDLIHTIPLEPFPVKSRYRKLYKA | fatty acid hydroperoxide lyase | CCATTCTTCTCCAACGGTGAAGATAAGAACCTTTGTTACTTTGTACGATCACAGGT CACAGCAATGGCTCTTCTCCCCTGAAACTTCTCTCGAACGCCAATTCCCGGTGGCTATGG CTTTCCCCCTTGCTCGGCTCCGGCTCCATCAAAGACCGTTACGAATTACGTTCCAAGGTAGAGA CGAATTCTTCCGTTCCGAATTACAACAAATACAACTCCACCGTCTTCCACGCAACATGCC |

| SEQ ID NOs | Organism | GENBANK reference | Amino acid sequence | Gene ID (Description) | Gene sequence |
|---|---|---|---|---|---|
| | | | | | TCGAACGGGCGGAGAGCGAGGGCTGCCATTGCCTGGAGGGGAAACAAGCAGTGCCCGGGAAGGAC ATGGTTGGGTGGTCGGTTGGGGCGGTCGATGGTTGGTCGGCCGAAGCTGTTCCTGGCCGGTACGACACGTTC GCCGCCGACGTTGGGTGTGGAGGGCCCGGTTGAGAACTCCGGTGCGTGGTGACGGTCACGTGCGCTGACGACGG GCTGCCGTCGGGGATAGGCACGACGCCGTCGACGTCACCGTCGCCGCCTCGCTGTGATTTAGTACT GTACTAGGTTGGGATGTTTTAATTGGTCGGTTAATTATTAATCACCGATAAAGTATTA ATCATGTTTATCATCTAACAACAATGAAAATATTAATCAT |
| 15 and 38 | Lactobacillus casei | AGP65310.1 | MSGYHFLKPFTKHCQTTLKNRIVIPPMATRLSFEDGTVTRDERRYYCQRAGGVGMAFT GTANVNALGKGFEEGELSVADDRFIPGLSKLAAAMKTGGTKAILQFSAGRMSNSKILRG EQPVSASAVAAPRAGYETPRALLTSAEIEATHDFGQAVRRAILAGFDGIELHGSANTYLIQ QFYSPNSNRRFIDEWGGDRDKMRRFPLAVVHEAEKYNATIADRPFLLGYRISPEELEQPFG HLDDTLALIDALKQITKIDYLHVSQSDVWRTSLRNPEDTAIMNREQRDHVAGAFPWVVG GIKTPADAEKAAESFDLVAIGHEMMREPHVVVQKVLDHDEKARYQDAPADLEELGIAPTF LBHESISGGAKKGVPLTTAQSVTSSNVTDJD | LCKS19_2632. [NADH-flavin oxidoreductase, Old Yellow Enzyme family] | ATGTCGGGTTATCATTTTTTAAAACGTTCACCTTCAAGCACCAAACCATCAGTTGAAA AATCCATTGTTCATTCCGCCGATGACAACCGCGCTGTCGTTGAAGACGGCACTGTGACG CGGGACGAAATCAGGTATTACCAGCAAGGGCTGGGCGTGGACGTAAGTCTCTGATGAT CGATTCATCCGGTTGAGCAAATCGCCCTGCGATGAATAGCAAGGCTGAAACACCAAGGCT ATTTGCAAATCTCAGCGCTGCCGCACGAGCAATAGCAACAGATTCGCGGGTGAGCAG CCAGTCAGTGCAGCAGTCGGCATGGCACCACTATTCACGATTTGGTCAGGTCGATTG ACATGGGCAAATGGAGGGCATGCAATCGAACTGCATGGGGCCAACACCTATCAGCACATTC CTTGCCGCTTTTGATGGCATCCGAACCGGCTGAGGCGCATGGCCGATGATCAGGGAAGGCGGATG CGTTTCGGCAGTCGTTCATGAAAGCACAAAGGAAAAAGTCGTGTGGAGCCGCCATATAAA CCATTTTGTTAGGCGACCGCATTTCGCCGAAAGTTGGAAACAAACCAAGATTGATTACTCGCATGTC GATGATACCTTGGCCTAATCGAGCTTTGGCGAACTCATTCGGCGAAGGGAACACAGCCATCATGAAT GAACAAATTCGTCACATGTCGCCGGGTGCCATCTTAGACCAGTCTAGACAGCATGGCCATTAAA ACCCCGCCATCGTGCTCTGGTTCAGAAGGGTCTCCCGTTAACACTGCCCGAGTCTGACA ATGAAAGTATTCGTCGGTGGGGCCAAAAGGTGTCCCGTTAACACTGCCCGAGTCTGACA TACCAAGTGGCCCCTGCGATCTGGAAGCATTGGCGCCGACGTTCCTCGATTTT ATCGAAAATTCCTGTGGCCAAAAGGTGTCCCGTTAACACTGCCCGAGTCTGACA TCAAGCAACGTGACTCAAGATTAA |
| 16 and 39 | Pseudomonas putida | AAN68878.1 | MSALFEPYTLKDVTLERMRNIAIPPMCQYMAEDGMMNDWNHVHLAGLARGGAGLLYVE ATAVAPEGRITPGCAGMSDAHACQAFPVVQAKAAGSVPGKQIAHAGRKASANRPW EGDDHHAADDARGWETIAPSAIAFGAHLPKVPREMTLDNARYKQDFVDAARRAFDA GFEWIELHPAHGYLGQSFPSESHSNRKTDAYGCPDMRSFLFETLAAVREVWPEWLPLT ARRFGVLEYDGRDEQTLEESIELARRPKAGGLDLLSVSVGFTIPPDTNHPWGPAFMGPIAER VRREAKLPVTSANWGFGTPQLAEAALQANQLDLVSVGRAHLADPHWAYFAAAKELGVEK ASWTLPAPYAHWLERYR | RPPX_02920 [NADH-flavin oxidoreductase] | ATGTCCGACTGTTCGAACCTACACCCTCAAAGAGTGCACCGTGCTAACGTATGCC ATTCCGCCGATGTGCCAGTGCCATGGCCAAGACGGCATGATCAACGACTGGCACGTG CACTTGGCCGGCCTGGCGCGCGGCGGTGCGGCTGCTGTACGTGGAAGCCACTGTG GCCCGGAAGGGCGGTATCACCCCCGGTTGCGCGGGATCCGAGAGCGAAGATCCTGCAGATC GCGTTCGTTCCGGTTGGTGCAAGGCATCAAGGCTGCGGTTCGGTCGCGGGTATCCAGATC GCCGACGACGGCGGCGGTTGGGAACGTCAGCGCAGCAATTGCCGCCGACCACCATTGCC TGCGAAAGTCCACCGGCCGCTGTGGAAATGACGCTGGACGACTATCGCCGGGTCAAGCAGGAGCTTC GTGGCGCAAGGTCCACCGGCCGCTGTGGAAATGACGCTGGACGACTATCGCCGGGTCAAGCAGGAGCTTC CATGCTACCTGCGCGAGCTCTTCCTGGCAGATCCCAACAAGGGCACGATGCCTAC GGTGCGCCTTGCGACAACGCCAGCCGCTTCCTGCTGAAAACGTGGCTGTCCGTGTG GTCTGGCCGGAGAACCTTGCGGATCGCCACCCGCCGGTTCCAGGCGATGGCCGACTCTGCCCGC GATGAGCAGAGCCCTGAGTGCGGGTTCCCAACTTGCGCGCCGAGCATTCCCTGGGGCTC GCTTCATGGGGCCTTGGCTGAGAGCGCGTTTGCGCCGAGGCAAAGCGCCGCAACCAGCTGGAT TGGTTCGGTGGCCTTTGGTACGCCGCAGTGGCGCACCTGGCGACTCGGCTTACTTGGCGGCAC GAGCGTGGGGTGGAAAGCGCGTCGTGACCTTGCCGGACCTTATGGCACTGGCGGCTCGAG CGTTACCGCTGA |
| 17 and 40 | Saccharomyces cerevisiae | AAC83700.1 | MSDQERRQNEKISYREEGFFIHHLMNPDNLMALEGEDYYLGELLELADRNRDVYFIRCSS GRFFSSGADFKGIAKACGGDDTNKYPSETSKVVVSNFVARNVPVTDAFIKHSKVLLCCLMG PANGLSAALVALCDIVYSINDKVYLLYPFANLGLITEGGTVSLPLKFGTNTTYECLMFNKP FKYDRMCENGFISKNFNMAPSSNAEAFRAVKVLEELREKVKGLYLPSCLGMKKLLKSNWHID AFNKANSVEVNESLKYWVDGEPLKRFRQLGSKQRKHRL | EC11 YLR284C | ATGTCCGAAGAAATTAGCAAATGAGAAAATCAGTTATCGTTATCGAAGACCATTCTC ATTATTCACTTAATGAACCCTGACAATTTGAATGCACTACGAAGGTGAAGACTATATTAT TTAGGAGCTTATCAGAACTAGCGCAGAAATCTGATGTATATATTTACCAATTACAA AGCAGTGGTAGATTTTTTCCAGTGGTGCGATTTCAAGGAGTATTGCAAAAGCCAAGGG GATGATACCAATAAATATCTTCGGAACAAAAGCCAAGTGGGGTGTCAATTTCTGCGGTAGA |

FIG. 8M

| SEQ ID NOs | Organism | GENBANK reference | Amino acid sequence | Gene ID (Description) | Gene sequence |
|---|---|---|---|---|---|
| | | | | (Peroxisomal delta3, delta2-enoyl-CoA isomerase) | AATGTTTATGTCACTGATGCCTTCATCAAGCATTCCAAAGTTTAATTTGCTGTTGAAT GTGACCAGCAATAGGGCTTGAGCGCGGCACTTGGTACGCATTGTGTACATTGTGCAGTATA AATGACAAGGTTCTTTGCTCATTGAAGTTTGCTATACCCTTTGCTAACTAGGACTAATTACCGAAGGTTGGT ACAACGGT:TCTTTGCTCATTGAAGTTTGCACAAATACGACGTATAGAATGCCTCATGTTC AACAAACCATTCAAGTACGATATATTATGCGAGAACGGATTATAAAGCAAGAATTTAAC ATGCCATTCTCAAACCTGCAACATACCTGCCCAGTTGCTTAGGGATGGAAGAAATTGCTGAAATCGAACCAC GTGAAAGGCTATACCTGCCCAGTTGCTTAGGGATGGAAGTAAATGAATCTCCAAGTATTGGGTA ATGGATGCATTCAATAAGGCTAACTCAGTGGAAGTAAATGAATCTCCAAGTATTGGGTA GATGGAGAGCCCTTAAAAAGATTTAGGCAGCTGGGCTCGAAACAAAGGAAGCATGGTTTA TGA |
| 18 and 41 | Clostridium perfringens |

FIG. 8N

| SEQ ID NOs | Organism | GENBANK reference | Amino acid sequence | Gene ID (Description) | Gene sequence |
|---|---|---|---|---|---|
| 21 and 44 | Geobacillus stearothermophilus | CAA81612.1 | MKAAVVEQFKEPLKIKEVKPTISYGEVLVRIKACGVCHTDLHAAHGDWPVKPKLPLIP GHEGVGIVEEVGPGVTHLKVGDRVGIPWLYSACGHCDYCLSGQETLCEHQKRNAGYSV DGGYAEYCRAAADYVVKIPDNLSFEEAAPIFCAGVTTYKALKVTGAKPGEWVATYGIGG LGHVAVQYAKAMGLNVVAVDIGDEKLELAKELGADLVVNPLKEDAAKFMKEKVGGVH AAVTAVSKPAFQSAYNSIRRGGACVLVGLPPEEMPIPIFDTVLNGIKIIGSIVGTRKDLQ EALQFAAEGKVKTIIEVQPLEKINEVFDRMLKGQINGRVVLTLEDK | alcohol dehydrogenase | ATGAAAGCCGCTGTAGTTGAACAATTTAAGGAACCATTAAAAATAAAAGAAGTAGAAAAA CCAACCATTTCATATGGAGAAGTATTAGTCCGCATTAAAGCATGCGGTGTTTGTCATCT GACTTGCATGGCCGTCACGGCGGATTGGCCGGTAAAACCAAAACTTCCTTAATCCCTGGC CATGAAGGAGTAGGAATTGTTGAAGAAGTAGGTCCAGGCGTAACCCATTAAAAGTGGGC GACCCGGTTGGAATTCCTTGGTTTATATTCTGCATGGCGGCCATTGTGATTATGTTTAAGC GGCCAAGAGACATTATGTGAGCACCAGAAAAACGCTGGCTACTCGTTGATGGAGGGTAT GCAGAATATTGCAGAGCGGCAGCAGATATGTGTAAAAATTCCGACAACTTATCATT GAAGAAGCTGCCCCAATTTTCTGCGCGGGAGTTACTACCTATAAAGGTAAAAGTAACA GGGGCAAAACCAGGAGAAATGGGTAGGACATGCGATATCGGCGGCGCCTTGGACACGTTGCC GTTCAAATACGGCGAAGCGCATGGGACTTAATGTCGTTGCTGTTGATATCGGCGACGAAAAA CTGAACTGCAAAAAGAACTGGCGCTGCATGGTTCAAGCCCTTGTAAACCCTTGAAAGAAGATGCA TCGAAATTTATGAAAGAAGGCGTTGGTGGTGTCCACGCGGCAGTTCAGACGCGTAACAGTGTATCT AAGCCACCGGTTTCAATCTGCGTACAATTCTATCTGCAGAGCGCGGAGCTTGTGTGCTGTTC TGGATTCTCACCGGAAGAAATGCCTATTCCGGATTTTTTGATACCGGTTTAAATGGAATCAAA ATCATCGGTTCCATTGTCGGCACGCGGAAAGACCTGCAAGAAGCGCTCCAATTCGCAGCG AAGGTAAAGTAAAGCATCAAATTAACGGTCGTGTAGTTTTAACGTTAGAAGATAAATAA GACAGAATGCTAAAAGGTCAAATTAACGGTCGTGTAGTTTAACGTTAAGTTAGAAGATAAATAA | 
| 22 and 45 | Lactobacillus plantarum WCFS1 | CCC78182.1 | MATLGANASLYSEQDHRITYYECDRITGRATILTLIDJAVLASEEQSDALGLTIEMVQSHIG VGWVVTQYAIDITRMPRCDEVVTIAVRGSAYNPYFAYREFVWIRDADGQQLAYITSIVV MMSQTTRRYKILPELVAPYCQSEVVKRIPRLPRPISFEATDTTHKPYHVRFFDIDPNRHV NNAHYFDWLVDTLPATFLLQHDLVHVDVRYENEVKYGQTVTAHANILPSEVADQVTT SHUEVDDEKCCEVTIQWRTLPEPIQ | lp_0708 (Acyl-ACP thioesterase) | ATGAAAGCCAACTTTAGGCGCAAATGGCGAGTCTTACAGTGAACAGCACGGATTACGTATTAT GAATGTGACCGACCACTGTCGCCGCAACTTAACGACTTTACTGATAATTGATATTGCTACTGCCA TCAGAGGATCAAAGCGACGACCCTTGGTTTTAACGACGGAAATGTGCAAAGCCATGGTGTC GGTTGGGTCGTCACGCAATATGCCATGCGATCCATCGATATTACGGATGCCGCAAGACGAAGTC GTTACGATTGCCGTTCGGGGTAGTGCTTAACGTGCTATAATCCATATTCTTGTCTACCGTGAATTTGG ATTCGGGACGGACAGCGAATTCGTAACAGTTACCAGAACCTGGCCTGATCGTCATGATGAGT CAAACGACCCGGCGGAATCGTAAAATTTACCGACAACTGCCGCCGATCAGTCGGAA GTCGTCAAGCGGTATTCCGCGCTTGCCAGCACGGATTAGTTTGAAGCGACGATAACACG ATTAGGAAGCGTACCATGTTGGCCTCGTAGATACGCTACCCGCCGACGGTCTTCTTCAACATGAT TAGTTCACGTTGACGTTCGCTATGAAAATGAAGTCAAGTACGGCCAAACGGTGACTGCT CATGCGAACATCTTACCGAGCGAAGTGGCCGATCAGGTCACGCAGGTCATTGATGAA GTTGATGAGAAGTGTGTGAGGCCAGATTCAATGGCGATCTTACCAGAGCCCGATT CAGTAA |
| 23 and 46 | Anaerococcus tetradius ATCC 35098 | EEI825564.1 | MKFKKFKGRMHVDPFNYISMRYLVALMNEVAFDQAEIILEKDJDMKNLRWWYSWDI QJENNRLGEEIEITTIPTHMDKFYAYRDFIVESRGNILARAKATFLLMDITRLRPIKIPCQN LSLAYGKENPIFDYDMEIRNDLAFIRDIQLRRADLLDNNFHINNAVYFDLIKETVDIYDK DISYIKLJYRNEIRDKSIDFALRGEDGRDYCLGKINTNV | HMPREF0077_1317 (Acyl-ACP thioesterase) | ATGAAATTCAAGAAGAAATTCAAAATAGGAAGGATGCATGTAGATCCTTTAATTATATC TCAATGAGATATCTAGTTGCTCTTATGAATGAAGTTGCCTTGATCAAGCAGAGATACTT GAAAAAGACATAGATATATGAAAAATCTAAGGTGGATAATTACTCTTGGATATACAAATC AAAACAATATTAGACTGGGAGAAGATAAATCGAAATTGAAATTCCACCATATGGAT AATTTATGCTATAGGGACTTTATAGTTGAAGATGAAGCTTGCTTCTCTATAAAATCCCCCAAAAT CTAAGCCGACCTTCCGCTAGACATTACTAGGCTTCGTCCTATAAATCCAGATATGAAATAAGA AATGACTAGCCTCATCAGAGATATTCAGTTAAGAAGACCAGATTGGATAATAATTTC ACATAAACAATGCCGTCATTCAAGCTAATCCTACAGAAGATGCAACCATATCGTCAAAATTGAA GCTTTCCAAGAAGAAGAAGATAAGTCCATAGACTTTGCCCTAAGAGGGAAGATGGAAGA GATTATTGTTTAGGAAAGATTAAAACTAATGTATAA | ical acid, lauryl sulfuric acid, gluconic acid, glutamic acid, hydroxynaphthoic acid, salicylic acid, stearic acid, muconic acid, and the like.

SEQUENCE LISTING

```
<160> NUMBER OF SEQ ID NOS: 48

<210> SEQ ID NO 1
<211> LENGTH: 1174
<212> TYPE: PRT
<213> ORGANISM: Mycobacterium marinum

<400> SEQUENCE: 1

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
```

```
                20                  25                  30
Ile Thr Ala Ala Ile Glu Arg Pro Gly Leu Pro Leu Pro Gln Ile Ile
             35                  40                  45
Glu Thr Val Met Thr Gly Tyr Ala Asp Arg Pro Ala Leu Ala Gln Arg
 50                  55                  60
Ser Val Glu Phe Val Thr Asp Ala Gly Thr His Thr Leu Arg
 65                  70                  75                  80
Leu Leu Pro His Phe Glu Thr Ile Ser Tyr Gly Glu Leu Trp Asp Arg
                 85                  90                  95
Ile Ser Ala Leu Ala Asp Val Leu Ser Thr Glu Gln Thr Val Lys Pro
            100                 105                 110
Gly Asp Arg Val Cys Leu Leu Gly Phe Asn Ser Val Asp Tyr Ala Thr
            115                 120                 125
Ile Asp Met Thr Leu Ala Arg Leu Gly Ala Val Ala Val Pro Leu Gln
            130                 135                 140
Thr Ser Ala Ala Ile Thr Gln Leu Gln Pro Ile Val Ala Glu Thr Gln
145                 150                 155                 160
Pro Thr Met Ile Ala Ala Ser Val Asp Ala Leu Ala Asp Ala Thr Glu
                165                 170                 175
Leu Ala Leu Ser Gly Gln Thr Ala Thr Arg Val Leu Val Phe Asp His
            180                 185                 190
His Arg Gln Val Asp Ala His Arg Ala Ala Val Glu Ser Ala Arg Glu
            195                 200                 205
Arg Leu Ala Gly Ser Ala Val Val Glu Thr Leu Ala Glu Ala Ile Ala
            210                 215                 220
Arg Gly Asp Val Pro Arg Gly Ala Ser Ala Gly Ser Ala Pro Gly Thr
225                 230                 235                 240
Asp Val Ser Asp Asp Ser Leu Ala Leu Leu Ile Tyr Thr Ser Gly Ser
                245                 250                 255
Thr Gly Ala Pro Lys Gly Ala Met Tyr Pro Arg Arg Asn Val Ala Thr
            260                 265                 270
Phe Trp Arg Lys Arg Thr Trp Phe Glu Gly Gly Tyr Glu Pro Ser Ile
            275                 280                 285
Thr Leu Asn Phe Met Pro Met Ser His Val Met Gly Arg Gln Ile Leu
            290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                325                 330                 335
Leu Thr Phe Val Pro Arg Val Trp Asp Met Val Phe Asp Glu Phe Gln
            340                 345                 350
Ser Glu Val Asp Arg Arg Leu Val Asp Gly Ala Asp Arg Val Ala Leu
            355                 360                 365
Glu Ala Gln Val Lys Ala Glu Ile Arg Asn Asp Val Leu Gly Gly Arg
            370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
            420                 425                 430
Ala Val Leu Asp Tyr Lys Leu Val Asp Val Pro Asp Leu Gly Tyr Phe
            435                 440                 445
```

```
Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
                500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
        530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
                580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
        610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Leu Leu Gly Gly Ser Ala Ser Asp Val
                660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
        690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
850                 855                 860
```

```
Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
            885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
        995                 1000                1005

Leu Ala Ala Thr Gly Ile Ala Pro Gly Ser Phe Tyr Glu Leu Ala
    1010                1015                1020

Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
    1085                1090                1095

Glu Thr Ala Leu Arg Ala Leu Pro Asp Arg Gln Arg His Ser Ser
    1100                1105                1110

Leu Leu Pro Leu Leu His Asn Tyr Arg Gln Pro Glu Arg Pro Val
    1115                1120                1125

Arg Gly Ser Ile Ala Pro Thr Asp Arg Phe Arg Ala Ala Val Gln
    1130                1135                1140

Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu
```

<210> SEQ ID NO 2
<211> LENGTH: 1173
<212> TYPE: PRT
<213> ORGANISM: Mycobacterium smegmatis

<400> SEQUENCE: 2

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
                20                  25                  30

Asp Pro Glu Phe Ala Ala Ala Pro Leu Pro Ala Val Val Asp Ala
            35                  40                  45
```

```
Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Arg Thr Val Thr Arg Leu Leu Pro Arg Phe
                85                  90                  95

Asp Thr Leu Thr Tyr Ala Gln Val Trp Ser Arg Val Gln Ala Val Ala
                100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
    355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
```

```
            465                 470                 475                 480
Lys Arg Pro Glu Val Thr Ala Ser Val Phe Asp Arg Asp Gly Tyr Tyr
                    485                 490                 495

His Thr Gly Asp Val Met Ala Glu Thr Ala Pro Asp His Leu Val Tyr
                    500                 505                 510

Val Asp Arg Arg Asn Asn Val Leu Lys Leu Ala Gln Gly Glu Phe Val
                    515                 520                 525

Ala Val Ala Asn Leu Glu Ala Val Phe Ser Gly Ala Ala Leu Val Arg
                    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                    565                 570                 575

Lys Ala Ala Leu Ala Asp Ser Leu Gln Arg Thr Ala Arg Asp Ala Glu
                    580                 585                 590

Leu Gln Ser Tyr Glu Val Pro Ala Asp Phe Ile Val Glu Thr Glu Pro
                    595                 600                 605

Phe Ser Ala Ala Asn Gly Leu Leu Ser Gly Val Gly Lys Leu Leu Arg
                    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                    645                 650                 655

Ala Ala Thr Gln Pro Val Ile Asp Thr Leu Thr Gln Ala Ala Ala Thr
                    660                 665                 670

Ile Leu Gly Thr Gly Ser Glu Val Ala Ser Asp Ala His Phe Thr Asp
                    675                 680                 685

Leu Gly Gly Asp Ser Leu Ser Ala Leu Thr Leu Ser Asn Leu Leu Ser
                    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                    725                 730                 735

Gly Asp Arg Arg Pro Ser Phe Thr Thr Val His Gly Ala Asp Ala Thr
                    740                 745                 750

Glu Ile Arg Ala Ser Glu Leu Thr Leu Asp Lys Phe Ile Asp Ala Glu
                    755                 760                 765

Thr Leu Arg Ala Ala Pro Gly Leu Pro Lys Val Thr Thr Glu Pro Arg
                    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                    805                 810                 815

Ile Val Arg Gly Arg Asp Asp Ala Ala Ala Arg Ala Arg Leu Thr Gln
                    820                 825                 830

Ala Tyr Asp Thr Asp Pro Glu Leu Ser Arg Arg Phe Ala Glu Leu Ala
                    835                 840                 845

Asp Arg His Leu Arg Val Val Ala Gly Asp Ile Gly Asp Pro Asn Leu
                    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                    885                 890                 895
```

```
Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
            915                 920                 925

Ala Met Gly Ile Pro Asp Phe Glu Asp Gly Asp Ile Arg Thr Val
            930                 935             940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
            1010                1015                1020

Gly Asp Gly Glu Arg Pro Arg Ala His Tyr Pro Gly Leu Thr Val
            1025                1030                1035

Asp Phe Val Ala Glu Ala Val Thr Thr Leu Gly Ala Gln Gln Arg
            1040                1045                1050

Glu Gly Tyr Val Ser Tyr Asp Val Met Asn Pro His Asp Asp Gly
            1055                1060                1065

Ile Ser Leu Asp Val Phe Val Asp Trp Leu Ile Arg Ala Gly His
            1070                1075                1080

Pro Ile Asp Arg Val Asp Asp Tyr Asp Asp Trp Val Arg Arg Phe
            1085                1090                1095

Glu Thr Ala Leu Thr Ala Leu Pro Glu Lys Arg Arg Ala Gln Thr
            1100                1105                1110

Val Leu Pro Leu Leu His Ala Phe Arg Ala Pro Gln Ala Pro Leu
            1115                1120                1125

Arg Gly Ala Pro Glu Pro Thr Glu Val Phe His Ala Ala Val Arg
            1130                1135                1140

Thr Ala Lys Val Gly Pro Gly Asp Ile Pro His Leu Asp Glu Ala
            1145                1150                1155

Leu Ile Asp Lys Tyr Ile Arg Asp Leu Arg Glu Phe Gly Leu Ile
            1160                1165                1170

<210> SEQ ID NO 3
<211> LENGTH: 1148
<212> TYPE: PRT
<213> ORGANISM: Segniliparus rugosus

<400> SEQUENCE: 3

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
                35                  40                  45

Leu Asp Thr Leu Met Arg Gly Tyr Ala Glu Arg Pro Ala Leu Ala His
        50                  55                  60

Arg Val Gly Ala Gly Tyr Glu Thr Ile Ser Tyr Gly Glu Leu Trp Ala
65              70                  75                  80

Arg Val Gly Ala Ile Ala Ala Ala Trp Gln Ala Asp Gly Leu Ala Pro
```

```
            85                  90                  95
Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
            115                 120                 125

Ala Gly Ala Ser Leu Ala Gln Leu Val Gly Ile Leu Glu Glu Thr Glu
            130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
            195                 200                 205

Val Glu Thr Leu Ala Asp Leu Ala Ala Arg Gly Glu Ala Leu Pro Glu
            210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
            290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
            340                 345                 350

Leu Gly Gly Arg Leu Leu Val Ala Val Cys Gly Ser Ala Pro Leu Ser
            355                 360                 365

Pro Glu Met Arg Ala Phe Met Glu Glu Val Leu Gly Phe Pro Leu Leu
            370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
            420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
            450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
            500                 505                 510
```

Gly Asn Ser Glu Arg Ser Phe Leu Leu Ala Val Val Pro Asn Ala
            515                 520                 525

Glu Val Leu Gly Ala Arg Asp Gln Glu Ala Lys Pro Leu Ile Ala
    530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                    565                 570                 575

Gly Leu Leu Ser Glu Val Gly Lys Leu Leu Arg Pro Lys Leu Lys Ala
                580                 585                 590

Arg Tyr Gly Glu Ala Leu Glu Ala Arg Tyr Asp Glu Ile Ala His Gly
            595                 600                 605

Gln Ala Asp Glu Leu Arg Ala Leu Arg Asp Gly Ala Gly Gln Arg Pro
        610                 615                 620

Val Val Glu Thr Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                    645                 650                 655

Ser Leu Ser Ala Leu Ser Leu Ala Asn Leu Leu His Asp Val Phe Glu
                660                 665                 670

Val Glu Val Pro Val Arg Ile Ile Ile Gly Pro Thr Ala Ser Leu Ala
            675                 680                 685

Gly Ile Ala Lys His Ile Glu Ala Glu Arg Ala Gly Ala Ser Ala Pro
        690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                    725                 730                 735

Lys Gly Leu Pro Ala Ala Asp Gln Val Arg Thr Val Leu Leu Thr Gly
                740                 745                 750

Ala Asn Gly Trp Leu Gly Arg Phe Leu Ala Leu Glu Gln Leu Glu Arg
            755                 760                 765

Leu Ala Arg Ser Gly Gln Asp Gly Gly Lys Leu Ile Cys Leu Val Arg
        770                 775                 780

Gly Lys Asp Ala Ala Ala Arg Arg Ile Glu Glu Thr Leu Gly
785                 790                 795                 800

Thr Asp Pro Ala Leu Ala Ala Arg Phe Ala Glu Leu Ala Glu Gly Arg
                    805                 810                 815

Leu Glu Val Val Pro Gly Asp Val Gly Glu Pro Lys Phe Gly Leu Asp
                820                 825                 830

Asp Ala Ala Trp Asp Arg Leu Ala Glu Glu Val Asp Val Ile Val His
            835                 840                 845

Pro Ala Ala Leu Val Asn His Val Leu Pro Tyr His Gln Leu Phe Gly
        850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                    885                 890                 895

Val Glu Pro Ser Ser Phe Glu Glu Asp Gly Asp Ile Arg Ala Val Val
                900                 905                 910

Pro Glu Arg Pro Leu Gly Asp Gly Tyr Ala Asn Gly Tyr Gly Asn Ser
            915                 920                 925

```
Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
            965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
            995                 1000                1005

Phe Thr Ala Glu Ala Ile Thr Thr Leu Gly Ala Glu Pro Ser Trp
    1010                1015                1020

Phe Asp Gly Gly Ala Gly Phe Arg Ser Phe Asp Val Phe Asn Pro
    1025                1030                1035

His His Asp Gly Val Gly Leu Asp Glu Phe Val Asp Trp Leu Ile
    1040                1045                1050

Glu Ala Gly His Pro Ile Ser Arg Ile Asp Asp His Lys Glu Trp
    1055                1060                1065

Phe Ala Arg Phe Glu Thr Ala Val Arg Gly Leu Pro Glu Ala Gln
    1070                1075                1080

Arg Gln His Ser Leu Leu Pro Leu Leu Arg Ala Tyr Ser Phe Pro
    1085                1090                1095

His Pro Pro Val Asp Gly Ser Val Tyr Pro Thr Gly Lys Phe Gln
    1100                1105                1110

Gly Ala Val Lys Ala Ala Gln Val Gly Ser Asp His Asp Val Pro
    1115                1120                1125

His Leu Gly Lys Ala Leu Ile Val Lys Tyr Ala Asp Asp Leu Lys
    1130                1135                1140

Ala Leu Gly Leu Leu
    1145

<210> SEQ ID NO 4
<211> LENGTH: 1168
<212> TYPE: PRT
<213> ORGANISM: Mycobacterium smegmatis

<400> SEQUENCE: 4

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
                20                  25                  30

Ile Ser Ala Ala Ala Asp Pro Glu Leu Arg Leu Pro Ala Ala Val
            35                  40                  45

Lys Gln Ile Leu Ala Gly Tyr Ala Asp Arg Pro Ala Leu Gly Lys Arg
50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
        130                 135                 140
```

```
Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Glu Thr Ile Thr Asp Ala Leu Asp Arg
210                 215                 220

Gly Arg Ser Leu Ala Asp Ala Pro Leu Tyr Val Pro Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
530                 535                 540

Tyr Leu Leu Ala Val Val Val Pro Thr Glu Glu Ala Leu Ser Arg Trp
545                 550                 555                 560
```

-continued

```
Asp Gly Asp Glu Leu Lys Ser Arg Ile Ser Asp Ser Leu Gln Asp Ala
                565                 570                 575
Ala Arg Ala Ala Gly Leu Gln Ser Tyr Glu Ile Pro Arg Asp Phe Leu
            580                 585                 590
Val Glu Thr Thr Pro Phe Thr Leu Glu Asn Gly Leu Leu Thr Gly Ile
        595                 600                 605
Arg Lys Leu Ala Arg Pro Lys Leu Lys Ala His Tyr Gly Glu Arg Leu
    610                 615                 620
Glu Gln Leu Tyr Thr Asp Leu Ala Glu Gly Gln Ala Asn Glu Leu Arg
625                 630                 635                 640
Glu Leu Arg Arg Asn Gly Ala Asp Arg Pro Val Val Glu Thr Val Ser
                645                 650                 655
Arg Ala Ala Val Ala Leu Leu Gly Ala Ser Val Thr Asp Leu Arg Ser
            660                 665                 670
Asp Ala His Phe Thr Asp Leu Gly Asp Ser Leu Ser Ala Leu Ser
        675                 680                 685
Phe Ser Asn Leu Leu His Glu Ile Phe Asp Val Asp Val Pro Val Gly
    690                 695                 700
Val Ile Val Ser Pro Ala Thr Asp Leu Ala Gly Val Ala Ala Tyr Ile
705                 710                 715                 720
Glu Gly Glu Leu Arg Gly Ser Lys Arg Pro Thr Tyr Ala Ser Val His
                725                 730                 735
Gly Arg Asp Ala Thr Glu Val Arg Ala Arg Asp Leu Ala Leu Gly Lys
            740                 745                 750
Phe Ile Asp Ala Lys Thr Leu Ser Ala Ala Pro Gly Leu Pro Arg Ser
        755                 760                 765
Gly Thr Glu Ile Arg Thr Val Leu Leu Thr Gly Ala Thr Gly Phe Leu
    770                 775                 780
Gly Arg Tyr Leu Ala Leu Glu Trp Leu Glu Arg Met Asp Leu Val Asp
785                 790                 795                 800
Gly Lys Val Ile Cys Leu Val Arg Ala Arg Ser Asp Asp Glu Ala Arg
                805                 810                 815
Ala Arg Leu Asp Ala Thr Phe Asp Thr Gly Asp Ala Thr Leu Leu Glu
            820                 825                 830
His Tyr Arg Ala Leu Ala Ala Asp His Leu Glu Val Ile Ala Gly Asp
        835                 840                 845
Lys Gly Glu Ala Asp Leu Gly Leu Asp His Asp Thr Trp Gln Arg Leu
    850                 855                 860
Ala Asp Thr Val Asp Leu Ile Val Asp Pro Ala Ala Leu Val Asn His
865                 870                 875                 880
Val Leu Pro Tyr Ser Gln Met Phe Gly Pro Asn Ala Leu Gly Thr Ala
                885                 890                 895
Glu Leu Ile Arg Ile Ala Leu Thr Thr Thr Ile Lys Pro Tyr Val Tyr
            900                 905                 910
Val Ser Thr Ile Gly Val Gly Gln Gly Ile Ser Pro Glu Ala Phe Val
        915                 920                 925
Glu Asp Ala Asp Ile Arg Glu Ile Ser Ala Thr Arg Arg Val Asp Asp
    930                 935                 940
Ser Tyr Ala Asn Gly Tyr Gly Asn Ser Lys Trp Ala Gly Glu Val Leu
945                 950                 955                 960
Leu Arg Glu Ala His Asp Trp Cys Gly Leu Pro Val Ser Val Phe Arg
                965                 970                 975
Cys Asp Met Ile Leu Ala Asp Thr Thr Tyr Ser Gly Gln Leu Asn Leu
```

```
                    980             985             990
Pro Asp Met Phe Thr Arg Leu Met  Leu Ser Leu Val Ala  Thr Gly Ile
            995                 1000                1005

Ala Pro Gly Ser Phe Tyr Glu  Leu Asp Ala Asp Gly  Asn Arg Gln
        1010                1015                1020

Arg Ala His Tyr Asp Gly Leu  Pro Val Glu Phe Ile  Ala Glu Ala
        1025                1030                1035

Ile Ser Thr Ile Gly Ser Gln  Val Thr Asp Gly Phe  Glu Thr Phe
        1040                1045                1050

His Val Met Asn Pro Tyr Asp  Asp Gly Ile Gly Leu  Asp Glu Tyr
        1055                1060                1065

Val Asp Trp Leu Ile Glu Ala  Gly Tyr Pro Val His  Arg Val Asp
        1070                1075                1080

Asp Tyr Ala Thr Trp Leu Ser  Arg Phe Glu Thr Ala  Leu Arg Ala
        1085                1090                1095

Leu Pro Glu Arg Gln Arg Gln  Ala Ser Leu Leu Pro  Leu Leu His
        1100                1105                1110

Asn Tyr Gln Gln Pro Ser Pro  Pro Val Cys Gly Ala  Met Ala Pro
        1115                1120                1125

Thr Asp Arg Phe Arg Ala Ala  Val Gln Asp Ala Lys  Ile Gly Pro
        1130                1135                1140

Asp Lys Asp Ile Pro His Val  Thr Ala Asp Val Ile  Val Lys Tyr
        1145                1150                1155

Ile Ser Asn Leu Gln Met Leu  Gly Leu Leu
        1160                1165

<210> SEQ ID NO 5
<211> LENGTH: 1185
<212> TYPE: PRT
<213> ORGANISM: Mycobacterium massiliense

<400> SEQUENCE: 5

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175
```

```
Ala Met Glu Ser Val Arg Ala Thr Pro Ser Ile Lys Gln Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
        210                 215                 220

Ala Val Ile Ala Arg Gly Ala Leu Pro Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
        275                 280                 285

Met Ile Gly Leu Asn Phe Met Pro Met Ser His Ile Met Gly Arg Gly
        290                 295                 300

Thr Leu Thr Ser Thr Leu Ser Thr Gly Thr Gly Tyr Phe Ala Ala
305                 310                 315                 320

Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
        355                 360                 365

Ala Glu Ala Val Ala Ala Glu Val Lys Ala Asp Ile Arg Asp Asn Leu
        370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
        530                 535                 540

Gly Ser Ser Glu Arg Ser Tyr Leu Leu Ala Val Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
```

```
                    595                 600                 605
Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
                660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
        690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
                740                 745                 750

Arg Ala Ala Asp Leu Thr Leu Asp Lys Phe Ile Asp Glu Ala Thr Leu
                755                 760                 765

His Ala Ala Pro Ser Leu Pro Lys Ala Ala Gly Ile Pro His Thr Val
        770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
                820                 825                 830

Asp Thr Gly Asp Thr Glu Leu Leu Ala His Phe Arg Ser Leu Ala Asp
                835                 840                 845

Lys His Leu Glu Val Leu Ala Gly Asp Ile Gly Asp Pro Asn Leu Gly
        850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
                900                 905                 910

Thr Thr Lys Ile Lys Pro Val Thr Tyr Leu Ser Thr Val Ala Val Ala
        915                 920                 925

Ala Tyr Val Asp Pro Thr Thr Phe Asp Glu Glu Ser Asp Ile Arg Leu
        930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
                980                 985                 990

Ser Arg Tyr Thr Gly Gln Leu Asn Val Pro Asp Gln Phe Thr Arg Leu
        995                1000                1005

Ile Leu Ser Leu Ile Ala Thr Gly Ile Ala Pro Gly Ser Phe Tyr
        1010                1015                1020
```

```
Gln Ala Gln Thr Thr Gly Glu Arg Pro Leu Ala His Tyr Asp Gly
    1025                1030                1035

Leu Pro Gly Asp Phe Thr Ala Glu Ala Ile Thr Thr Leu Gly Thr
    1040                1045                1050

Gln Val Pro Glu Gly Ser Gly Phe Val Thr Tyr Asp Cys Val
    1055                1060                1065

Asn Pro His Ala Asp Gly Ile Ser Leu Asp Asn Phe Val Asp Trp
    1070                1075                1080

Leu Ile Glu Ala Gly Tyr Pro Ile Ala Arg Ile Asp Asn Tyr Thr
    1085                1090                1095

Glu Trp Phe Thr Arg Phe Asp Thr Ala Ile Arg Gly Leu Ser Glu
    1100                1105                1110

Lys Gln Lys Gln His Ser Leu Leu Pro Leu Leu His Ala Phe Glu
    1115                1120                1125

Gln Pro Ser Ala Ala Glu Asn His Gly Val Val Pro Ala Lys Arg
    1130                1135                1140

Phe Gln His Ala Val Gln Ala Ala Gly Ile Gly Pro Val Gly Gln
    1145                1150                1155

Asp Gly Thr Thr Asp Ile Pro His Leu Ser Arg Arg Leu Ile Val
    1160                1165                1170

Lys Tyr Ala Lys Asp Leu Glu Gln Leu Gly Leu Leu
    1175                1180                1185

<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala Ala His Ser
1               5                   10                  15

Arg Leu Ala Arg Arg Ala Ala Glu Leu Leu Ala Thr Asp Pro Gln Ala
                20                  25                  30

Ala Ala Thr Leu Pro Asp Pro Glu Val Val Arg Gln Ala Thr Arg Pro
            35                  40                  45

Gly Leu Arg Leu Ala Glu Arg Val Asp Ala Ile Leu Ser Gly Tyr Ala
        50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
```

```
                195                 200                 205
Asp Arg Glu Ala Val Glu Ala Lys Arg Lys Ile Ala Asp Ala Gly
210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
                260                 265                 270

Gly Ala Met Tyr Pro Glu Arg Asn Val Ala His Phe Trp Gly Gly Val
                275                 280                 285

Trp Ala Ala Ala Phe Asp Glu Asp Ala Ala Pro Pro Val Pro Ala Ile
                290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
                340                 345                 350

Leu Phe Leu Val Pro Arg Val Val Glu Met Leu Tyr Gln His Tyr Gln
                355                 360                 365

Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
                420                 425                 430

Glu Ala Gly Pro Val Trp Arg Asp Gly Tyr Leu Val Lys Pro Pro Val
                435                 440                 445

Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
                500                 505                 510

Glu Gln Phe Ala Tyr Val Asp Arg Arg Lys Asn Val Leu Lys Leu Ser
                515                 520                 525

Gln Gly Glu Phe Val Thr Leu Ala Lys Leu Glu Ala Ala Tyr Ser Ser
                530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
                580                 585                 590

Ile Ala Arg Asp Glu Gly Leu Gln Ser Tyr Glu Val Pro Arg Asp Phe
                595                 600                 605

Ile Ile Glu Thr Asp Pro Phe Thr Val Glu Asn Gly Leu Leu Ser Asp
                610                 615                 620
```

```
Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
    690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
    850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
        915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
            980                 985                 990

Phe Arg Ser Asp Met Ile Leu Ala His Gln Lys Tyr Thr Gly Gln Val
        995                 1000                1005

Asn Ala Thr Asp Gln Phe Thr Arg Leu Val Gln Ser Leu Leu Ala
    1010                1015                1020

Thr Gly Leu Ala Pro Lys Ser Phe Tyr Glu Leu Asp Ala Gln Gly
    1025                1030                1035
```

```
Asn Arg Gln Arg Ala His Tyr Asp Gly Ile Pro Val Asp Phe Thr
    1040                1045                1050

Ala Glu Ser Ile Thr Thr Leu Gly Gly Asp Gly Leu Glu Gly Tyr
    1055                1060                1065

Arg Ser Tyr Asn Val Phe Asn Pro His Arg Asp Gly Val Gly Leu
    1070                1075                1080

Asp Glu Phe Val Asp Trp Leu Ile Glu Ala Gly His Pro Ile Thr
    1085                1090                1095

Arg Ile Asp Asp Tyr Asp Gln Trp Leu Ser Arg Phe Glu Thr Ser
    1100                1105                1110

Leu Arg Gly Leu Pro Glu Ser Lys Arg Gln Ala Ser Val Leu Pro
    1115                1120                1125

Leu Leu His Ala Phe Ala Arg Pro Gly Pro Ala Val Asp Gly Ser
    1130                1135                1140

Pro Phe Arg Asn Thr Val Phe Arg Thr Asp Val Gln Lys Ala Lys
    1145                1150                1155

Ile Gly Ala Glu His Asp Ile Pro His Leu Gly Lys Ala Leu Val
    1160                1165                1170

Leu Lys Tyr Ala Asp Asp Ile Lys Gln Leu Gly Leu Leu
    1175                1180                1185

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
        210                 215                 220
```

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Met Ala Arg Thr
65                  70                  75                  80

Val Ala Glu Gln Thr Arg Leu Leu Ala Tyr Ser Asn Pro Phe Cys Asp
            85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
            115                 120                 125

Ala Val Asp Thr Ala Ile Arg Leu Met His Tyr Tyr Gln Asn Cys Arg

```
            130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 9
<211> LENGTH: 454
<212> TYPE: PRT
<213> ORGANISM: Pseudomonas syringae

<400> SEQUENCE: 9

Met Ser Ala Asn Asn Pro Gln Thr Leu Glu Trp Gln Ala Leu Ser Ser
1               5                   10                  15

Glu His Leu Ala Pro Phe Ser Asp Tyr Lys Gln Leu Lys Glu Lys
                20                  25                  30
```

```
Gly Pro Arg Ile Ile Thr Arg Ala Glu Gly Val Tyr Leu Trp Asp Ser
         35                  40                  45

Glu Gly Asn Lys Ile Leu Asp Gly Met Ser Gly Leu Trp Cys Val Ala
 50                  55                  60

Ile Gly Tyr Gly Arg Glu Leu Ala Asp Ala Ala Ser Lys Gln Met
 65                  70                  75                  80

Arg Glu Leu Pro Tyr Tyr Asn Leu Phe Phe Gln Thr Ala His Pro Pro
                 85                  90                  95

Val Leu Glu Leu Ala Lys Ala Ile Ser Asp Ile Ala Pro Glu Gly Met
             100                 105                 110

Asn His Val Phe Phe Thr Gly Ser Gly Ser Glu Gly Asn Asp Thr Met
             115                 120                 125

Leu Arg Met Val Arg His Tyr Trp Ala Leu Lys Gly Gln Pro Asn Lys
 130                 135                 140

Lys Thr Ile Ile Ser Arg Val Asn Gly Tyr His Gly Ser Thr Val Ala
 145                 150                 155                 160

Gly Ala Ser Leu Gly Gly Met Thr Tyr Met His Glu Gln Gly Asp Leu
                 165                 170                 175

Pro Ile Pro Gly Val Val His Ile Pro Gln Pro Tyr Trp Phe Gly Glu
             180                 185                 190

Gly Gly Asp Met Thr Pro Asp Glu Phe Gly Ile Trp Ala Ala Glu Gln
             195                 200                 205

Leu Glu Lys Lys Ile Leu Glu Leu Gly Val Glu Asn Val Gly Ala Phe
 210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                 245                 250                 255

Phe Ala Ala Asp Glu Val Ile Cys Gly Phe Gly Arg Thr Ser Glu Trp
             260                 265                 270

Phe Gly Ser Asp Phe Tyr Gly Leu Arg Pro Asp Met Met Thr Ile Ala
             275                 280                 285

Lys Gly Leu Thr Ser Gly Tyr Val Pro Met Gly Gly Leu Ile Val Arg
 290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                 325                 330                 335

Ile Arg Ile Leu Arg Glu Glu Lys Ile Val Glu Arg Val Arg Ser Glu
             340                 345                 350

Thr Ala Pro Tyr Leu Gln Lys Arg Leu Arg Glu Leu Ser Asp His Pro
             355                 360                 365

Leu Val Gly Glu Val Arg Gly Val Gly Leu Leu Gly Ala Ile Glu Leu
 370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                 405                 410                 415

Val Gly Asp Thr Met Ile Ile Ala Pro Pro Leu Val Ile Ser Phe Ala
             420                 425                 430

Gln Ile Asp Glu Leu Val Glu Lys Ala Arg Thr Cys Leu Asp Leu Thr
             435                 440                 445

Leu Ala Val Leu Gln Gly
```

<210> SEQ ID NO 10
<211> LENGTH: 467
<212> TYPE: PRT
<213> ORGANISM: Rhodobacter sphaeroides

<400> SEQUENCE: 10

```
Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Ala Leu Ala Ser Leu
        355                 360                 365
```

```
Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
                420                 425                 430

Ile Ile Ser Arg Ala Gln Ile Asp Glu Met Val Ala Ile Met Arg Gln
            435                 440                 445

Ala Ile Thr Glu Val Ser Ala Ala His Gly Leu Thr Ala Lys Glu Pro
450                 455                 460

Ala Ala Val
465

<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
                20                  25                  30

Ala Leu Asn Arg Glu Val Ile Glu Tyr Phe Lys Glu His Val Asn Pro
            35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Val Ser Ala Val Gln Asn Gln Leu Ala
                100                 105                 110

Lys Gln Pro Leu His Ser Gln Glu Leu Leu Asp Pro Leu Arg Ala Met
            115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
    195                 200                 205

His Val Pro Phe Gly Asn Ile Glu Ala Met Arg Thr Ala Leu Asn Glu
210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Pro Gly Tyr Leu Thr Ala
                245                 250                 255

Val Arg Lys Leu Cys Asp Glu Phe Gly Ala Leu Met Ile Leu Asp Glu
            260                 265                 270
```

```
Val Gln Thr Gly Met Gly Arg Thr Gly Lys Met Phe Ala Cys Glu His
            275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
                340                 345                 350

Gln Asn Leu Pro Ala Gln Ala Glu Gln Lys Gly Asp Met Leu Leu Asp
            355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
    435                 440                 445

Leu Ala Ala Met Arg Val Ser Val Glu Glu Ala
450                 455

<210> SEQ ID NO 12
<211> LENGTH: 453
<212> TYPE: PRT
<213> ORGANISM: Vibrio fluvialis

<400> SEQUENCE: 12

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
```

```
            180             185             190
Thr Glu Gln Phe Val Ala Arg Leu Ala Arg Glu Leu Glu Glu Thr
        195                 200                 205
Ile Gln Arg Glu Gly Ala Asp Thr Ile Ala Gly Phe Phe Ala Glu Pro
    210                 215                 220
Val Met Gly Ala Gly Val Ile Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
            275                 280                 285
Ala Gly Phe Phe Pro Met Gly Ala Val Ile Leu Gly Pro Glu Leu Ser
            290                 295                 300
Lys Arg Leu Glu Thr Ala Ile Glu Ala Ile Glu Glu Phe Pro His Gly
305                 310                 315                 320
Phe Thr Ala Ser Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Ala Val
                370                 375                 380
Lys Asp Lys Ala Ser Lys Thr Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
                420                 425                 430
Gln Met Asp Glu Met Phe Asp Lys Leu Glu Lys Ala Leu Asp Lys Val
            435                 440                 445
Phe Ala Glu Val Ala
        450

<210> SEQ ID NO 13
<211> LENGTH: 478
<212> TYPE: PRT
<213> ORGANISM: Cucumis sativus

<400> SEQUENCE: 13

Met Ala Ser Ser Pro Glu Leu Pro Leu Lys Pro Ile Pro Gly Gly
1               5                   10                  15
Tyr Gly Phe Pro Phe Leu Gly Pro Ile Lys Asp Arg Tyr Asp Tyr Phe
                20                  25                  30
Tyr Phe Gln Gly Arg Asp Glu Phe Arg Ser Arg Ile Thr Lys Tyr
            35                  40                  45
Asn Ser Thr Val Phe His Ala Asn Met Pro Pro Gly Pro Phe Ile Ser
        50                  55                  60
Ser Asp Ser Arg Val Val Leu Leu Asp Ala Leu Ser Phe Pro Ile
65                  70                  75                  80
Leu Phe Asp Thr Thr Lys Val Glu Lys Arg Asn Ile Leu Asp Gly Thr
                85                  90                  95
```

```
Tyr Met Pro Ser Leu Ser Phe Thr Gly Gly Ile Arg Thr Cys Ala Tyr
            100                 105                 110

Leu Asp Pro Ser Glu Thr Glu His Thr Val Leu Lys Arg Leu Phe Leu
        115                 120                 125

Ser Phe Leu Ala Ser His His Asp Arg Phe Ile Pro Leu Phe Arg Ser
    130                 135                 140

Ser Leu Ser Glu Met Phe Val Lys Leu Glu Asp Lys Leu Ala Asp Lys
145                 150                 155                 160

Asn Lys Ile Ala Asp Phe Asn Ser Ile Ser Asp Ala Val Ser Phe Asp
                165                 170                 175

Tyr Val Phe Arg Leu Phe Ser Asp Gly Thr Pro Asp Ser Thr Leu Ala
            180                 185                 190

Ala Asp Gly Pro Gly Met Phe Asp Leu Trp Leu Gly Leu Gln Leu Ala
        195                 200                 205

Pro Leu Ala Ser Ile Gly Leu Pro Lys Ile Phe Ser Val Phe Glu Asp
    210                 215                 220

Leu Ile Ile His Thr Ile Pro Leu Pro Phe Phe Pro Val Lys Ser Arg
225                 230                 235                 240

Tyr Arg Lys Leu Tyr Lys Ala Phe Tyr Ser Ser Gly Ser Phe Leu
                245                 250                 255

Asp Glu Ala Glu Lys Gln Gly Ile Asp Arg Glu Lys Ala Cys His Asn
            260                 265                 270

Leu Val Phe Leu Ala Gly Phe Asn Ala Tyr Gly Met Lys Val Leu
        275                 280                 285

Phe Pro Thr Ile Leu Lys Trp Val Gly Thr Gly Glu Asp Leu His
290                 295                 300

Arg Lys Leu Ala Glu Glu Val Arg Thr Thr Val Lys Glu Glu Gly Gly
305                 310                 315                 320

Leu Thr Phe Ser Ala Leu Glu Lys Met Ser Leu Leu Lys Ser Val Val
                325                 330                 335

Tyr Glu Ala Leu Arg Ile Glu Pro Pro Val Pro Phe Gln Tyr Gly Lys
            340                 345                 350

Ala Lys Glu Asp Ile Val Ile Gln Ser His Asp Ser Cys Phe Lys Ile
        355                 360                 365

Lys Lys Gly Glu Thr Ile Phe Gly Tyr Gln Pro Phe Ala Thr Lys Asp
    370                 375                 380

Pro Lys Ile Phe Lys Asp Ser Glu Lys Phe Val Gly Asp Arg Phe Val
385                 390                 395                 400

Gly Glu Glu Gly Glu Lys Leu Leu Lys Tyr Val Tyr Trp Ser Asn Glu
                405                 410                 415

Arg Glu Thr Val Glu Pro Thr Ala Glu Asn Lys Gln Cys Pro Gly Lys
            420                 425                 430

Asn Leu Val Val Met Met Gly Arg Ile Ile Val Val Glu Phe Phe Leu
        435                 440                 445

Arg Tyr Asp Thr Phe Thr Val Asp Val Ala Asp Leu Ala Leu Gly Pro
    450                 455                 460

Ala Val Lys Phe Lys Ser Leu Thr Arg Ala Thr Ala Ser Val
465                 470                 475

<210> SEQ ID NO 14
<211> LENGTH: 500
<212> TYPE: PRT
<213> ORGANISM: Oryza sativa

<400> SEQUENCE: 14
```

Met Ala Pro Pro Val Asn Ser Gly Asp Ala Ala Ala Ala Thr
1               5                   10                  15

Gly Glu Lys Ser Lys Leu Ser Pro Ser Gly Leu Pro Ile Arg Glu Ile
            20                  25                  30

Pro Gly Gly Tyr Gly Val Pro Phe Phe Ser Pro Leu Arg Asp Arg Leu
        35                  40                  45

Asp Tyr Phe Tyr Phe Gln Gly Ala Glu Glu Tyr Phe Arg Ser Arg Val
        50                  55                  60

Ala Arg His Gly Gly Ala Thr Val Leu Arg Val Asn Met Pro Pro Gly
65                  70                  75                  80

Pro Phe Ile Ser Gly Asn Pro Arg Val Val Ala Leu Leu Asp Ala Arg
                85                  90                  95

Ser Phe Arg Val Leu Leu Asp Asp Ser Met Val Asp Lys Ala Asp Thr
                100                 105                 110

Leu Asp Gly Thr Tyr Met Pro Ser Arg Ala Leu Phe Gly Gly His Arg
            115                 120                 125

Pro Leu Ala Phe Leu Asp Ala Asp Pro Arg His Ala Lys Ile Lys
            130                 135                 140

Arg Val Val Met Ser Leu Ala Ala Arg Met His His Val Ala Pro
145                 150                 155                 160

Ala Phe Arg Ala Ala Phe Ala Ala Met Phe Asp Ala Val Glu Ala Gly
                165                 170                 175

Leu Gly Ala Ala Val Glu Phe Asn Lys Leu Asn Met Arg Tyr Met Leu
                180                 185                 190

Asp Phe Thr Cys Ala Ala Leu Phe Gly Gly Pro Pro Ser Lys Val
                195                 200                 205

Val Gly Asp Gly Ala Val Thr Lys Ala Met Ala Trp Leu Ala Phe Gln
210                 215                 220

Leu His Pro Ile Ala Ser Lys Val Val Lys Pro Trp Pro Leu Glu Glu
225                 230                 235                 240

Leu Leu Leu His Thr Phe Ser Leu Pro Pro Phe Leu Val Arg Arg Gly
                245                 250                 255

Tyr Ala Asp Leu Lys Ala Tyr Phe Ala Asp Ala Ala Ala Val Leu
                260                 265                 270

Asp Asp Ala Glu Lys Ser His Thr Gly Ile Pro Arg Asp Glu Leu Leu
                275                 280                 285

Asp Asn Leu Val Phe Val Ala Ile Phe Asn Ala Phe Gly Gly Phe Lys
                290                 295                 300

Ile Phe Leu Pro His Ile Val Lys Trp Leu Ala Arg Ala Gly Pro Glu
305                 310                 315                 320

Leu His Ala Lys Leu Ala Thr Glu Val Arg Ala Thr Val Pro Thr Gly
                325                 330                 335

Glu Asp Asp Gly Ile Thr Leu Ala Ala Val Glu Arg Met Pro Leu Val
            340                 345                 350

Lys Ser Val Val Trp Glu Ala Leu Arg Met Asn Pro Pro Val Glu Phe
                355                 360                 365

Gln Tyr Gly His Ala Arg Arg Asp Met Val Val Glu Ser His Asp Ala
    370                 375                 380

Ala Tyr Glu Val Arg Lys Gly Glu Met Leu Phe Gly Tyr Gln Pro Leu
385                 390                 395                 400

Ala Thr Arg Asp Glu Lys Val Phe Asp Arg Ala Gly Glu Phe Val Ala
                405                 410                 415

```
Asp Arg Phe Val Ala Gly Gly Ala Ala Gly Asp Arg Pro Leu Leu Glu
                420                 425                 430

His Val Val Trp Ser Asn Gly Pro Glu Thr Arg Ala Pro Ser Glu Gly
            435                 440                 445

Asn Lys Gln Cys Pro Gly Lys Asp Met Val Val Ala Val Gly Arg Leu
450                 455                 460

Met Val Ala Glu Leu Phe Arg Arg Tyr Asp Thr Phe Ala Ala Asp Val
465                 470                 475                 480

Val Glu Ala Pro Val Glu Pro Val Val Thr Phe Thr Ser Leu Thr Arg
                485                 490                 495

Ala Ser Ser Gly
            500

<210> SEQ ID NO 15
<211> LENGTH: 387
<212> TYPE: PRT
<213> ORGANISM: Lactobacillus casei

<400> SEQUENCE: 15

Met Ser Gly Tyr His Phe Leu Lys Pro Phe Thr Phe Lys His Gln Thr
1               5                   10                  15

Ile Thr Leu Lys Asn Arg Ile Val Ile Pro Pro Met Thr Thr Arg Leu
                20                  25                  30

Ser Phe Glu Asp Gly Thr Val Thr Arg Asp Glu Ile Arg Tyr Tyr Gln
            35                  40                  45

Gln Arg Ala Gly Gly Val Gly Met Phe Ile Thr Gly Thr Ala Asn Val
        50                  55                  60

Asn Ala Leu Gly Lys Gly Phe Glu Gly Glu Leu Ser Val Ala Asp Asp
65                  70                  75                  80

Arg Phe Ile Pro Gly Leu Ser Lys Leu Ala Ala Ala Met Lys Thr Gly
                85                  90                  95

Gly Thr Lys Ala Ile Leu Gln Ile Phe Ser Ala Gly Arg Met Ser Asn
            100                 105                 110

Ser Lys Ile Leu Arg Gly Glu Gln Pro Val Ser Ala Ser Ala Val Ala
        115                 120                 125

Ala Pro Arg Ala Gly Tyr Glu Thr Pro Arg Ala Leu Thr Ser Ala Glu
    130                 135                 140

Ile Glu Ala Thr Ile His Asp Phe Gly Gln Ala Val Arg Arg Ala Ile
145                 150                 155                 160

Leu Ala Gly Phe Asp Gly Ile Glu Leu His Gly Ala Asn Thr Tyr Leu
                165                 170                 175

Ile Gln Gln Phe Tyr Ser Pro Asn Ser Asn Arg Arg Thr Asp Glu Trp
            180                 185                 190

Gly Gly Asp Arg Asp Lys Arg Met Arg Phe Pro Leu Ala Val Val His
        195                 200                 205

Glu Ala Glu Lys Val Ile Ala Thr Ile Ala Asp Arg Pro Phe Leu Leu
    210                 215                 220

Gly Tyr Arg Ile Ser Pro Glu Glu Leu Glu Gln Pro Gly Ile Thr Leu
225                 230                 235                 240

Asp Asp Thr Leu Ala Leu Ile Asp Ala Leu Lys Gln Thr Lys Ile Asp
                245                 250                 255

Tyr Leu His Val Ser Gln Ser Asp Val Trp Arg Thr Ser Leu Arg Asn
            260                 265                 270

Pro Glu Asp Thr Ala Ile Met Asn Glu Gln Ile Arg Asp His Val Ala
        275                 280                 285
```

```
Gly Ala Phe Pro Val Ile Val Gly Gly Ile Lys Thr Pro Ala Asp
            290                 295                 300

Ala Glu Lys Ala Ala Glu Ser Phe Asp Leu Val Ala Ile Gly His Glu
305                 310                 315                 320

Met Ile Arg Glu Pro His Trp Val Gln Lys Val Leu Asp His Asp Glu
                325                 330                 335

Lys Ala Ile Arg Tyr Gln Ile Ala Pro Ala Asp Leu Glu Glu Leu Gly
            340                 345                 350

Ile Ala Pro Thr Phe Leu Asp Phe Ile Glu Ser Ile Ser Gly Gly Ala
        355                 360                 365

Lys Gly Val Pro Leu Thr Thr Ala Gln Ser Val Thr Ser Ser Asn Val
370                 375                 380

Thr Gln Asp
385

<210> SEQ ID NO 16
<211> LENGTH: 363
<212> TYPE: PRT
<213> ORGANISM: Pseudomonas putida

<400> SEQUENCE: 16

Met Ser Ala Leu Phe Glu Pro Tyr Thr Leu Lys Asp Val Thr Leu Arg
1               5                   10                  15

Asn Arg Ile Ala Ile Pro Pro Met Cys Gln Tyr Met Ala Glu Asp Gly
            20                  25                  30

Met Ile Asn Asp Trp His His Val His Leu Ala Gly Leu Ala Arg Gly
        35                  40                  45

Gly Ala Gly Leu Leu Val Val Glu Ala Thr Ala Val Ala Pro Glu Gly
    50                  55                  60

Arg Ile Thr Pro Gly Cys Ala Gly Ile Trp Ser Asp Ala His Ala Gln
65                  70                  75                  80

Ala Phe Val Pro Val Val Gln Ala Ile Lys Ala Ala Gly Ser Val Pro
                85                  90                  95

Gly Ile Gln Ile Ala His Ala Gly Arg Lys Ala Ser Ala Asn Arg Pro
            100                 105                 110

Trp Glu Gly Asp Asp His Ile Ala Ala Asp Ala Arg Gly Trp Glu
        115                 120                 125

Thr Ile Ala Pro Ser Ala Ile Ala Phe Gly Ala His Leu Pro Lys Val
    130                 135                 140

Pro Arg Glu Met Thr Leu Asp Asp Ile Ala Arg Val Lys Gln Asp Phe
145                 150                 155                 160

Val Asp Ala Ala Arg Arg Ala Arg Asp Ala Gly Phe Glu Trp Ile Glu
                165                 170                 175

Leu His Phe Ala His Gly Tyr Leu Gly Gln Ser Phe Phe Ser Glu His
            180                 185                 190

Ser Asn Lys Arg Thr Asp Ala Tyr Gly Gly Ser Phe Asp Asn Arg Ser
        195                 200                 205

Arg Phe Leu Leu Glu Thr Leu Ala Ala Val Arg Glu Val Trp Pro Glu
    210                 215                 220

Asn Leu Pro Leu Thr Ala Arg Phe Gly Val Leu Glu Tyr Asp Gly Arg
225                 230                 235                 240

Asp Glu Gln Thr Leu Glu Glu Ser Ile Glu Leu Ala Arg Arg Phe Lys
                245                 250                 255

Ala Gly Gly Leu Asp Leu Leu Ser Val Ser Val Gly Phe Thr Ile Pro
```

```
                    260                 265                 270
Asp Thr Asn Ile Pro Trp Gly Pro Ala Phe Met Gly Pro Ile Ala Glu
        275                 280                 285

Arg Val Arg Arg Glu Ala Lys Leu Pro Val Thr Ser Ala Trp Gly Phe
    290                 295                 300

Gly Thr Pro Gln Leu Ala Glu Ala Ala Leu Gln Ala Asn Gln Leu Asp
305                 310                 315                 320

Leu Val Ser Val Gly Arg Ala His Leu Ala Asp Pro His Trp Ala Tyr
                325                 330                 335

Phe Ala Ala Lys Glu Leu Gly Val Glu Lys Ala Ser Trp Thr Leu Pro
            340                 345                 350

Ala Pro Tyr Ala His Trp Leu Glu Arg Tyr Arg
        355                 360

<210> SEQ ID NO 17
<211> LENGTH: 280
<212> TYPE: PRT
<213> ORGANISM: Saccharomyces cerevisiae

<400> SEQUENCE: 17

Met Ser Gln Glu Ile Arg Gln Asn Glu Lys Ile Ser Tyr Arg Ile Glu
1               5                   10                  15

Gly Pro Phe Phe Ile Ile His Leu Met Asn Pro Asp Asn Leu Asn Ala
            20                  25                  30

Leu Glu Gly Glu Asp Tyr Ile Tyr Leu Gly Glu Leu Leu Glu Leu Ala
        35                  40                  45

Asp Arg Asn Arg Asp Val Tyr Phe Thr Ile Ile Gln Ser Ser Gly Arg
    50                  55                  60

Phe Phe Ser Ser Gly Ala Asp Phe Lys Gly Ile Ala Lys Ala Gln Gly
65                  70                  75                  80

Asp Asp Thr Asn Lys Tyr Pro Ser Glu Thr Ser Lys Trp Val Ser Asn
                85                  90                  95

Phe Val Ala Arg Asn Val Tyr Val Thr Asp Ala Phe Ile Lys His Ser
            100                 105                 110

Lys Val Leu Ile Cys Cys Leu Asn Gly Pro Ala Ile Gly Leu Ser Ala
        115                 120                 125

Ala Leu Val Ala Leu Cys Asp Ile Val Tyr Ser Ile Asn Asp Lys Val
    130                 135                 140

Tyr Leu Leu Tyr Pro Phe Ala Asn Leu Gly Leu Ile Thr Glu Gly Gly
145                 150                 155                 160

Thr Thr Val Ser Leu Pro Leu Lys Phe Gly Thr Asn Thr Thr Tyr Glu
                165                 170                 175

Cys Leu Met Phe Asn Lys Pro Lys Tyr Asp Ile Met Cys Glu Asn
            180                 185                 190

Gly Phe Ile Ser Lys Asn Phe Asn Met Pro Ser Ser Asn Ala Glu Ala
        195                 200                 205

Phe Asn Ala Lys Val Leu Glu Glu Leu Arg Glu Lys Val Lys Gly Leu
    210                 215                 220

Tyr Leu Pro Ser Cys Leu Gly Met Lys Lys Leu Leu Lys Ser Asn His
225                 230                 235                 240

Ile Asp Ala Phe Asn Lys Ala Asn Ser Val Glu Val Asn Glu Ser Leu
                245                 250                 255

Lys Tyr Trp Val Asp Gly Glu Pro Leu Lys Arg Phe Arg Gln Leu Gly
            260                 265                 270
```

```
Ser Lys Gln Arg Lys His Arg Leu
        275                 280

<210> SEQ ID NO 18
<211> LENGTH: 246
<212> TYPE: PRT
<213> ORGANISM: Clostridium perfringens

<400> SEQUENCE: 18

Met Gly Lys Ala Tyr Glu Lys Val Tyr Glu Val Thr Tyr Gly Glu Thr
1               5

```
Phe Phe Ser Ser Gly Ala Asp Phe Lys Gly Ile Ala Lys Ala Gln Gly
 65                  70                  75                  80

Asp Asp Thr Asn Lys Tyr Pro Ser Glu Thr Ser Lys Trp Val Ser Asn
                 85                  90                  95

Phe Val Ala Arg Asn Val Tyr Val Thr Asp Ala Phe Ile Lys His Ser
            100                 105                 110

Lys Val Leu Ile Cys Cys Leu Asn Gly Pro Ala Ile Gly Leu Ser Ala
        115                 120                 125

Ala Leu Val Ala Leu Cys Asp Ile Val Tyr Ser Ile Asn Asp Lys Val
130                 135                 140

Tyr Leu Leu Tyr Pro Phe Ala Asn Leu Gly Leu Ile Thr Glu Gly Gly
145                 150                 155                 160

Thr Thr Val Ser Leu Pro Leu Lys Phe Gly Thr Asn Thr Thr Tyr Glu
                165                 170                 175

Cys Leu Met Phe Asn Lys Pro Phe Lys Tyr Asp Ile Met Cys Glu Asn
            180                 185                 190

Gly Phe Ile Ser Lys Asn Phe Asn Met Pro Ser Ser Asn Ala Glu Ala
        195                 200                 205

Phe Asn Ala Lys Val Leu Glu Glu Leu Arg Glu Lys Val Lys Gly Leu
210                 215                 220

Tyr Leu Pro Ser Cys Leu Gly Met Lys Lys Leu Leu Lys Ser Asn His
225                 230                 235                 240

Ile Asp Ala Phe Asn Lys Ala Asn Ser Val Glu Val Asn Glu Ser Leu
                245                 250                 255

Lys Tyr Trp Val Asp Gly Glu Pro Leu Lys Arg Phe Arg Gln Leu Gly
            260                 265                 270

Ser Lys Gln Arg Lys His Arg Leu
        275                 280

<210> SEQ ID NO 20
<211> LENGTH: 247
<212> TYPE: PRT
<213> ORGANISM: Bacteroides thetaiotaomicron

<400> SEQUENCE: 20

Met Ser Glu Glu Asn Lys Ile Gly Thr Tyr Gln Phe Val Ala Glu Pro
1               5                   10                  15

Phe His Val Asp Phe Asn Gly Arg Leu Thr Met Gly Val Leu Gly Asn
            20                  25                  30

His Leu Leu Asn Cys Ala Gly Phe His Ala Ser Asp Arg Gly Phe Gly
        35                  40                  45

Ile Ala Thr Leu Asn Glu Asp Asn Tyr Thr Trp Val Leu Ser Arg Leu
    50                  55                  60

Ala Ile Glu Leu Asp Glu Met Pro Tyr Gln Tyr Glu Lys Phe Ser Val
65                  70                  75                  80

Gln Thr Trp Val Glu Asn Val Tyr Arg Leu Phe Thr Asp Arg Asn Phe
                85                  90                  95

Ala Val Ile Asp Lys Asp Gly Lys Lys Ile Gly Tyr Ala Arg Ser Val
            100                 105                 110

Trp Ala Met Ile Asn Leu Asn Thr Arg Lys Pro Ala Asp Leu Leu Ala
        115                 120                 125

Leu His Gly Gly Ser Ile Val Asp Tyr Ile Cys Asp Glu Pro Cys Pro
130                 135                 140

Ile Glu Lys Pro Ser Arg Ile Lys Val Thr Ser Asn Gln Pro Val Ala
145                 150                 155                 160
```

Thr Leu Thr Ala Lys Tyr Ser Asp Ile Asp Ile Asn Gly His Val Asn
                165                 170                 175

Ser Ile Arg Tyr Ile Glu His Ile Leu Asp Leu Phe Pro Ile Glu Leu
            180                 185                 190

Tyr Gln Thr Lys Arg Ile Arg Arg Phe Glu Met Ala Tyr Val Ala Glu
        195                 200                 205

Ser Tyr Phe Gly Asp Glu Leu Ser Phe Phe Cys Asp Glu Val Ser Glu
    210                 215                 220

Asn Glu Phe His Val Glu Val Lys Lys Asn Gly Ser Glu Val Val Cys
225                 230                 235                 240

Arg Ser Lys Val Ile Phe Glu
                245

<210> SEQ ID NO 21
<211> LENGTH: 339
<212> TYPE: PRT
<213> ORGANISM: Geobacillus stearothermophilus

<400> SEQUENCE: 21

Met Lys Ala Ala Val Val Glu Gln Phe Lys Glu Pro Leu Lys Ile Lys
1               5                   10                  15

Glu Val Glu Lys Pro Thr Ile Ser Tyr Gly Glu Val Leu Val Arg Ile
            20                  25                  30

Lys Ala Cys Gly Val Cys His Thr Asp Leu His Ala Ala His Gly Asp
        35                  40                  45

Trp Pro Val Lys Pro Lys Leu Pro Leu Ile Pro Gly His Glu Gly Val
    50                  55                  60

Gly Ile Val Glu Glu Val Gly Pro Gly Val Thr His Leu Lys Val Gly
65                  70                  75                  80

Asp Arg Val Gly Ile Pro Trp Leu Tyr Ser Ala Cys Gly His Cys Asp
                85                  90                  95

Tyr Cys Leu Ser Gly Gln Glu Thr Leu Cys Glu His Gln Lys Asn Ala
            100                 105                 110

Gly Tyr Ser Val Asp Gly Gly Tyr Ala Glu Tyr Cys Arg Ala Ala Ala
        115                 120                 125

Asp Tyr Val Val Lys Ile Pro Asp Asn Leu Ser Phe Glu Glu Ala Ala
    130                 135                 140

Pro Ile Phe Cys Ala Gly Val Thr Thr Tyr Lys Ala Leu Lys Val Thr
145                 150                 155                 160

Gly Ala Lys Pro Gly Glu Trp Val Ala Ile Tyr Gly Ile Gly Gly Leu
                165                 170                 175

Gly His Val Ala Val Gln Tyr Ala Lys Ala Met Gly Leu Asn Val Val
            180                 185                 190

Ala Val Asp Ile Gly Asp Glu Lys Leu Glu Leu Ala Lys Glu Leu Gly
        195                 200                 205

Ala Asp Leu Val Val Asn Pro Leu Lys Glu Asp Ala Ala Lys Phe Met
    210                 215                 220

Lys Glu Lys Val Gly Gly Val His Ala Ala Val Val Thr Ala Val Ser
225                 230                 235                 240

Lys Pro Ala Phe Gln Ser Ala Tyr Asn Ser Ile Arg Arg Gly Gly Ala
                245                 250                 255

Cys Val Leu Val Gly Leu Pro Pro Glu Glu Met Pro Ile Pro Ile Phe
            260                 265                 270

Asp Thr Val Leu Asn Gly Ile Lys Ile Ile Gly Ser Ile Val Gly Thr

```
              275                 280                 285
Arg Lys Asp Leu Gln Glu Ala Leu Gln Phe Ala Ala Glu Gly Lys Val
290                 295                 300

Lys Thr Ile Ile Glu Val Gln Pro Leu Glu Lys Ile Asn Glu Val Phe
305                 310                 315                 320

Asp Arg Met Leu Lys Gly Gln Ile Asn Gly Arg Val Val Leu Thr Leu
                325                 330                 335

Glu Asp Lys

<210> SEQ ID NO 22
<211> LENGTH: 261
<212> TYPE: PRT
<213> ORGANISM: Lactobacillus plantarum

<400> SEQUENCE: 22

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
    130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Gln Thr Val Thr Ala His Ala Asn Ile
    210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 23
<211> LENGTH: 231
<212> TYPE: PRT
<213> ORGANISM: Anaerococcus tetradius

<400> SEQUENCE: 23
```

```
Met Lys Phe Lys Lys Lys Phe Lys Ile Gly Arg Met His Val Asp Pro
1               5                   10                  15

Phe Asn Tyr Ile Ser Met Arg Tyr Leu Val Ala Leu Met Asn Glu Val
            20                  25                  30

Ala Phe Asp Gln Ala Glu Ile Leu Glu Lys Asp Ile Asp Met Lys Asn
        35                  40                  45

Leu Arg Trp Ile Ile Tyr Ser Trp Asp Ile Gln Ile Glu Asn Asn Ile
    50                  55                  60

Arg Leu Gly Glu Glu Ile Glu Ile Thr Thr Ile Pro Thr His Met Asp
65                  70                  75                  80

Lys Phe Tyr Ala Tyr Arg Asp Phe Ile Val Glu Ser Arg Gly Asn Ile
                85                  90                  95

Leu Ala Arg Ala Lys Ala Thr Phe Leu Leu Met Asp Ile Thr Arg Leu
            100                 105                 110

Arg Pro Ile Lys Ile Pro Gln Asn Leu Ser Leu Ala Tyr Gly Lys Glu
        115                 120                 125

Asn Pro Ile Phe Asp Ile Tyr Asp Met Glu Ile Arg Asn Asp Leu Ala
    130                 135                 140

Phe Ile Arg Asp Ile Gln Leu Arg Arg Ala Asp Leu Asp Asn Asn Phe
145                 150                 155                 160

His Ile Asn Asn Ala Val Tyr Phe Asp Leu Ile Lys Glu Thr Val Asp
                165                 170                 175

Ile Tyr Asp Lys Asp Ile Ser Tyr Ile Lys Leu Ile Tyr Arg Asn Glu
            180                 185                 190

Ile Arg Asp Lys Lys Gln Ile Gln Ala Phe Ala Arg Arg Glu Asp Lys
        195                 200                 205

Ser Ile Asp Phe Ala Leu Arg Gly Glu Asp Gly Arg Asp Tyr Cys Leu
    210                 215                 220

Gly Lys Ile Lys Thr Asn Val
225                 230
```

<210> SEQ ID NO 24
<211> LENGTH: 3525
<212> TYPE: DNA
<213> ORGANISM: Mycobacterium marinum

<400> SEQUENCE: 24

```
atgtcgccaa tcacgcgtga agagcggctc gagcgccgca tccaggacct ctacgccaac      60
gacccgcagt tcgccgccgc caaacccgcc acggcgatca ccgcagcaat cgagcggccg     120
ggtctaccgc taccccagat catcgagacc gtcatgaccg gatacgccga tcggccggct     180
ctcgctcagc gctcggtcga attcgtgacc gacgccggca ccggccacac cacgctgcga     240
ctgctccccc acttcgaaac catcagctac ggcgagcttt gggaccgcat cagcgcactg     300
gccgacgtgc tcagcaccga acagacggtg aaaccgggcg accgggtctg cttgttgggc     360
ttcaacagcg tcgactacgc cacgatcgac atgactttgg cgcggctggg cgcggtggcc     420
gtaccactgc agaccagcgc ggcgataacc cagctgcagc cgatcgtcgc cgagacccag     480
cccaccatga tcgcggccag cgtcgacgca ctcgctgacg ccaccgaatt ggctctgtcc     540
ggtcagaccg ctacccgagt cctggtgttc gaccaccacc ggcaggttga cgcacaccgc     600
gcagcggtcg aatccgcccg ggagcgcctg gccggctcgg cggtcgtcga aaccctggcc     660
gaggccatcg cgcgcggcga cgtgccccgc ggtgcgtccg ccggctcggc gcccggcacc     720
gatgtgtccg acgactcgct cgcgctactg atctacacct cgggcagcac gggtgcgccc     780
```

```
aagggcgcga tgtacccccg acgcaacgtt gcgaccttct ggcgcaagcg cacctggttc      840
gaaggcggct acgagccgtc gatcacgctg aacttcatgc aatgagcca cgtcatgggc      900 cgccaaatcc tgtacggcac gctgtgcaat ggcggcaccg cctacttcgt ggcgaaaagc      960
gatctctcca ccttgttcga agacctggcg ctggtgcggc ccaccgagct gaccttcgtg     1020
ccgcgcgtgt gggacatggt gttcgacgag tttcagagtg aggtcgaccg ccgcctggtc     1080 gacgcgccg accgggtcgc gctcgaagcc caggtcaagg ccgagatacg caacgacgtg      1140
ctcggtggac ggtataccag cgcactgacc ggctccgccc ctatctccga cgagatgaag     1200
gcgtgggtcg aggagctgct cgacatgcat ctggtcgagg gctacggctc caccgaggcc     1260
gggatgatcc tgatcgacgg agccattcgg cgcccggcgg tactcgacta caagctggtc     1320
gatgttcccg acctgggtta cttcctgacc gaccggccac atccgcgggg cgagttgctg     1380
gtcaagaccg atagtttgtt cccgggctac taccagcgag ccgaagtcac cgccgacgtg     1440
ttcgatgctg acgcttcta ccggaccggc gacatcatgg ccgaggtcgg ccccgaacag      1500
ttcgtgtacc tcgaccgccg caacaacgtg ttgaagctgt cgcagggcga gttcgtcacc     1560
gtctccaaac tcgaagcggt gtttggcgac agcccactgg tacggcagat ctacatctac     1620
ggcaacagcg cccgtgccta cctgttggcg gtgatcgtcc ccacccagga ggcgctggac     1680
gccgtgcctg tcgaggagct caaggcgcgg ctgggcgact cgctgcaaga ggtcgcaaag     1740
gccgccggcc tgcagtccta cgagatcccg cgcgacttca tcatcgaaac aacaccatgg     1800
acgctggaga acggcctgct caccggcatc cgcaagttgg ccaggccgca gctgaaaaag     1860
cattacggcg agcttctcga gcagatctac acggacctgg cacacggcca ggccgacgaa     1920
ctgcgctcgc tgcgccaaag cggtgccgat gcgccggtgc tggtgacggt gtgccgtgcg     1980
gcggccgcgc tgttgggcgg cagcgcctct gacgtccagc ccgatgcgca cttcaccgat     2040
ttgggcggcg actcgctgtc ggcgctgtcg ttcaccaacc tgctgcacga gatcttcgac     2100
atcgaagtgc cggtgggcgt catcgtcagc cccgccaacg acttgcaggc cctggccgac     2160
tacgtcgagg cggctcgcaa acccggctcg tcacggccga ccttcgcctc ggtccacggc     2220
gcctcgaatg ggcaggtcac cgaggtgcat gccggtgacc tgtccctgga caaattcatc     2280
gatgccgcaa ccctggccga agctccccgg ctgcccgccg caaacaccca agtgcgcacc     2340
gtgctgctga ccgcgccac cggcttcctc gggcgctacc tggccctgga atggctggag     2400
cggatggacc tggtcgacgg caaactgatc tgcctggtcc gggccaagtc cgacaccgaa     2460
gcacgggcgc ggctggacaa gacgttcgac agcggcgacc ccgaactgct ggcccactac     2520
cgcgcactgg ccggcgacca cctcgaggtg ctcgccggtg acaagggcga agccgacctc     2580
ggactggacc ggcagacctg gcaacgcctg gccgacacgg tcgacctgat cgtcgacccc     2640
gcggccctgg tcaaccacgt actgccatac agccagctgt cgggcccaa cgcgctgggc      2700 accgccgagc tgctgcggct ggcgctcacc tccaagatca agccctacag ctacacctcg     2760
acaatcggtg tcgccgacca gatcccgccg tcggcgttca ccgaggacgc cgacatccgg     2820
gtcatcagcg ccaccccgcg cggtcgacgac agctacgcca atggctactc gaacagcaag     2880
tgggccggca aggtgctgtt gcgcgaggcg catgacctgt gtggcctgcc ggttgcggtg     2940
ttccgctgcg acatgatcct ggccgacacc acatgggcgg acagctcaa tgtgccggac      3000 atgttcaccc ggatgatcct gagcctggcg gccaccggta tcgcgccggg ttcgttctat     3060
gagcttgcgg ccgacggcgc ccggcaacgc gcccactatg acggtctgcc cgtcgagttc     3120
```

| | |
|---|---|
| atcgccgagg cgatttcgac tttgggtgcg cagagccagg atggtttcca cacgtatcac | 3180 |
| gtgatgaacc cctacgacga cggcatcgga ctcgacgagt tcgtcgactg gctcaacgag | 3240 |
| tccggttgcc ccatccagcg catcgctgac tatggcgact ggctgcagcg cttcgaaacc | 3300 |
| gcactgcgcg cactgcccga tcggcagcgg cacagctcac tgctgccgct gttgcacaac | 3360 |
| tatcggcagc cggagcggcc cgtccgcggg tcgatcgccc taccgatcg cttccgggca | 3420 |
| gcggtgcaag aggccaagat cggccccgac aaagacattc cgcacgtcgg cgcgccgatc | 3480 |
| atcgtgaagt acgtcagcga cctgcgccta ctcggcctgc tctga | 3525 |

<210> SEQ ID NO 25
<211> LENGTH: 3522
<212> TYPE: DNA
<213> ORGANISM: Mycobacterium smegmatis

<400> SEQUENCE: 25

| | |
|---|---|
| atgaccagcg atgttcacga cgccacagac ggcgtcaccg aaaccgcact cgacgacgag | 60 |
| cagtcgaccc gccgcatcgc cgagctgtac gccaccgatc ccgagttcgc cgccgccgca | 120 |
| ccgttgcccg ccgtggtcga cgcggcgcac aaacccgggc tgcggctggc agagatcctg | 180 |
| cagaccctgt tcaccggcta cggtgaccgc ccggcgctgg gataccgcgc ccgtgaactg | 240 |
| gccaccgacg agggcgggcg caccgtgacg cgtctgctgc gcgcggttcga caccctcacc | 300 |
| tacgcccagg tgtggtcgcg cgtgcaagcg gtcgccgcgg ccctgcgcca caacttcgcg | 360 |
| cagccgatct accccggcga cgccgtcgcg acgatcggtt tcgcgagtcc cgattacctg | 420 |
| acgctggatc tcgtatgcgc ctacctgggc ctcgtgagtg ttccgctgca gcacaacgca | 480 |
| ccggtcagcc ggctcgcccc gatcctggcc gaggtcgaac gcggatcct caccgtgagc | 540 |
| gccgaatacc tcgacctcgc agtcgaatcc gtgcgggacg tcaactcggt gtcgcagctc | 600 |
| gtggtgttcg accatcaccc cgaggtcgac gaccaccgcg acgcactggc ccgcgcgcgt | 660 |
| gaacaactcg ccggcaaggg catcgccgtc accaccctgg acgcgatcgc cgacgagggc | 720 |
| gccgggctgc cggccgaacc gatctacacc gccgaccatg atcagcgcct cgcgatgatc | 780 |
| ctgtacacct cgggttccac cggcgcaccc aagggtgcga tgtacaccga ggcgatggtg | 840 |
| gcgcggctgt ggaccatgtc gttcatcacg ggtgacccca cgccggtcat caacgtcaac | 900 |
| ttcatgccgc tcaaccacct gggcgggcgc atcccatt ccaccgccgt gcagaacggt | 960 |
| ggaaccagtt acttcgtacc ggaatccgac atgtccacgc tgttcgagga tctcgcgctg | 1020 |
| gtgcgcccga ccgaactcgg cctggttccg cgcgtcgccg acatgctcta ccagcaccac | 1080 |
| ctcgccaccg tcgaccgcct ggtcacgcag ggcgccgacg aactgaccgc cgagaagcag | 1140 |
| gccggtgccg aactgcgtga gcaggtgctc ggcggacgcg tgatcaccgg attcgtcagc | 1200 |
| accgcaccgc tggccgcgga gatgagggcg ttcctcgaca tcaccctggg cgcacacatc | 1260 |
| gtcgacggct acgggctcac cgagaccggc gccgtgacac gcgacggtgt gatcgtgcgg | 1320 |
| ccaccggtga tcgactacaa gctgatcgac gttcccgaac tcggctactt cagcaccgac | 1380 |
| aagccctacc gcgtggcga actgctggtc aggtcgcaaa cgctgactcc cgggtactac | 1440 |
| aagcgccccg aggtcaccgc gagcgtcttc gaccgggacg gctactacca caccggcgac | 1500 |
| gtcatggccg agaccgcacc cgaccacctg gtgtacgtgg accgtcgcaa caacgtcctc | 1560 |
| aaactcgcgc agggcgagtt cgtggccggt c gccaacctgg aggcggtgtt ctccggcgcg | 1620 |
| gcgctggtgc ccagatcttc cgtgtacggc aacagcgagc gcagtttcct tctgccgtg | 1680 |
| gtggtcccga cgccggaggc gctcgagcag tacgatccgg ccgcgctcaa ggccgcgctg | 1740 |

```
gccgactcgc tgcagcgcac cgcacgcgac gccgaactgc aatcctacga ggtgccggcc    1800
gatttcatcg tcgagaccga gccgttcagc gccgccaacg ggctgctgtc gggtgtcgga    1860
aaactgctgc ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg agcgaggtg     2040 gcatccgacg cccacttcac cgacctgggc ggggattccc tgtcggcgct gacactttcg    2100
aacctgctga gcgatttctt cggtttcgaa gttcccgtcg gcaccatcgt gaacccggcc    2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cggtctgcc caaggtcacc     2340 accgagccac ggacggtgtt gctctcgggc gccaacggct ggctgggccg gttcctcacg    2400
ttgcagtggc tggaacgcct ggcacctgtc ggcggcaccc tcatcacgat cgtgcggggc    2460
cgcgacgacg ccgcggcccg cgcacggctg acccaggcct acgacaccga tcccgagttg    2520
tcccgccgct tcgccgagct ggccgaccgc cacctgcggg tggtcgccgg tgacatcggc    2580
gacccgaatc tgggcctcac acccgagatc tggcaccggc tcgccgccga ggtcgacctg    2640
gtggtgcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatcccg acttcgagga ggacggcgac    2820
atccggaccg tgagcccggt gcgcccgctc gacggcggat acgccaacgg ctacggcaac    2880
agcaagtggg ccggcgaggt gctgctgcgg gaggcccacg atctgtgcgg gctgcccgtg    2940
gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg agacggtga gcgcccgcgg gcgcactacc ccggcctgac ggtcgatttc     3120
gtggccgagg cggtcacgac gctcggcgcg cagcagcgcg agggatacgt gtcctacgac    3180
gtgatgaacc cgcacgacga cgggatctcc ctggatgtgt cgtggactg gctgatccgg     3240 gcgggccatc cgatcgaccg ggtcgacgac tacgacgact gggtgcgtcg gttcgagacc    3300
gcgttgaccg cgcttcccga gaagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggcccggga gacatcccgc acctcgacga ggcgctgatc    3480
gacaagtaca tacgcgatct gcgtgagttc ggtctgatct ga                      3522
```

<210> SEQ ID NO 26
<211> LENGTH: 3447
<212> TYPE: DNA
<213> ORGANISM: Segniliparus rugosus

<400> SEQUENCE: 26

```
atgggcgacg cgaagagcg ggcgaagcgt ttcttccaga ggatcgggga gctgagcgcg      60 acggaccccgc agttcgcggc cgccgcgccg gaccccgccg tggtcgaggc cgtgtcggac    120
ccctcgctct cgttcacccg ctacttggac acgctgatgc gcgggtacgc cgagcgcccg    180
gcgctcgccc accgggtcgg cgcgggatac gagacgatca gctacgggga gctgtgggcg    240 cggggtcgggg cgattgcggc ggcgtggcag gcggacggcc tcgcgccggg cgacttcgtc    300
```

```
gccacggtcg gtttcaccag cccggactac gtcgccgtcg accttgcggc cgcgaggtcg    360
gggctggtgt ccgtgccgtt gcaggcgggt gcttcgctcg cccagctcgt cgggatcctc    420
gaggagaccg agccgaaggt gctcgcggcg agcgcgagca gtctcgaagg ggccgttgcc    480
tgcgcgctgg cggccccgag cgtgcagcgg ctcgtcgtgt tcgacctgcg cggcccggac    540
gcttcggaga gcgcggcgga cgagcgccga ggcgccctcg ccgatgccga ggagcagctg    600
gcgcgggccg ggcgggccgt ggtcgtcgag accctcgccg acctggcggc ccgaggcgag    660
gcgctgccgg aagcccgct gttcgagccc gccgagggcg aagacccgct ggccctcttg     720
atctacacgt ccggctcgac cggggccccg aaggggggcga tgtactcgca gcgcctggtg   780
tcccagctct gggggcgcac gccggtggtg ccggggatgc cgaacatctc gctgcattac    840
atgccgctga ccactccta cgggcggcg gtcctcgccg gggcgctctc ggcgggcggg      900
accgcccact tcaccgcgaa cagcgaccgtt ccaccctct tcgaggacat cgcgctcgcc    960
cgcccccacct cctcgccct ggtccccagg gtctgcgaga tgctgttcca ggagagccag    1020
cgcggccagg acgtcgcgga gctgcgcgaa cgggtgctcg gcggtcggct gctggtcgcg    1080
gtgtgcggct ccgccccgct gtcgccggag atgcgcgcgt tcatggagga ggtgctcggc    1140
ttcccgctgc tcgacggcta cggctcgacc gaggcgctcg gcgtcatgcg caacgggatc    1200
atccagcgcc cgccggtcat cgactacaag ctggtcgacg tgcccgagct gggctatcgc    1260
accactgaca agccctaccc gaggggcgag ctgtgcatcc gctcgacgag cctgatctcc    1320
ggctactaca gcgccccga gatcacagcg gaggtgttcg acgcgcaggg ctactacaag    1380
accggcgacg tgatggccga gatcgcgccg gaccacctgg tgtacgtgga ccggagcaag    1440
aacgtcctca aactctccca aggcgagttc gtcgccgtcg cgaagctcga agccgcgtac    1500
ggcacgagcc cgtacgtgaa gcagatcttc gtctacggca acagcgagcg ctccttcctg    1560
ctcgcggtcg tcgtgccgaa cgccgaagtc ctcggcgcgc gggaccagga ggaggccaag    1620
ccgctcatcg ccgcctcgct gcagaagatc gcgaaagagg ctggcctgca gtcttacgag    1680
gtcccgcgcg acttcttgat cgagaccgag ccgttcacca gcagaacgg cctgctctcc    1740
gaggtcggca agctgctgcg cccgaagctc aaggcccggt acggcgaggc gctggaggcg    1800
cgctacgacg agatcgcgca cggccaggcg gacgagctgc gcgcgctgcg ggacggcgcg    1860
ggacagcgcc cggtggtcga gccgtcgtg cgggccgccg tcgcgatctc cggctccgag    1920
ggcgcggagg tcggccctga ggcgaacttc gccgacctcg gcggggactc gctctccgcg    1980
ttgagccttg cgaacttgct gcacgacgtc ttcgaagtcg aggtgccggt gcggatcatc    2040
atcggcccga ccgcctcgct cgccgggatc gccaagcaca tcgaggccga gcgcgccggg    2100
gcgagcgccc cgacggcggc ctccgtgcac ggcgcggggg cgacgaggat ccgagcgagc    2160
gagctgacgc tggagaaatt cctccctgaa gacctgcttg ccgccgcgaa gggccttccg    2220
gccgccgacc aggtccgcac ggtgctcttg acgggcgcga acggctggct cgggcgtttc    2280
ctcgcgttgg aacagctcga acggctcgcc cgatcgggc aggacggcgg gaagctgatc    2340
tgcctggtcc gggggaaaga cgcggctgcg gcgcgcaggc ggatcgaaga aacgctcggc    2400
acggacccgg ccctggccgc caggttcgcc gaacttgccg aggggcggtt ggaagtggtc    2460
ccgggggacg tgggcgagcc gaagttcggc ttggacgacg cggcatggga ccggctggcc    2520
gaggaggtgg acgtcatcgt ccacccggcg gcccttgtga accacgttct gccgtaccac    2580
cagctgttcg ggccgaacgt ggtcggcacg gcggagatca tccggctcgc gatcaccgcc    2640
aagcgcaagc cggtcaccta cctctccacg gtggcggtcg cggcgggcgt ggagccctcc    2700
```

-continued

| | |
|---|---|
| tccttcgagg aggacggcga catccgggcc gtggtcccg aacgcccttt gggcgatggg | 2760 |
| tacgcgaacg gctacggcaa cagcaaatgg gcggggagg tgctgctgcg cgaagcgcac | 2820 |
| gagcttgtgg gcctgccggt ggcggtgttc cgctcggaca tgatcctcgc gcacacccgg | 2880 |
| tacaccggac agctcaacgt cccgaccag ttcaccaggc tcgtcctgag ccttttggcc | 2940 |
| accgggatcg cgcccaagtc cttctaccag cagggcgcgg cgggcgaacg ccagcgggcg | 3000 |
| cattacgacg gcatccccgt ggacttcacc gccgaggcca tcaccacgct cggcgcggag | 3060 |
| ccgagctggt tcgacggcgg cgcggggttc cgcagcttcg acgtgttcaa cccgcaccac | 3120 |
| gacggggtgg gcttggacga gttcgtggac tggctcatcg aggcccgggca tccgatctcc | 3180 |
| aggatcgacg accacaagga atggttcgcc cggttcgaga ccgccgtgcg cggcctgccc | 3240 |
| gaagcgcagc gccagcattc cctgctgccg ctgttgcgcg cctactcgtt cccgcatccg | 3300 |
| cccgtggacg gcagtgtcta tccgaccggg aagttccagg gcgcggtcaa agccgcgcag | 3360 |
| gtgggctccg accacgacgt gccgcatctc ggcaaggcgc tgatcgtgaa atacgcggac | 3420 |
| gacctgaagg ctctcggact cctctga | 3447 |

<210> SEQ ID NO 27
<211> LENGTH: 3507
<212> TYPE: DNA
<213> ORGANISM: Mycobacterium smegmatis

<400> SEQUENCE: 27

| | |
|---|---|
| atgacgatcg aaacgcgcga agaccgcttc aaccggcgca ttgaccactt gttcgaaacc | 60 |
| gacccgcagt tcgccgccgc ccgtcccgac gaggcgatca gcgcggctgc cgccgatccg | 120 |
| gagttgcgcc ttcctgccgc ggtcaaacag attctggccg gctatgcgga ccgccctgcg | 180 |
| ctgggcaagc gcgccgtcga gttcgtcacc gacgaagaag gccgcaccac cgcgaagctc | 240 |
| ctgccccgct tcgacaccat cacctaccgt cagctcgcag gccggatcca ggccgtgacc | 300 |
| aatgcctggc acaaccatcc ggtgaatgcc ggtgaccgcg tggccatcct gggtttcacc | 360 |
| agtgtcgact acacgacgat cgacatcgcc ctgctcgaac tcggcgccgt gtccgtaccg | 420 |
| ctgcagacca gtgcgccggt ggcccaactg cagccgatcg tcgccgagac cgagcccaag | 480 |
| gtgatcgcgt cgagcgtcga cttcctcgcc gacgcagtcg ctctcgtcga gtccgggccc | 540 |
| gcgccgtcgc gactggtggt gttcgactac agccacgagg tcgacgatca gcgtgaggcg | 600 |
| ttcgaggcgg ccaagggcaa gctcgcaggc accggcgtcg tcgtcgagac gatcaccgac | 660 |
| gcactggacc gcgggcggtc actcgccgac gcaccgctct acgtgcccga cgaggccgac | 720 |
| ccgctgaccc ttctcatcta cacctccggc agcaccggca ctcccaaggg cgcgatgtac | 780 |
| cccgagtcca agaccgccac gatgtggcag gccgggtcca aggccggtg ggacgagacc | 840 |
| ctcggcgtga tgccgtcgat caccctgaac ttcatgccca tgagtcacgt catggggcgc | 900 |
| ggcatcctgt gcagcacact cgccagcggc ggaaccgcgt acttcgccgc acgcagcgac | 960 |
| ctgtccacct tcctggagga cctcgccctc gtgcggccca cgcagctcaa cttcgttcct | 1020 |
| cgcatctggg acatgctgtt ccaggagtac cagagccgcc tcgacaaccg ccgcgccgag | 1080 |
| ggatccgagg accgagccga agccgcagtc ctcgaagagg tccgcaccca actgctcggc | 1140 |
| gggcgattcg tttcggccct gaccggatcg gctcccatct cggcggagat gaagagctgg | 1200 |
| gtcgaggacc tgctcgacat gcatctgctg gagggctacg gctccaccga ggccggcgcg | 1260 |
| gtgttcatcg acggcagat ccagcgcccg ccggtcatcg actacaagct ggtcgacgtg | 1320 |

```
cccgatctcg gctacttcgc cacggaccgg ccctacccgc gcggcgaact tctggtcaag    1380
tccgagcaga tgttccccgg ctactacaag cgtccggaga tcaccgccga gatgttcgac    1440
gaggacgggt actaccgcac cggcgacatc gtcgccgagc tcgggcccga ccatctcgaa    1500
tacctcgacc gccgcaacaa cgtgctgaaa ctgtcgcagg gcgaattcgt cacggtctcc    1560
aagctggagg cggtgttcgg cgacagcccc ctggtacgcc agatctacgt ctacggcaac    1620
agcgcgcggt cctatctgct ggcggtcgtg gtcccgaccg aagaggcact gtcacgttgg    1680
gacggtgacg aactcaagtc gcgcatcagc gactcactgc aggacgcggc acgagccgcc    1740
ggattgcagt cgtatgagat cccgcgtgac ttcctcgtcg agacaacacc tttcacgctg    1800
gagaacggcc tgctgaccgg tatccgcaag ctggcccggc cgaaactgaa ggcgcactac    1860
ggcgaacgcc tcaacagct ctacaccgac ctggccgagg gcaggccaa cgagttgcgc    1920 gagttgcgcc gcaacggagc cgaccggccc gtggtcgaga ccgtcagccg cgccgcggtc    1980
gcactgctcg gtgcctccgt cacggatctg cggtccgatg cgcacttcac cgatctgggt    2040
ggagattcgt tgtcggcctt gagcttctcg aacctgttgc acgagatctt cgatgtcgac    2100
gtgccggtcg gcgtcatcgt cagcccggcc accgacctgg caggcgtcgc ggcctacatc    2160
gagggcgaac tgcgcggctc caagcgcccc acatacgcgt cggtgcacgg gcgcgacgcc    2220
accgaggtgc gcgcgcgtga tctcgccctg gcaagttca tcgacgccaa gaccctgtcc    2280
gccgcgccgg gtctgccgcg ttcgggcacc gagatccgca ccgtgctgct gaccggcgcc    2340
accgggttcc tgggccgcta tctggcgctg gaatggctgg agcgcatgga cctggtggac    2400
ggcaaggtga tctgcctggt gcgcgcccgc agcgacgacg aggcccgggc gcgtctggac    2460
gccacgttcg acaccgggga cgcgacactg ctcgagcact accgcgcgct ggcagccgat    2520
cacctcgagg tgatcgccgg tgacaagggc gaggccgatc tgggtctcga ccacgacacg    2580
tggcagcgac tggccgacac cgtcgatctg atcgtcgatc cggccgccct ggtcaatcac    2640
gtcctgccgt acagccagat gttcggaccc aatgcgctcg gcaccgccga actcatccgg    2700
atcgcgctga ccaccacgat caagccgtac gtgtacgtct cgacgatcgg tgtgggacag    2760
ggcatctccc ccgaggcgtt cgtcgaggac gccgacatcc gcgagatcag cgcgacgcgc    2820
cgggtcgacg actcgtacgc caacggctac ggcaacagca gtgggccgg cgaggtcctg    2880 ctgcgggagg cgcacgactg gtgtggtctg ccggtctcgg tgttccgctg cgacatgatc    2940
ctggccgaca cgacctactc gggtcagctg aacctgccgg acatgttcac ccgcctgatg    3000
ctgagcctcg tggcgaccgg catcgcgccc ggttcgttct acgaactcga tcggacggc    3060 aaccggcagc gcgcccacta cgacgggctg cccgtggagt tcatcgccga ggcgatctcc    3120
accatcggct cgcaggtcac cgacggattc gagacgttcc acgtgatgaa cccgtacgac    3180
gacggcatcg gcctcgacga gtacgtggac tggctgatcg aggccggcta ccccgtgcac    3240
cgcgtcgacg actacgccac ctggctgagc cggttcgaaa ccgcactgcg ggccctgccg    3300
gaacggcaac gtcaggcctc gctgctgccg ctgctgcaca actatcagca gccctcaccg    3360
cccgtgtgcg gtgccatggc acccaccgac cggttccgtg ccgcggtgca ggacgcgaag    3420
atcggccccg acaaggacat tccgcacgtc acggccgacg tgatcgtcaa gtacatcagc    3480
aacctgcaga tgctcggatt gctgtaa    3507
```

<210> SEQ ID NO 28
<211> LENGTH: 3564
<212> TYPE: DNA
<213> ORGANISM: Mycobacterium massiliense

<400> SEQUENCE: 28

```
atgaccgtga ccaacgaaac caacccacag caggagcagc tatcccgccg tattgaaagt    60
ctgcgcgaaa gcgatccgca gttccgggcg gcccagcccg accggcggt cgccgaacag    120
gtgctgcgcc cgggcctgca tctttctgaa gccattgcgg cgttgatgac tggttgcgcc    180
gagcgcccgg cgctcggtga gcgcgcacgc gagttggtca tcgaccagga tggccgcacc    240
acgctgcgcc tgttgccacg cttcgacacc accacatacg gcgaattatg gtcccgcaca    300
acatcagtcg ccgctgcatg gcaccacgac gccacccacc cggtcaaggc cggcgatctg    360
gtggccaccc tgggattcac cagcatcgac tacaccgtgc tggatctggc gatcatgatc    420
ctcggtggcg tggcggttcc gctacagacc agcgccccgg cttcgcagtg gacgaccatt    480
ctggccgaag cggaacccaa cactctcgcg gtaagcatcg aattgatctg cgctgcaatg    540
gaatctgtgc gggccacgcc ttccatcaag caggtcgtcg tgttcgacta cacccccgag    600
gtcgatgatc aacgggaggc attcgaggca gcaagcacac aactcgccgg caccggcatc    660
gcccttgaga ccctcgatgc cgtcatcgcc cgcggcgccg cacttccggc ggcaccgctc    720
tacgcaccat cggccggcga cgatccgctg gcgctactca tctacacctc cggcagcacc    780
ggggctccaa agggcgccat gcacagcgaa acatcgtgc gccgctggtg gattcgtgag    840
gacgtcatgg ccggcaccga gaacctgccc atgatcgggc tgaacttcat gccgatgagt    900
cacatcatgg gacgcggcac cctcaccctcc accctgtcta ccggcggaac cggatacttc    960
gcggcgtcca gtgacatgtc aacgctcttc gaggacatgg agctgatccg cccgacggcg    1020
ctggccttgg ttccacgcgt gtgcgacatg gtgttccagc gattccagac cgaggtggac    1080
cggcgtctgg cgagcggcga caccgccagt gccgaggccg ttgcggccga ggtcaaggcc    1140
gatatccgtg acaacctctt cggtggacgc gtatcggcgg tcatggtcgg ttctgctcca    1200
ttatccgagg agctgggtga gttcatcgaa tcctgcttcg agctgaatct gaccgatggc    1260
tacggctcca ccgaggccgg catggtgttc cgcgacggca tcgtgcaacg cccgccggtc    1320
attgactaca aactggttga cgtgcccgaa ctgggctact ctccaccga caagccgcac    1380
ccgcgcggtg agctgctgct gaagaccgac ggcatgttcc tcgggtacta caaacgcccc    1440
gaggtgactg ccagcgtctt cgacgcggac ggttttttaca tgaccggcga catcgtcgcc    1500
gagctggccc acgacaacat cgagatcatc gatcgccgca acaacgtgct caaactctcg    1560
cagggagagt ttgtcgcggt cgccaccttg gaggccgagt acgccaatag ccctgtggtg    1620
caccagatct acgtctacgg cagcagcgaa cggtcctacc tgctagcagt cgtggtgccg    1680
acgccggagg ccgtggccgc cgccaagggc gacgcggcgg cactcaagac gaccatcgcg    1740
gactcgctgc aggacattgc caaagagatc cagctgcagt cctacgaagt cccccgcgac    1800
ttcatcatcg aaccgcagcc attcacccag ggcaacggcc tgctaacggg tatcgccaag    1860
ctggcgcgcc cgaacctgaa ggcgcactat ggaccgcggc tggagcagat gtacgccgaa    1920
atcgccgagc agcaggctgc cgagcttcgg gcgttgcacg gagtggaccc ggacaagccc    1980
gcgctggaaa cggtcctcaa ggcggcgcag gccctgctcg gcgtctcgtc ggccgaactg    2040
gccgcggacg cgcatttcac cgatctgggt ggcgattcgc tgtccgcact gtccttctcg    2100
gatctgctgc gcgatatctt cgcggtcgaa gtaccggtcg gagtcatcgt cagtgccgcg    2160
aacgatctcg gcggtgttgc gaaatttgtt gatgaacaac gccattcggg cgggacgcgg    2220
ccgaccgcgg agacggtgca cggcgccggg catacggaga tccgggccgc ggacctgacc    2280
```

```
ctggacaagt tcatcgacga ggccaccctg catgcggcac cgtcgcttcc gaaggccgcc    2340
gggatcccac acaccgtcct gctcaccggg tccaacggct acctgggcca ctacctggca    2400
ctggaatggc ttgaacgcct ggacaagaca gacggcaagc tgatcgtcat catccgcggt    2460
aagaatgccg aggccgccta cggccgcctc gaggaagcct tcgacaccgg cgacacgcag    2520
ctgttggcgc acttccggtc gctggccgac aagcacctcg aagtactggc cggcgatatc    2580
ggcgacccca accttggcct ggatgccgac acctggcagc gcctggccga caccgtcgac    2640
gtcatcgtgc accccgccgc cctggtcaac cacgtactgc cctacagcca gctgttcgga    2700
ccgaatgtcg ttggcaccgc cgagatcatc aagctggcca tcaccaccaa gatcaagccg    2760
gtcacctacc tgtccacggt cgcggtcgcg gcatacgtcg atccgacgac attcgacgaa    2820
gagtccgata tccggctcat cagcgcggtg cgtcccgtgg acgagctgta cgcgaacggc    2880
tacggcaaca gcaagtgggc cggagaggta ctgctgcgcg aagcccatga cctgtgcggc    2940
ctgcccgtcg cggtcttccg ctccgacatg atcttggccc acagccgcta caccggccag    3000
ctcaacgtcc cagaccagtt cacccgactg atcctgagcc tcatcgccac cggcatcgcc    3060
cccggctcct tctaccaagc acaaaccacc ggcgaacgcc cactcgcgca ctacgacgga    3120
ttaccgggtg acttcaccgc cgaggcgatc accaccctgg gcacacaagt acccgaaggg    3180
agcgaggggt tgtgacgta tgactgcgtg aacccgcacg ccgacgggat ctcactggac    3240
aacttcgtcg actggctcat cgaagcggga taccccatcg cacgcatcga caactacacc    3300
gaatggttca cccgcttcga caccgccatc cgaggcctac ccgaaaaaca gaaacaacac    3360
tccctactgc cactgctcca cgcattcgaa cagccgtccg ccgccgagaa ccatggcgtc    3420
gtcccggcaa agcggttcca gcacgctgtg caggccgccg gaatcggtcc ggtcgggcaa    3480
gacggcacta ccgacattcc ccacctgtcg cggcgactga tcgtgaaata cgccaaggac    3540
ctcgaacagc tcggactcct atga                                          3564
```

<210> SEQ ID NO 29
<211> LENGTH: 3561
<212> TYPE: DNA
<213> ORGANISM: Segniliparus rotundus

<400> SEQUENCE: 29

```
atgactcagt cgcacactca aggtccgcaa gcgtctgcgg cgcacagccg tctcgcccgt     60
cgcgcggcgg agcttctcgc gacggacccg caggccgccg cgaccctccc cgacccggag    120
gtcgtgcggc aggcgacgcg tccagggctg cggctcgcgg agcgggtcga cgcgatcctc    180
agcggctacg ccgaccgccc ggctctcggg cagcgctctt ttcagaccgt caaagatccc    240
atcaccggac gctcctcggt cgagttgctc ccacgttcg acaccatcac ctaccgcgag    300
ctgcgagagc gcgccacagc gatcgcaagc gacctggcgc atcacccgca ggccccggcc    360
aagcccggag atttcctcgc gagcatcggc ttcatcagcg tcgattacgt cgccatcgac    420
atcgccgggg tcttcgccgg gctcaccgcc gtcccgctcc agaccggcgc gacactcgcg    480
acgttgacgg cgatcaccgc agagaccgcg ccaaccctgt cgcggcgag catcgagcac    540 ctgccgaccg ccgtggacgc cgttctcgcc acgccctcag tgcgccggtt gctcgtcttc    600
gactaccgcg ccgggtcgga cgaggaccgc gaggcggtcg aggcggccaa gcggaaaatc    660 gccgacgcg gcagctcggt gctcgtggac gttttggacg aggtgatcgc acgcgggaaa    720
tcggcgccga aggcgccgct gccccccgcc accgacgcgg cgacgactc gctgtccttg    780 ctcatctaca cctccggctc caccgggacg cccaaggggg cgatgtaccc ggagcgcaac    840
```

```
gtcgcgcact tctggggcgg cgtctgggcc gccgcgttcg acgaggacgc cgccccgccc      900
gtcccagcga tcaacatcac gttcctgccg ctcagccacg tcgccagcag actttcgctc      960
atgccgaccc tcgcccgggg cggcctcatg cacttcgtcg cgaagagcga cctgtccacc     1020
ctcttcgagg acttgaaact cgctcgtccg acgaacctgt tcctggtgcc cagagtggtc     1080
gagatgctgt accagcacta ccagagcgaa ttagaccgca ggggagtgca ggacggcacc     1140
cgcgaagccg aagcggtgaa ggacgacctg cgcacgggc cctcggcgg ccggatcctc      1200 actgcgggct tcggctcggc gccgctgtcc gccgagctgg ctggcttcat cgaatccctg     1260
ctgcagatcc acctggtgga cggctacggg tccaccgagg cggggccggt gtggcgcgac     1320
ggctacctcg tcaaaccgcc ggtgaccgac tacaagctca tcgacgtgcc cgagctcggg     1380
tacttctcca ccgactcccc gcatcccgg ggcgagctgg ccatcaagac gcagaccatc     1440
ctccccggct attacaagcg ccccgagacg accgcggaag tcttcgacga ggacggcttc     1500
tacctcaccg gggacgtggt cgcgcagatc gggccggaac agttcgcgta cgtcgaccgg     1560
cgcaagaacg tcctcaagct ctcccagggc gagttcgtga ccctcgcgaa gctcgaggcc     1620
gcgtacagct ccagcccgct ggtgcgacag ctcttcgtct acggctccag cgaacgctcg     1680
tacttgctcg ccgtgatcgt gcccaccccg gacgccctga agaagttcgg cgtcggcgag     1740
gcggcgaaag ccgcgctcgg ggagtctctg cagaagatcg ctcgcgacga gggcctgcaa     1800
tcctacgagg tgccgcgcga cttcatcatc gaaacggatc cgttcacggt cgagaacggc     1860
ctgctctccg acgcccgcaa gtcgttgcgc ccgaagctca aggagcatta cggcgaacgg     1920
ctcgaagcga tgtacaaaga gctcgcggac ggtcaggcga acgagctgcg cgacatccgc     1980
agaggcgtgc aacaacgccc gacgctcgaa accgtgcggc gcgccgcggc cgcgatgctg     2040
ggcgcgagcg ccgcggaaat caagccggac gcccatttca ccgacctcgg cggcgactcg     2100
ctctccgcgc tgacgttctc gaacttcctg cacgacctct tcgaagtcga tgtgcccgtc     2160
ggggtgatcg tgagcgccgc gaacacattg ggctccgtgg ccgagcacat cgacgcgcag     2220
ctcgcggggg gccgtgcccg gccgacgttc gcgaccgtgc acggcaaagg ctccaccacg     2280
atcaaggcca gcgatctgac cttggacaag ttcatcgacg agcagaccct cgaggccgcg     2340
aagcacttgc ccaagcccgc cgacccgccg cgcaccgtgc tgctcaccgg cgcgaacggc     2400
tggctcggcc ggttcctcgc ccttgaatgg ctcgaaaggc tcgcccccgc cggcggcaag     2460
ctcatcacga tcgtgcgcgg caaggacgcg gcacaggcaa aggctcggct cgacgccgcg     2520
tacgagagcg cgacccgaa gctcgccggt cattaccagg atttggccgc gacgacgctc     2580
gaagtgctcg cgggcgattt cagcgagccg cgtctcgggc tggacgaggc gacctggaac     2640
cggctggccg acgaggtgga cttcatctcg caccccggcg ctctggtcaa ccatgtcctg     2700
ccgtacaacc agctgttcgg gccgaacgtg gccggtgtgg ccgagatcat caagctcgcg     2760
atcaccacac ggatcaagcc cgtcacgtac ctgtccacag tcgccgtcgc ggcgggcgtc     2820
gagccgtcgg ccttagacga ggacggcgac atccggacgg tgagcgctga gcgctcggtc     2880
gacgagggct acgccaacgg gtacgggaac agcaaatggg gcggcgaggt gctgctgcgc     2940
gaagcgcacg atcgcacggg actgccggtt cgggtgttcc gctcggacat gatcctcgcg     3000
catcagaaat acaccggaca agtgaacgcg accgaccagt tcacccggct cgtccagagc     3060
cttttggcaa ccgggctcgc accgaagtcc ttctacgagc tcgacgccca gggcaaccgg     3120
cagcgggccc actacgacgg gatacccgtg gacttcaccg ccgagtcgat caccacgctc     3180
```

| | |
|---|---|
| ggcggcgacg gtttggaagg ctaccgcagc tacaacgtgt caacccgca tcgcgacggc | 3240 |
| gtcggtttgg acgagttcgt cgactggctc atcgaagccg acacccgat cacacggatc | 3300 |
| gacgactacg accagtggct ctcgcgcttc gagacctcgt tgcgcggcct gcccgaatcc | 3360 |
| aagcgccaag cctccgtgct cccgttgctg cacgccttcg cccggccagg gcccgccgtg | 3420 |
| gacggctcgc ctttccggaa cacggtgttc cgcaccgacg tgcagaaggc gaagatcggc | 3480 |
| gcggaacacg acatccccca cctgggcaaa gcgctcgtgc tcaagtacgc cgacgacatc | 3540 |
| aagcagctcg gtctgctctg a | 3561 |

<210> SEQ ID NO 30
<211> LENGTH: 1380
<212> TYPE: DNA
<213> ORGANISM: Chromobacterium violaceum

<400> SEQUENCE: 30

| | |
|---|---|
| atgcagaagc aacgtacgac cagccaatgg cgcgaactgg atgccgccca tcacctgcat | 60 |
| ccgttcaccg ataccgcatc gctgaaccag gcgggcgcgc gcgtgatgac gcgcggagag | 120 |
| ggcgtctacc tgtgggattc ggaaggcaac aagatcatcg acggcatggc cggactgtgg | 180 |
| tgcgtgaacg tcggctacgg ccgcaaggac tttgccgaag cggcgcgccg gcagatggaa | 240 |
| gagctgccgt tctacaacac cttcttcaag accacccatc cggcggtggt cgagctgtcc | 300 |
| agcctgctgc tgaagtgac gccggccggt ttcgaccgcg tgttctatac caattccggt | 360 |
| tccgaatcgg tggacaccat gatccgcatg gtgcgccgct actgggacgt gcagggcaag | 420 |
| ccggagaaga gacgctgat cggccgctgg aacggctatc acggctccac catcggcggc | 480 |
| gccagcctgg gcggcatgaa gtacatgcac gagcagggcg acttgccgat tccgggcatg | 540 |
| gcccacatcg agcagccttg gtggtacaag cacggcaagg acatgacgcc ggacgagttc | 600 |
| ggcgtggtgg ccgcgcgctg gctggaagag aagattctgg aaatcggcgc cgacaaggtg | 660 |
| gccgccttcg tcggcgaacc catccagggc gccggcggtg tgatcgtccc gccggccacc | 720 |
| tactggccgg aaatcgagcg catttgccgc aagtacgacg tgctgctggt ggccgacgaa | 780 |
| gtgatctgcg gcttcgggcg taccggcgaa tggttcggcc atcagcattt cggcttccag | 840 |
| cccgacctgt tcaccgccgc caagggcctg tcctccggct atctgccgat aggcgcggtc | 900 |
| tttgtcggca gcgcgtggc cgaaggcctg atcgccggcg cgacttcaa ccacggcttc | 960 |
| acctactccg gccacccggt ctgcgccgcc gtcgcccacg ccaacgtggc ggcgctgcgc | 1020 |
| gacgagggca tcgtccagcg cgtcaaggac gacatcggcc gtacatgca aaagcgctgg | 1080 |
| cgtgaaacct tcagccgttt cgagcatgtg gacgacgtgc gcggcgtcgg catggtgcag | 1140 |
| gcgttcaccc tggtgaagaa caaggcgaag cgcgagctgt tccccgattt cggcgagatc | 1200 |
| ggcacgctgt gccgcgacat cttcttccgc aacaacctga tcatgcgggc atgcggcgac | 1260 |
| cacatcgtgt cggcgccgcc gctggtgatg acgcgggcgg aagtggacga gatgctggcg | 1320 |
| gtggcggaac gctgtctgga ggaattcgag cagacgctga aggcgcgcgg gctggcttag | 1380 |

<210> SEQ ID NO 31
<211> LENGTH: 1407
<212> TYPE: DNA
<213> ORGANISM: Pseudomonas aeruginosa

<400> SEQUENCE: 31

| | |
|---|---|
| atgaacgcaa gactgcacgc cacgtccccc ctcggcgacg ccgacctggt ccgtgccgac | 60 |
| caggcccact acatgcacgg ctaccacgtg ttcgacgacc accgcgtcaa cggctcgctg | 120 |

```
aacatcgccg ccggcgacgg cgcctatatc tacgacaccg ccggcaaccg ctacctcgac      180
gcggtgggcg gcatgtggtg caccaacatc ggcctggggc gcgaggaaat ggctcgcacc      240
gtggccgagc agacccgcct gctggcctat tccaatccct tctgcgacat ggccaacccg      300
cgcgccatcg aactctgccg caagctcgcc gagctggccc ccggcgacct cgaccacgtg      360
ttcctcacca ccggcggttc caccgccgtg acaccgcga tccgcctcat gcactactac       420
cagaactgcc gcggcaagcg cgccaagaag cacgtcatca cgcggatcaa cgcctaccac      480
ggctcgacct tcctcggcat gtcgctgggc ggcaagagcg ccgaccggcc ggccgagttc      540
gacttcctcg acgagcgcat ccaccacctc gcctgtccct attactaccg cgctccggaa      600
gggctgggcg aagccgagtt cctcgatggc ctggtggacg agttcgaacg caagatcctc      660
gaactgggcg ccgaccgggt gggggcgttc atctccgagc cggtgttcgg ctccggcggc      720
gtgatcgtcc cgcccgcggg ctaccacagg cggatgtggg agctgtgcca gcgctacgac      780
gtgctgtaca tctccgacga agtggtgacc tccttcggcc gcctcggcca cttcttcgcc      840
agccaggcgg tgttcggcgt acagccggac atcatcctca ccgccaaggg cctcacctcc      900
ggctaccagc cgctgggcgc gtgcatcttc tcccggcgca tctgggaggt gatcgccgag      960
ccggacaagg gccgctgctt cagccatggt ttcacctact ccggccaccc ggtggcctgc     1020
gcggcggcgc tgaagaacat cgagatcatc gagcgcgagg gcttgctcgc ccacgccgac     1080
gaggtcggcc gctacttcga ggagcgcctg caaagcctcc gcgacctgcc catcgtcggc     1140
gacgtgcgcg gatgcgcttc catggcctgt gtcgagttcg tcgccgacaa ggcgagcaag     1200
gcgctgtttc cggaaagcct gaacatcggc gagtgggtcc acctgcgggc gcagaagcgc     1260
ggcctgctgg ttcgtccgat cgtccacctg aacgtgatgt cgccgccgct gatcctcacc     1320
cgcgaacagg tcgataccgt ggtccgggtg ctgcgcgaga gcatcgagga aaccgtggag     1380
gatcttgtcc gcgccggtca ccggtaa                                        1407
```

<210> SEQ ID NO 32
<211> LENGTH: 1365
<212> TYPE: DNA
<213> ORGANISM: Pseudomonas syringae

<400> SEQUENCE: 32

```
atgagtgcca acaacccgca aaccctcgaa tggcaggccc tgagcagcga gcatcacctg       60
gcaccgttca gcgactacaa acaactgaaa gagaaaggcc cgcgcatcat caccegtgcc      120 gagggcgttt atctgtggga cagcgagggc aacaagatcc tcgatggcat gtccggcctg      180
tggtgcgtgg ccatcggtta tggccgcgaa gaactggccg acgcagccag caaacagatg      240
cgcgagctgc cgtactacaa cctgttcttc cagaccgccc accegccggt gctggaactg      300 gccaaggcca tctccgacat cgctcccgag ggcatgaacc atgtgttctt caccggttca      360
ggctctgaag gcaatgacac gatgctgcgc atggttcgtc attactgggc gctgaaaggc      420
cagccgaaca agaaaaccat catcagccgc gtcaatggct accacggctc caccgtcgcc      480
ggtgccagcc tgggtggcat gacctacatg cacgaacagg gcgacctgcc gatcccgggg     540
gtggtgcaca ttccacagcc ttactggttc ggcgaaggcg cgacatgac gccggacgag      600 ttcggcatct gggcggccga gcaactggaa agaaaattc tcgagctggg cgtcgagaac       660
gtcggtgcgt tcattgccga gccaatccag ggcgcgggcg tgtgattgt cccgcctgat      720 tcctactggc cgaagatcaa ggaaatcctt tcccgctacg acatcctgtt cgccgccgat     780
```

```
gaggtgattt gtggcttcgg gcgtaccagt gagtggttcg gtagcgattt ctatggcctc    840
aggccggaca tgatgaccat cgccaaaggc ctgacctccg gttacgtacc gatgggcggc    900
ctgatcgtgc gcgatgaaat cgttgcggtg ctcaatgagg gtggcgattt caatcacggc    960
tttacctact ccgggcaccc ggtggcggcc gcggttgcgc tggagaacat ccgtatcctg   1020
cgcgaagaaa agatcgtcga acgggtcagg tcggaaacgg caccgtattt gcaaaagcgt   1080
ttgcgtgagt tgagcgatca tccgctggtg ggcgaagtcc ggggtgtcgg gctgctcggg   1140
gccattgagc tggtgaagga caagaccacc cgcgagcgct ataccgacaa gggcgcggga   1200
atgatctgtc gaaccttctg cttcgacaat ggcctgatca tgcgggctgt gggcgatacc   1260
atgatcattg cgccgccact ggtgatcagt tttgcgcaaa tcgatgagct ggtagagaag   1320
gcgcgcacgt gtctggatct gacgctggcg gtgttgcagg gctga                  1365
```

<210> SEQ ID NO 33
<211> LENGTH: 1404
<212> TYPE: DNA
<213> ORGANISM: Rhodobacter sphaeroides

<400> SEQUENCE: 33

```
atgacgcgga atgacgcgac gaatgctgcc ggagcggtgg gcgcggcgat gcgggatcac     60
atcctcttgc ctgcacagga aatggcgaag ctcggcaagt ccgcgcagcc ggtgctgact    120
catgccgagg gcatctatgt ccataccgag gacggccgcc gctgatcga cgggccggcg    180 ggcatgtggt gcgcgcaggt gggctacggc cgccgcgaga tcgtcgatgc catggcgcat    240
caggcgatgg tgctgcccta tgcctcgccc tggtatatgg ccacgagccc cgcggcgcgg    300
ctggcggaga agatcgccac gctgacgccg ggcgatctca accggatctt tttcaccacg    360
ggcgggtcga ccgcggtgga cagcgcgctg cgcttctcgg aattctacaa caacgtgctg    420
ggccggccgc agaagaagcg catcatcgtg cgctacgacg gctatacggg ctcgacggcg    480
ctcaccgccg cctgcaccgg ccgcaccggc aactggccga acttcgacat cgcgcaggac    540
cggatctcgt tcctctcgag ccccaatccg cgccacgccg gcaaccgcag ccaggaggcg    600
ttcctcgacg atctggtgca ggaattcgag gaccggatcg agagcctcgg ccccgacacg    660
atcgcggcct tcctggccga gccgatcctc gcctcgggcg gcgtcattat tccgcccgca    720
ggctatcatg cgcgcttcaa ggcgatctgc gagaagcacg catcctcta tatctcggac    780 gaggtggtga cgggcttcgg ccgttgcggc gagtggttcg cctcggagaa ggtgttcggg    840
gtggtgccgg acatcatcac cttcgccaag ggcgtgacct cgggctatgt gccgctcggc    900
ggccttgcga tctccgaggc ggtgctggcg cggatctcgg gcgagaatgc caagggaagc    960 tggttccacca acggctatac ctacagcaat cagccggtgg cctgcgccgc ggcgcttgcc   1020
aacatcgagc tgatggagcg cgagggcatc gtcgatcagg cgcgcgagat ggcggactat   1080
ttcgccgcgg cgctggcttc gctgcgcgat ctgccgggcg tggcggaaac ccggtcggtg   1140
ggcctcgtgg gttgcgtgca atgcctgctc gacccgaccc gggcggacgg cacggccgag   1200
gacaaggcct tcaccctgaa gatcgacgag cgctgcttcg agctcgggct gatcgtgcgc   1260
ccgctgggca tctctgcgt gatctcgccg ccgctcatca tctcgcgcgc gcagatcgac   1320
gagatggtcg cgatcatgcg gcaggccatc accgaagtga gcgccgccca cggtctgacc   1380
gcgaaagaac cggccgccgt ctga                                          1404
```

<210> SEQ ID NO 34
<211> LENGTH: 1380

<212> TYPE: DNA
<213> ORGANISM: Escherichia coli

<400> SEQUENCE: 34

| | | | | | |
|---|---|---|---|---|---|
| ttgaacaggt | taccttcgag | cgcatcggct | ttagcgtgca | gcgcccacgc | cctgaatctc | 60 |
| attgagaagc | gaacgctgga | tcatgaggag | atgaaagcac | ttaaccgaga | ggtgattgaa | 120 |
| tacttcaaag | agcatgtcaa | tccggggttt | ttagagtatc | gcaaatctgt | taccgccggc | 180 |
| ggggattacg | gagccgtaga | gtggcaagcg | ggaagtttaa | atacgcttgt | cgacacccag | 240 |
| ggccaggagt | ttatcgactg | cctgggaggt | tttggaattt | tcaacgtggg | gcaccgtaat | 300 |
| ccagttgtgg | tttccgccgt | acagaatcaa | cttgcgaaac | aaccgctgca | cagccaggag | 360 |
| ctgctcgatc | cgttacgggc | gatgttggcg | aaaaccttg | ctgcgctaac | gcccggtaaa | 420 |
| ctgaaataca | gcttcttctg | taatagcggc | accgagtccg | ttgaagcagc | gctgaagctg | 480 |
| gcgaaagctt | accagtcacc | gcgcggcaag | tttactttta | ttgccaccag | cggcgcgttc | 540 |
| cacggtaaat | cacttggcgc | gctgtcggcc | acggcgaaat | cgaccttccg | caaaccgttt | 600 |
| atgccgttac | tgccgggctt | ccgtcatgtg | ccgtttggca | atatcgaagc | catgcgcacg | 660 |
| gctcttaacg | agtgcaaaaa | aaccggtgat | gatgtggctg | cggtgatcct | cgaaccgatt | 720 |
| cagggtgaag | gtggcgtaat | tctgccgccg | ccgggctatc | tcaccgccgt | acgtaagcta | 780 |
| tgcgatgagt | tcggcgcact | gatgatcctc | gatgaagtac | aaacgggcat | ggggcgcacg | 840 |
| ggcaagatgt | tcgcctgcga | gcatgagaac | gtacagccgg | atatcctctg | ccttgccaaa | 900 |
| gcgctcggcg | gcggcgtgat | gccgattggc | gcgaccatcg | ccactgaaga | ggtgttttca | 960 |
| gttctgttcg | acaacccatt | cctgcatacc | accacctttg | gcggcaaccc | gctggcctgt | 1020 |
| gcggcggcgc | tggcgaccat | caatgtgttg | ctggagcaga | acttaccggc | tcaggctgag | 1080 |
| caaaaaggcg | atatgttgct | ggacggtttc | cgtcaactgg | cgcgggaata | tcccgatctg | 1140 |
| gtacaggaag | cgcgtggtaa | agggatgttg | atggcgattg | agtttgttga | taacgaaatc | 1200 |
| ggctataact | ttgccagcga | gatgttccgc | cagcgcgtac | tggtggccgg | aacgctcaat | 1260 |
| aacgccaaaa | cgatccgcat | tgaaccgcca | ctgacactga | ccattgaaca | gtgtgaactg | 1320 |
| gtgatcaaag | cggcgcgtaa | ggcgctggcg | gccatgcgag | taagtgtcga | agaagcgtaa | 1380 |

<210> SEQ ID NO 35
<211> LENGTH: 1362
<212> TYPE: DNA
<213> ORGANISM: Vibrio fluvialis

<400> SEQUENCE: 35

| | | | | | |
|---|---|---|---|---|---|
| atgaacaaac | cgcaaagctg | ggaagcccgg | gccgagacct | attcgctcta | tggtttcacc | 60 |
| gacatgcctt | cgctgcatca | gcgcggcacg | gtcgtcgtga | cccatggcga | gggaccctat | 120 |
| atcgtcgatg | tgaatggccg | gcgttatctg | gacgccaact | cgggcctgtg | gaacatggtc | 180 |
| gcgggctttg | accacaaggg | gctgatcgac | gccgccaagg | cccaatacga | gcgttttccc | 240 |
| ggttatcacg | ccttttttcgg | ccgcatgtcc | gatcagacgg | taatgctgtc | ggaaaagctg | 300 |
| gtcgaggtgt | cgcccttga | ttcgggccgg | gtgttctata | caaactcggg | gtccgaggcg | 360 |
| aatgacacca | tggtcaagat | gctatggttc | ctgcatgcag | ccgagggcaa | accgcaaaag | 420 |
| cgcaagatcc | tgacccgctg | gaacgcctat | cacggcgtga | ccgccgtttc | ggccagcatg | 480 |
| accggcaagc | cctataattc | ggtctttggc | ctgccgctgc | cgggctttgt | gcatctgacc | 540 |
| tgcccgcatt | actggcgcta | tggcgaagag | ggcgaaaccg | aagagcagtt | cgtcgcccgc | 600 |

```
ctcgcccgcg agctggagga aacgatccag cgcgagggcg ccgacaccat cgccggtttc      660
tttgccgaac cggtgatggg cgcggccggc gtgattcccc cggccaaggg gtatttccag      720
gcgatcctgc caatcctgcg caaatatgac atcccggtca tctcggacga ggtgatctgc      780
ggtttcggac gcaccggtaa cacctggggc tgcgtgacct atgactttac acccgatgca      840
atcatctcgt ccaagaatct tacagcgggc ttttttccca tggggcggt gatccttggc       900 ccggaacttt ccaaacggct ggaaaccgca atcgaggcga tcgaggaatt ccccatggc       960 tttaccgcct cgggccatcc ggtcggctgt gctattgcgc tgaaagcaat cgacgtggtg     1020
atgaatgaag gctggctga aacgtccgc cgccttgccc ccgtttcga ggaaaggctg       1080 aaacatatcg ccgagcgccc gaacatcggt gaatatcgcg gcatcggctt catgtgggcg     1140
ctggaggctg tcaaggacaa ggcaagcaag acgccgttcg acggcaacct gtcggtcagc     1200
gagcgtatcg ccaatacctg caccgatctg gggctgattt ccggccgct tggtcagtcc     1260 gtcgtccttt gtccgccctt tatcctgacc gaggcgcaga tggatgagat gttcgataaa     1320
ctcgaaaaag cccttgataa ggtctttgcc gaggttgcct ga                        1362
```

<210> SEQ ID NO 36
<211> LENGTH: 1813
<212> TYPE: DNA
<213> ORGANISM: Cucumis sativus

<400> SEQUENCE: 36

```
ccattctctt ccaacgtgaa gataagaaac cttttgttta cttttgtac gatcacaggt        60 cacagcaatg gcttcttcct cccctgaact tcctctcaaa cccattcccg gtggctatgg      120
cttccccttc ctcggtccca tcaaagaccg ttacgattac ttctatttcc aaggtagaga      180
cgaattcttc cgttcccgaa ttaccaaata caactccacc gtcttccacg ccaacatgcc      240
accgggcccc ttcatctcct ccgattccag agtcgttgtc ctcctcgatg ccctcagttt      300
tcccatcctc ttcgacacca ccaaagtcga gaaacgcaac attctcgacg gaacttacat      360
gccctccttg tccttcaccg gcggcattcg cacctgtgct tatttggacc catcggaaac      420
agagcacact gttctcaaac gcctctttct ctcctttctc gcttctcacc atgacaggtt      480
catccctctg tttcgaagct ccttgtctga gatgtttgtt aagcttgaag ataaactcgc      540
cgacaaaaat aagatcgctg atttcaactc gattagtgat gccgtgtcgt ttgattatgt      600
tttccgttta ttctccgatg gaacccctga ttcgacatta gctgctgatg gacctggaat      660
gttcgattta tggcttgggc ttcaacttgc cccattggct tccattggcc ttcccaaaat      720
tttctctgtt tttgaagatc tcattattca caccattccc ctgcctttct tcccagtcaa      780
gagtcgttac aggaagcttt ataaagcgtt ttactcctcc tctggctcat ttctagacga      840
agcagagaaa caggggatag acagagagaa agcatgtcac aatttagtgt tcttgctgg       900 attcaacgca tacgggggaa tgaaagtcct ttttcccact atactgaaat gggtcggcac      960
cggtggcgag gatctccacc gtaaactggc ggaggaagtg aggacaaccg tgaaggaaga     1020 aggggactg acttctctccg ccttggagaa aatgagtctg ctgaagtcgg tcgtgtacga     1080
agctctgaga tcgaaccgc cggtgccgtt ccagtacggg aaagcgaagg aggatatcgt     1140
gattcagagc cacgattctt gtttcaagat caaaaaaggg gagacgattt tggttatca     1200 gccgttttgct actaaagatc cgaagatttt taaggactcg gagaagttcg tgggcgatag     1260
gttcgtggga gaagaagggg agaagctttt gaagtatgtt tactggtcaa atgagcggga     1320
gacggtggag ccgacggcgg agaacaagca gtgtccgggg aagaatctgg tggtgatgat     1380
```

```
gggcaggatt attgtggtgg aattcttcct ccgttatgat acgttcactg tggacgtcgc    1440
agatttggcg ctgggcccgg cggtgaagtt caagtccttg accagagcca ccgcttcggt    1500
ttagaagcta atgacaaaat tagtttttaa tcattttaca gaataaagga agggtgttcg    1560
tgattggttg atgcagggaa gctgtggtgg acttgagcac acatgacaca tcattgattt    1620
gttggggtta taaagtaatt tcctcgtgat ccgcgtcgtt tttaatttga gatctcattg    1680
tgtgttgtaa cccgcgggtg atcttatttt tatagtttct tttttctcaa ctatgctcca    1740 attttaaat taaataaata ccaaatatca acttcataga caaaaaaaaa aaaaaaaaa     1800 aaaaaaaaaa aaa                                                      1813

<210> SEQ ID NO 37
<211> LENGTH: 1721
<212> TYPE: DNA
<213> ORGANISM: Oryza sativa

<400> SEQUENCE: 37
ctcctcgaac caacccaaca caacacttgc acttgcacta cgtactctca tttcatccgc      60
tcccggccgg caatggcgcc accgccagtg aactccggcg acgccgccgc cgccgccacg     120
ggagagaaga gcaagctctc gccgtcgggc ctccccatac gcgagatacc cggcggctac     180
ggcgtgccct tcttctcgcc gctgcgcgac cgcctcgact acttctactt ccagggcgcc     240
gaggagtact tccgatcacg cgtcgcccgc cacgcggcg ccaccgtgct ccgcgtcaac      300
atgccgcccg gcccttcat ctccggcaac cccgcgtcg tcgccctcct cgacgcgcgc       360
agcttccgcg tcctcctcga cgactccatg gtggacaagg ccgacacgct cgacggcacc     420
tacatgccgt cgcgcgcgct cttcggcgg caccgcccgc tcgccttcct cgacgccgcc     480
gacccgcgcc acgccaagat caagcgcgtc gtgatgtcgc tcgccgccgc gcggatgcac     540
cacgtcgcgc cggcgttccg cgccgccttt gccgccatgt tcgacgccgt cgaggccggc   600
ctcggcgccg ccgtcgagtt caacaagctc aacatgaggt acatgctcga cttcacctgc     660
gccgcgctgt tcggcggcga ccgccgagc aaggtggtcg cgacggcgc cgtgacgaag       720 gccatggcgt ggctcgcgtt ccagctgcac ccgatcgcga gcaaggtcgt caagccatgg     780
ccgctcgagg agctactcct gcacaccttc tccctgccgc cgttcctggt gcggcgtggc     840
tacgccgacc tgaaggcgta cttcgccgac gccgccgcgg ccgtcctcga cgacgccgag     900
aagagccaca cgggaatccc gcgcgacgag ctcctcgaca accttgtgtt cgtcgccatt     960
ttcaacgcct tcggcggctt caagatcttc ctgccacaca tcgtcaagtg gctcgcccgc    1020
gccggcccgg agctccacgc caagcttgcc accgaggtcc gcgccaccgt gcccaccggc    1080
gaggacgacg gcatcaccct cgccgccgtc gagcggatgc cgctggtgaa gtcggtggtg    1140
tgggaggcgc tgcgcatgaa cccgccggtg gagttccagt acggccacgc gcggcgcgac    1200
atggtggtcg agagccacga cgcggcgtac gaggtgcgca agggggagat gctgttcggc    1260
taccagccgc tcgccacccg cgacgagaag gtgttcgacc gcgccggcga ttcgtcgcc    1320 gaccggttcg tcgccggcgg cgccgccggc gaccggccgc tgctggagca cgtggtgtgg    1380
tcgaacgggc cggagacgag ggcgccatcg gaggggaaca agcagtgccc cgggaaggac    1440
atggtggtgg cggtggggcg gctgatggtg gcggagctgt tccggcggta cgacacgttc    1500
gccgccgacg tggtggaggc gccggtggag ccggtggtga cgttcacgtc gctgacacgg    1560
gcgtcgtcgg gatagcacgc acgtcgacgt cacgtgcgcg ccgtgctgtg atttagtact    1620
```

| | |
|---|---|
| gtactaggtt ggtggatgtt ttaattgcgt ggttaattat taatcacgca taaagtatta | 1680 |
| atcatgtttt atcatctaac aacaatgaaa atattaatca t | 1721 |

<210> SEQ ID NO 38
<211> LENGTH: 1164
<212> TYPE: DNA
<213> ORGANISM: Lactobacillus casei

<400> SEQUENCE: 38

| | |
|---|---|
| atgtcgggtt atcatttttt aaaaccgttc accttcaagc accaaaccat cacgttgaaa | 60 |
| aatcgcattg tcattccgcc gatgacaacg cgcctgtcgt ttgaagacgg cactgtgacg | 120 |
| cgggacgaaa tcaggtatta ccagcaacgg gccggtggcg tcggcatgtt tattaccggt | 180 |
| accgccaatg tcaatgcgct tggcaaagga ttcgaaggtg agctaagtgt cgctgatgat | 240 |
| cgattcatcc ccggtttgag caaactcgcc gctgcgatga aaacaggcgg caccaaggct | 300 |
| attttgcaaa tcttcagcgc tggccgcatg agcaatagca agattctgcg cggtgagcag | 360 |
| ccagtcagtg ccagtgcggt tgctgcgcca cgggcgggtt acgaaacacc gcgcgcattg | 420 |
| acatcggcag aaatcgaggc cactattcac gattttggtc aggctgtgcg ccgcgccatc | 480 |
| cttgctggtt ttgatggcat cgaactgcat ggtgccaaca cctatctgat acagcaattc | 540 |
| tattcgccaa actctaatcg ccgaaccgat gaatgggggcg gtgaccgcga taagcggatg | 600 |
| cgttttccgt tggcagtcgt tcatgaagca gaaaaagtga ttgccacaat tgctgaccgg | 660 |
| ccattttttgt taggctaccg catttcgccg gaagagttgg aacagcctgg cattaccttg | 720 |
| gatgatacct tggccttaat cgacgctttg aaacaaacca agattgatta cctgcatgtc | 780 |
| tcccaaagtg acgtttggcg aacctcattg cgcaaccccg aggacacagc catcatgaat | 840 |
| gaacaaattc gtgaccatgt cgccggtgct tttccagtga ttgtggtcgg tgcattaaaa | 900 |
| accccccgccg atgctgagaa agcggcagaa tcctttgatt tggtcgcgat tggtcacgaa | 960 |
| atgattcgcg agccgcactg ggttcagaag gtcttagacc atgacgaaaa ggcgatccgt | 1020 |
| taccagatcg cccctgctga tcttgaagaa cttggcattg cgccgacctt cctcgatttt | 1080 |
| atcgaaagta tttccggtgg ggcaaaaggt gtcccgttaa caactgcgca gtctgtgaca | 1140 |
| tcaagcaacg tgactcaaga ttaa | 1164 |

<210> SEQ ID NO 39
<211> LENGTH: 1092
<212> TYPE: DNA
<213> ORGANISM: Pseudomonas putida

<400> SEQUENCE: 39

| | |
|---|---|
| atgtccgcac tgttcgaacc ctacaccctc aaagacgtca ccctgcgtaa ccgtatcgcc | 60 |
| attccgccga tgtgccagta catggccgaa gacggcatga tcaacgactg gcaccacgta | 120 |
| cacttggccg gcctggcccg tgtggtggcc ggcttgctgg tggtcgaagc cactgctgtg | 180 |
| gccccggaag ggcgtatcac ccccggttgc gccgggatct ggagcgatgc ccacgctcag | 240 |
| gcgttcgttc cggtggtgca ggccatcaag gctgccggtt cggtgccggg tatccagatc | 300 |
| gcccacgccg ggcgcaaggc cagcgccaac cgcccgtggg agggtgacga ccacattgcc | 360 |
| gccgacgacg cgcgcggctg ggagaccatt gccccgtctg ccattgcctt ggcgcgcac | 420 |
| ctgccgaaag tgccacggga aatgacgctg gacgatatcg cccgggtcaa gcaggacttc | 480 |
| gtcgatgccg cccgccgtgc gcgtgatgcc ggcttcgagt ggatagaact gcactttgcc | 540 |
| catggctacc tgggccagag cttcttctcc gagcattcca acaagcgcac cgatgcctac | 600 |

```
ggtggcagct tcgacaaccg cagccgcttc ctgctggaaa cactggctgc cgtgcgcgaa    660
gtgtggccgg agaacctgcc gctgaccgcg cgctttggtg tgttggaata cgatggccgc    720
gatgagcaga ccctggaaga gtcgatcgaa ctggcccgcc gtttcaaggc cggtgggctc    780
gacctgctga gcgtgagtgt cggcttcacc attcccgaca ccaacattcc ctggggccca    840
gcgttcatgg ggccgattgc cgagcgcgtg cgccgcgaag cgaagctgcc cgtgacgtcg    900
gcgtggggct ttggtacgcc gcagttggcg gaggccgcat tgcaggccaa ccagctggat    960
ctggtttcgg tagggcgcgc gcacctggcc gacccgcact gggcttactt tgcggccaag   1020
gagctggggg tggaaaaagc gtcctggacc ttgccggcgc cttatgcgca ctggctcgag   1080
cgttaccgct ga                                                       1092

<210> SEQ ID NO 40
<211> LENGTH: 843
<212> TYPE: DNA
<213> ORGANISM: Saccharomyces cerevisiae

<400> SEQUENCE: 40

```
atgtcgcaag aaattaggca aaatgagaaa atcagttatc gtattgaagg accattcttc     60
attattcact taatgaaccc tgacaatttg aatgcactag aaggtgaaga ctatatttat    120
ttaggagagt tactagaact agcggacaga aatcgtgatg tatattttac aattatacaa    180
agcagtggta gatttttttc cagtggtgct gatttcaagg gtattgcaaa agcccaaggg    240
gatgatacca ataaatatcc ttcggaaaca agcaagtggg tgtcaaattt tgtcgctaga    300
aatgtttatg tcactgatgc cttcatcaag cattccaaag ttttaatttg ctgtttgaat    360
ggaccagcaa tagggttgag cgcggcactg gtagcgttat gtgacattgt gtacagtata    420
aatgacaagg tttatttgct ataccccttt gctaacttag gactaattac cgaaggtggt    480
acaacggtct ctttgccatt gaagtttggc acaaatacga cgtatgaatg cctcatgttc    540
aacaaaccat tcaagtacga tataatgtgc gagaacggat ttataagcaa gaattttaac    600
atgccatctt caaacgctga agcgttcaat gcaaaggtct tagaagaatt gagggagaaa    660
gtgaaagggc tatacctgcc cagttgctta gggatgaaaa aattgctgaa atcgaaccac    720
atcgatgcat tcaataaggc taactcagtg gaagtaaatg aatctctcaa gtattgggta    780
gatggagagc ccttaaaaag atttaggcag ctgggctcga aacaaaggaa gcatcgttta    840
tga                                                                  843
```

<210> SEQ ID NO 41
<211> LENGTH: 741
<212> TYPE: DNA
<213> ORGANISM: Clostridium perfringens

<400> SEQUENCE: 41

```
atggggaaag cttatgaaaa agtttatgaa gttacttatg gagaaacaga tggaagaaaa     60
gactgtagaa taacttcaat gatgaacttc ttttcagact gttgcttaag tcaagaagaa    120
aagaattcaa tgaactatgc agataatagc agtgaaacta cttgggtatt ttttgattat    180
gaaataatag ttaatagata tccaagatat agagagaaaa ttaaggtaaa aacttatgtt    240
gaatctataa gaaagtttta ttctaacaga gtatttgagg cttatgatat ggatggggcc    300
ttagtagcta gggctgatgt attagccttc ttaataaaca aaaaaactag aagaccagct    360
agaataagcg atgaagaata tgagattcat ggattaagta aggagtcttc aaaattatta    420
```

```
agaaaaaaat taaactttga gaaatttgat aaagaagatt tagagatgaa ttttcacata    480
agatatttag atatagatct aaatatgcat gtaagtaata ttaagtatgt agagtggatt    540
ttagaaacag taccagttga tattgttcta aattacaaaa tgaaaaaat aaaaataaaa     600 tttgaaaaag aaattacata tggtcataat gtaattataa agtcaaaaat aattaagggt   660
gaagatgaag taaaggttct tcataaagta gaaaatgaag agggagaaag cattacttta   720
gcagaaactt attggtatta a                                              741
```

<210> SEQ ID NO 42
<211> LENGTH: 843
<212> TYPE: DNA
<213> ORGANISM: Saccharomyces cerevisiae

<400> SEQUENCE: 42

```
atgtcgcaag aaattaggca aaatgagaaa atcagttatc gtattgaagg accattcttc    60
attattcact taatgaaccc tgacaatttg aatgcactag aaggtgaaga ctatatttat   120
ttaggagagt tactagaact agcggacaga atcgtgatg tatattttac aattatacaa    180
agcagtggta gatttttttc cagtggtgct gatttcaagg gtattgcaaa agcccaaggg   240
gatgatacca ataaatatcc ttcggaaaca agcaagtggg tgtcaaattt tgtcgctaga   300
aatgtttatg tcactgatgc cttcatcaag cattccaaag ttttaatttg ctgtttgaat   360
ggaccagcaa tagggttgag cgcggcactg gtagcgttat gtgacattgt gtacagtata   420
aatgacaagg tttatttgct ataccccttt gctaacttag gactaattac cgaaggtggt   480
acaacggtct ctttgccatt gaagtttggc acaaatacga cgtatgaatg cctcatgttc   540
aacaaaccat tcaagtacga tataatgtgc gagaacggat ttataagcaa gaattttaac   600
atgccatctt caaacgctga agcgttcaat gcaaggtct tagaagaatt gagggagaaa   660
gtgaaagggc tatacctgcc cagttgctta gggatgaaaa aattgctgaa atcgaaccac   720
atcgatgcat tcaataaggc taactcagtg gaagtaaatg aatctctcaa gtattgggta   780
gatggagagc ccttaaaaag atttaggcag ctgggctcga acaaaggaa gcatcgttta    840 tga                                                                  843
```

<210> SEQ ID NO 43
<211> LENGTH: 744
<212> TYPE: DNA
<213> ORGANISM: Bacteroides thetaiotaomicron

<400> SEQUENCE: 43

```
atgagtgaag aaaataaaat agggacttat cagtttgtgg cagagccgtt tcacgtagat    60
tttaacggcc gtctgaccat gggcgtgctg gaaatcatc tgctgaattg cgcaggtttt   120
catgccagcg accgtggatt tggtattgct acgctgaacg aggacaatta cacatgggtg   180
cttccccgcc tggctatcga gctggatgag atgccttacc agtacgagaa gttctcggtt   240
cagacatggg tggagaatgt ctatcgtctc tttaccgacc gtaactttgc cgtcattgac   300
aaggatggaa agaagatcgg ctatgcccgt tccgtatggg cgatgatcaa tctgaatacc   360
cgtaagcctg ccgatctgtt ggcattgcat ggaggaagca tcgtcgatta tatatgcgat   420
gaaccttgcc cgatagaaaa gccttcgcgt atcaaggtga caagcaatca gcctgttgcg   480
acgctgacgg caaatacag tgatatcgat attaacggac acgtaaacag tattcgttat   540
atcgagcaca tacttgactt gtttccgata gaactgtatc agacgaaacg tatccgccgg   600
tttgaaatgg cgtatgtggc tgaaagttat ttcggagatg aactctcttt cttctgtgat   660
```

| | |
|---|---:|
| gaggtgagtg aaaacgagtt tcatgtagag gtgaagaaaa acggcagcga ggtagtatgc | 720 |
| cgttccaaag tgatatttga ataa | 744 |

<210> SEQ ID NO 44
<211> LENGTH: 1020
<212> TYPE: DNA
<213> ORGANISM: Geobacillus stearothermophilus

<400> SEQUENCE: 44

| | |
|---|---:|
| atgaaagccg ctgtagttga acaatttaag gaaccattaa aaataaaaga agtagaaaaa | 60 |
| ccaaccattt catatggaga agtattagtc cgcattaaag catgcggtgt ttgtcatact | 120 |
| gacttgcatg ccgctcacgg cgattggccg gtaaaaccaa aacttccttt aatccctggc | 180 |
| catgaaggag taggaattgt tgaagaagta ggtccaggcg taacccattt aaaagtgggc | 240 |
| gaccgcgttg gaattccttg gttatattct gcatgcggcc attgtgatta ttgtttaagc | 300 |
| ggccaagaga cattatgtga gcaccaaaaa aacgctggct actctgttga tggagggtat | 360 |
| gcagaatatt gcagagcggc agcagactat gtggttaaaa ttcctgacaa cttatcattt | 420 |
| gaagaagctg cccccaatttt ctgcgccgga gttactacct ataaagcgtt aaaagtaaca | 480 |
| ggggcaaaac caggagaatg ggtagcaatt tacggtatcg gcggccttgg acacgttgcc | 540 |
| gttcaatacg cgaaggcgat gggacttaat gtcgttgctg ttgatatcgg cgacgaaaaa | 600 |
| cttgaacttg caaaagaact tggcgctgat cttgttgtaa accctttgaa agaagatgca | 660 |
| gcgaaattta tgaaagagaa agtcggcgga gttcacgcag cagtcgtaac agctgtatct | 720 |
| aagccagcgt ttcaatctgc gtacaattct atccgcagag gcggagcttg tgtgcttgtc | 780 |
| ggattgccac cggaagaaat gcctattcca atttttgata cggttttaaa tggaatcaaa | 840 |
| atcatcggtt ccattgtcgg cacgcggaaa gacctgcaag aagcgctcca attcgcagcg | 900 |
| gaaggtaaag taaaaaccat tattgaagtg caacctcttg aaaaaattaa tgaagtattt | 960 |
| gacagaatgc taaaaggtca aattaacggg cgtgtagttt taacgttaga agataaataa | 1020 |

<210> SEQ ID NO 45
<211> LENGTH: 786
<212> TYPE: DNA
<213> ORGANISM: Lactobacillus plantarum

<400> SEQUENCE: 45

| | |
|---|---:|
| atggcaactt taggcgcaaa tgcgagtctt tacagtgaac agcaccggat tacgtattat | 60 |
| gaatgtgacc gcactggtcg cgcaaccttta acgacattaa ttgatattgc cgtactggca | 120 |
| tcagaggatc aaagcgacgc ccttggttta acgacggaaa tggtgcaaag ccatggtgtc | 180 |
| ggttgggtcg tcacgcaata tgccatcgat attacacgga tgccccgcca agacgaagtc | 240 |
| gttacgattg ccgttcgggg tagtgcttat aatccatatt ttgcttaccg tgaattttgg | 300 |
| attcgggacg cagatggtca acagttggcc tatattacga gtatctgggt catgatgagt | 360 |
| caaacgaccc ggcgaatcgt aaaaatttta ccagaactgg tcgcgccgta tcagtcggaa | 420 |
| gtcgtcaagc gtattccgcg cttgccacga ccgattagtt ttgaagcgac cgatacaacg | 480 |
| attacgaagc cgtaccatgt ccgcttcttt gacattgatc ccaaccggca tgttaataat | 540 |
| gcacactatt ttgattggct cgtagatacg ctacccgcga cgttcttgct tcaacatgat | 600 |
| ttagttcacg ttgacgttcg ctatgaaaat gaagtcaagt acgggcaaac ggtgactgct | 660 |
| catgcgaaca tcttaccgag cgaagtggcc gatcaggtca cgacgagtca tttgatcgaa | 720 |

-continued

```
gttgatgatg agaagtgttg tgaggtcacg attcaatggc ggactttacc agagccgatt    780
cagtaa                                                               786
```

<210> SEQ ID NO 46
<211> LENGTH: 696
<212> TYPE: DNA
<213> ORGANISM: Anaerococcus tetradius

<400> SEQUENCE: 46

```
atgaaattca agaagaaatt caaaatagga aggatgcatg tagatccttt taattatatc     60
tcaatgagat atctagttgc tcttatgaat gaagttgcct ttgatcaagc agagatactt    120 gaaaagaca tagatatgaa aaatctaagg tggataattt actcttggga tatacaaatc     180
gaaaacaata ttagactggg agaagaaata gaaatcacca caattcccac ccatatggat    240
aaattttatg cttataggga ctttatagtt gaaagtaggg gaaatatcct agcaagggct    300
aaagcgacct tcctattgat ggacattact aggcttcgtc ctataaaaat ccccaaaat    360 ctaagcctag catatggaaa ggaaaatcca atctttgata tctacgatat ggaaataaga    420
aatgacttag ccttcatcag agatattcag ttaagaagag cagatttgga taataatttc    480
cacataaaca atgccgtcta ttttgatttg attaaagaaa ctgtcgatat ttatgacaag    540
gatataagtt atatcaagct aatctacaga aatgaaatta gggataaaaa acaaattcaa    600
gctttcgcaa gaagagaaga taagtccata gactttgccc taagagggga agatggaaga    660
gattattgtt taggaaagat taaaactaat gtataa                              696
```

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 47

His His His His His His His
1               5

<210> SEQ ID NO 48
<211> LENGTH: 496
<212> TYPE: PRT
<213> ORGANISM: Escherichia coli

<400> SEQUENCE: 48

Met Ile Thr Glu Phe Val Phe Ile Pro Ile Phe Ala Ile Ala Ala Gly
1               5                   10                  15

Val Ala Gln Ser Leu Gln Tyr Leu Asn Arg Tyr His Val Ile Arg Glu
            20                  25                  30

Pro Pro Glu His Ile Leu Asn Arg Leu Pro Ser Ser Ala Ser Ala Leu
        35                  40                  45

Ala Cys Ser Ala His Ala Leu Asn Leu Ile Glu Lys Arg Thr Leu Asp
    50                  55                  60

His Glu Glu Met Lys Ala Leu Asn Arg Glu Val Ile Glu Tyr Phe Lys
65                  70                  75                  80

Glu His Val Asn Pro Gly Phe Leu Glu Tyr Arg Lys Ser Val Thr Ala
                85                  90                  95

Gly Gly Asp Tyr Gly Ala Val Glu Trp Gln Ala Gly Ser Leu Asn Thr
            100                 105                 110

```
Leu Val Asp Thr Gln Gly Gln Glu Phe Ile Asp Cys Leu Gly Gly Phe
            115                 120                 125
Gly Ile Phe Asn Val Gly His Arg Asn Pro Val Val Ser Ala Val
        130                 135                 140
Gln Asn Gln Leu Ala Lys Gln Pro Leu His Ser Gln Glu Leu Leu Asp
145                 150                 155                 160
Pro Leu Arg Ala Met Leu Ala Lys Thr Leu Ala Ala Leu Thr Pro Gly
                    165                 170                 175
Lys Leu Lys Tyr Ser Phe Phe Cys Asn Ser Gly Thr Glu Ser Val Glu
                180                 185                 190
Ala Ala Leu Lys Leu Ala Lys Ala Tyr Gln Ser Pro Arg Gly Lys Phe
            195                 200                 205
Thr Phe Ile Ala Thr Ser Gly Ala Phe His Gly Lys Ser Leu Gly Ala
            210                 215                 220
Leu Ser Ala Thr Ala Lys Ser Thr Phe Arg Lys Pro Phe Met Pro Leu
225                 230                 235                 240
Leu Pro Gly Phe Arg His Val Pro Phe Gly Asn Ile Glu Ala Met Arg
                    245                 250                 255
Thr Ala Leu Asn Glu Cys Lys Lys Thr Gly Asp Asp Val Ala Ala Val
                260                 265                 270
Ile Leu Glu Pro Ile Gln Gly Glu Gly Gly Val Ile Leu Pro Pro Pro
            275                 280                 285
Gly Tyr Leu Thr Ala Val Arg Lys Leu Cys Asp Glu Phe Gly Ala Leu
            290                 295                 300
Met Ile Leu Asp Glu Val Gln Thr Gly Met Gly Arg Thr Gly Lys Met
305                 310                 315                 320
Phe Ala Cys Glu His Glu Asn Val Gln Pro Asp Ile Leu Cys Leu Ala
                    325                 330                 335
Lys Ala Leu Gly Gly Gly Val Met Pro Ile Gly Ala Thr Ile Ala Thr
                340                 345                 350
Glu Glu Val Phe Ser Val Leu Phe Asp Asn Pro Phe Leu His Thr Thr
            355                 360                 365
Thr Phe Gly Gly Asn Pro Leu Ala Cys Ala Ala Ala Leu Ala Thr Ile
            370                 375                 380
Asn Val Leu Leu Glu Gln Asn Leu Pro Ala Gln Ala Glu Gln Lys Gly
385                 390                 395                 400
Asp Met Leu Leu Asp Gly Phe Arg Gln Leu Ala Arg Glu Tyr Pro Asp
                    405                 410                 415
Leu Val Gln Glu Ala Arg Gly Lys Gly Met Leu Met Ala Ile Glu Phe
                420                 425                 430
Val Asp Asn Glu Ile Gly Tyr Asn Phe Ala Ser Glu Met Phe Arg Gln
            435                 440                 445
Arg Val Leu Val Ala Gly Thr Leu Asn Asn Ala Lys Thr Ile Arg Ile
    450                 455                 460
Glu Pro Pro Leu Thr Leu Thr Ile Glu Gln Cys Glu Leu Val Ile Lys
465                 470                 475                 480
Ala Ala Arg Lys Ala Leu Ala Ala Met Arg Val Ser Val Glu Glu Ala
                485                 490                 495
```

METHODS AND MATERIALS FOR THE ENZYMATIC CONVERSION OF A NON-3-ENAL TO AZELAIC ACID

CROSS-REFERENCE TO RELATED APPLICATIONS

The present application is a continuation of U.S. patent application Ser. No. 16/351,324, filed Mar. 12, 2019, which is a continuation of U.S. patent application Ser. No. 15/421,164, filed Jan. 31, 2017, which claims the benefit of U.S. Provisional Application No. 62/289,877, filed Feb. 1, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 31, 2017, submitted Jan. 31, 2017 in parent U.S. application Ser. No. 15/421,164, and is named 12444_0626-00000_SL.txt and is 176,758 bytes in size.

TECHNICAL FIELD

This invention provides methods for biosynthesizing 7-carbon monomers. For example, the present invention provides methods for making two 9-carbon monomers from an 18-carbon intermediate and enzymatically converting the two 9-carbon monomers to 7-carbon monomers. For example, the present invention provides methods for making non-3-enal and 9-oxononanoate using a polypeptide having the activity of a hydroperoxide lyase and enzymatically converting non-3-enal and 9-oxononanoate to pimeloyl-CoA or a salt thereof using one or more polypeptides having the activity of a dehydrogenase, a CoA ligase, an isomerase, a reductase, a thioesterase, a monooxygenase, a hydratase, and/or a thiolase, or methods using microorganisms expressing one or more of such polypeptides. This invention also provides methods for converting pimeloyl-CoA or a salt thereof to one or more of pimelic acid, 7-aminoheptanoic acid, 7-hydroxyheptanoic acid, heptamethylenediamine, and 1,7-heptanediol, or corresponding salts thereof, using one or more polypeptides having the activity of a thioesterase, a CoA ligase, a CoA transferase, a dehydrogenase, a reductase, an acetyltransferase, a deacylase, and/or a transaminase or methods using recombinant microorganisms expressing one or more such polypeptides.

BACKGROUND

Nylons are synthetic polymers composed of polyamides, which are generally synthesized by the condensation polymerization of a diamine with a dicarboxylic acid. Similarly, nylons also may be produced by the condensation polymerization of lactams. Nylon 7 is produced by polymerisation of 7-aminoheptanoic acid, whereas Nylon 7,7 is produced by condensation polymerisation of pimelic acid and heptamethylenediamine. No economically cost competitive petrochemical routes exist to producing the monomers for Nylon 7 and Nylon 7,7.

Given the lack of economically cost competitive petrochemical monomer feedstocks, biotechnology offers an alternative approach via biocatalysis. Biocatalysis is the use of biological catalysts, such as enzymes, to perform biochemical transformations of, for example, bioderived feedstocks and petrochemical feedstocks, which can both be viable starting materials for the biocatalysis processes.

SUMMARY

Accordingly, against this background, it is clear that there is a need for sustainable methods for producing one or more of pimelic acid, 7-aminoheptanoate, 7-hydroxyheptanoate, heptamethylenediamine, and 1,7-heptanediol, or derivatives thereof, wherein the methods are biocatalyst based. This document is based at least in part on the discovery that it is possible to construct biochemical pathways using, inter alia, a polypeptide having the activity of a hydroperoxide lyase to produce two C9 (9-carbon) aliphatic molecules from a single C18 (18-carbon) molecule, and converting the two C9 molecules in one or more enzymatic steps to pimelic acid, 7-aminoheptanoic acid, 7-hydroxyheptanoic acid, heptamethylenediamine, or 1,7-heptanediol, or corresponding salts thereof. In particular, this document is based at least in part on the discovery that it is possible to construct biochemical pathways using, inter alia, a polypeptide having the activity of a hydroperoxide lyase to produce non-3-enal and 9-oxononanoate from 9-hydroxyperoxyoctadec-10,12-dienoate and converting at least one of non-3-enal and 9-oxononanoate in one or more enzymatic steps to pimelic acid, 7-aminoheptanoic acid, 7-hydroxyheptanoic acid, heptamethylenediamine or 1,7-heptanediol. Pimelic acid and pimelate, 7-hydroxyheptanoic acid and 7-hydroxyheptanoate, 9-oxononanoate and 9-oxononanoic acid, and 7-aminoheptanoic and 7-aminoheptanoate are used interchangeably herein to refer to the compounds in any of their neutral or ionized forms, including any salt forms thereof. It is understood by those skilled in the art that the specific form will depend on pH.

For compounds containing carboxylic acid groups such as organic monoacids, hydroxyacids, aminoacids, and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as, but not limited to, organic amines, aminoacids, and diamines, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as, but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include aluminum hydroxide, calcium hydroxide, potassium hydroxide, sodium carbonate, sodium hydroxide, and the like; or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

It has been discovered that appropriate non-natural pathways, feedstocks, microorganisms, attenuation strategies to the microorganism's biochemical network, and cultivation strategies may be combined to efficiently produce pimeloyl-CoA as a C7 (7-carbon) building block, or convert pimeloyl-CoA to other C7 building blocks such as pimelic acid, 7-aminoheptanoic acid, 7-hydroxyheptanoic acid, heptamethylenediamine, or 1,7-heptanediol.

In some embodiments, a terminal carboxyl group can be enzymatically formed using a polypeptide having the activity of a thioesterase, a CoA transferase, a CoA ligase, an aldehyde dehydrogenase, a succinate-semialdehyde dehydrogenase, a 5-oxopentanoate dehydrogenase, a 6-oxohexanoate dehydrogenase, or a 7-oxoheptanoate dehydrogenase. See FIG. 3.

In some embodiments, a terminal amine group can be enzymatically formed using a polypeptide having the activity of a ω-transaminase or a deacylase. See FIG. 4 and FIG. 5. The polypeptide having the activity of a ω-transaminase can have at least 70% sequence identity to any one of the amino acid sequences set forth in SEQ ID NOs: 7-12. Furthermore, the polypeptide having the activity of a ω-transaminase can have at least 70% sequence identity to any one of the amino acid sequences set forth in SEQ ID NOs: 7-12 and be capable of transferring at least one amine group separated from a carbonyl group by at least one methylene insertion.

In some embodiments, a terminal hydroxyl group can be enzymatically formed using a polypeptide having the activity of an alcohol dehydrogenase. See FIG. 4 and FIG. 7.

In one aspect, this document features a method of producing non-3-enal and 9-oxononanoate from 9-hydroxyperoxyoctadec-10,12-dienoate using a polypeptide having the activity of a hydroperoxide lyase classified under EC 4.2.99.-.

In any of the methods, non-3-enal and 9-oxononanoate can be enzymatically produced from 9-hydroxyperoxyoctadec-10,12-dienoate, which itself can be enzymatically produced from octadecanoyl-CoA using one or more polypeptides having the activity of a delta9-desaturase, a delta12-desaturase, a thioesterase, and/or a 9-lipoxygenase. The polypeptide having the activity of a delta9-desaturase can be classified under EC 1.14.19.1, such as, for example, the gene product of Le-FAD1 from *Lentinula edodes* (UniProtKB Accession No. Q76C19), the gene product of SCD1 from *Mesocricetus auratus* (UniProtKB Accession No. A7LCI9), an acyl-CoA-delta9-3a-desaturase from *Dendrolimus punctatus* (UniProtKB Accession No. B7SB75), the gene product of scd1 from *Rattus norvegicus* (UniProtKB Accession No. P07308), the gene product of PF3D7_0511200 from *Plasmodium falciparum* (UniProtKB Accession No. Q8I0W9), or the gene product of desB1 from *Bombus lucorum* (UniProtKB Accession No. A5CKE1).

The polypeptide having the activity of a delta12-desaturase can be classified under EC 1.14.19.6, such as, for example, the gene product of D12Des from *Acheta domesticus* (UniProtKB Accession No. B7SB91), the gene product of FAD2 from *Gossypium hirsutum* (UniProtKB Accession No. Q8W2B9), the gene product of CFad6 from *Chlorella vulgaris* (UniProtKB Accession No. D3U658), a delta12 fatty acid desaturase from *Triadica sebifera* (UniProtKB Accession No. A5J295), the gene product of Pc-fad2 from *Phanerochaete chrysosporium* (UniProtKB Accession No. D4Q8H2), the gene product of Cs-fad2 from *Ceriporiopsis subvermispora* (UniProtKB Accession No. D4Q8S6), or the gene product of AN1037.2 from *Emericella nidulans* (UniProtKB Accession No. Q5BEJ3).

The polypeptide having the activity of a thioesterase can be classified under EC 3.1.2.-, such as, for example, the gene product of BT_2075 from *Bacteroides thetaiotaomicron* (strain ATCC 29148/DSM 2079/NCTC 10582/E50/VPI-5482) (GenBank Accession No. AAO77182.1, SEQ ID NO: 20), the gene product of lp_0708 from *Lactobacillus plantarum* (strain ATCC BAA-793/NCIMB8826/WCFS1) (GenBank Accession No. CCC78182.1, SEQ ID NO: 22), the gene product of CPF_2954 from *Clostridium perfringens* (strain ATCC 13124/DSM 756/JCM 1290/NCIMB 6125/NCTC 8237/Type A) (GenBank Accession No. ABG82470.1, SEQ ID NO: 18), or the gene product of HMPREF0077_1317 from *Anaerococcus tetradius* ATCC 35098 (GenBank Accession No. EEI82564.1, SEQ ID NO: 23).

The polypeptide having the activity of a 9-lipoxygenase can be classified, for example, under EC 1.13.11.58, EC 1.13.11.60, EC 1.13.11.61, or EC 1.13.11.62, such as, for example, an allene oxide synthase-lipoxygenase protein from *Plexaura homomalla* (UniProtKB Accession No. O16025), a Psi-producing oxygenase A from *Emericella nidulans* (UniProtKB Accession No. Q6RET3), a 5,8-linoleate diol synthase from *Aspergillus fumigatus* (UniProtKB Accession No. C1KH66), or a linoleate diol synthase from *Gaeumannomyces graminis* (UniProtKB Accession No. Q9UUS2).

The method includes enzymatically converting non-3-enal to azelaic acid via two alternative enzymatic pathways. The method also includes enzymatically converting 9-oxononanoate to azelaic acid.

In one aspect, the method includes converting non-3-enal to azelaic acid using one or more polypeptides having the enzymatic activities of an aldehyde dehydrogenase, a CoA ligase, a dodecenoyl-CoA isomerase, a trans-2-enoyl-CoA reductase, a thioesterase, a monooxygenase, an alcohol dehydrogenase, a succinate semialdehyde dehydrogenase, a 5-oxopentanoate dehydrogenase, a 6-oxohexanoate dehydrogenase, and/or a 7-oxoheptanoate dehydrogenase.

The polypeptide having the activity of an aldehyde dehydrogenase can be classified under EC 1.2.1.-, for example, EC 1.2.1.3, EC 1.2.1.4, EC 1.2.1.5, or EC 1.2.1.48, such as, for example, the gene product of Bt-aldh from *Geobacillus thermoleovorans* B23 (UniProtKB Accession No. Q9FAB1), the gene product of dhaS from *Bacillus subtilis* (UniProtKB Accession No. O34660), the gene product of ALD5 from *Saccharomyces cerevisiae* (UniProtKB Accession No. A6ZR27), the gene product of ALDH2C4 from *Arabidopsis thaliana* (UniProtKB Accession No. Q56YU0), the gene product of aldh7 from *Rhodococcus ruber* (UniProtKB Accession No. Q840S9), the gene product of alkH from *Pseudomonas oleovorans* (UniProtKB Accession No. P12693), the gene product of ald1 from *Acinetobacter* sp. M-1 (UniProtKB Accession No. Q9FDS1), or the gene product of acoD from *Ralstonia eutropha* (UniProtKB Accession No. P46368).

The polypeptide having the activity of a CoA ligase can be classified under EC 6.2.1.-, such as, for example, the gene product of acs6 from *Brassica napus* (UniProtKB Accession No. Q9FNT6), the gene product of PCS60 from *Saccharomyces cerevisiae* (UniProtKB Accession No. P38137), the gene product of alkK from *Pseudomonas oleovorans* (UniProtKB Accession No. Q00594), the gene product of ACSM5 from *Homo sapiens* (UniProtKB Accession No. Q6NUN0), or the gene product of alkK from *Aeropyrum pernix* (UniProtKB Accession No. Q9YF45).

The polypeptide having the activity of a dodecenoyl-CoA isomerase can be classified under EC 5.3.3.8, such as, for example, the gene product of ECI1 from *Saccharomyces cerevisiae* (SEQ ID NO: 17 and SEQ ID NO: 19).

The polypeptide having the activity of a trans-2-enoyl-CoA reductase can be classified under EC 1.3.1.38, EC 1.3.1.44, or EC 1.3.1.8. The polypeptide having the activity of a thioesterase can be classified under EC 3.1.2.-. The polypeptide having the activity of a monooxygenase can be classified under EC 1.14.14.1, EC 1.14.14.3, EC 1.14.15.1, or EC 1.14.15.3. The polypeptide having the activity of an alcohol dehydrogenase can be classified under EC 1.1.1.-, such as, for example, a 4-hydroxybutanoate dehydrogenase classified under EC 1.1.1.61, such as, for example, the gene product of gbd, or a 6-hydroxyhexanoate dehydrogenase classified under EC 1.1.1.258, such as, for example, the gene product of chnD from *Acinetobacter* sp. NCIMB9871 (Donoghue et al., Eur. J. Biochem, 1975, 60: 1-7). The polypeptide having the activity of a succinate semialdehyde dehydrogenase can be classified under EC 1.2.1.16, EC 1.2.1.24, or EC 1.2.1.79. The polypeptide having the activity of a 5-oxopentanoate dehydrogenase can be classified under EC 1.2.1.20, such as that encoded by cpnE from *Comamonas* sp. The polypeptide having the activity of a 6-oxohexanoate dehydrogenase can be classified under EC 1.2.1.63, such as that encoded by chnE from *Acinetobacter* sp., and the polypeptide having the activity of a 7-oxoheptanoate dehydrogenase can be classified under EC 1.2.1.- (e.g., the gene product of thnG from *Sphingomonas macrogolitabida*).

In an alternative aspect, the method includes converting non-3-enal to azelaic acid using one or more polypeptides having the enzymatic activities of an enal isomerase, an enoate reductase, an aldehyde dehydrogenase, a monooxygenase, an alcohol dehydrogenase, a succinate semialdehyde dehydrogenase, a 5-oxopentanoate dehydrogenase, a 6-oxohexanoate dehydrogenase, and/or a 7-oxoheptanoate dehydrogenase. The polypeptide having the activity of an enal isomerase can be classified under EC 5.3.3.-, such as, for example, the gene product of ECI1 from *Saccharomyces cerevisiae* (SEQ ID NO: 17 and SEQ ID NO: 19); Geisbrecht et al J. Biol. Chem, 1998 273 (50) 33184-33191.) The polypeptide having the activity of an enoate reductase can be classified under EC 1.3.1.31. The polypeptide having the activity of an aldehyde dehydrogenase can be classified under EC 1.2.1.-, for example, EC 1.2.1.3, EC 1.2.1.4, EC 1.2.1.5, or EC 1.2.1.48. The polypeptide having the activity of a monooxygenase can be classified under EC 1.14.14.1, EC 1.14.14.3, EC 1.14.15.1, or EC 1.14.15.3. The polypeptide having the activity of an alcohol dehydrogenase can be classified under EC 1.1.1.-, for example, a 4-hydroxybutanoate dehydrogenase classified under EC 1.1.1.61, such as, for example, the gene product of gbd, or a 6-hydroxyhexanoate dehydrogenase classified under EC 1.1.1.258, such as, for example, the gene product of chnD from *Acinetobacter* sp. NCIMB9871 (Donoghue et al., Eur. J. Biochem, 1975, 60:1-7).

The polypeptide having the activity of a succinate semialdehyde dehydrogenase can be classified under EC 1.2.1.16, EC 1.2.1.24, or EC 1.2.1.79, such as, for example, the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from *Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9).

The polypeptide having the activity of a 5-oxopentanoate dehydrogenase can be classified under EC 1.2.1.20, such as that encoded by cpnE from *Comamonas* sp. The polypeptide having the activity of a 6-oxohexanoate dehydrogenase can be classified under EC 1.2.1.63, such as that encoded by chnE from *Acinetobacter* sp., and the polypeptide having the activity of a 7-oxoheptanoate dehydrogenase can be classified under EC 1.2.1.- (e.g., the gene product of thnG from *Sphingomonas macrogolitabida*).

In a further aspect, the method includes converting 9-oxononanoate to azelaic acid using a polypeptide classified under EC 1.2.1.-, such as EC 1.2.1.3, EC 1.2.1.16, EC 1.2.1.20, EC 1.2.1.24, EC 1.2.1.63, or EC 1.2.1.79. The polypeptides classified under EC 1.2.1.3 have the activity of an aldehyde dehydrogenase. The polypeptides classified under EC 1.2.1.16, EC 1.2.1.24, or EC 1.2.1.79 have the activity of a succinate semialdehyde dehydrogenase, such as, for example, the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from *Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9). The polypeptides classified under EC 1.2.1.20 have the activity of a 5-oxopentanoate dehydrogenase, such as that encoded by cpnE from *Comamonas* sp. The polypeptides classified under EC 1.2.1.63 have the activity of a 6-oxohexanoate dehydrogenase, such as that encoded by chnE from *Acinetobacter* sp. Further polypeptides classified under EC 1.2.1.- have the activity of a 7-oxoheptanoate dehydrogenase (e.g., the gene product of thnG from *Sphingomonas macrogolitabida*).

In the above-described enzymatic pathways, both non-3-enal and 9-oxononanoate are converted to azelaic acid. Azelaic acid is then converted to pimeloyl-CoA using one or more polypeptides having the enzymatic activities of a CoA ligase, an acyl-CoA dehydrogenase, an enoyl-CoA hydratase, a 3-hydroxyacyl-CoA dehydrogenase, a 3-oxoacyl-ACP reductase, and/or a β-ketothiolase.

The polypeptide having the activity of a CoA ligase can be classified under EC 6.2.1.-, such as, for example, the gene product of acs6 from *Brassica napus* (UniProtKB Accession No. Q9FNT6), the gene product of PCS60 from *Saccharomyces cerevisiae* (UniProtKB Accession No. P38137), the gene product of alkK from *Pseudomonas oleovorans* (UniProtKB Accession No. Q00594), the gene product of ACSM5 from *Homo sapiens* (UniProtKB Accession No. Q6NUN0), or the gene product of alkK from *Aeropyrum pernix* (UniProtKB Accession No. Q9YF45). The polypeptide having the activity of an acyl-CoA dehydrogenase can be classified under EC 1.3.8.-, such as EC 1.3.8.6, EC 1.3.8.7, or EC 1.3.8.8. The polypeptide having the activity of an enoyl-CoA hydratase can be classified under EC 4.2.1.17 or EC 4.2.1.119. The polypeptide having the activity of a 3-hydroxyacyl-CoA dehydrogenase can be classified under EC 1.1.1.35, EC 1.1.1.36, or EC 1.1.1.157, and the polypeptide having the activity of a 3-oxoacyl-ACP reductase may be classified, for example, under EC 1.1.1.100. The polypeptide having the activity of a f-ketothiolase can be classified under EC 2.3.1.16 or EC 2.3.1.174. The polypeptide having the activity of a β-ketothiolase is capable of converting 3-oxo-azelaoyl-CoA to pimeloyl-CoA.

Any of the methods further can include enzymatically converting pimeloyl-CoA to pimelic acid, 7-aminoheptanoate, 7-hydroxyheptanoate, heptamethylenediamine, or 1,7-heptanediol or their corresponding salts in one or more steps.

For example, pimeloyl-CoA can be enzymatically converted to pimelic acid using one or more polypeptides having the activity of a thioesterase, a CoA ligase, a CoA transferase, an aldehyde dehydrogenase, a 5-oxopentanoate dehydrogenase, a 6-oxohexanoate dehydrogenase, a 7-oxoheptanoate dehydrogenase, and/or a succinate-semialdehyde dehydrogenase. See FIG. 3.

For example, pimeloyl-CoA can be enzymatically converted to 7-aminoheptanoate using one or more polypeptides having the activity of an acetylating aldehyde dehydrogenase and/or a ω-transaminase. See FIG. 4.

For example, pimeloyl-CoA can be enzymatically converted to pimelate (pimelic acid) as previously described in FIG. 3, and pimelate can be enzymatically converted to 7-aminoheptanoate using one or more polypeptides having the enzymatic activity of a carboxylate reductase and/or a ω-transaminase. See FIG. 4. The polypeptide having the activity of a ω-transaminase can have at least 70% sequence identity to any one of the amino acid sequences set forth in SEQ ID NOs: 7-12.

For example, pimeloyl-CoA can be enzymatically converted to 7-hydroxyheptanoate using one or more polypeptides having the enzymatic activity of an acetylating aldehyde dehydrogenase and/or an alcohol dehydrogenase. In particular, pimeloyl-CoA can be enzymatically converted to 7-hydroxyheptanoate using one or more polypeptides having the enzymatic activity of an acetylating aldehyde dehydrogenase and one or more polypeptides having the enzymatic activity of a 4-hydroxybutanoate dehydrogenase, a 5-hydroxypentanoate dehydrogenase, and/or a 6-hydroxyhexanoate dehydrogenase. See FIG. 6.

For example, pimeloyl-CoA can be enzymatically converted to pimelate (pimelic acid) as previously described in FIG. 3, and pimelate can be enzymatically converted to 7-hydroxyheptanoate using one or more polypeptides having the enzymatic activity of a carboxylate reductase and/or an alcohol dehydrogenase. In particular, pimelate can be enzymatically converted to 7-hydroxyheptanoate using one or more polypeptides having the enzymatic activity of a carboxylate reductase and one or more polypeptides having the enzymatic activity of a 4-hydroxybutanoate dehydrogenase, a 5-hydroxypentanoate dehydrogenase, and/or a 6-hydroxyhexanoate dehydrogenase. See FIG. 6.

For example, 7-aminoheptanoate and 7-hydroxyheptanoate can be converted to heptamethylenediamine using one or more polypeptides having the activity of a carboxylate reductase, a ω-transaminase, an alcohol dehydrogenase, an N-acetyltransferase, and/or a deacylase. See FIG. 5. The polypeptide having the activity of a carboxylate reductase can have at least 70% sequence identity to any one of the amino acid sequences set forth in SEQ ID NOs: 1-6. The polypeptide having the activity of a ω-transaminase can have at least 70% sequence identity to any one of the amino acid sequences set forth in SEQ ID NOs: 7-12. For example, pimeloyl-CoA can be converted to pimelate semialdehyde (see FIG. 3, FIG. 4, and FIG. 6), and subsequently pimelate semialdehyde can be converted to heptamethylenediamine using one or more polypeptides having the activity of a carboxylate reductase and/or a ω-transaminase. See FIG. 5.

The polypeptide having the activity of a carboxylate reductase can have at least 70% sequence identity to any one of the amino acid sequences set forth in SEQ ID NO: 1-6. The polypeptide having the activity of a ω-transaminase can have at least 70% sequence identity to any one of the amino acid sequences set forth in SEQ ID NOs: 7-12.

For example, pimeloyl-CoA can be converted to 7-hydroxyheptanoate (see FIG. 6), and subsequently 7-hydroxyheptanoate can be converted to 1,7-heptanediol using polypeptides having the activity of a carboxylate reductase and an alcohol dehydrogenase. See FIG. 7.

The polypeptide having the activity of a carboxylate reductase can have at least 70% sequence identity to any one of the amino acid sequences set forth in SEQ ID NOs: 1-6.

In any of the methods described herein, pimelic acid can be produced by forming the second terminal functional group in pimeloyl-CoA using a polypeptide having the activity of: (i) a thioesterase classified under EC 3.1.2.-, (ii) a CoA ligase classified under EC 6.2.1.-, such as EC 6.2.1.5 or EC 6.2.1.15, and/or (iii) a CoA transferase classified under EC 2.8.3.-, such as EC 2.8.3.8 or EC 2.8.3.12.

In any of the methods described herein, pimelic acid can be produced by forming the second terminal functional group in pimelate semialdehyde (also known as 7-oxoheptanoate) using a polypeptide having the activity of (i) an aldehyde dehydrogenase classified under EC 1.2.1.3, or (ii) a succinate semialdehyde dehydrogenase classified under EC 1.2.1.16, EC 1.2.1.24, or EC 1.2.1.79, a 5-oxopentanoate dehydrogenase classified under EC 1.2.1.-, for example, EC 1.2.1.20, such as that encoded by cpnE from *Comamonas* sp., a 6-oxohexanoate dehydrogenase classified under EC 1.2.1.63, such as that encoded by chnE from *Acinetobacter* sp., or a 7-oxoheptanoate dehydrogenase classified under EC 1.2.1.- (e.g., the gene product of thnG from *Sphingomonas macrogolitabida*). See FIG. 3.

In any of the methods described herein, 7-aminoheptanoic acid can be produced by forming the second terminal functional group in pimelate semialdehyde using a polypeptide having the activity of a ω-transaminase classified under EC 2.6.1.-. See FIG. 4.

In any of the methods described herein, 7-hydroxyheptanoic acid can be produced by forming the second terminal functional group in pimelate semialdehyde using a polypeptide having the activity of an alcohol dehydrogenase classified under EC 1.1.1.-, a 6-hydroxyhexanoate dehydrogenase classified under EC 1.1.1.258, such as, for example, the gene product of chnD from *Acinetobacter* sp. NCIMB9871 (Donoghue et al., Eur. J. Biochem, 1975, 60: 1-7); a 5-hydroxypentanoate dehydrogenase classified under EC 1.1.1.-, such as, for example, the gene product of cpnD from *Comamonas* sp. (Iwaki et al., *Appl. Environ. Microbiol.*, 1999, 65(11):5158-5162), or a 4-hydroxybutanoate dehydrogenase classified under EC 1.1.1.61, such as, for example, the gene product of gbd. See FIG. 6.

In any of the methods described herein, heptamethylenediamine can be produced by forming a second terminal functional group in (i) 7-aminoheptanal using a polypeptide having the activity of a co-transaminase classified under EC 2.6.1.-, such as, for example, EC 2.6.1.18, EC 2.6.1.19, EC 2.6.1.29, EC 2.6.1.48, or EC 2.6.1.82 or in (ii) N7-acetyl-1,7-diaminoheptane using a deacylase classified, for example, under EC 3.5.1.-, such as, for example, EC 3.5.1.62 or EC 3.5.1.82, such as that encoded by dag from *Alcaligenes xylosoxydans* xylosoxydans (*Achromobacter xylosoxidans*) (UniProtKB Accession No. P94211). See FIG. 5.

In any of the methods described herein, 1,7-heptanediol can be produced by forming the second terminal functional group in 7-hydroxyheptanal using a polypeptide having the activity of an alcohol dehydrogenase classified under EC 1.1.1.- (e.g., EC 1.1.1.1, EC 1.1.1.2, EC 1.1.1.21, or EC 1.1.1.184), such as that encoded by YMR318C from *Saccharomyces cerevisiae*, yqhD from *Escherichia coli*, or as represented by GenBank Accession No. CAA81612.1 (SEQ ID NO: 21). See FIG. 7.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, plant oils, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

In some embodiments, the microorganism's tolerance to high concentrations of one or more C7 (7-carbon) building blocks is improved through continuous cultivation in a selective environment.

In some embodiments, the microorganism's biochemical network is attenuated or augmented to (1) ensure the intracellular availability of acetyl-CoA or malonyl-CoA, (2) create an NADH or NADPH imbalance that may only be balanced via the formation of one or more C7 building blocks, (3) prevent degradation of central metabolites, central precursors leading to and including C7 building blocks, and/or (4) ensure efficient efflux from the cell.

As used herein, "attenuation" refers to downregulation or inactivation of gene expression.

In some embodiments, a cultivation strategy is used to achieve anaerobic, micro-aerobic, or aerobic cultivation conditions.

In some embodiments, the cultivation strategy includes limiting nutrients, such as limiting nitrogen, phosphate, or oxygen.

In some embodiments, one or more C7 building blocks are produced by a single type of microorganism, e.g., a recombinant microorganism containing one or more exogenous nucleic acids, using, for example, a fermentation strategy. In some embodiments, one or more C7 building blocks are produced by a single type of microorganism having one or more exogenous nucleic acids which encode polypeptides having the activity of a hydroxperoxide lyase, aldehyde dehydrogenase, a CoA ligase, a dodecenoyl-CoA isomerase, a trans-2-enoyl-CoA reductase, a thioesterase, a monooxygenase, an alcohol dehydrogenase, a succinate-semialdehyde dehydrogenase, a 5-oxopentanoate dehydrogenase, a 6-oxohexanoate dehydrogenase, a 7-oxoheptanoate dehydrogenase, an acyl-CoA dehydrogenase, an enoyl-CoA hydratase, a 3-hydroxyacyl-CoA dehydrogenase, a 3-oxoacyl CoA dehydrogenase, and/or a β-ketothiolase. Said microorganism produces pimeloyl-CoA from 9-hydroxyperoxyoctadec-10,12-dienoate. See FIG. 1.

In another aspect, this document features a recombinant microorganism that includes at least one exogenous nucleic acid encoding a polypeptide having the activity of a hydroxperoxide lyase, an enal isomerase, an enoate reductase, an aldehyde dehydrogenase, a monoxygenase, an alcohol dehydrogenase, a succinate-semialdehyde dehydrogenase, a 5-oxopentanoate dehydrogenase, a 6-oxohexanoate dehydrogenase, a 7-oxoheptanoate dehydrogenase, a CoA ligase, an acyl-CoA dehydrogenase, an enoyl-CoA hydratase, a 3-hydroxyacyl-CoA dehydrogenase, a 3-oxoacyl CoA dehydrogenase, and/or a β-ketothiolase. Said microorganism produces pimeloyl-CoA from 9-hydroxyperoxyoctadec-10, 12-dienoate. See FIG. 2.

In another aspect, this document features a recombinant microorganism that includes at least one exogenous nucleic acid encoding a polypeptide having the activity of an aldehyde dehydrogenase, a succinate-semialdehyde dehydrogenase, a 5-oxopentanoate dehydrogenase, a 6-oxohexanoate dehydrogenase, a 7-oxoheptanoate dehydrogenase, a CoA ligase, an acyl-CoA dehydrogenase, an enoyl- CoA hydratase, a 3-hydroxyacyl-CoA dehydrogenase, a 3-oxoacyl CoA dehydrogenase, and a β-ketothiolase. Said microorganism produces pimeloyl-CoA from 9-oxononanoate. See FIG. 1 and FIG. 2.

A microorganism producing pimeloyl-CoA further can include one or more polypeptides having the activity of: (i) a thioesterase, (ii) a CoA ligase, (iii) a CoA transferase, and/or (iv) an acetylating aldehyde dehydrogenase and one of a succinate-semialdehyde dehydrogenase, a 5-oxopentanoate dehydrogenase, a 6-oxohexanoate dehydrogenase, and/or a 7-oxoheptanoate dehydrogenase; the microorganism further producing pimelic acid or a salt thereof. See FIG. 3.

A microorganism producing pimeloyl-CoA further can include one or more polypeptides having the activity of an acetylating aldehyde dehydrogenase and/or a co-transaminase, the microorganism further producing 7-aminoheptanoate or a salt thereof. A microorganism producing pimeloyl-CoA further can include one or more of the exogenous polypeptides as described directly above for producing pimelate, and a microorganism producing pimelate further can include one or more exogenous polypeptides having the activity of: carboxylate reductase and/or a co-transaminase, the microorganism further producing 7-aminoheptanoate or a salt thereof. See FIG. 4.

A microorganism producing pimeloyl-CoA further can include one or more of the following exogenous polypeptides having the activity of: an acetylating aldehyde dehydrogenase, an alcohol dehydrogenase, a 4-hydroxybutanoate dehydrogenase, a 5-hydroxypentanoate dehydrogenase, and a 6-hydroxyhexanoate dehydrogenase, the microorganism further producing 7-hydroxyheptanoate or a salt thereof. A microorganism producing pimeloyl-CoA further can include one or more of the exogenous polypeptides as described directly above for producing pimelate, and a microorganism producing pimelate further can include one or more polypeptides having the activity of carboxylate reductase and/or a co-transaminase, the microorganism further producing 7-aminoheptanoate or a salt thereof. A microorganism producing pimeloyl-CoA further can include one or more exogenous polypeptides having the activity of: an acetylating aldehyde dehydrogenase, an alcohol dehydrogenase, a 4-hydroxybutanoate dehydrogenase, a 5-hydroxypentanoate dehydrogenase, and/or a 6-hydroxyhexanoate dehydrogenase, the microorganism further producing 7-hydroxyheptanoate or a salt thereof. A microorganism producing pimeloyl-CoA further can include one or more of the exogenous polypeptides as described directly above for producing pimelate, and a microorganism producing pimelate further can include one or more exogenous polypeptides having the activity of: a carboxylate reductase and an alcohol dehydrogenase, a 4-hydroxybutanoate dehydrogenase, a 5-hydroxypentanoate dehydrogenase, and/or a 6-hydroxyhexanoate dehydrogenase, the microorganism further producing 7-hydroxyheptanoate or a salt thereof. See FIG. 6.

A microorganism producing pimeloyl-CoA further can include one or more of the exogenous polypeptides as described above for producing 7-aminoheptanoate or 7-hydroxyheptanoate, and a microorganism producing 7-aminoheptanoate or 7-hydroxyheptanoate can further include one or more of the exogenous polypeptides having the activity of: a carboxylate reductase, a co-transaminase, an alcohol dehydrogenase, an N-acetyltransferase, and/or a deacylase, said microorganism further producing heptamethylenediamine. A microorganism producing pimelate semialdehyde (see FIG. 3, FIG. 4, and FIG. 6) can further include one or more polypeptides having the activity of a carboxylate reductase and/or a co-transaminase, said microorganism further producing heptamethylenediamine or a salt thereof. See FIG. 5.

A microorganism producing pimeloyl-CoA further can include one or more of the exogenous polypeptides as described above for producing 7-hydroxyheptanoate, and a microorganism producing 7-hydroxyheptanoate can further include one or more of the exogenous polypeptides having the activity of a carboxylate reductase and/or an alcohol dehydrogenase, the microorganism further producing 1,7-heptanediol. See FIG. 7.

Any of the recombinant microorganisms described herein further can include one or more of exogenous polypeptides having the activity of: a delta9-desaturase, a delta12-desaturase, a thioesterase, and/or a 9-lipoxygenase.

Any of the recombinant microorganisms can be a prokaryote, such as a prokaryote from a genus selected from *Escherichia*, *Clostridia*, *Corynebacteria*, *Cupriavidus*, *Pseudomonas*, *Delftia*, *Bacillus*, *Lactobacillus*, *Lactococcus*, and *Rhodococcus*. For example, the prokaryote can be selected from *Escherichia coli*, *Clostridium ljungdahlii*, *Clostridium autoethanogenum*, *Clostridium kluyveri*, *Corynebacterium glutamicum*, *Cupriavidus necator*, *Cupriavidus metallidurans*. *Pseudomonas fluorescens*, *Pseudomonas putida*, *Pseudomonas oleavorans*, *Delftia acidovorans*, *Bacillus subtillis*, *Lactobacillus delbrueckii*, *Lactococcus lactis*, and *Rhodococcus equi*. Such prokaryotes also can be sources of genes for constructing recombinant cells described herein that are capable of producing C7 building blocks.

Any of the recombinant microorganisms can be a eukaryote such as a eukaryote from a genus selected from *Aspergillus*, *Saccharomyces*, *Pichia*, *Yarrowia*, *Issatchenkia*, *Debaryomyces*, *Arxula*, and *Kluyveromyces*. For example, the eukaryote can be selected from *Aspergillus niger, Saccharomyces cerevisiae*, *Pichia pastoris*, *Yarrowia lipolytica*, *Issathenkia orientalis*, *Debaryomyces hansenii*, *Arxula adenoinivorans*, and *Kluyveromyces lactis*. Such eukaryotes also can be sources of genes for constructing recombinant cells described herein that are capable of producing C7 building blocks.

Any of the recombinant microorganisms described herein further can include attenuation of one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, an NADH-consuming transhydrogenase, an NADH-specific glutamate dehydrogenase, an NADH/NADPH-utilizing glutamate dehydrogenase, a pimeloyl-CoA dehydrogenase, an acyl-CoA dehydrogenase accepting C7 building blocks and central precursors as substrates, a butyryl-CoA dehydrogenase, or an adipyl-CoA synthetase.

Any of the recombinant microorganisms described herein further can overexpress one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

In another aspect, this document features a non-naturally occurring microorganism comprising at least one exogenous nucleic acid encoding at least one polypeptide having the activity of at least one enzyme, at least one substrate, and at least one product, as depicted in any one of FIG. 1 to 7.

In another aspect, this document features a nucleic acid construct or expression vector comprising a polynucleotide encoding a polypeptide having carboxylate reductase activity, wherein the polynucleotide is operably linked to one or more heterologous control sequences that direct production of the polypeptide and wherein the polypeptide having carboxylate reductase activity is selected from: (a) a polypeptide having at least 70% sequence identity to the polypeptide of SEQ ID NO: 1; (b) a polypeptide having at least 70% sequence identity to the polypeptide of SEQ ID NO: 2; (c) a polypeptide having at least 70% sequence identity to the polypeptide of SEQ ID NO: 3; (d) a polypeptide having at least 70% sequence identity to the polypeptide of SEQ ID NO: 4, (e) a polypeptide having at least 70% sequence identity to the polypeptide of SEQ ID NO: 5 and (f) a polypeptide having at least 70% sequence identity to the polypeptide of SEQ ID NO: 6.

In another aspect, this document features a nucleic acid construct or expression vector comprising a polynucleotide encoding a polypeptide having ω-transaminase activity, wherein the polynucleotide is operably linked to one or more heterologous control sequences that direct production of the polypeptide and wherein the polypeptide having ω-transaminase activity is selected from: (a) a polypeptide having at least 70% sequence identity to the polypeptide of SEQ ID NO: 7; (b) a polypeptide having at least 70% sequence identity to the polypeptide of SEQ ID NO: 8; (c) a polypeptide having at least 70% sequence identity to the polypeptide of SEQ ID NO: 9; (d) a polypeptide having at least 70% sequence identity to the polypeptide of SEQ ID NO: 10; (e) a polypeptide having at least 70% sequence identity to the polypeptide of SEQ ID NO: 11 or SEQ ID NO: 48; and (f) a polypeptide having at least 70% sequence identity to the polypeptide of SEQ ID NO: 12.

In another aspect, this document features a nucleic acid construct or expression vector comprising a polynucleotide encoding a polypeptide having hydroperoxide lyase activity, wherein the polynucleotide is operably linked to one or more heterologous control sequences that direct production of the polypeptide and wherein the polypeptide having hydroperoxide lyase activity is selected from: (a) a polypeptide having at least 70% sequence identity to the polypeptide of SEQ ID NO: 13 and (b) a polypeptide having at least 70% sequence identity to the polypeptide of SEQ ID NO: 14.

In another aspect, this document features a nucleic acid construct or expression vector comprising a polynucleotide encoding a polypeptide having enoate reductase activity, wherein the polynucleotide is operably linked to one or more heterologous control sequences that direct production of the polypeptide and wherein the polypeptide having enoate reductase activity is selected from: (a) a polypeptide having at least 70% sequence identity to the polypeptide of SEQ ID NO: 15 and (b) a polypeptide having at least 70% sequence identity to the polypeptide of SEQ ID NO: 16.

In another aspect, this document features a nucleic acid construct or expression vector comprising a polynucleotide encoding a polypeptide having isomerase activity, wherein the polynucleotide is operably linked to one or more heterologous control sequences that direct production of the polypeptide and wherein the polypeptide having isomerase activity is a polypeptide having at least 70% sequence identity to the polypeptide of SEQ ID NO: 17.

In another aspect, this document features a nucleic acid construct or expression vector comprising a polynucleotide encoding a polypeptide having thioesterase activity, wherein the polynucleotide is operably linked to one or more heterologous control sequences that direct production of the polypeptide and wherein the polypeptide having thioesterase activity is selected from: (a) a polypeptide having at least 70% sequence identity to the polypeptide of SEQ ID NO: 18, (b) a polypeptide having at least 70% sequence identity to the polypeptide of SEQ ID NO: 20, (c) a polypeptide having at least 70% sequence identity to the polypeptide of SEQ ID NO: 22, and (d) a polypeptide having at least 70% sequence identity to the polypeptide of SEQ ID NO: 23.

In another aspect, this document features a nucleic acid construct or expression vector comprising a polynucleotide encoding a polypeptide having alcohol dehydrogenase activity, wherein the polynucleotide is operably linked to one or more heterologous control sequences that direct production of the polypeptide and wherein the polypeptide having alcohol dehydrogenase activity is a polypeptide having at least 70% sequence identity to the polypeptide of SEQ ID NO: 21.

In another aspect, this document features a composition comprising the nucleic acid construct or expression vector of embodiment 103 or 104.

In another aspect, this document features a culture medium comprising the nucleic acid construct or expression vector of embodiment 103 or 104.

In another aspect, this document features a non-naturally occurring biochemical network comprising 9-hydroxyperoxyoctadec-10,12-dienoate, an exogenous nucleic acid encoding a polypeptide having the activity of a hydroperoxide lyase classified under EC 4.2.99.-, and non-3-enal and 9-oxononanoate.

In another aspect, this document features a non-naturally occurring biochemical network comprising non-3-enoyl-CoA, an exogenous nucleic acid encoding a polypeptide having the activity of a dodecenoyl-CoA isomerase classified under EC 5.3.3.8, and non-2-enoyl-CoA.

In another aspect, this document features a non-naturally occurring biochemical network comprising non-2-enal, an exogenous nucleic acid encoding a polypeptide having the activity of an enoate reductase classified under EC 1.3.1.31, and nonanal.

In another aspect, this document features a non-naturally occurring biochemical network comprising nonanoic acid, an exogenous nucleic acid encoding a polypeptide having the activity of a monooxygenase classified under EC 1.14.14.- or EC 1.14.15.-, and a 9-hydroxynonanoic acid.

In another aspect, this document features means for producing pimeloyl-CoA, comprising culturing a non-naturally occurring microorganism comprising at least one exogenous nucleic acid encoding a polypeptide having the enzymatic activity of (i) a hydroperoxide lyase, (ii) an acetylating aldehyde dehydrogenase, (iii) a CoA ligase, (iv) a dodecenoyl-CoA isomerase or an enoate reductase, (v) a trans-2-enoyl-CoA reductase, (vi) a thioesterase, (vii) a monooxygenase, (viii) an alcohol dehydrogenase, (ix) an aldehyde dehydrogenase classified under any of EC 1.2.1.3, EC 1.2.1.16, EC 1.2.1.20, EC 1.2.1.24, EC 1.2.1.63, or EC 1.2.1.79, (x) an acyl-CoA dehydrogenase, (xi) an enoyl-CoA hydratase, (xii) a 3-hydroxyacyl-CoA dehydrogenase or a 3-oxoacyl ACP reductase, and/or (xiii) a β-ketothiolase, expressed in a sufficient amount in said microorganism to produce pimeloyl-CoA.

In another aspect, this document features a bio-derived, bio-based or fermentation-derived product, wherein said product comprises: (i) a composition comprising at least one bio-derived, bio-based, or fermentation-derived compound according to embodiment 112; (ii) a bio-derived, bio-based, or fermentation-derived polymer comprising the bio-derived, bio-based, or fermentation-derived composition or compound of (i), or any combination thereof; (iii) a bio-derived, bio-based, or fermentation-derived resin comprising the bio-derived, bio-based, or fermentation-derived compound or bio-derived, bio-based, or fermentation-derived composition of (i) or any combination thereof or the bio-derived, bio-based, or fermentation-derived polymer of (ii) or any combination thereof; (iv) a molded substance obtained by molding the bio-derived, bio-based, or fermentation-derived polymer of (ii) or the bio-derived, bio-based, or fermentation-derived resin of (iii), or any combination thereof; (v) a bio-derived, bio-based, or fermentation-derived formulation comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), or bio-derived, bio-based, or fermentation-derived molded substance of (iv), or any combination thereof; and (vi) a bio-derived, bio-based, or fermentation-derived semi-solid or a non-semi-solid stream, comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), bio-derived, bio-based, or fermentation-derived formulation of (v), or bio-derived, bio-based, or fermentation-derived molded substance of (iv), or any combination thereof.

Embodiments 1-112 recite non-limiting example embodiments of the disclosure.

1. A method of producing non-3-enal and 9-oxononanoate in a recombinant microorganism, said method comprising enzymatically converting 9-hydroxyperoxyoctadec-10,12-dienoate to non-3-enal and 9-oxononanoate using an exogenous polypeptide having the activity of a hydroperoxide lyase classified under EC 4.2.99.-.
2. The method of embodiment 1, wherein said exogenous polypeptide is the gene product of *Cucumis sativus* (GenBank Accession No. AAF64041.1, SEQ ID NO: 13) or a polypeptide having at least 70%, at least 80%, or at least 85% sequence identity with the same or the gene product of *Oryza sativa* (GenBank Accession No. BAG97978.1, SEQ ID NO: 14) or a polypeptide having at least 70%, at least 80%, or at least 85% sequence identity with the same.
3. The method of embodiment 1, further comprising enzymatically converting non-3-enal to azelaic acid using one or more polypeptides, comprising at least one polypeptide having the activity of a dodecenoyl-CoA isomerase classified under EC 5.3.3.8.
4. The method of embodiment 3, wherein said at least one polypeptide having the activity of a dodecenoyl-CoA isomerase classified under EC 5.3.3.8 enzymatically converts non-3-enoyl-CoA to non-2-enoyl-CoA.
5. The method of embodiment 1, further comprising enzymatically converting non-3-enal to azelaic acid using one or more polypeptides, comprising at least one polypeptide having the activity of an enoate reductase classified under EC 1.3.1.31.
6. The method of embodiment 5, wherein said at least one polypeptide having the activity of an enoate reductase classified under EC 1.3.1.31 enzymatically is an enzymatic step in converting non-3-enal to nonanal.
7. The method of embodiment 3 or embodiment 5, wherein said one or more polypeptides comprises a polypeptide having the activity of a monooxygenase classified under EC 1.14.14.- or EC 1.14.15.-, such as EC 1.14.14.1, EC 1.14.14.3, EC 1.14.15.1, or EC 1.14.15.3.
8. The method of embodiment 7, wherein said polypeptide having the activity of a monooxygenase converts nonanoic acid to 9-hydroxynonanoic acid.
9. A method of producing azelaic acid in a recombinant microorganism, said method comprising the steps of enzymatically converting 9-hydroxyperoxyoctadec-10,12-dienoate to non-3-enal and 9-oxononanoate using an exogenous polypeptide having the activity of a hydroperoxide lyase classified under EC 4.2.99.- and enzymatically converting non-3-enal to azelaic acid using one or more polypeptides, including at least one polypeptide having the activity of a dodecenoyl-CoA isomerase classified under EC 5.3.3.8 or at least one polypeptide having the activity of an enoate reductase classified under EC 1.3.1.31.
10. The method of embodiment 9, wherein said one or more polypeptides further comprises a polypeptide having the activity of a monooxygenase classified under EC 1.14.14.- or EC 1.14.15.-, wherein said monooxygenase enzymatically converts nonanoic acid to 9-hydroxynonanoic acid.
11. The method of embodiment 9, wherein said non-3-enal is converted to azelaic acid using one or more polypeptides having the enzymatic activities of an enal isomerase, an aldehyde dehydrogenase, a CoA ligase, a dodecenoyl-CoA isomerase, a trans-2-enoyl-CoA reductase, a thioesterase, a monooxygenase, and/or an alcohol dehydrogenase.
12. The method of embodiment 11, wherein said aldehyde dehydrogenase is classified under EC 1.2.1.3, EC 1.2.1.4, EC 1.2.1.5, or EC 1.2.1.48.
13. The method of embodiment 11, wherein said CoA ligase is classified under EC 6.2.1.-, such as EC 6.2.1.5 or EC 6.2.1.15.
14. The method of embodiment 11, wherein said trans-2-enoyl-CoA reductase is classified under EC 1.3.1.38, EC 1.3.1.44, or EC 1.3.1.8.
15. The method of embodiment 11, wherein said thioesterase is classified under EC 3.1.2.-.
16. The method of embodiment 11, wherein said alcohol dehydrogenase is classified under EC 1.1.1.-, such as EC 1.1.1.61 or EC 1.1.1.258.
17. The method of embodiment 11, wherein said aldehyde dehydrogenase is classified under EC 1.2.1.3, EC 1.2.1.16, EC 1.2.1.20, EC 1.2.1.24, EC 1.2.1.63, or EC 1.2.1.79, wherein said aldehyde dehydrogenase classified under EC 1.2.1.16, EC 1.2.1.24, or EC 1.2.1.79 is a succinate-semialdehyde dehydrogenase, wherein said aldehyde dehydrogenase classified under EC 1.2.1.20 is a 5-oxopentanoate dehydrogenase, wherein said aldehyde dehydrogenase classified under EC 1.2.1.63 is a 6-oxohexanoate dehydrogenase, and wherein said aldehyde dehydrogenase classified under EC 1.2.1.- is a 7-oxoheptanoate dehydrogenase.
18. The method of embodiment 9, wherein said non-3-enal is converted to azelaic acid using one or more polypeptides having the enzymatic activities of an enoate reductase, an aldehyde dehydrogenase, a monooxygenase, and/or an alcohol dehydrogenase.

19. The method of embodiment 18, wherein said aldehyde dehydrogenase is classified under EC 1.2.1.3, EC 1.2.1.4, EC 1.2.1.5, or EC 1.2.1.48.
20. The method of embodiment 18, wherein said alcohol dehydrogenase is classified under EC 1.1.1.-, such as EC 1.1.1.61 or EC 1.1.1.258.
21. The method of embodiment 18, wherein said aldehyde dehydrogenase is classified under EC 1.2.1.3, EC 1.2.1.16, EC 1.2.1.20, EC 1.2.1.24, EC 1.2.1.63, or EC 1.2.1.79, wherein said aldehyde dehydrogenase classified under EC 1.2.1.16, EC 1.2.1.24, or EC 1.2.1.79 is a succinate-semialdehyde dehydrogenase, wherein said aldehyde dehydrogenase classified under EC 1.2.1.20 is a 5-oxopentanoate dehydrogenase, wherein said aldehyde dehydrogenase classified under EC 1.2.1.63 is a 6-oxohexanoate dehydrogenase and wherein said aldehyde dehydrogenase classified under EC 1.2.1.- is a 7-oxoheptanoate dehydrogenase.
22. The method of embodiment 9, wherein said 9-oxononanoate is converted to azelaic acid using a polypeptide having the enzymatic activity of an aldehyde dehydrogenase.
23. The method of embodiment 22, wherein said aldehyde dehydrogenase is classified under EC 1.2.1.3, EC 1.2.1.16, EC 1.2.1.20, EC 1.2.1.24, EC 1.2.1.63, or EC 1.2.1.79, wherein said aldehyde dehydrogenase classified under EC 1.2.1.16, EC 1.2.1.24, or EC 1.2.1.79 is a succinate-semialdehyde dehydrogenase, wherein said aldehyde dehydrogenase classified under EC 1.2.1.20 is a 5-oxopentanoate dehydrogenase, wherein said aldehyde dehydrogenase classified under EC 1.2.1.63 is a 6-oxohexanoate dehydrogenase, and wherein said aldehyde dehydrogenase classified under EC 1.2.1.- is a 7-oxoheptanoate dehydrogenase.
24. The method of any of embodiments 11, 18, or 22, wherein said azelaic acid is converted to pimeloyl-CoA using one or more polypeptides having the enzymatic activities of a CoA ligase, an acyl-CoA dehydrogenase, an enoyl-CoA hydratase, a 3-hydroxyacyl-CoA dehydrogenase, and/or a β-ketothiolase.
25. The method of embodiment 24, wherein said CoA ligase is classified under EC 6.2.1.-.
26. The method of embodiment 24, wherein said acyl-CoA dehydrogenase is classified under EC 1.3.8.-.
27. The method of embodiment 26, wherein said acyl-CoA dehydrogenase is classified under EC 1.3.8.6, EC 1.3.8.7, or EC 1.3.8.8.
28. The method of embodiment 24, wherein said enoyl-CoA hydratase is classified under EC 4.2.1.17 or EC 4.2.1.119.
29. The method of embodiment 24, wherein said 3-hydroxyacyl-CoA dehydrogenase is classified under EC 1.1.1.35, EC 1.1.1.36, or EC 1.1.1.157.
30. The method of embodiment 24, wherein said β-ketothiolase is classified under EC 2.3.1.16 or EC 2.3.1.174.
31. A method for biosynthesizing azelaic acid, said method comprising enzymatically synthesizing non-3-enal and 9-oxononanoate from 9-hydroxyperoxyoctadec-10,12 dienoate using a polypeptide having the activity of a hydroperoxide lyase classified under EC 4.2.99.- and enzymatically converting non-3-enal and/or 9-oxononanoate to azelaic acid.
32. The method of embodiment 31, wherein said non-3-enal is converted to non-3-enoate using a polypeptide having the activity of an aldehyde dehydrogenase; non-3-enoate is converted to non-3-enoyl-CoA using a polypeptide having the activity of a CoA ligase; non-3-enoyl-CoA is converted to non-2-enoyl-CoA using a polypeptide having the activity of a dodecenoyl-CoA isomerase; non-2-enoyl-CoA is converted to nonanoyl-CoA using a polypeptide having the activity of a trans-2-enoyl-CoA reductase; nonanoyl-CoA is converted to nonanoic acid using a polypeptide having the activity of a thioesterase; nonanoic acid is converted to 9-hydroxynonanoic using a polypeptide having the activity of a monooxygenase; 9-hydroxynonanoic is converted to 9-oxononanoate using a polypeptide having the activity of an alcohol dehydrogenase; and 9-oxononanoate is converted to azelaic acid using a polypeptide having the activity of an aldehyde dehydrogenase.
33. The method of embodiment 31, wherein non-3-enal is converted to nonanal using a polypeptide having the activity of an enoate reductase; nonanal is converted to nonanoic acid using a polypeptide having the activity of an aldehyde dehydrogenase; nonanoic acid is converted to 9-hydroxynonanoic acid using a polypeptide having the activity of a monooxygenase; 9-hydroxynonanoic acid is converted to 9-oxononanoic acid using a polypeptide having the activity of an alcohol dehydrogenase; and 9-oxononanoic acid is converted to azelaic acid using a polypeptide having the activity of an aldehyde dehydrogenase.
34. The method of embodiment 31, wherein said 9-oxononanoate is converted to azelaic acid using a polypeptide having the activity of an aldehyde dehydrogenase.
35. The method of any one of embodiments 31 to 34, further comprising the following steps to convert azelaic acid to pimeloyl-CoA: azelaic acid is converted to azelaoyl-CoA using a polypeptide having the activity of a CoA ligase; azelaoyl-CoA is converted to 2,3-dehydro-azelaoyl-CoA using a polypeptide having the activity of an acyl-CoA dehydrogenase; 2,3-dehydro-azelaoyl-CoA is converted to 3-hydroxy-azelaoyl-CoA using a polypeptide having the activity of an enoyl-CoA hydratase; 3-hydroxy-azelaoyl-CoA is converted to 3-oxo-azelaoyl-CoA using a polypeptide having the activity of a 3-hydroxyacyl-CoA dehydrogenase; and 3-oxo-azelaoyl-CoA is converted to pimeloyl-CoA using a polypeptide having the activity of a β-ketothiolase.
36. A method of producing one or more of pimelic acid, 7-aminoheptanoate, 7-hydroxyheptanoate, heptamethylenediamine, or 1,7-heptanediol, or corresponding salts thereof, said method comprising the step of converting 9-hydroxyperoxyoctadec-10,12-dienoate to non-3-enal and 9-oxononanoate using a polypeptide having the enzymatic activity of a hydroperoxide lyase and subsequently converting non-3-enal or 9-oxononanoate to pimeloyl-CoA.
37. The method of embodiment 36, wherein said non-3-enal is converted to pimeloyl-CoA using an enzymatic pathway comprising a polypeptide having the activity of a dodecenoyl-CoA isomerase classified under EC 5.3.3.8 and a polypeptide having the activity of a monooxygenase classified under EC 1.14.14.- or EC 1.14.15.-.
38. The method of embodiment 36, wherein said non-3-enal is converted to pimeloyl-CoA using an enzymatic pathway comprising a polypeptide having the activity of an enoate reductase classified under EC 1.3.1.31 and a polypeptide having the activity of a monooxygenase classified under EC 1.14.14.- or EC 1.14.15.-.

39. The method of embodiment 36, wherein said pimeloyl-CoA is converted to pimelate semialdehyde using one or more polypeptides having the activity of an acetylating aldehyde dehydrogenase.

40. The method of embodiment 39, wherein said pimeloyl-CoA is converted to pimelate semialdehyde using one or more polypeptides having at least 70%, at least 80%, or at least 85% sequence identity to an acetylating aldehyde dehydrogenase encoded by pduB from *Salmonella typhimurium* or encoded by pduP from *Klebsiella pneumoniae*.

41. The method of embodiment 36, wherein said pimelate is converted to pimelate semialdehyde using one or more polypeptides having the activity of a carboxylate reductase classified under EC 1.2.99.6.

42. The method of embodiment 41, wherein said one or more polypeptides have at least 70%, at least 80%, or at least 85% sequence identity to a polypeptide having the activity of a carboxylate reductase classified under EC 1.2.99.6.

43. The method of embodiment 36, wherein said pimeloyl-CoA is converted to one or more of pimelic acid, 7-aminoheptanoate, 7-hydroxyheptanoate, heptamethylenediamine, or 1,7-heptanediol, or corresponding salts thereof, in one or more steps.

44. The method of embodiment 43, wherein said pimeloyl-CoA is converted to pimelic acid using at least one polypeptide having the enzymatic activity of a thioesterase encoded by any one of yciA from *Escherichia coli*, acot13 from *Mus musculus*, or tesB from *Escherichia coli*.

45. The method of embodiment 44, wherein said pimeloyl-CoA is converted to pimelic acid using a polypeptide having at least 70%, at least 80%, or at least 85% sequence identity to a polypeptide encoded by any one of yciA from *Escherichia coli*, acot13 from *Mus musculus* or tesB from *Escherichia coli*.

46. The method of embodiment 43, wherein said pimeloyl-CoA is converted to pimelic acid using a polypeptide having the activity of a CoA ligase classified under EC 6.2.1.- or a polypeptide having the activity of a CoA transferase classified under EC 2.8.3.-.

47. The method of embodiment 46, wherein said pimeloyl-CoA is converted to pimelic acid using a polypeptide having at least 70%, at least 80%, or at least 85% sequence identity to a CoA ligase classified under EC 6.2.1.- or at least 70%, at least 80%, or at least 85% sequence identity to a CoA transferase classified under EC 2.8.3.-.

48. The method of embodiment 39 or 40, wherein said pimelate semialdehyde is converted to pimelic acid using one or more polypeptides having the activity of an aldehyde dehydrogenase classified under EC 1.2.1.3, EC 1.2.1.16, EC 1.2.1.20, EC 1.2.1.24, EC 1.2.1.63, or EC 1.2.1.79, wherein said aldehyde dehydrogenase classified under EC 1.2.1.16, EC 1.2.1.24, or EC 1.2.1.79 is a succinate-semialdehyde dehydrogenase, wherein said aldehyde dehydrogenase classified under EC 1.2.1.20 is a 5-oxopentanoate dehydrogenase, wherein said aldehyde dehydrogenase classified under EC 1.2.1.63 is a 6-oxohexanoate dehydrogenase and wherein said aldehyde dehydrogenase classified under EC 1.2.1.- is a 7-oxoheptanoate dehydrogenase.

49. The method of embodiment 48, wherein said pimelate semialdehyde is converted to pimelic acid using one or more polypeptides having at least 70%, at least 80%, or at least 85% sequence identity to an aldehyde dehydrogenase classified under EC 1.2.1.3, EC 1.2.1.16, EC 1.2.1.20, EC 1.2.1.24, EC 1.2.1.63, or EC 1.2.1.79.

50. The method of any one of embodiments 39 to 41, wherein said pimelate semialdehyde is converted to 7-aminoheptanoate using one or more polypeptides having the activity of a ω-transaminase classified under EC 2.6.1.-.

51. The method of embodiment 50, wherein said pimelate semialdehyde is converted to 7-aminoheptanoate using one or more polypeptides having at least 70%, at least 80%, or at least 85% sequence identity to a polypeptide having the activity of a w-transaminase classified under EC 2.6.1.-.

52. The method of any one of embodiments 39 to 41, wherein said pimelate semialdehyde is converted to 7-hydroxyheptanoate using one or more polypeptides having the enzymatic activity of an alcohol dehydrogenase, wherein said alcohol dehydrogenase is a 4-hydroxybutanoate dehydrogenase, a 5-hydroxypentanoate dehydrogenase, or a 6-hydroxyhexanoate dehydrogenase.

53. The method of embodiment 52, wherein said alcohol dehydrogenase is encoded by any one of chnD from *Acinetobacter* sp. NCIMB9871, cpnD from *Comamonas* sp., or gbd.

54. The method of embodiment 53, wherein said alcohol dehydrogenase is encoded by a polypeptide having at least 70%, at least 80%, or at least 85% sequence identity to a polypeptide encoded by any one chnD from *Acinetobacter* sp. NCIMB9871, cpnD from *Comamonas* sp., or gbd.

55. The method of embodiment 50 or 51, wherein said 7-aminoheptanoate is converted to 7-aminoheptanal using one or more polypeptides having the activity of a carboxylate reductase classified under EC 1.2.99.6, and wherein said 7-aminoheptanal is converted to heptamethylenediamine using one or more polypeptides having the activity of a ω-transaminase classified under EC 2.6.1.-.

56. The method of embodiment 55, wherein said carboxylate reductase classified under EC 1.2.99.6 is encoded by griC or griD from *Streptomyces griseus*.

57. The method of embodiment 56, wherein said carboxylate reductase classified under EC 1.2.99.6 is a polypeptide having at least 70%, at least 80%, or at least 85% sequence identity to a polypeptide encoded by griC or griD from *Streptomyces griseus*.

58. The method of embodiment 55, wherein said 7-aminoheptanal is converted to heptamethylenediamine using one or more polypeptides having at least 70%, at least 80%, or at least 85% sequence identity to a polypeptide having the activity of a w-transaminase classified under EC 2.6.1.-.

59. The method of embodiment 50 or 51, wherein said 7-aminoheptanoate is converted to N7-acetyl-7-aminoheptanoate using one or more polypeptides having the activity of an N-acetyltransferase classified under EC 2.3.1.32; wherein N7-acetyl-7-aminoheptanoate is converted to N7-acetyl-7-aminoheptanal using one or more polypeptides having the activity of a carboxylate reductase classified under EC 1.2.99.6; wherein N7-acetyl-7-aminoheptanal is converted to N7-acetyl-1,7-diaminoheptane using one or more polypeptides having the activity of a w-transaminase classified under EC 2.6.1.-; and wherein N7-acetyl-1,7-diaminoheptane is converted to heptamethylenediamine using one or more polypeptides having the activity of a deacylase classified under EC 3.5.1.-.

60. The method of any one of embodiments 52 to 54, wherein said 7-hydroxyheptanoate is converted to 7-hydroxyheptanal using one or more polypeptides having the activity of a carboxylate reductase classified under EC 1.2.99.6; wherein 7-hydroxyheptanal is converted to 7-aminoheptanol using one or more polypeptides having the activity of a w-transaminase classified under EC 2.6.1.18, EC 2.6.1.19, or EC 2.6.1.48; wherein 7-aminoheptanol is converted to 7-aminoheptanal using one or more polypeptides having the activity of an alcohol dehydrogenase classified under EC 1.1.1.-; and wherein said 7-aminoheptanal is converted to heptamethylenediamine using one or more polypeptides having the activity of a w-transaminase classified under EC 2.6.1.-.

61. The method of embodiment 60, wherein said alcohol dehydrogenase has at least 70%, at least 80%, or at least 85% sequence identity to a polypeptide encoded by yqhD from *Escherichia coli*.

62. The method of embodiment 61, wherein said alcohol dehydrogenase has at least 70% sequence identity to a polypeptide encoded by yqhD from *Escherichia coli*.

63. The method of any one of embodiments 39 to 41, wherein said pimelate semialdehyde is converted to heptanedial using one or more polypeptides having the activity of a carboxylate reductase classified under EC 1.2.99.6; wherein heptanedial is converted to 7-aminoheptanal using one or more polypeptides having the activity of a ω-transaminase classified under EC 2.6.1.18, EC 2.6.1.19, EC 2.6.1.48, EC 2.6.1.29, or EC 2.6.1.82; and wherein 7-aminoheptanal is converted to heptamethylenediamine using one or more polypeptides having the activity of a w-transaminase classified under EC 2.6.1.-.

64. The method of any of embodiments 52 to 54, wherein said 7-hydroxyheptanoate is converted to 7-hydroxyheptanal using a carboxylate reductase classified under EC 1.2.99.6; and wherein 7-hydroxyheptanal is converted to 1,7 heptanediol using one or more polypeptides having the activity of an alcohol dehydrogenase classified under EC 1.1.1.-.

65. The method of embodiment 1, wherein said 9-hydroxyperoxyoctadec-10,12-dienoate is enzymatically produced from octadecanoyl-CoA.

66. The method of embodiment 65, wherein said 9-hydroxyperoxyoctadec-10,12-dienoate is enzymatically produced from octadecanoyl-CoA using one or more polypeptides having the activity of a delta9-desaturase, a delta12-desaturase, a thioesterase, and/or a 9-lipoxygenase.

67. The method of embodiment 66, wherein said polypeptide having the activity of a stearoyl-CoA delta9-desaturase is classified under EC 1.14.19.1.

68. The method of embodiment 66, wherein said polypeptide having the activity of a delta12-desaturase is classified under EC 1.14.19.6.

69. The method of embodiment 66, wherein said polypeptide having the activity of a thioesterase is classified under EC 3.1.2.-.

70. The method of embodiment 66, wherein said polypeptide having the activity of a 9-lipoxygenase is classified under EC 1.13.11.58, EC 1.13.11.60, EC 1.13.11.61, or EC 1.13.11.62.

71. The method of any of the preceding embodiments, wherein said method is performed in a recombinant microorganism.

72. The method of embodiment 71, wherein said microorganism is subjected to a cultivation strategy under aerobic, anaerobic or micro-aerobic cultivation conditions.

73. The method of embodiment 71 or 72, wherein said microorganism is cultured under conditions of nutrient limitation.

74. The method according to any one of embodiments 71 to 73, wherein said microorganism is retained using a ceramic membrane to maintain a high cell density during fermentation.

75. The method of any one of embodiments 71 to 74, wherein the principal carbon source fed to the fermentation derives from a biological feedstock.

76. The method of embodiment 75, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, plant oils, or municipal waste.

77. The method of any one of embodiments 71 to 74, wherein the principal carbon source fed to the fermentation derives from a non-biological feedstock.

78. The method of embodiment 77, wherein the non-biological feedstock is, or derives from, natural gas, syngas, C02/H2, methanol, ethanol, benzoate, non-volatile residue (NVR) caustic wash waste stream from cycloheptane oxidation processes, or terephthalic acid/isophthalic acid mixture waste streams.

79. The method of embodiment 71, wherein the microorganism is a prokaryote.

80. The method of embodiment 79, wherein said prokaryote is from a genus selected from *Escherichia, Clostridia, Corynebacteria, Cupriavidus, Pseudomonas, Delftia, Bacillus, Lactobacillus, Lactococcus*, and *Rhodococcus*.

81. The method of embodiment 80, wherein said prokaryote is selected from *Escherichia coli, Clostridium ljungdahlii, Clostridium autoethanogenum, Clostridium kluyveri, Corynebacterium glutamicum, Cupriavidus necator, Cupriavidus metallidurans. Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*.

82. The method of embodiment 71, wherein the microorganism is a eukaryote.

83. The method of embodiment 82, wherein said eukaryote is from a genus selected from *Aspergillus, Saccharomyces, Pichia, Yarrowia, Issatchenkia, Debaryomyces, Arxula*, and *Kluyveromyces*.

84. The method of embodiment 83, wherein said eukaryote is selected from *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*.

85. The method of embodiment 71, wherein the microorganism's tolerance to high concentrations of a C7 building block is improved relative to a wild type organism.

86. The method of embodiment 71, wherein the microorganism's tolerance to high concentrations of a C7 building block is improved relative to a wild type organism through continuous cultivation in a selective environment.

87. The method of embodiment 71, wherein said microorganism comprises an attenuation to one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, an NADH-consuming transhydrogenase, an NADH-specific glutamate dehydrogenase, an NADH/NADPH-utilizing glutamate dehydrogenase, a pimeloyl-CoA dehydrogenase; an acyl-CoA dehydrogenase accepting C7 building blocks and central precursors as substrates; a butaryl-CoA dehydrogenase; or an adipyl-CoA synthetase.

88. The method of any one of embodiments 71 to 87, wherein said microorganism overexpresses one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

89. A recombinant microorganism comprising at least one exogenous nucleic acid encoding a polypeptide having the enzymatic activity of (i) a hydroperoxide lyase, (ii) an aldehyde dehydrogenase, (iii) a CoA ligase, (iv) a dodecenoyl-CoA isomerase, (v) a trans-2-enoyl-CoA reductase, (vi) a thioesterase, (vii) a monooxygenase, and/or (viii) an alcohol dehydrogenase, said microorganism producing azelaic acid.

90. A recombinant microorganism comprising at least one exogenous nucleic acid encoding a polypeptide having the enzymatic activity of (i) a hydroperoxide lyase, (ii) an enoate reductase, (iii) an aldehyde dehydrogenase, (iv) a monooxygenase, and/or (v) an alcohol dehydrogenase, said microorganism producing azelaic acid.

91. A recombinant microorganism comprising at least one exogenous nucleic acid encoding a polypeptide having the enzymatic activity of (i) a hydroperoxide lyase, and/or (ii) an aldehyde dehydrogenase, said microorganism producing azelaic acid.

92. The recombinant microorganism of any of embodiments 89 to 91, said microorganism further comprising one or more exogenous polypeptides having the enzymatic activity of: (i) a CoA ligase, (ii) an acyl-CoA dehydrogenase, (iii) an enoyl-CoA hydratase, (iv) a 3-hydroxyacyl-CoA dehydrogenase or a 3-oxoacyl ACP reductase, and/or (v) a β-ketothiolase, said microorganism further producing pimeloyl-CoA.

93. The recombinant microorganism of embodiment 92, said microorganism further comprising one or more exogenous polypeptides having the enzymatic activity of a thioesterase, a CoA ligase, a CoA transferase, an acetylating aldehyde dehydrogenase, and/or an aldehyde dehydrogenase, said microorganism further producing pimelic acid.

94. The recombinant microorganism of embodiment 92 or 93, said microorganism further comprising one or more polypeptides having the activity of an aldehyde dehydrogenase and/or a ω-transaminase, said microorganism further producing 7-aminoheptanoate.

95. The recombinant microorganism of embodiment 92 or 93, said microorganism further comprising one or more exogenous polypeptides having the activity of a carboxylate reductase and/or a ω-transaminase, said microorganism further producing 7-aminoheptanoate.

96. The recombinant microorganism of embodiment 92 or 93, said microorganism further comprising one or more of the following exogenous enzymes: a carboxylate reductase, an alcohol dehydrogenase, or an acetylating aldehyde dehydrogenase, said microorganism further producing 7-hydroxyheptanoate.

97. The recombinant microorganism of any one of embodiments 92 to 96, said microorganism comprising one or more of the following exogenous enzymes: a carboxylate reductase, a ω-transaminase, an alcohol dehydrogenase, an N-acetyltransferase, or a deacylase, said microorganism further producing heptamethylenediamine.

98. The recombinant microorganism of embodiment 92 or 93, wherein said pimeloyl-CoA or said pimelic acid is converted to pimelate semialdehyde using an acetylating aldehyde dehydrogenase encoded by pduB from *Salmonella typhimurium* or pduP from *Klebsiella pneumoniae* or one or more polypeptides having the activity of a carboxylate reductase classified under EC 1.2.99.6.

99. The recombinant microorganism of embodiment 98, said microorganism comprising polypeptides having the activity of a carboxylate reductase and one or more w-transaminases, said microorganism producing heptamethylenediamine.

100. The recombinant microorganism of embodiment 96, said microorganism further comprising polypeptides having the activity of a carboxylate reductase and an alcohol dehydrogenase, said microorganism further producing 1,7 heptanediol.

101. The recombinant microorganism of any one of embodiments 89 to 100, said microorganism further comprising one or more exogenous enzymes: a delta9-desaturase, a delta12-desaturase, a thioesterase, or a 9-lipoxygenase.

102. A non-naturally occurring microorganism comprising at least one exogenous nucleic acid encoding at least one polypeptide having the activity of at least one enzyme, at least one substrate, and at least one product, depicted in any one of FIG. 1 to 7.

103. A nucleic acid construct or expression vector comprising a polynucleotide encoding a polypeptide having carboxylate reductase activity, wherein the polynucleotide is operably linked to one or more heterologous control sequences that direct production of the polypeptide and wherein the polypeptide having carboxylate reductase activity is selected from: (a) a polypeptide having at least 70% sequence identity to the polypeptide of SEQ ID NO: 1; (b) a polypeptide having at least 70% sequence identity to the polypeptide of SEQ ID NO: 2; (c) a polypeptide having at least 70% sequence identity to the polypeptide of SEQ ID NO: 3; (d) a polypeptide having at least 70% sequence identity to the polypeptide of SEQ ID NO: 4, (e) a polypeptide having at least 70% sequence identity to the polypeptide of SEQ ID NO: 5 and (f) a polypeptide having at least 70% sequence identity to the polypeptide of SEQ ID NO: 6.

104. A nucleic acid construct or expression vector comprising a polynucleotide encoding a polypeptide having ω-transaminase activity, wherein the polynucleotide is operably linked to one or more heterologous control sequences that direct production of the polypeptide and wherein the polypeptide having ω-transaminase activity is selected from: (a) a polypeptide having at least 70% sequence identity to the polypeptide of SEQ ID NO: 7; (b) a polypeptide having at least 70% sequence identity to the polypeptide of SEQ ID NO: 8; (c) a polypeptide having at least 70% sequence identity to the polypeptide of SEQ ID NO: 9; (d) a polypeptide having at least 70% sequence identity to the polypeptide of SEQ ID NO: 10; (e) a polypeptide having at least 70% sequence identity to the polypeptide of SEQ ID NO: 11 or SEQ ID NO: 48; and (f) a polypeptide having at least 70% sequence identity to the polypeptide of SEQ ID NO: 12.

105. A composition comprising the nucleic acid construct or expression vector of embodiment 103 or 104.
106. A culture medium comprising the nucleic acid construct or expression vector of embodiment 103 or 104.
107. A non-naturally occurring biochemical network comprising a 9-hydroxyperoxyoctadec-10,12-dienoate, an exogenous nucleic acid encoding a polypeptide having the activity of a hydroperoxide lyase classified under EC 4.2.99.-, and non-3-enal and 9-oxononanoate.
108. A non-naturally occurring biochemical network comprising non-3-enoyl-CoA, an exogenous nucleic acid encoding a polypeptide having the activity of a dodecenoyl-CoA isomerase classified under EC 5.3.3.8 and non-2-enoyl-CoA.
109. A non-naturally occurring biochemical network comprising non-3-enal, an exogenous nucleic acid encoding a polypeptide having the activity of an enoate reductase classified under EC 1.3.1.31 and nonanal.
110. A non-naturally occurring biochemical network comprising nonanoic acid, an exogenous nucleic acid encoding a polypeptide having the activity of a monooxygenase classified under EC 1.14.14.- or EC 1.14.15.- and 9-hydroxynonanoic acid.
111. Means for producing pimeloyl-CoA, comprising culturing a non-naturally occurring microorganism comprising at least one exogenous nucleic acid encoding a polypeptide having the enzymatic activity of (i) a hydroperoxide lyase, (ii) an aldehyde dehydrogenase, (iii) a CoA ligase, (iv) a dodecenoyl-CoA isomerase, (iv) a trans-2-enoyl-CoA reductase, (v) a thioesterase, (vi) an enoate reductase, (vii) a monooxygenase, (viii) an alcohol dehydrogenase, (ix) an acyl-CoA dehydrogenase, (x) an enoyl-CoA hydratase, (xi) a 3-hydroxyacyl-CoA dehydrogenase and (xii) a β-ketothiolase, expressed in a sufficient amount in said microorganism to produce pimeloyl-CoA.
112. A bio-derived, bio-based, or fermentation-derived product, wherein said product comprises:
 (i) a composition comprising at least one bio-derived, bio-based, or fermentation-derived compound according to any one of embodiments 6-8, 36, or 39 or any combination thereof,
 (ii) a bio-derived, bio-based, or fermentation-derived polymer comprising the bio-derived, bio-based or fermentation-derived composition or compound of (i), or any combination thereof,
 (iii) a bio-derived, bio-based, or fermentation-derived resin comprising the bio-derived, bio-based, or fermentation-derived compound or bio-derived, bio-based, or fermentation-derived composition of (i) or any combination thereof or the bio-derived, bio-based, or fermentation-derived polymer of (ii) or any combination thereof,
 (iv) a molded substance obtained by molding the bio-derived, bio-based, or fermentation-derived polymer of (ii) or the bio-derived, bio-based, or fermentation-derived resin of (iii), or any combination thereof,
 (v) a bio-derived, bio-based, or fermentation-derived formulation comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), or bio-derived, bio-based, or fermentation-derived molded substance of (v), or any combination thereof, or
 (vi) a bio-derived, bio-based, or fermentation-derived semi-solid or a non-semi-solid stream, comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), bio-derived, bio-based, or fermentation-derived formulation of (v), or bio-derived, bio-based, or fermentation-derived molded substance of (iv), or any combination thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the application, including the written description and drawings, and the claims. The word "comprising" in the claims may be replaced by "consisting essentially of" or with "consisting of," according to standard practice in patent law.

DESCRIPTION OF DRAWINGS

FIGS. 8A-8N contain the amino acid sequences of a *Mycobacterium marinum* carboxylate reductase (see GenBank Accession No. ACC40567.1, SEQ ID NO: 1), a *Mycobacterium smegmatis* carboxylate reductase (see GenBank Accession No. ABK71854.1, SEQ ID NO: 2), a *Segniliparus rugosus* carboxylate reductase (see GenBank Accession No. EFV11917.1, SEQ ID NO: 3), a *Mycobacterium smegmatis* carboxylate reductase (see GenBank Accession No. ABK75684.1, SEQ ID NO: 4), a *Mycobacterium massiliense* carboxylate reductase (see GenBank Accession No. EIV11143.1, SEQ ID NO: 5), a *Segniliparus rotundus* carboxylate reductase (see GenBank Accession No. ADG98140.1, SEQ ID NO: 6), a *Chromobacterium violaceum* co-transaminase (see GenBank Accession No. AAQ59697.1, SEQ ID NO: 7), a *Pseudomonas aeruginosa* co-transaminase (see GenBank Accession No. AAG08191.1, SEQ ID NO: 8), a *Pseudomonas syringae* co-transaminase (see GenBank Accession No. AAY39893.1, SEQ ID NO: 9), a *Rhodobacter sphaeroides* co-transaminase (see GenBank Accession No. ABA81135.1, SEQ ID NO: 10), an *Escherichia coli* co-transaminase (see GenBank Accession No. AAA57874.1, SEQ ID NO: 11, SEQ ID NO: 48), a *Vibrio fluvialis* co-transaminase (see GenBank Accession No. AEA39183.1, SEQ ID NO: 12), a *Cucumis sativus* hydroperoxide lyase (see GenBank Accession No. AAF64041.1, SEQ ID NO: 13), a *Oryza sativa* hydroperoxide lyase (see GenBank Accession No. BAG97978.1, SEQ ID NO: 14), a *Lactobacillus casei* enoate reductase (see GenBank Accession No. AGP69310.1, SEQ ID NO: 15), a *Pseudomonas putida* enoate reductase (see GenBank Accession No. AAN66878.1, SEQ ID NO: 16), a *Saccharomyces cerevisiae* isomerase (see GenBank Accession No. AAC83700.1, SEQ ID NO: 17), a *Clostridium perfringens* thioesterase (see GenBank Accession ABG82470.1, SEQ ID NO: 18), a *Saccharomyces cerevisiae* isomerase (see GenBank Accession No. AAC83700.1, SEQ ID NO: 19), a *Bacteroides thetaiotaomicron* thioesterase (see GenBank Accession No. AAO77182.1, SEQ ID NO: 20), a *Geobacillus stearothermophilus* alcohol dehydrogenase (see GenBank Accession No. CAA81612.1, SEQ ID NO: 21), a *Lactobacillus plantarum* WCFS1 thioesterase (see GenBank Accession No. CCC78182.1, SEQ ID NO: 22), and an *Anaerococcus tetradius* ATCC 35098 thioesterase (see GenBank Accession No. EEI82564.1, SEQ ID NO: 23). In addition, gene ID and gene sequences (SEQ ID NOs: 24-46) corresponding to the amino acid sequences are provided in FIGS. 8A-8N.

DETAILED DESCRIPTION

Figure 1:
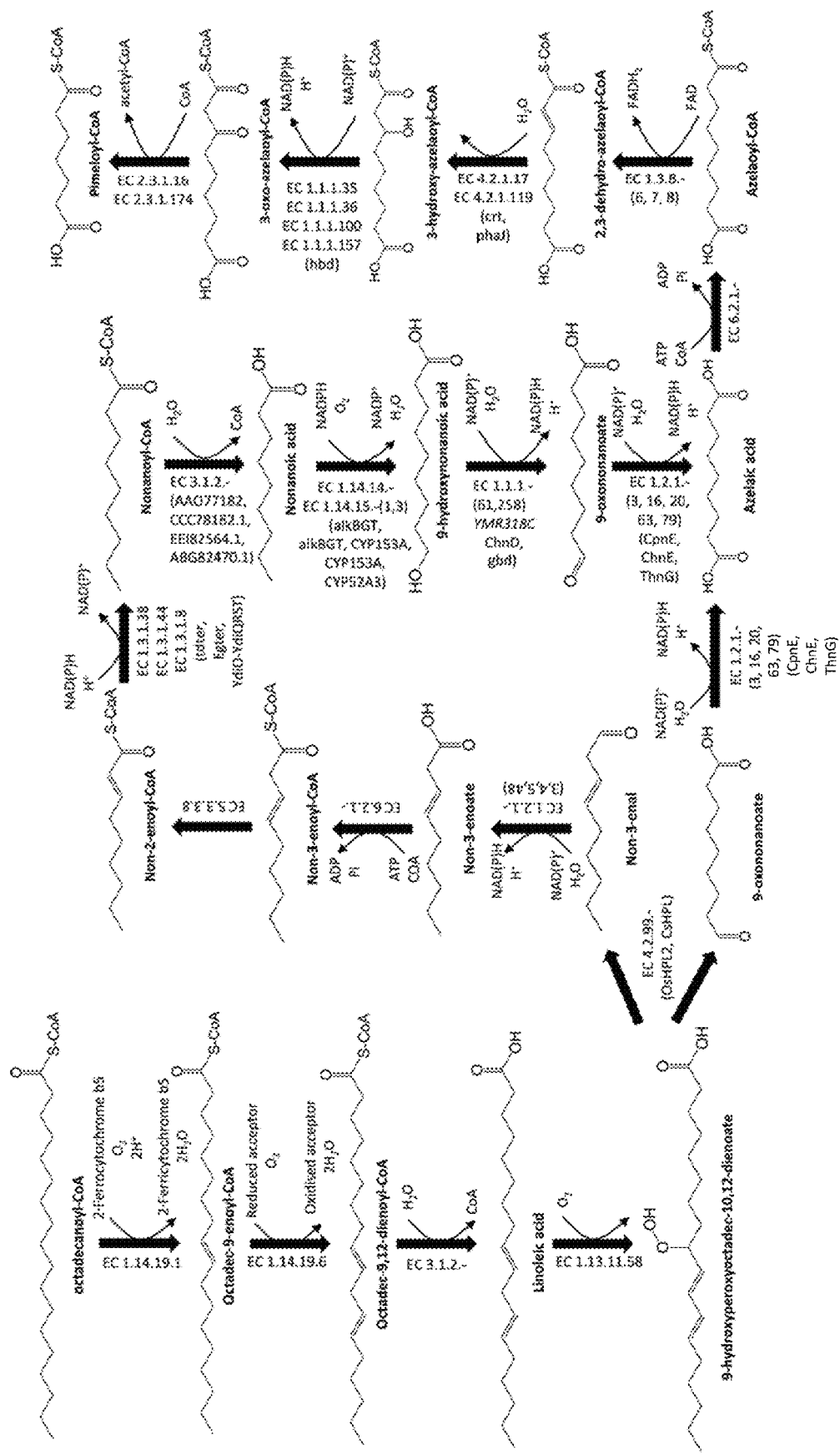
FIG. 1 is a schematic of exemplary biochemical pathways leading to pimeloyl-CoA via isomerase activity using octadecanoyl-CoA as a central metabolite.

In general, this document provides enzymes, non-natural pathways, cultivation strategies, feedstocks, microorganisms, and attenuations to the microorganism's biochemical network, for producing pimeloyl-CoA or one or more of pimelic acid, 7-aminoheptanoate, 7-hydroxyheptanoic acid, heptamethylenediamine, or 1,7-heptanediol, or corresponding salts thereof, all of which are referred to as C7 building blocks herein.

As used herein, a "bio-based product" is a product in which both the feedstock (e.g., sugars from sugar cane, corn, wood; biomass; waste streams from agricultural processes) and the conversion process to the product are biologically based (e.g., fermentation/enzymatic transformation involving a biological host/organism/enzyme). As used herein, a "bio-derived product" is a product in which one of the feedstocks (e.g., sugars from sugar cane, corn, wood; biomass; waste streams from agricultural processes) or the conversion process to the product is biologically based (e.g., fermentation/enzymatic transformation involving a biological host/organism/enzyme).

As used herein, a "fermentation-derived product" is a product produced by fermentation involving a biological host or organism.

The term "C7 building block" is used to denote a seven (7) carbon chain aliphatic backbone. As used herein, the term "central precursor" is used to denote any metabolite in any metabolic pathway shown herein leading to the synthesis of a C7 building block. The term "central metabolite" is used herein to denote a metabolite that is produced in all microorganisms to support growth.

Microorganisms described herein can include endogenous pathways that can be manipulated such that pimeloyl-CoA or one or more other C7 building blocks can be produced. In an endogenous pathway, the microorganism naturally expresses all of the enzymes catalyzing the reactions within the pathway. A microorganism containing an engineered pathway does not naturally express all of the enzymes catalyzing the reactions within the pathway but has been engineered such that all of the enzymes within the pathway are expressed in the microorganism.

The term "exogenous" as used herein with reference to a nucleic acid (or a protein) and a microorganism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a microorganism once in the microorganism. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is a non-naturally-occurring nucleic acid, and thus is exogenous to a microorganism once introduced into the microorganism, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is a non-naturally-occurring nucleic acid. A nucleic acid that is naturally-occurring can be exogenous to a particular microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a microorganism refers to a nucleic acid (or protein) that does occur in (and can be obtained from) that particular microorganism as it is found in nature. Moreover, a cell "endogenously expressing" a nucleic acid (or protein) expresses that nucleic acid (or protein) as does a microorganism of the same particular type as it is found in nature. Moreover, a microorganism "endogenously producing" or that "endogenously produces" a nucleic acid, protein, or other compound produces that nucleic acid, protein, or compound as does a microorganism of the same particular type as it is found in nature.

For example, depending on the microorganism and the compounds produced by the microorganism, one or more polypeptides having the following specific enzymatic activities may be expressed in the microorganism in addition to a hydroperoxide lyase: an acetylating aldehyde dehydrogenase, a CoA ligase, a dodecenoyl-CoA isomerase or an enoate reductase, a trans-2-enoyl-CoA reductase, a thioesterase, a monooxygenase, an enoyl-CoA hydratase, a deacetylase, an acyl-CoA dehydrogenase, an enoyl-CoA hydratase, an alcohol dehydrogenase, a 4-hydroxybutanoate dehydrogenase, a 6-hydroxyhexanoate dehydrogenase, an aldehyde dehydrogenase, a succinate-semialdehyde dehydrogenase, a 5-oxopentanoate dehydrogenase, a 6-oxohexanoate dehydrogenase, a 7-oxoheptanoate dehydrogenase, an acyl-CoA dehydrogenase, an enoyl-CoA hydratase, a 3-hydroxyacyl-CoA dehydrogenase, a 3-oxoacyl ACP reductase, a β-ketothiolase, a CoA transferase, a carboxylate reductase, a ω-transaminase, an N-acetyltransferase, and/or a deacylase. In recombinant microorganisms expressing a polypeptide having the activity of a carboxylate reductase, a polypeptide having the activity of a phosphopantetheinyl transferase also can be expressed as it enhances activity of the carboxylate reductase.

For example, a recombinant microorganism can include a polypeptide having the activity of an exogenous hydroperoxide lyase and produce non-3-enal and 9-oxononanoate from 9-hydroxyperoxyoctadec-10,12-dienoate. The non-3-enal and 9-oxononanoate can be converted enzymatically to pimeloyl-CoA and subsequently to one or more of pimelic acid, 7-aminoheptanoate, 7-hydroxyheptanoic acid, heptamethylenediamine, or 1,7-heptanediol, or corresponding salts thereof.

For example, a recombinant microorganism producing pimeloyl-CoA can include one or more of exogenous polypeptides having the enzymatic activity of: a thioesterase, a CoA ligase, a CoA transferase, an acetylating aldehyde dehydrogenase, a succinate-semialdehyde dehydrogenase, a 5-oxopentanoate dehydrogenase, a 6-oxohexanoate dehydrogenase, and/or a 7-oxoheptanoate dehydrogenase, and further produce pimelic acid. See FIG. 3.

For example, a recombinant microorganism producing pimeloyl-CoA can include an exogenous polypeptide having the activity of a thioesterase and produce pimelic acid. For example, a recombinant microorganism producing pimeloyl-CoA can include an exogenous polypeptide having the activity of a CoA ligase or a CoA transferase, and further produce pimelic acid. For example, a recombinant microorganism producing pimeloyl-CoA can include an exogenous polypeptide having the activity of an acetylating aldehyde dehydrogenase and one or more polypeptides having the enzymatic activity of: an aldehyde dehydrogenase, a succinate-semialdehyde dehydrogenase, a 5-oxopentanoate dehydrogenase, a 6-oxohexanoate dehydrogenase, and/or a 7-oxoheptanoate dehydrogenase, and produce pimelic acid. See FIG. 3.

For example, a recombinant microorganism can include one or more exogenous polypeptides having the enzymatic activity of an aldehyde dehydrogenase, a ω-transaminase, and/or a carboxylate reductase, and produce 7-aminoheptanoate. See FIG. 4.

For example, a recombinant microorganism producing pimeloyl-CoA can include an exogenous polypeptide having the activity of an acetylating aldehyde dehydrogenase and an exogenous polypeptide having the activity of a ω-transaminase, and produce 7-aminoheptanoate. For example, a recombinant microorganism producing pimelate (see FIG. 3) can include an exogenous polypeptide having the activity of a carboxylate reductase and an exogenous polypeptide having the activity of a ω-transaminase, and produce 7-aminoheptanoate. See FIG. 4.

For example, a recombinant microorganism producing pimeloyl-CoA can include one or more exogenous polypeptides having the enzymatic activity of a carboxylate reductase, an alcohol dehydrogenase, a 4-hydroxybutanoate dehydrogenase, a 5-hydroxypentanoate dehydrogenase, a 6-hydroxyhexanoate dehydrogenase, and/or an aldehyde dehydrogenase and further produce 7-hydroxyheptanoate. See FIG. 6.

For example, a recombinant microorganism producing pimeloyl-CoA can include an exogenous polypeptide having the activity of a carboxylate reductase and an exogenous polypeptide having the activity of a 4-hydroxybutanoate dehydrogenase, and produce 7-hydroxyheptanoate. For example, a recombinant microorganism producing pimeloyl-CoA can include an exogenous polypeptide having the activity of a carboxylate reductase and an exogenous polypeptide having the activity of a 5-hydroxypentanoate dehydrogenase, and produce 7-hydroxyheptanoate. For example, a recombinant microorganism producing pimeloyl-CoA can include an exogenous polypeptide having the activity of a carboxylate reductase and an exogenous polypeptide having the activity of a 6-hydroxyhexanoate dehydrogenase, and produce 7-hydroxyheptanoate. For example, a recombinant microorganism producing pimelate (see FIG. 3) can include an exogenous polypeptide having the activity of a carboxylate reductase and an exogenous polypeptide having the activity of either a 4-hydroxybutanoate dehydrogenase, a 5-hydroxypentanoate dehydrogenase, or a 6-hydroxyhexanoate dehydrogenase, and produce 7-hydroxyheptanoate. See FIG. 6.

For example, a recombinant microorganism producing pimeloyl-CoA can include one or more exogenous polypeptides to produce 7-aminoheptanoate or 7-hydroxyheptanoate. See FIG. 4 and FIG. 6. A recombinant microorganism producing 7-aminoheptanoate or 7-hydroxyheptanoate can include one or more exogenous polypeptides having the activity of: a carboxylate reductase, a ω-transaminase, an alcohol dehydrogenase, an N-acetyltransferase, and/or a deacylase, and produce heptamethylenediamine. See FIG. 5.

For example, a recombinant microorganism producing pimeloyl-CoA can include the polypeptides necessary to convert pimeloyl-CoA to 7-aminoheptanoate and can include an exogenous polypeptide having the activity of a carboxylate reductase and one or more exogenous polypeptides having the activity of ω-transaminases (e.g., one transaminase or two different transaminases) and produce heptamethylenediamine. For example, a recombinant microorganism producing pimeloyl-CoA can include the polypeptides necessary to convert pimeloyl-CoA to 7-aminoheptanoate and can include one or more exogenous polypeptides having the activity of an N-acetyltransferase, a carboxylate reductase, a ω-transaminase, and/or a deacylase, and produce heptamethylenediamine. For example, a recombinant microorganism producing pimeloyl-CoA can include the polypeptides necessary to convert pimeloyl-CoA to 7-hydroxyheptanoate and can include one or more exogenous polypeptides having the activity of a carboxylate reductase, a ω-transaminase (e.g., one transaminase or two different transaminases), and/or an alcohol dehydrogenase, and produce heptamethylenediamine. See FIG. 5.

For example, a recombinant microorganism producing pimeloyl-CoA can include the polypeptides having the necessary enzymatic activity for conversion of pimeloyl-CoA to 7-hydroxyheptanoate (see FIG. 6) as described above and can also include one or more exogenous polypeptides having the enzymatic activity of a carboxylate reductase and/or an alcohol dehydrogenase, and further produce 1,7-heptanediol from 7-hydroxyheptanoate. See FIG. 7.

In any of the recombinant microorganisms, the recombinant microorganism also can include one or more (e.g., one, two, or three) of the following exogenous enzymes used to convert either octadecanoyl-CoA to 9-hydroxyperoxyoctadec-10,12-dienoate: a delta9-desaturase, a delta12-desaturase, a thioesterase, or a 9-lipoxygenase. For example, a recombinant microorganism can include a delta9-desaturase, a delta12-desaturase, a thioesterase, and a 9-lipoxygenase.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL. Enzyme Commission (EC) numbers for many enzymes are also provided. EC numbers are well known in the art and provide a numerical classification scheme for enzymes based on the chemical reactions they catalyze. An enzyme classified with an EC number to the fourth level is discretely and specifically classified on the basis of the reactions that its members are able to perform. Well known nomenclature databases such as ENZYME, maintained by the Swiss Institute of Bioinformatics, provide examples of specific enzymes corresponding to specific EC numbers.

Any of the enzymes described herein that can be used for production of one or more C7 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide having the activity of a carboxylate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see GenBank Accession No. ACC40567.1, SEQ ID NO: 1), a *Mycobacterium smegmatis* (see GenBank Accession No. ABK71854.1, SEQ ID NO: 2), a *Segniliparus rugosus* (see GenBank Accession No. EFV11917.1, SEQ ID NO: 3), a *Mycobacterium smegmatis* (see GenBank Accession No. ABK75684.1, SEQ ID NO: 4), a *Mycobacterium massiliense* (see GenBank Accession No. EIV11143.1, SEQ ID NO: 5), or a *Segniliparus rotundus* (see GenBank Accession No. ADG98140.1, SEQ ID NO: 6) carboxylate reductase. See FIGS. 8A-8G.

For example, a polypeptide having the activity of a ω-transaminase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see GenBank Accession No. AAQ59697.1, SEQ ID NO: 7), a *Pseudomonas aeruginosa* (see GenBank Accession No. AAG08191.1, SEQ ID NO: 8), a *Pseudomonas syringae* (see GenBank Accession No. AAY39893.1, SEQ ID NO: 9), a *Rhodobacter sphaeroides* (see GenBank Accession No. ABA81135.1, SEQ ID NO: 10), an *Escherichia coli* (see GenBank Accession No. AAA57874.1, SEQ ID NO: 11, SEQ ID NO: 48), or a *Vibrio fluvialis* (see GenBank Accession No. AEA39183.1, SEQ ID NO: 12) ω-transaminase. Some of these ω-transaminases are diamine ω-transaminases. See FIGS. 8G-8J.

Figure 8G:
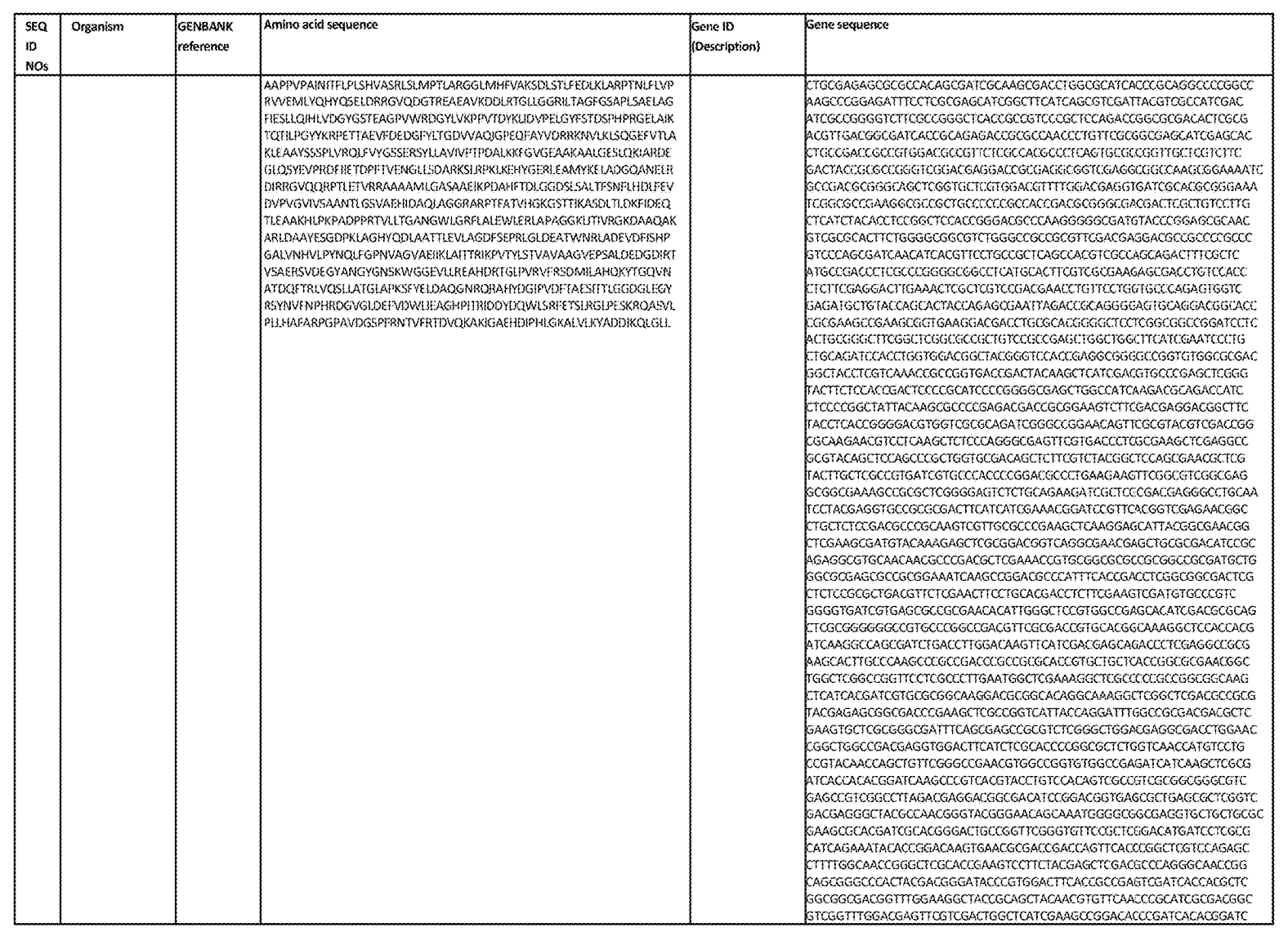
Figure 8K:
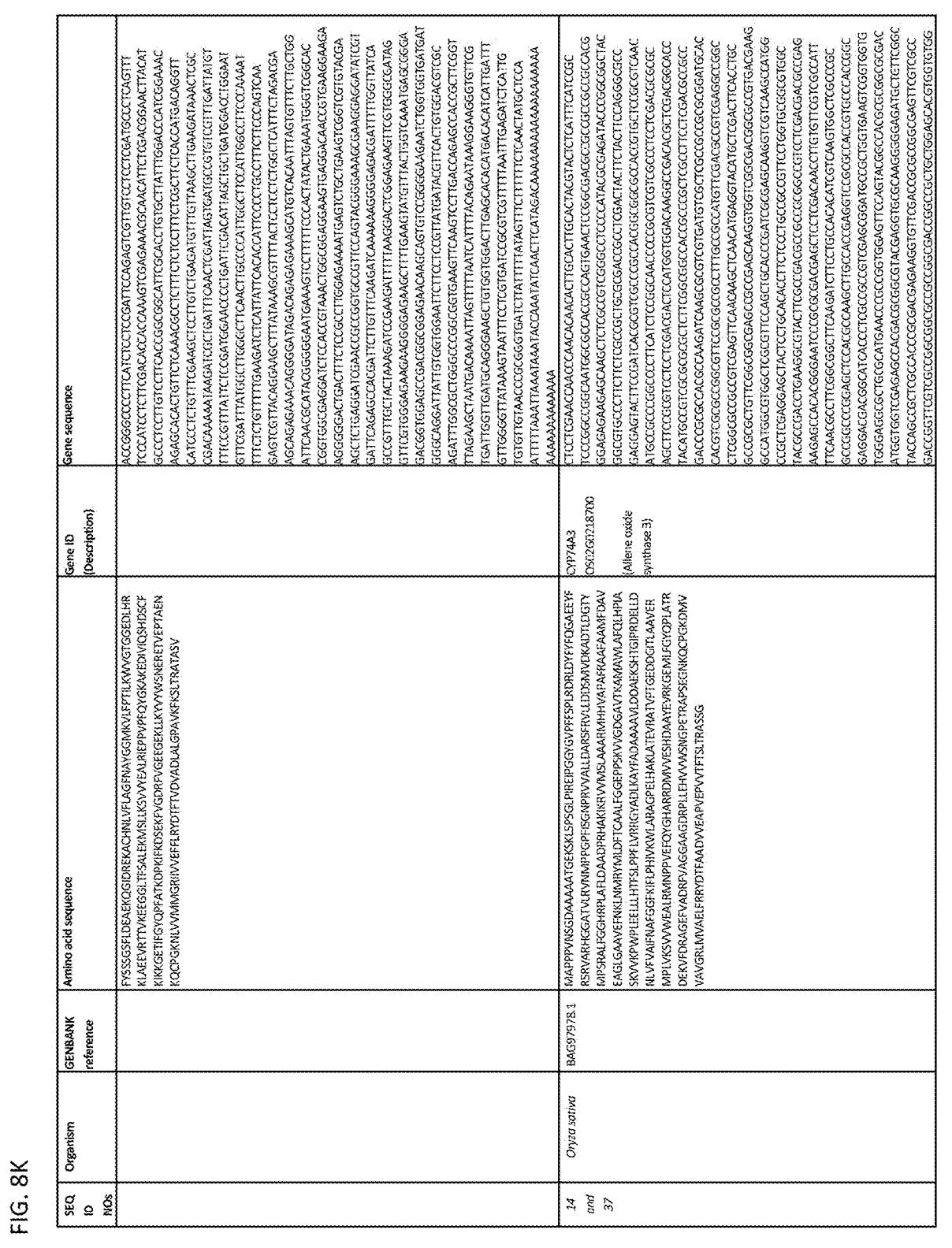

For example, a polypeptide having the activity of a hydroperoxide lyase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Cucumis sativus* (see GenBank Accession No. AAF64041.1, SEQ ID NO: 13) or a *Oryza sativa* hydroperoxide lyase (see GenBank Accession No. BAG97978.1, SEQ ID NO: 14). See FIGS. 8J-8K.

For example, a polypeptide having the activity of an enoate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Lactobacillus casei* (see GenBank Accession No. AGP69310.1, SEQ ID NO: 15) or a *Pseudomonas putida* enoate reductase (see GenBank Accession No. AAN66878.1, SEQ ID NO: 16). See FIGS. 8K-8L.

For example, a polypeptide having the activity of an isomerase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Saccharomyces cerevisiae* isomerase (see GenBank Accession No. AAC83700.1, SEQ ID NO: 17 and SEQ ID NO: 19). See FIGS. 8L-8M.

For example, a polypeptide having the activity of a thioesterase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Clostridium perfringens* (see GenBank Accession No. ABG82470.1, SEQ ID NO: 18), a *Bacteroides thetaiotaomicron* VPI-5482 (see GenBank Accession No. AAO77182.1, SEQ ID NO: 20), a *Lactobacillus plantarum* WCFS1 (see GenBank Accession No. CCC78182.1, SEQ ID NO: 22), or a *Anaerococcus tetradius* ATCC 35098 (see GenBank Accession No. EEI82564.1, SEQ ID NO: 23). See FIGS. 8L-8N.

For example, a polypeptide having the activity of an alcohol dehydrogenase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Geobacillus stearothermophilus* (see GenBank Accession No. CAA81612.1, SEQ ID NO: 21). See FIG. 8M.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 100 (e.g., not more than one, two, three, four, five, six, seven, eight, nine, ten, 12, 15, 20, 25, 30, 35, 40, 50, 60, 70, 80, 90 or 100) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, 20, 30, 40, or 50 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., heptahistidine (SEQ ID NO: 47)), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain microorganisms (e.g., yeast cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered microorganisms can naturally express none or some (e.g., one or more, two or more, three or more, four or more, five or more, or six or more) of the enzymes of the pathways described herein. Thus, a pathway within an engineered microorganism can include all exogenous enzymes, or can include both endogenous and exogenous enzymes. Endogenous genes of the engineered microorganisms also can be disrupted to prevent the formation of undesirable metabolites or prevent the loss of intermediates in the pathway through other enzymes acting on such intermediates. Engineered microorganisms can be referred to as recombinant microorganisms or recombinant cells. As described herein recombinant microorganisms can include nucleic acids encoding one or more of a hydroperoxide lyase, an aldehyde dehydrogenase, a CoA ligase, a dodecenoyl-CoA isomerase or an enoate reductase, a trans-2-enoyl-CoA reductase, a thioesterase, a monooxygenase, an enoyl-CoA hydratase, a deacetylase, an acyl-CoA dehydrogenase, an enoyl-CoA hydratase, an alcohol dehydrogenase, a 4-hydroxybutanoate dehydrogenase, a 6-hydroxyhexanoate dehydrogenase, an aldehyde dehydrogenase, a succinate-semialdehyde dehydrogenase a 5-oxopentanoate dehydrogenase, a 6-oxohexanoate dehydrogenase, a 7-oxoheptanoate dehydrogenase, an acyl-CoA dehydrogenase, an enoyl-CoA hydratase, a 3-hydroxyacyl-CoA dehydrogenase, a 3-oxoacyl ACP reductase, a β-ketothiolase, a delta9-desaturase, a delta12-desaturase, a thioesterase, or a 9-lipoxygenase, as described herein.

In addition, the production of C7 building blocks can be performed in vitro using the isolated enzymes described herein, using a lysate (e.g., a cell lysate) from a microorganism as a source of the enzymes, or using one or more lysates from different microorganisms as the source of the enzymes.

The reactions of the pathways described herein can be performed in one or more microorganisms (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be isolated, purified or extracted from of the above types of microorganism cells and used in a purified or semi-purified form. Moreover, such extracts include lysates (e.g., cell lysates) that can be used as sources of relevant enzymes. In the methods provided by the document, all the steps can be performed in microorganism cells, all the steps can be performed using extracted enzymes, or some of the steps can be performed in cells and others can be performed using extracted enzymes.

Enzymes
Enzymes Generating Pimeloyl-CoA

Figure 2:
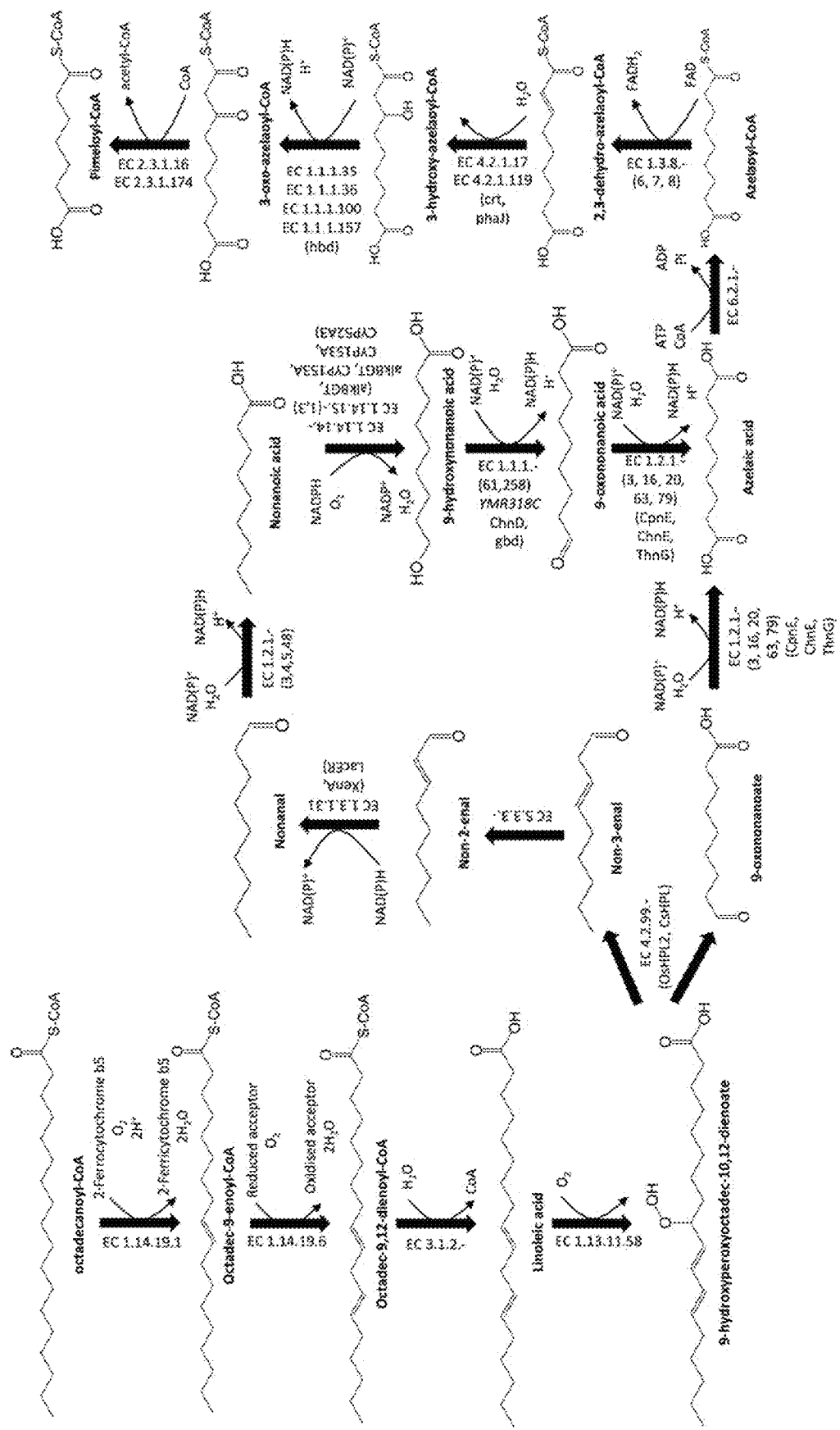
FIG. 2 is a schematic of further exemplary biochemical pathways leading to pimeloyl-CoA via enoate reductase activity using octadecanoyl-CoA as a central metabolite.
Figure 9:
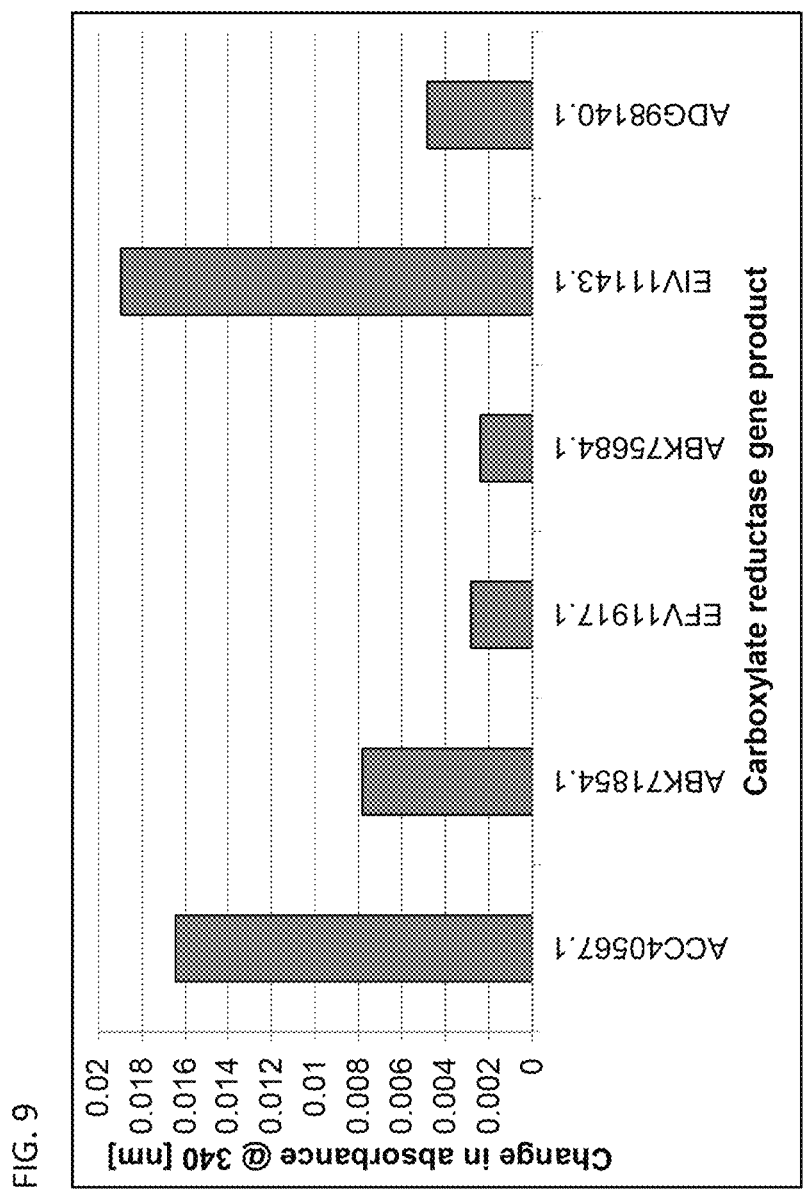
FIG. 9 is a bar graph summarizing the change in absorbance at 340 nm after 20 minutes, which is a measure of the consumption of NADPH and activity of six carboxylate reductase preparations in enzyme only controls (no substrate).

As depicted in FIG. 1 and FIG. 2, 9-hydroxyperoxyoctadec-10,12-dienoate can be enzymatically synthesized from the central metabolite octadecanoyl-CoA using one or more exogenous polypeptides having the enzymatic activity of: a delta9-desaturase, a delta12-desaturase, a thioesterase, and/or a 9-lipoxygenase.

In some embodiments, a polypeptide having the activity of a delta9-desaturase may be classified under EC 1.14.19.1, such as, for example, the gene product of Le-FAD1 from *Lentinula edodes* (UniProtKB Accession No. Q76C19), the gene product of SCD1 from *Mesocricetus auratus* (UniProtKB Accession No. A7LCI9), an acyl-CoA-delta9-3a-desaturase from *Dendrolimus punctatus* (UniProtKB Accession No. B7SB75), the gene product of scd1 from *Rattus norvegicus* (UniProtKB Accession No. P07308), the gene product of PF3D7_0511200 from *Plasmodium falciparum* (UniProtKB Accession No. Q8I0W9), or the gene product of desB1 from *Bombus lucorum* (UniProtKB Accession No. A5CKE1).

A polypeptide having the activity of a delta12-desaturase may be classified under EC 1.14.19.6, such as, for example, the gene product of D12Des from *Acheta domesticus* (UniProtKB Accession No. B7SB91), the gene product of FAD2 from *Gossypium hirsutum* (UniProtKB Accession No. Q8W2B9), the gene product of CFad6 from *Chlorella vulgaris* (UniProtKB Accession No. D3U658), a delta12 fatty acid desaturase from *Triadica sebifera* (UniProtKB Accession No. A5J295), the gene product of Pc-fad2 from *Phanerochaete chrysosporium* (UniProtKB Accession No. D4Q8H2), the gene product of Cs-fad2 from *Ceriporiopsis subvermispora* (UniProtKB Accession No. D4Q8S6), or the gene product of AN1037.2 from *Emericella nidulans* (UniProtKB Accession No. Q5BEJ3).

A polypeptide having the activity of a thioesterase may be classified under EC 3.1.2.-, such as, for example, the gene product of BT_2075 from *Bacteroides thetaiotaomicron* (strain ATCC 29148/DSM 2079/NCTC 10582/E50/VPI-5482) (GenBank Accession No. AAO77182.1, SEQ ID NO: 20), the gene product of lp_0708 from *Lactobacillus plantarum* (strain ATCC BAA-793/NCIMB 8826/WCFS1) (GenBank Accession No. CCC78182.1, SEQ ID NO: 22), the gene product of HMPREF0077_1317 from *Anaerococcus tetradius* ATCC 35098 (GenBank Accession No. EEI82564.1, SEQ ID NO: 23), or the gene product of CPF_2954 from *Clostridium perfringens* (strain ATCC 13124/DSM 756/JCM 1290/NCIMB 6125/NCTC 8237/Type A) (GenBank Accession No. ABG82470.1, SEQ ID NO: 18).

A polypeptide having the activity of a 9-lipoxygenase may be classified, for example, under EC 1.13.11.58, EC 1.13.11.60, EC 1.13.11.61, or EC 1.13.11.62, such as, for example, an allene oxide synthase-lipoxygenase protein from *Plexaura homomalla* (UniProtKB Accession No. O16025), a Psi-producing oxygenase A from *Emericella nidulans* (UniProtKB Accession No. Q6RET3), a 5,8-linoleate diol synthase from *Aspergillus fumigatus* (UniProtKB Accession No. C1KH66), or a linoleate diol synthase from *Gaeumannomyces graminis* (UniProtKB Accession No. Q9UUS2).

As further depicted in FIG. 1 and FIG. 2, 9-hydroperoxyoctadec-10,12-dienoate may be enzymatically cleaved into non-3-enal and 9-oxononanoate using a polypeptide having the activity of a hydroperoxide lyase. In some embodiments, a polypeptide having the activity of a hydroperoxide lyase may be classified under EC 4.2.99.-, such as, for example, the gene product of *Cucumis sativus* (GenBank Accession No. AAF64041.1, SEQ ID NO: 13) or the gene product of *Oryza sativa* (GenBank Accession No. BAG97978.1, SEQ ID NO: 14).

As shown in FIG. 1 and FIG. 2, non-3-enal and 9-oxononanoate may be converted by separate enzymatic pathways to azelaic acid. Azelaic acid, regardless of its origination from non-3-enal or 9-oxononanoate, may then be converted to pimeloyl-CoA. The enzymes involved in the conversion of non-3-enal to azelaic acid, 9-oxononanoate to azelaic acid and azelaic acid to pimeloyl-CoA are as described in the following paragraphs.

As shown in FIG. 1, non-3-enal may be converted to azelaic acid by one or more exogenous polypeptides having the enzymatic activities of: (i) an aldehyde dehydrogenase, (ii) a CoA ligase, (iii) a dodecenoyl-CoA isomerase, (iv) a trans-2-enoyl-CoA reductase, (v) a thioesterase, (vi) a monooxygenase, (vii) an alcohol dehydrogenase, and/or (viii) a succinate-semialdehyde dehydrogenase, a 5-oxopentanoate dehydrogenase, a 6-oxohexanoate dehydrogenase, and/or a 7-oxoheptanoate dehydrogenase.

As shown in FIG. 2, non-3-enal may be converted to azelaic acid by one or more exogenous polypeptides having the enzymatic activities of: (i) an enal isomerase, (ii) an enoate reductase, (iii) an aldehyde dehydrogenase, (iv) a monooxygenase, (v) an alcohol dehydrogenase, and/or (vi) a succinate-semialdehyde dehydrogenase, a 7-oxoheptanoate dehydrogenase, a 6-oxohexanoate dehydrogenase, and/or a 5-oxopentanoate dehydrogenase.

In some embodiments, a polypeptide having the activity of an aldehyde dehydrogenase may be classified under EC 1.2.1.-, such as EC 1.2.1.3, EC 1.2.1.4, EC 1.2.1.5, or EC 1.2.1.48, such as, for example, the gene product of Bt-aldh from *Geobacillus thermoleovorans* B23 (UniProtKB Accession No. Q9FAB1), the gene product of dhaS from *Bacillus subtilis* (UniProtKB Accession No. O34660), the gene product of ALD5 from *Saccharomyces cerevisiae* (UniProtKB Accession No. A6ZR27), the gene product of ALDH2C4 from *Arabidopsis thaliana* (UniProtKB Accession No. Q56YU0), the gene product of aldh7 from *Rhodococcus ruber* (UniProtKB Accession No. Q840S9), the gene product of alkH from *Pseudomonas oleovorans* (UniProtKB Accession No. P12693), the gene product of ald1 from *Acinetobacter* sp. M-1 (UniProtKB Accession No. Q9FDS1), or the gene product of acoD from *Ralstonia eutropha* (UniProtKB Accession No. P46368).

In some embodiments, a polypeptide having the activity of an enoate reductase may be classified, for example, under EC 1.3.1.31, such as, for example, the gene product of xenA from *Pseudomonas putida* (GenBank Accession No. AAN66878.1, SEQ ID NO: 16) or the gene product of LOCK919_2632 from *Lactobacillus casei* (GenBank Accession No. AGP69310.1, SEQ ID NO: 15).

In some embodiments, a polypeptide having the activity of a CoA ligase may be classified under EC 6.2.1.-, such as, for example, the gene product of acs6 from *Brassica napus* (UniProtKB Accession No. Q9FNT6), the gene product of PCS60 from *Saccharomyces cerevisiae* (UniProtKB Accession No. P38137), the gene product of alkK from *Pseudomonas oleovorans* (UniProtKB Accession No. Q00594), the gene product of ACSM5 from *Homo sapiens* (UniProtKB Accession No. Q6NUN0), or the gene product of alkK from *Aeropyrum pernix* (UniProtKB Accession No. Q9YF45).

In some embodiments, a polypeptide having the activity of a dodecenoyl-CoA isomerase may be classified under EC 5.3.3.8, such as, for example, the gene product of ECI1 from *Saccharomyces cerevisiae* (GenBank Accession No. AAC83700.1, SEQ ID NO: 17 and SEQ ID NO: 19, Geisbrecht et al J. Biol. Chem, 1998 273 (50) 33184-33191).

In some embodiments, a polypeptide having the activity of a trans-2-enoyl-CoA reductase may be classified under EC 1.3.1.38 or EC 1.3.1.44, such as, for example, the gene product of ter from *Escherichia coli, Fibrobacter succinogenes*, or *Treponema denticola* (Nishimaki et al., J. Biochem., 1984, 95:1315-1321; Shen et al., 2011, supra) or tdter from *Treponema denticola* (Bond-Watts et al., *Biochemistry*, 2012, 51:6827-6837) or EC 1.3.1.8 (Inui et al., *Eur. J. Biochem.*, 1984, 142, 121-126).

In some embodiments, a polypeptide having the activity of a thioesterase may be classified under EC 3.1.2.-, such as, for example, the gene product of BT_2075 from *Bacteroides thetaiotaomicron* (strain ATCC 29148/DSM 2079/NCTC 10582/E50/VPI-5482) (GenBank Accession No. AAO77182.1, SEQ ID NO: 20), the gene product of lp_0708 from *Lactobacillus plantarum* (strain ATCC BAA-793/NCIMB 8826/WCFS1) (GenBank Accession No. CCC78182.1, SEQ ID NO: 22), the gene product of HMPREF0077_1317 from *Anaerococcus tetradius* ATCC 35098 (GenBank Accession No. EEI82564.1, SEQ ID NO: 23), or the gene product of CPF_2954 from *Clostridium perfringens* (strain ATCC 13124/DSM 756/JCM 1290/NCIMB 6125/NCTC 8237/Type A) (GenBank Accession No. ABG82470.1, SEQ ID NO: 18).

In some embodiments, a polypeptide having the activity of a monooxygenase may be classified in the cytochrome P450 family under EC 1.14.14.- or EC 1.14.15.-, such as EC 1.14.14.1, EC 1.14.14.3, EC 1.14.15.1, or EC 1.14.15.3 or as the gene products of alkBGT from *Pseudomonas putida*, CYP153A from *Polaromonas* sp., or CYP52A3 from *Saccharomyces cerevisiae*.

In some embodiments, a polypeptide having the activity of an alcohol dehydrogenase may be classified under EC 1.1.1.-, such as a 6-hydroxyhexanoate dehydrogenase classified, for example, under EC 1.1.1.258, such as, for example, the gene product of chnD from *Acinetobacter* sp. NCIMB9871 (Donoghue et al., Eur. J. Biochem, 1975, 60: 1-7); or a 4-hydroxybutanoate dehydrogenase classified, for example, under EC 1.1.1.61 such as, for example, the gene product of gbd (e.g., from *Sorangium cellulosum*). In some embodiments, a polypeptide having the activity of an aldehyde dehydrogenase may be classified under, for example, EC 1.2.1.-, such as a 7-oxoheptanoate dehydrogenase (e.g., the gene product of thnG from *Sphingomonas macrogolitabida*), a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (e.g., the gene product of cpnE *Comamonas* sp.), a succinate-semialdehyde dehydrogenase classified, for example, under EC 1.2.1.16, EC 1.2.1.24, or EC 1.2.1.79 (e.g., the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from *Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9)), or an aldehyde dehydrogenase classified under EC 1.2.1.3.

As shown in FIG. 1 and FIG. 2, 9-oxononanoate may be converted to azelaic acid by one or more exogenous polypeptides having the following enzymatic activities; for example, a 7-oxoheptanoate dehydrogenase (e.g., the gene product of thnG from *Sphingomonas macrogolitabida*) classified under EC 1.2.1.-, a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (the gene product of cpnE from *Comamonas* sp.), a succinate-semialdehyde dehydrogenase classified, for example, under EC 1.2.1.16, EC 1.2.1.24, or EC 1.2.1.79, and/or an aldehyde dehydrogenase classified under EC 1.2.1.3.

As shown in FIG. 1 and FIG. 2, azelaic acid may be converted to pimeloyl-CoA by one or more exogenous polypeptides having the enzymatic activities of: a CoA ligase, an acyl-CoA dehydrogenase, an enoyl-CoA hydratase, a 3-hydroxyacyl-CoA dehydrogenase, a 3-oxoacyl-ACP reductase, and/or a β-ketothiolase. In some embodiments, a polypeptide having the activity of a CoA ligase may be classified under, for example, EC 6.2.1.-.

In some embodiments, a polypeptide having the activity of an acyl-CoA dehydrogenase may be classified under, for example, EC 1.3.8.-, such as EC 1.3.8.6, EC 1.3.8.7, or EC 1.3.8.8.

In some embodiments, a polypeptide having the activity of an enoyl-CoA hydratase may be classified under, for example, EC 4.2.1.17, such as, for example, the gene product of crt from *Clostridium acetobutylicum*, or classified under EC 4.2.1.119, such as, for example, the gene product of phaJ from *Pseudomonas aeruginosa*. In some embodiments, a polypeptide having the activity of a 3-hydroxyacyl-CoA dehydrogenase may be classified for example, under EC 1.1.1.-, such as EC 1.1.1.35 (e.g., the gene product of fadB from *Escherichia coli*), EC 1.1.1.36 (e.g., the gene product of phaB from *Cupriavidus* necator), or EC 1.1.1.157 (e.g., the gene product of hbd from *Clostridium acetobutylicum*), and a polypeptide having the activity of a 3-oxoacyl-ACP reductase may be classified, for example, under EC 1.1.1.100, such as, for example, the gene product of fabG from *Escherichia coli*.

In some embodiments, a polypeptide having the activity of a β-ketothiolase may be classified, for example, under EC 2.3.1.16 or EC 2.3.1.174 such as, for example, the gene product of bktB from *Cupriavidus* necator or paaJ from *Escherichia coli*.

Figure 3:
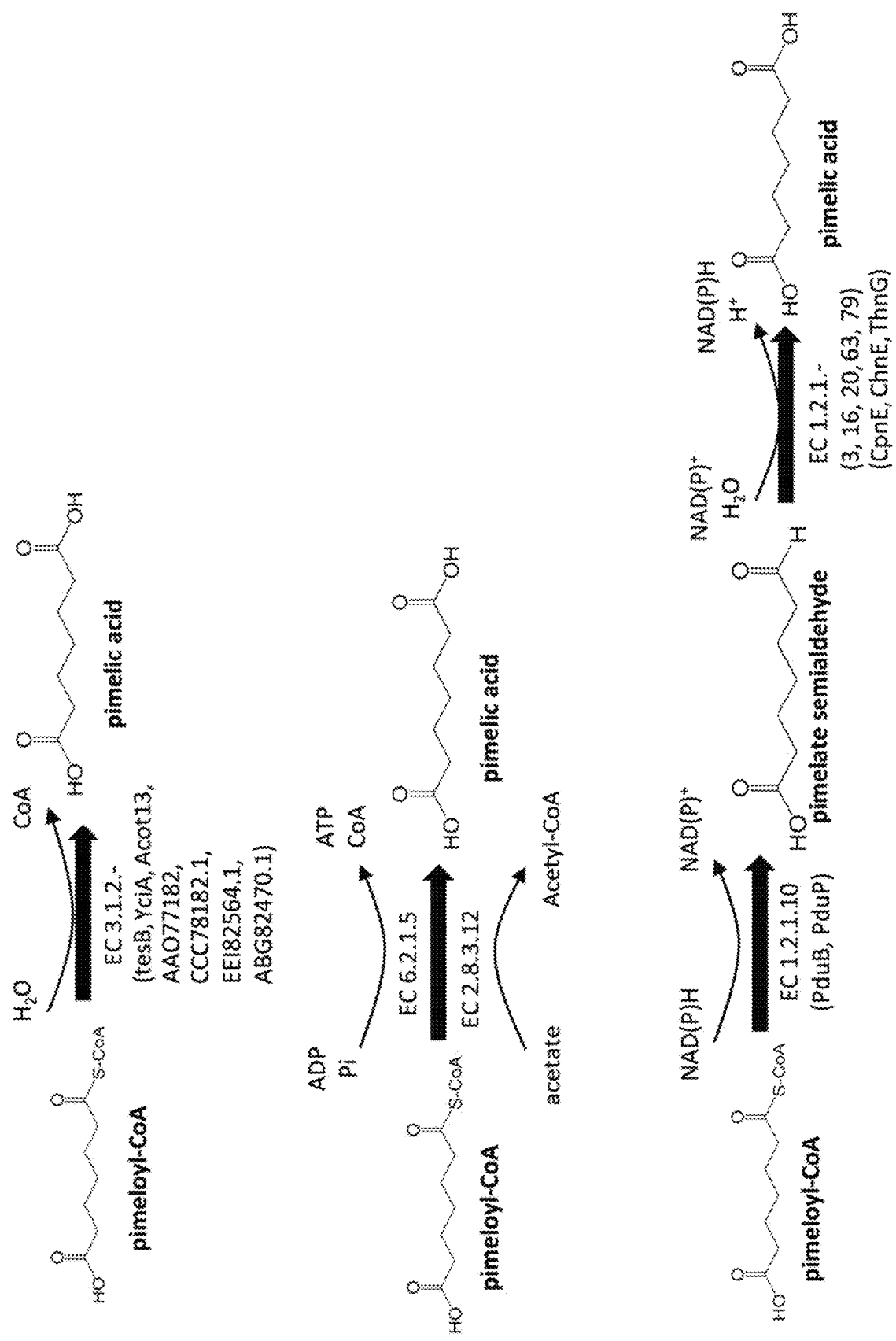
FIG. 3 is a schematic of exemplary biochemical pathways leading to pimelic acid using pimeloyl-CoA as a central precursor.

Enzymes Generating the Terminal Carboxyl Groups in the Biosynthesis of Pimelic Acid As depicted in FIG. 3, pimeloyl-CoA can be enzymatically converted to pimelic acid. The terminal carboxyl group leading to the production of pimelic acid can be enzymatically formed using polypeptides having the activity of a thioesterase, a CoA ligase, a CoA transferase, an aldehyde dehydrogenase, a succinate-semialdehyde dehydrogenase, a 5-oxopentanoate dehydrogenase, a 6-oxohexanoate dehydrogenase, and/or a 7-oxoheptanoate dehydrogenase.

In some embodiments, the second terminal carboxyl group leading to the synthesis of pimelic acid can be enzymatically formed in pimeloyl-CoA by a polypeptide having the activity of a thioesterase classified under EC 3.1.2.-. The polypeptide having the activity of a thioesterase can be, for example, the gene product of yciA from *Escherichia coli* or acot13 from *Mus musculus* (Cantu et al., Protein Science, 2010, 19, 1281-1295; Zhuang et al., Biochemistry, 2008, 47(9):2789-2796; Naggert et al., J. Biol. Chem., 1991, 266(17):11044-11050), or tesB from *Escherichia coli*, or the gene product of BT_2075 from *Bacteroides thetaiotaomicron* (strain ATCC 29148/DSM 2079/NCTC 10582/E50/VPI-5482) (GenBank Accession No. AAO77182.1, SEQ ID NO: 20), the gene product of lp_0708 from *Lactobacillus plantarum* (strain ATCC BAA-793/NCIMB 8826/WCFS1) (GenBank Accession No. CCC78182.1, SEQ ID NO: 22), the gene product of HMPREF0077_1317 from *Anaerococcus tetradius* ATCC 35098 (GenBank Accession No. EEI82564.1, SEQ ID NO: 23), or the gene product of CPF_2954 from *Clostridium perfringens* (strain ATCC 13124/DSM 756/JCM 1290/NCIMB 6125/NCTC 8237/Type A) (GenBank Accession No. ABG82470.1, SEQ ID NO: 18)).

In some embodiments, the second terminal carboxyl group leading to the synthesis of pimelic acid can be enzymatically formed in pimeloyl-CoA by a polypeptide having the activity of a CoA ligase classified under EC 6.2.1.-, such as EC 6.2.1.5 or EC 6.2.1.15, or a polypeptide having the activity of a CoA transferase classified under EC 2.8.3.-, such as EC 2.8.3.8 or EC 2.8.3.12 (e.g., a succinyl-CoA:acetate CoA-transferase from *Acetobacter aceti* (UniProtKB Accession No. B3EY95), the gene product of ANACAC_01149 from *Anaerostipes caccae* (UniProtKB Accession No. B0MC58), a butyryl-CoA:acetate CoA-transferase from *Butyrivibrio fibrisolvens* (UniProtKB Accession No. D2WEY7), a butyryl-CoA:acetate CoA-transferase from *Eubacterium hallii* (UniProtKB Accession No. D2WEY8), the gene product of FAEPRAA2165_01575 from *Faecalibacterium prausnitzii* (UniProtKB Accession No. C7H5K4), a butyryl-CoA:acetate CoA-transferase from *Faecalibacterium prausnitzii* (UniProtKB Accession No. D2WEZ2), the gene product of FAEPRAM212_02812 from *Faecalibacterium prausnitzii* (UniProtKB Accession No. A8SFP6), a butyryl-CoA transferase from *Roseburia hominis* (UniProtKB Accession No. Q2TME9), or a butyryl-CoA:acetate CoA-transferase from *Roseburia inulinivorans* (UniProtKB Accession No. D2WEY6)).

In some embodiments, pimeloyl-CoA can be enzymatically converted to pimelate semialdehyde by a polypeptide having the activity of an aldehyde dehydrogenase classified under, for example, EC 1.2.1.10, such as an acetaldehyde dehydrogenase encoded by pduB from *Salmonella typhimurium*. The second terminal carboxyl group leading to the synthesis of pimelic acid can be enzymatically formed in pimelate semialdehyde by a polypeptide having the activity of an aldehyde dehydrogenase classified under EC 1.2.1.3 (Guerrillot & Vandecasteele, *Eur. J. Biochem.*, 1977, 81, 185-192); a 7-oxoheptanoate dehydrogenase (e.g., the gene product of thnG from *Sphingomonas macrogolitabida*; López-Sanchez et al., *Appl. Environ. Microbiol.*, 2010, 76(1), 110-118) classified under EC 1.2.1.-; a 6-oxohexanoate dehydrogenase (e.g., the gene product of chnE from *Acinetobacter* sp.) classified, for example, under EC 1.2.1.63; a 5-oxopentanoate dehydrogenase classified, for example, under EC 1.2.1.20 (e.g., the gene product of cpnE from *Comamonas* sp.) or a succinate-semialdehyde dehydrogenase classified, for example, under EC 1.2.1.16, EC 1.2.1.24, or EC 1.2.1.79 (e.g., the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from *Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9)).

Enzymes Generating 7-Aminoheptanoate

Figure 4:
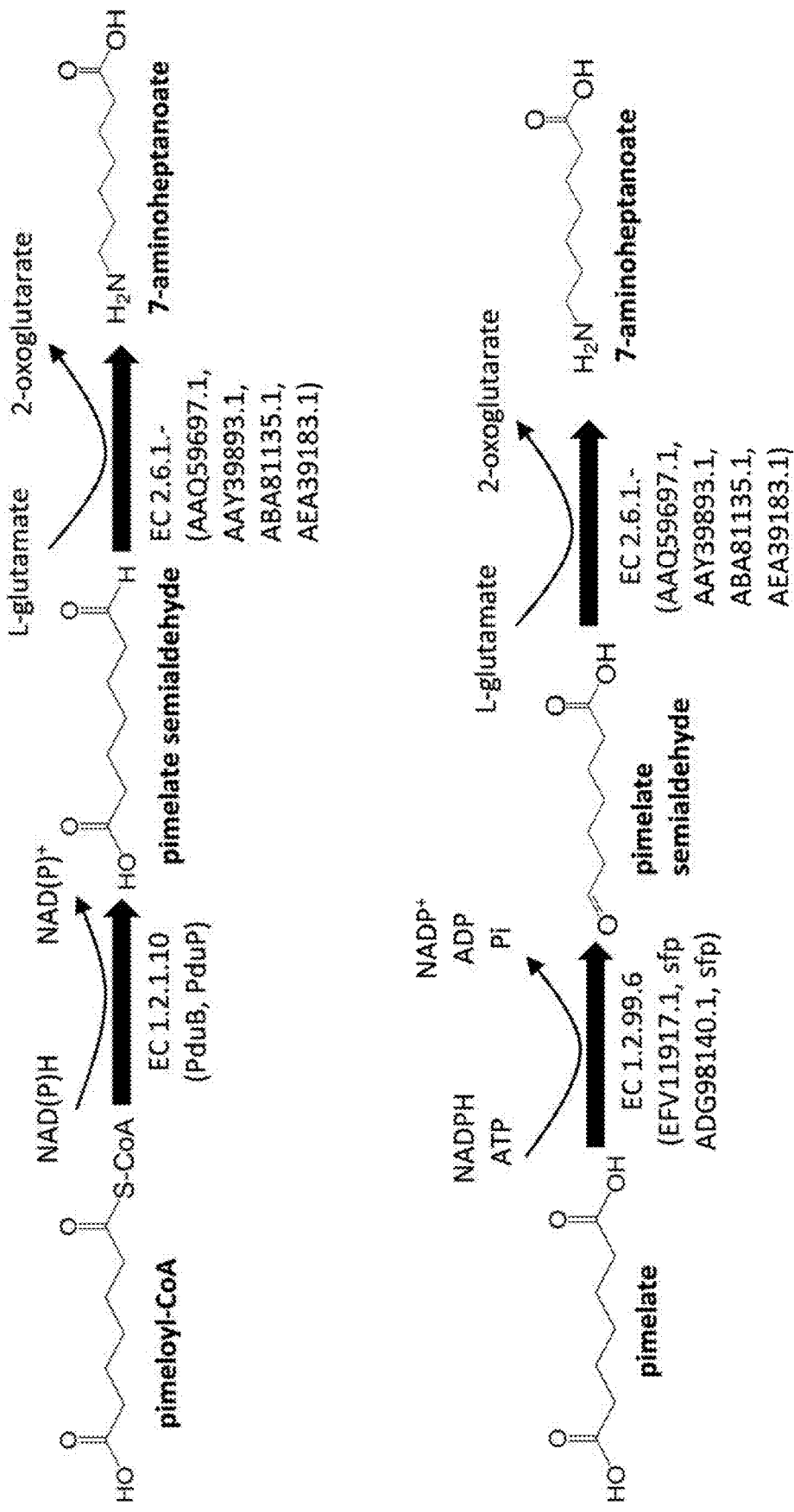
FIG. 4 is a schematic of exemplary biochemical pathways leading to 7-aminoheptanoate using pimeloyl-CoA and pimelate as central precursors.

As depicted in FIG. 4, pimeloyl-CoA is converted to pimelate semialdehyde by a polypeptide having the enzymatic activity of an aldehyde dehydrogenase classified under, for example, EC 1.2.1.10, such as an acetaldehyde dehydrogenase encoded by pduB from *Salmonella typhimurium* or pduP from *Klebsiella pneumoniae*. A terminal amine group may then be enzymatically formed or removed using one or more polypeptides having the activity of a ω-transaminase classified under, for example, EC 2.6.1.-, e.g., EC 2.6.1.18, EC 2.6.1.19, EC 2.6.1.29, EC 2.6.1.48, or EC 2.6.1.82, such as, for example, that obtained from *Chromobacterium violaceum* (GenBank Accession No. AAQ59697.1, SEQ ID NO: 7), *Pseudomonas aeruginosa* (GenBank Accession No. AAG08191.1, SEQ ID NO: 8), *Pseudomonas syringae* (GenBank Accession No. AAY39893.1, SEQ ID NO: 9), *Rhodobacter sphaeroides* (GenBank Accession No. ABA81135.1, SEQ ID NO: 10), *Escherichia coli* (GenBank Accession No. AAA57874.1, SEQ ID NO: 11, SEQ ID NO: 48), *Vibrio fluvialis* (GenBank Accession No. AEA39183.1, SEQ ID NO: 12), *Streptomyces griseus*, or *Clostridium viride*. See FIGS. 8G-8J. The reversible ω-transaminase from *Chromobacterium violaceum* (GenBank Accession No. AAQ59697.1, SEQ ID NO: 7) has demonstrated analogous activity accepting 7-aminoheptanoic acid as amino donor, thus forming the first terminal amine group in pimelate semialdehyde (Kaulmann et al., *Enzyme and Microbial Technology*, 2007, 41, 628-637).

Alternatively, pimelate (pimelic acid) as shown in FIG. 3, may be enzymatically converted to pimelate semialdehyde by a polypeptide having the activity of a carboxylate reductase classified, for example, under EC 1.2.99.6 such as polypeptides represented by the following GenBank Accession Nos: EFV11917.1 (SEQ ID NO: 3) and ADG98140.1 (SEQ ID NO: 6). A terminal amine group may then be enzymatically formed or removed from pimelate semialdehyde using one or more polypeptides having the activity of a ω-transaminase classified under, for example, EC 2.6.1.-, e.g., EC 2.6.1.18, EC 2.6.1.19, EC 2.6.1.29, EC 2.6.1.48, or EC 2.6.1.82, such as, for example, that obtained from *Chromobacterium violaceum* (GenBank Accession No. AAQ59697.1, SEQ ID NO: 7), *Pseudomonas aeruginosa* (GenBank Accession No. AAG08191.1, SEQ ID NO: 8), *Pseudomonas syringae* (GenBank Accession No. AAY39893.1, SEQ ID NO: 9), *Rhodobacter sphaeroides* (GenBank Accession No. ABA81135.1, SEQ ID NO: 10), *Vibrio fluvialis* (GenBank Accession No. AEA39183.1, SEQ ID NO: 12), *Streptomyces griseus*, or *Clostridium viride*. See FIGS. 8G-8J. The reversible ω-transaminase from *Chromobacterium violaceum* (GenBank Accession No. AAQ59697.1, SEQ ID NO: 7) has demonstrated analogous activity accepting 7-aminoheptanoic acid as amino donor, thus forming the first terminal amine group in pimelate semialdehyde (Kaulmann et al., *Enzyme and Microbial Technology*, 2007, 41, 628-637).

An additional ω-transaminase that can be used in the methods and microorganisms described herein is from *Escherichia coli* (GenBank Accession No. AAA57874.1, SEQ ID NO: 11, SEQ ID NO: 48). Some of the ω-transaminases classified, for example, under EC 2.6.1.29 or EC 2.6.1.82 are diamine ω-transaminases (e.g., SEQ ID NO: 11, SEQ ID NO: 48).

The reversible ω-transaminase from *Chromobacterium violaceum* (GenBank Accession No. AAQ59697.1, SEQ ID NO: 7) has demonstrated analogous activity accepting 7-aminoheptanoic acid as amino donor, thus forming the first terminal amine group in pimelate semialdehyde (Kaulmann et al., *Enzyme and Microbial Technology*, 2007, 41, 628-637).

Figure 5:
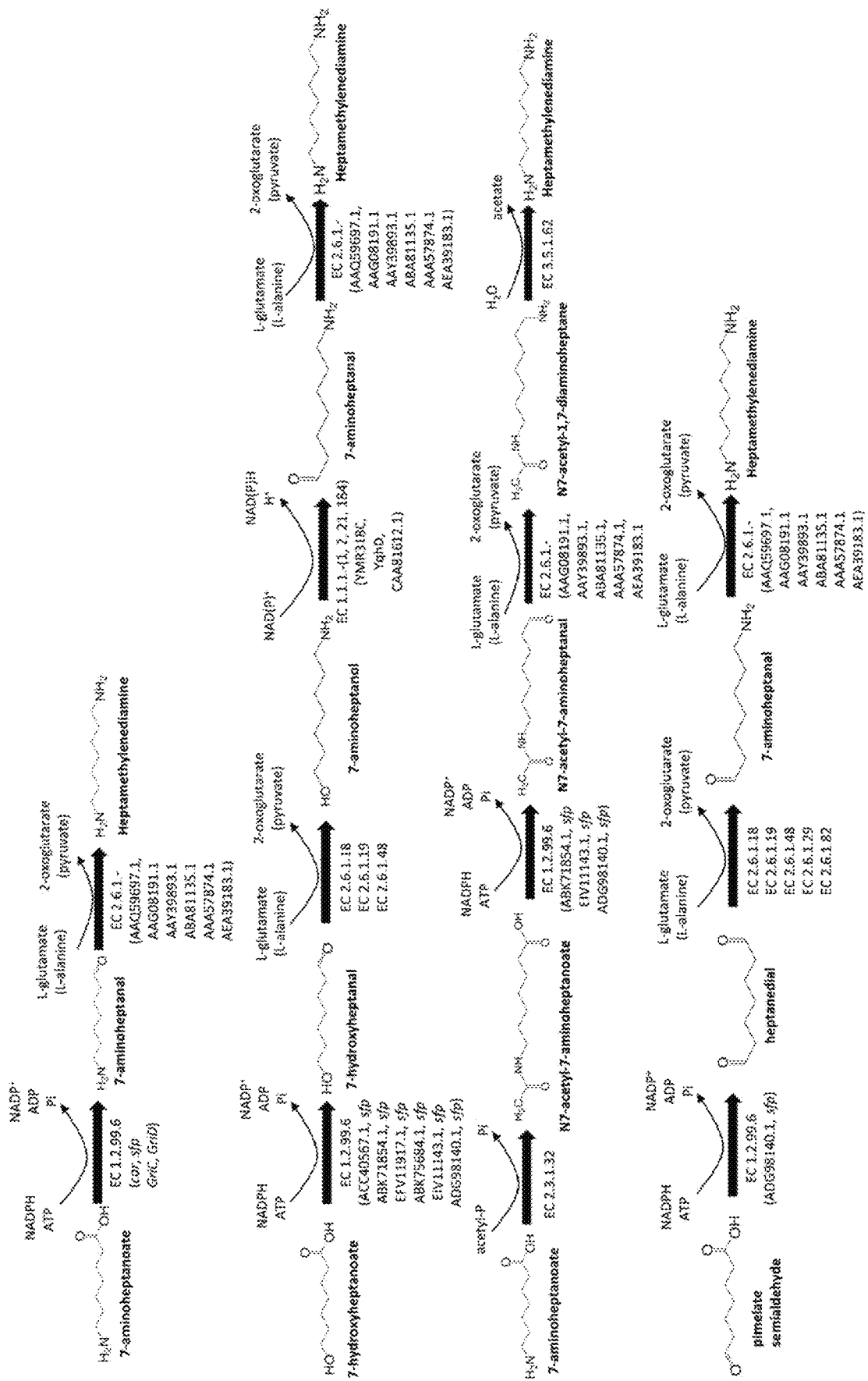
FIG. 5 is a schematic of exemplary biochemical pathways leading to heptamethylenediamine using 7-aminoheptanoate, 7-hydroxyheptanoate, and pimelate semialdehyde as central precursors.

Enzymes Generating the Terminal Amine Groups in the Biosynthesis of Heptamethylenediamine As depicted in FIG. 5, terminal amine groups can be enzymatically formed or removed using polypeptides having the activity of a ω-transaminase or a deacylase.

In some embodiments, a terminal amine group leading to the synthesis of 7-aminoheptanoic acid is enzymatically formed in 7-aminoheptanal by a polypeptide having the activity of a ω-transaminase classified, for example, under EC 2.6.1.-, e.g., EC 2.6.1.18, EC 2.6.1.19, EC 2.6.1.29, EC 2.6.1.48, or EC 2.6.1.82, such as that obtained, for example, from *Chromobacterium violaceum* (GenBank Accession No. AAQ59697.1, SEQ ID NO: 7), *Pseudomonas aeruginosa* (GenBank Accession No. AAG08191.1, SEQ ID NO: 8), *Pseudomonas syringae* (GenBank Accession No. AAY39893.1, SEQ ID NO: 9), *Rhodobacter sphaeroides* (GenBank Accession No. ABA81135.1, SEQ ID NO: 10), *Vibrio fluvialis* (GenBank Accession No. AEA39183.1, SEQ ID NO: 12), *Streptomyces griseus*, or *Clostridium viride*. See FIGS. 8G-8J.

An additional polypeptide having the activity of a ω-transaminase that can be used in the methods and microorganisms described herein is from *Escherichia coli* (GenBank Accession No. AAA57874.1, SEQ ID NO: 11, SEQ ID NO: 48). Some of the polypeptides having the activity of ω-transaminases classified, for example, under EC 2.6.1.29 or EC 2.6.1.82 are diamine ω-transaminases (e.g., SEQ ID NO: 11, SEQ ID NO: 48).

The reversible ω-transaminase from *Chromobacterium violaceum* (GenBank Accession No. AAQ59697.1, SEQ ID NO: 7) has demonstrated analogous activity accepting 7-aminoheptanoic acid as amino donor, thus forming the first terminal amine group in pimelate semialdehyde (Kaulmann et al., *Enzyme and Microbial Technology*, 2007, 41, 628-637).

The reversible 4-aminobubyrate:2-oxoadipate transaminase from *Streptomyces griseus* has demonstrated activity for the conversion of 7-aminoheptanoate to pimelate semialdehyde (Yonaha et al., *Eur. J. Biochem.*, 1985, 146, 101-106).

The reversible 5-aminovalerate transaminase from *Clostridium viride* has demonstrated activity for the conversion of 7-aminoheptanoate to pimelate semialdehyde (Barker et al., *J. Biol. Chem.*, 1987, 262(19), 8994-9003).

In some embodiments, the second terminal amine group leading to the synthesis of heptamethylenediamine is enzymatically formed in 7-aminoheptanal by a polypeptide having the activity of a diamine transaminase classified, for example, under EC 2.6.1.29 or classified, for example, under EC 2.6.1.82, such as, for example, the gene product of ygjG from *E. coli* (GenBank Accession No. AAA57874.1, SEQ ID NO: 11, SEQ ID NO: 48). The polypeptides having the activity of a transaminase set forth in SEQ ID NOs: 7-10 and 12 also can be used to produce heptamethylenediamine. See FIGS. 8G-8J.

The gene product of ygG from *Escherichia coli* accepts a broad range of diamine carbon chain length substrates, such as putrescine, cadaverine and spermidine (Samsonova et al., *BMC Microbiology*, 2003, 3:2).

The diamine transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed in N7-acetyl-1,7-diaminoheptane by a polypeptide having the activity of a deacylase classified, for example, under EC 3.5.1.-, such as, for example, EC 3.5.1.62 or EC 3.5.1.82.

Figure 6:
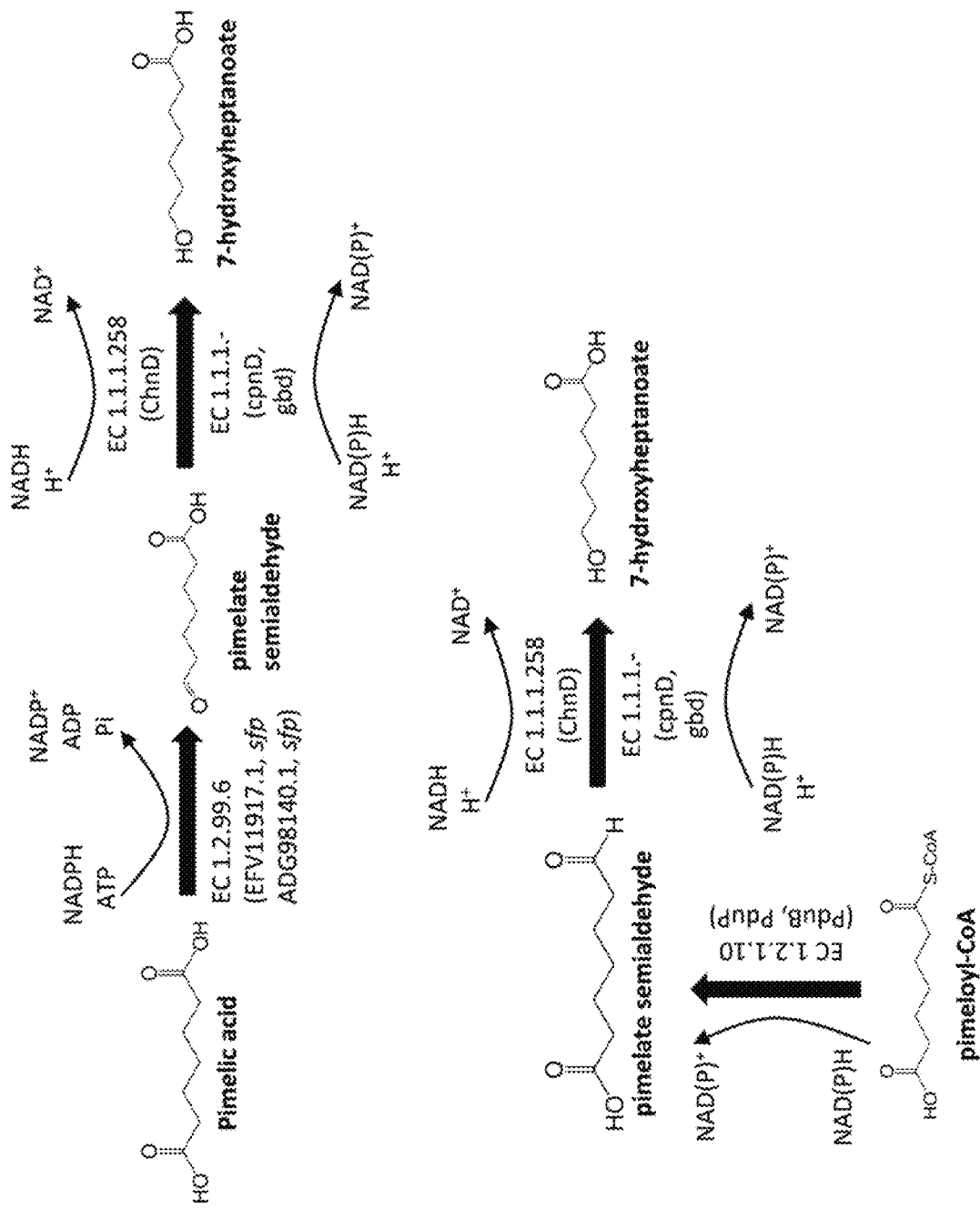
FIG. 6 is a schematic of exemplary biochemical pathways leading to 7-hydroxyheptanoate using pimeloyl-CoA and pimelate as central precursors.

Enzymes Generating the Terminal Hydroxyl Groups in the Biosynthesis of 7-Hydroxyheptanoate As depicted in FIG. 6, pimelic acid, as shown in FIG. 3, may be converted to pimelate semialdehyde by a polypeptide having the activity of a carboxylate reductase classified, for example, under EC 1.2.99.6, such as, for example, the polypeptides represented by the following GenBank Accession Numbers: EFV11917.1 (SEQ ID NO: 3) or ADG98140.1 (SEQ ID NO: 6). Having formed pimelate semialdehyde, a terminal hydroxyl group can then be enzymatically formed (or removed) using one or more polypeptides having the activity of an alcohol dehydrogenase classified, for example, under EC 1.1.1.-, such as, for example, a 5-hydroxypentanoate dehydrogenase, such as, for example, the gene product of cpnD from *Comamonas* sp (Iwaki et al., *Appl. Environ. Microbiol.*, 1999, 65(11):5158-5162), or a 4-hydroxybutanoate dehydrogenase, such as, for example, the gene product of gbd. The polypeptide having the activity of an alcohol dehydrogenase may also be classified under EC 1.1.1.258, such as a 6-hydroxyhexanoate dehydrogenase, such as, for example, the gene product of chnD from *Acinetobacter* sp. NCIMB9871 (Donoghue et al., *Eur. J. Biochem*, 1975, 60: 1-7).

Alternatively, as shown in FIG. 6, pimeloyl-CoA may be converted to pimelate semialdehyde by an polypeptide having the activity of an alcohol dehydrogenase classified, for example, under EC 1.2.1.10, such as a polypeptide having the activity of an acetaldehyde dehydrogenase encoded by pduB from *Salmonella typhimurium* or pduP from *Klebsiella pneumoniae*. Having formed pimelate semialdehyde, a terminal hydroxyl group can then be enzymatically formed (or removed) using one or more polypeptides having the activity of an alcohol dehydrogenase classified, for example, under EC 1.1.1.- such as a 5-hydroxypentanoate dehydrogenase, such as, for example, the gene product of cpnD from *Comamonas* sp. (Iwaki et al., *Appl. Environ. Microbiol.*, 1999, 65(11):5158-5162), or a 4-hydroxybutanoate dehydrogenase, such as, for example, the gene product of gbd. The polypeptide having the activity of an alcohol dehydrogenase may also be classified under EC 1.1.1.258, such as a 6-hydroxyhexanoate dehydrogenase, such as, for example, the gene product of chnD from *Acinetobacter* sp. NCIMB9871 (Donoghue et al., *Eur. J. Biochem*, 1975, 60: 1-7).

Figure 7:
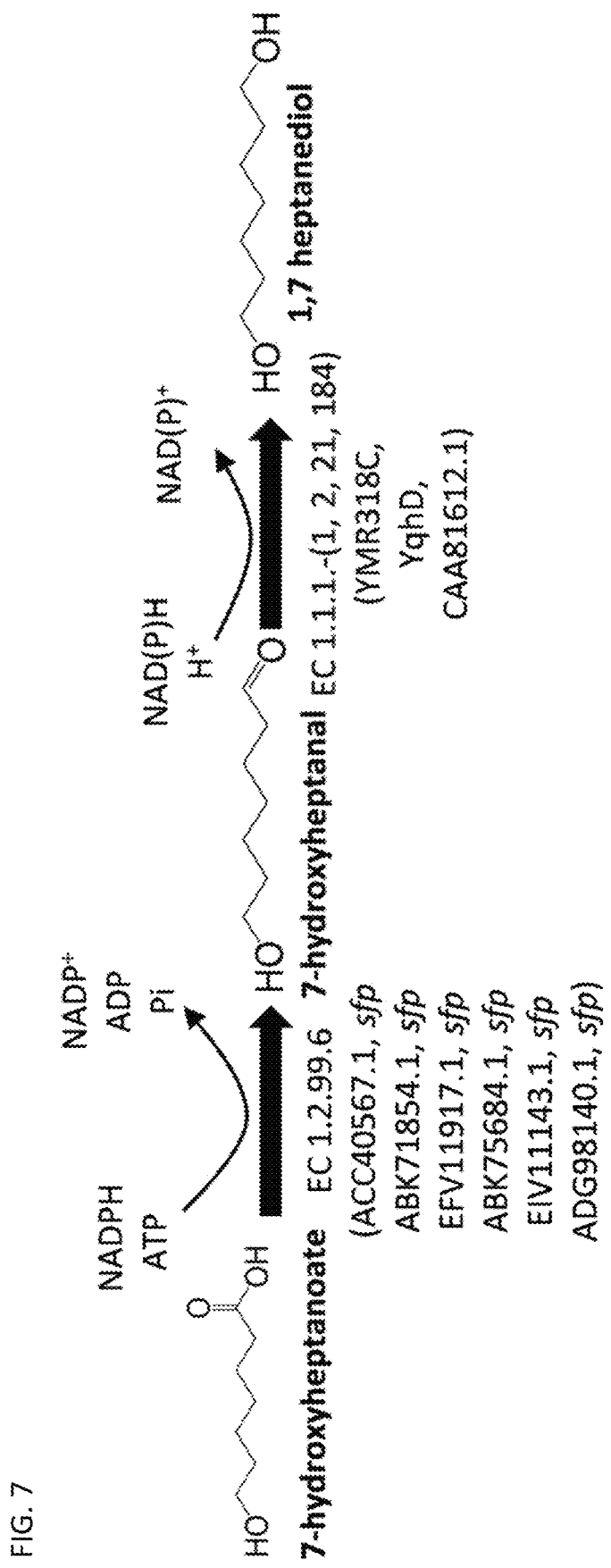
FIG. 7 is a schematic of an exemplary biochemical pathway leading to 1,7-heptanediol using 7-hydroxyheptanoate as a central precursor.

Enzymes Generating the Terminal Hydroxyl Groups in the Biosynthesis of 1,7 Heptanediol As depicted in FIG. 7, the terminal hydroxyl group can be enzymatically formed using a polypeptide having the activity of an alcohol dehydrogenase. For example, the second terminal hydroxyl group leading to the synthesis of 1,7 heptanediol can be enzymatically formed in 7-hydroxyheptanal by a polypeptide having the activity of an alcohol dehydrogenase classified under EC 1.1.1.- (e.g., EC 1.1.1.1, EC 1.1.1.2, EC 1.1.1.21, or EC 1.1.1.184), such as, for example, the gene product of YMR318C from *Saccharomyces cerevisiae* or yqhD from *Escherichia coli* (Liu et al., *Microbiology*, 2009, 155, 2078-2085; Larroy et al., 2002, *Biochem J*, 361(Pt 1), 163-172; Jarboe, 2011, *Appl. Microbiol. Biotechnol.*, 89(2), 249-257) or the polypeptide represented by GenBank Accession No. CAA81612.1 (SEQ ID NO: 21). The alcohol dehydrogenase encoded by YMR318C has broad substrate specificity, including the oxidation of C7 alcohols. The polypeptide having the activity of an alcohol dehydrogenase classified under EC 1.1.1.- may also be a polypeptide represented by GenBank Accession CAA81612.1 (SEQ ID NO: 21).

Biochemical Pathways

Pathways to Pimeloyl-CoA

In some embodiments, and as shown in FIG. 1 and FIG. 2, the central metabolite octadecanoyl-CoA is converted to octadec-9-enoyl-CoA using a polypeptide having the enzymatic activity of a delta9-desaturase classified under, for example, EC 1.14.19.1; followed by conversion of octadec-9-enoyl-CoA to octadec-9,12-dienoyl-CoA using a polypeptide having the enzymatic activity of a delta12-desaturase classified under, for example, EC 1.14.19.6; followed by conversion of octadec-9,12-dienoyl-CoA to linoleic acid using a polypeptide having the enzymatic activity of a thioesterase classified under, for example, EC 3.1.2.-; followed by conversion of linoleic acid using a polypeptide having the enzymatic activity of a 9-lipoxygenase classified under, for example, EC 1.13.11.58, EC 1.13.11.60, EC 1.13.11.61, or EC 1.13.11.62.

In some embodiments, and as shown in FIG. 1 and FIG. 2, 9-hydroxyperoxyoctadec-10,12-dienoate is cleaved by a polypeptide having the enzymatic activity of a hydroperoxide lyase classified, for example, under EC 4.2.99.-, such as, for example, a polypeptide represented by GenBank Accession No. AAF64041.1 (SEQ ID NO: 13) or a polypeptide represented by GenBank Accession No. BAG97978.1 (SEQ ID NO: 14), to produce non-3-enal and 9-oxononanoate.

In some embodiments, and as shown in FIG. 1, non-3-enal is converted to non-3-enoate by one or more polypeptides having the enzymatic activity of an aldehyde dehydrogenase classified, for example, under EC 1.2.1.- such as EC 1.2.1.3, EC 1.2.1.4, EC 1.2.1.5, or EC 1.2.1.48, such as, for example, the gene product of Bt-aldh from *Geobacillus thermoleovorans* B23 (UniProtKB Accession No. Q9FAB1), the gene product of dhaS from *Bacillus subtilis* (UniProtKB Accession No. O34660), the gene product of ALD5 from *Saccharomyces cerevisiae* (UniProtKB Accession No. A6ZR27), the gene product of ALDH2C4 from *Arabidopsis thaliana* (UniProtKB Accession No. Q56YU0), the gene product of aldh7 from *Rhodococcus ruber* (UniProtKB Accession No. Q840S9), the gene product of alkH from *Pseudomonas oleovorans* (UniProtKB Accession No. P12693), the gene product of ald1 from *Acinetobacter* sp. M-1 (UniProtKB Accession No. Q9FDS1), or the gene product of acoD from *Ralstonia eutropha* (UniProtKB Accession No. P46368); followed by conversion of non-3-enoate to non-3-enoyl-CoA by a polypeptide having the enzymatic activity of a CoA ligase classified, for example, under EC 6.2.1.-, such as, for example, the gene product of acs6 from *Brassica napus* (UniProtKB Accession No. Q9FNT6), the gene product of PCS60 from *Saccharomyces cerevisiae* (UniProtKB Accession No. P38137), the gene product of alkK from *Pseudomonas oleovorans* (UniProtKB Accession No. Q00594), the gene product of ACSM5 from *Homo sapiens* (UniProtKB Accession No. Q6NUN0), or the gene product of alkK from *Aeropyrum pernix* (UniProtKB Accession No. Q9YF45); followed by conversion of non-3-enoyl-CoA to non-2-enoyl-CoA by a polypeptide having the enzymatic activity of a dodecenoyl-CoA isomerase classified, for example, under EC 5.3.3.8; followed by conversion of non-2-enoyl-CoA to nonanoyl-CoA by a trans-2-enoyl-CoA reductase classified, for example, under EC 1.3.1.38, EC 1.3.1.44 such as, for example, the gene product of ter from *Escherichia coli, Fibrobacter succinogenes,* or *Treponema denticola* (Nishimaki et al., *J. Biochem.,* 1984, 95:1315-1321; Shen et al., 2011, supra) or tdter from *Treponema denticola* (Bond-Watts et al., *Biochemistry,* 2012, 51:6827-6837) or EC 1.3.1.8 (Inui et al., *Eur. J. Biochem.,* 1984, 142, 121-126); followed by conversion of nonanoyl-CoA to nonanoic acid using a polypeptide having the enzymatic activity of a thioesterase classified, for example, under EC 3.1.2.-, such as, for example, the gene product of BT_2075 from *Bacteroides thetaiotaomicron* (strain ATCC 29148/DSM 2079/NCTC 10582/E50/VPI-5482) (GenBank Accession No. AAO77182.1, SEQ ID NO: 20), the gene product of lp_0708 from *Lactobacillus plantarum* (strain ATCC BAA-793/NCIMB 8826/WCFS1) (GenBank Accession No. CCC78182.1, SEQ ID NO: 22), the gene product of HMPREF0077_1317 from *Anaerococcus tetradius* ATCC 35098 (GenBank Accession No. EEI82564.1, SEQ ID NO: 23), or the gene product of CPF_2954 from *Clostridium perfringens* (strain ATCC 13124/DSM 756/JCM 1290/NCIMB 6125/NCTC 8237/Type A) (GenBank Accession No. ABG82470.1), SEQ ID NO: 18); followed by conversion of nonanoic acid to 9-hydroxynonanoic acid using a polypeptide having the enzymatic activity of a monooxygenase classified, for example, under EC 1.14.14- or EC 1.14.15.-, such as EC 1.14.14.1, EC 1.14.14.3, EC 1.14.15.1 or EC 1.14.15.3 and as encoded by alkBGT from *Pseudomonas putida*, CYP153A from *Polaromonas* sp., or CYP52A3 from *Saccharomyces cerevisiae*; followed by conversion of 9-hydroxynonanoic acid to 9-oxononanoate using a polypeptide having the enzymatic activity of an alcohol dehydrogenase classified under EC 1.1.1.-, a 6-hydroxyhexanoate dehydrogenase classified under EC 1.1.1.258, such as, for example, the gene product of chnD from *Acinetobacter* sp. NCIMB9871 (Donoghue et al., Eur. J. Biochem, 1975, 60: 1-7); or a 4-hydroxybutanoate dehydrogenase classified under EC 1.1.1.61, such as, for example, the gene product of gbd; followed by conversion of 9-oxononanoate to azelaic acid using a polypeptide having the enzymatic activity of an aldehyde dehydrogenase classified under, for example, EC 1.2.1.- such as a 7-oxoheptanoate dehydrogenase (e.g., the gene product of thnG from *Sphingomonas macrogolitabida*), a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (e.g., the gene product of cpnE from *Comamonas* sp.), a succinate-semialdehyde dehydrogenase classified, for example, under EC 1.2.1.16, EC 1.2.1.24, or EC 1.2.1.79, or an aldehyde dehydrogenase classified under EC 1.2.1.3.

In some embodiments, and as shown in FIG. 2, non-3-enal is converted to non-2-enal by a polypeptide having the enzymatic activity of an enal isomerase classified, for example, under EC 5.3.3.-; followed by conversion of non-2-al to nonanal by a polypeptide having the enzymatic activity of an enoate reductase classified, for example, under EC 1.3.1.31; followed by conversion of nonanal to nonanoic acid by a polypeptide having the enzymatic activity of an aldehyde dehydrogenase classified, for example, under EC 1.2.1.-. such as EC 1.2.1.3, EC 1.2.1.4, EC 1.2.1.5, or EC 1.2.1.48, such as, for example, the gene product of Bt-aldh from *Geobacillus thermoleovorans* B23 (UniProtKB Accession No. Q9FAB1), the gene product of dhaS from *Bacillus subtilis* (UniProtKB Accession No. O34660), the gene product of ALD5 from *Saccharomyces cerevisiae* (UniProtKB Accession No. A6ZR27), the gene product of ALDH2C4 from *Arabidopsis thaliana* (UniProtKB Accession No. Q56YU0), the gene product of aldh7 from *Rhodococcus ruber* (UniProtKB Accession No. Q840S9), the gene product of alkH from *Pseudomonas oleovorans* (UniProtKB Accession No. P12693), the gene product of ald1 from *Acinetobacter* sp. M-1 (UniProtKB Accession No. Q9FDS1), or the gene product of acoD from *Ralstonia eutropha* (UniProtKB Accession No. P46368); followed by conversion of nonanoic acid to 9-hydroxynonanoic acid by a monooxygenase classified, for example, under EC 1.14.14- or EC 1.14.15.-, such as EC 1.14.14.1, EC 1.14.14.3, EC 1.14.15.1, or EC 1.14.15.3 or encoded by alkBGT from *Pseudomonas putida*, CYP153A from *Polaromonas* sp., or CYP52A3 from *Saccharomyces cerevisiae*; followed by conversion of 9-hydroxynonanoic acid to 9-oxononanoic acid by a polypeptide having the enzymatic activity of an alcohol dehydrogenase classified under EC 1.1.1.-, a 6-hydroxyhexanoate dehydrogenase classified under EC 1.1.1.258, such as, for example, the gene product of chnD from *Acinetobacter* sp. NCIMB9871 (Donoghue et al., *Eur. J. Biochem,* 1975, 60: 1-7); or a 4-hydroxybutanoate dehydrogenase classified under EC 1.1.1.61, such as, for example, the gene product of gbd; followed by conversion of 9-oxononanoate to azelaic acid using a polypeptide having the enzymatic activity of an aldehyde dehydrogenase classified under, for example, EC 1.2.1.-, such as a 7-oxoheptanoate dehydrogenase (e.g., the gene product of thnG from *Sphingomonas macrogolitabida*), a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (e.g., the gene product of cpnE from *Comamonas* sp.), a succinate-semialdehyde dehydrogenase classified, for example, under EC 1.2.1.16, EC 1.2.1.24, or EC 1.2.1.79 (e.g., the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from

*Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9)), or an aldehyde dehydrogenase classified under EC 1.2.3.

In some embodiments, and as shown in FIGS. 1 and 2, 9-oxononanoate is converted to azelaic acid using a polypeptide having the activity of an aldehyde dehydrogenase classified under, for example, EC 1.2.1.-, such as a 7-oxoheptanoate dehydrogenase (e.g., the gene product of thnG from *Sphingomonas macrogolitabida*), a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (e.g., the gene product of cpnE from *Comamonas* sp.), a succinate-semialdehyde dehydrogenase classified, for example, under EC 1.2.1.16, EC 1.2.1.24, or EC 1.2.1.79 (e.g., the gene product of ALDH5F1 from *Arabidopsis thaliana* (UniProtKB Accession No. Q9SAK4), the gene product of araE from *Azospirillum brasilense* (UniProtKB Accession No. Q1JUP4), the gene product of Ssadh from *Drosophila melanogaster* (UniProtKB Accession No. Q9VBP6), the gene product of ALDH5A1 from *Gorilla gorilla* (UniProtKB Accession No. Q6A2H1), the gene product of ALDH5A1 from *Hylobates lar* (UniProtKB Accession No. Q3MSM3), the gene product of ssadh from *Lucilia cuprina* (UniProtKB Accession No. B0JFD4), the gene product of ALDH5A1 from *Pan paniscus* (UniProtKB Accession No. Q3MSM4), the gene product of ALDH5A1 from *Pan troglodytes* (UniProtKB Accession No. Q6A2H0), the gene product of ALDH5A1 from *Pongo abelii* (UniProtKB Accession No. Q6A2H2), the gene product of ALDH5A1 from *Pongo pygmaeus* (UniProtKB Accession No. Q6A2H2), or the gene product of gapN-1 from *Sulfolobus solfataricus* (UniProtKB Accession No. Q97XS9)), or an aldehyde dehydrogenase classified under EC 1.2.1.3.

In some embodiments, and as shown in FIG. 1 and FIG. 2, azelaic acid is converted to azelaoyl-CoA by a polypeptide having the enzymatic activity of a CoA ligase classified, for example, under EC 6.2.1.-, such as, for example, the gene product of acs6 from *Brassica napus* (UniProtKB Accession No. Q9FNT6), the gene product of PCS60 from *Saccharomyces cerevisiae* (UniProtKB Accession No. P38137), the gene product of alkK from *Pseudomonas oleovorans* (UniProtKB Accession No. Q00594), the gene product of ACSM5 from *Homo sapiens* (UniProtKB Accession No. Q6NUN0), or the gene product of alkK from *Aeropyrum pernix* (UniProtKB Accession No. Q9YF45); followed by conversion of azelaoyl-CoA to 2,3-dehydroazelaoyl-CoA using a polypeptide having the enzymatic activity of an acyl-CoA dehydrogenase classified, for example, under EC 1.3.8.-, such as EC 1.3.8.6, EC 1.3.8.7 or EC 1.3.8.8; followed by conversion of 2,3-dehydroazelaoyl-CoA to 3-hydroxy-azelaoyl-CoA by a polypeptide having the enzymatic activity of an enoyl-CoA hydratase classified, for example, under EC 4.2.1.17, such as, for example, the gene product of crt from *Clostridium acetobutylicum*, or classified under EC 4.2.1.119, such as, for example, the gene product of phaJ from *Pseudomonas aeruginosa*; followed by conversion of 3-hydroxy-azelaoyl-CoA to 3-oxo-azelaoyl-CoA by a polypeptide having the enzymatic activity of a 3-hydroxyacyl-CoA dehydrogenase classified for example, under EC 1.1.1.-, such as EC 1.1.1.35 (e.g., the gene product of fadB from *Escherichia coli*), EC 1.1.1.36 (e.g., the gene product of phaB from *Cupriavidus necator*), or EC 1.1.1.157 (e.g., the gene product of hbd from *Clostridium acetobutylicum*) or a 3-oxoacyl-ACP reductase classified, for example, under EC 1.1.1.100, such as, for example, the gene product of fabG from *Escherichia coli*; followed by conversion of 3-oxo-azelaoyl-CoA to pimeloyl-CoA by a polypeptide having the enzymatic activity of a β-ketothiolase classified, for example, under EC 2.3.1.16 or EC 2.3.1.174 such as, for example, the gene product of bktB from *Cupriavidus necator* or paaJ from *Escherichia coli*.

Pathways Using Pimeloyl-CoA as Central Precursor to Pimelic Acid

In some embodiments, pimelic acid is synthesized from pimeloyl-CoA by a polypeptide having the activity of a thioesterase classified under, for example, EC 3.1.2.-. The polypeptide having the activity of a thioesterase can be the gene product of yciA from *Escherichia coli* or acot13 from *Mus musculus* (Cantu et al., *Protein Science*, 2010, 19, 1281-1295; Zhuang et al., *Biochemistry*, 2008, 47(9):2789-2796; Naggert et al., *J. Biol. Chem.*, 1991, 266(17):11044-11050), or tesB from *Escherichia coli* or a polypeptide represented by one of the following GenBank accession numbers: AAO77182.1 (SEQ ID NO: 20); CCC78182.1 (SEQ ID NO: 22); EEI82564.1 (SEQ ID NO: 23); or ABG82470.1 (SEQ ID NO: 18).

In some embodiments, pimelic acid is synthesized from pimeloyl-CoA by a polypeptide having the activity of a CoA ligase classified under, for example, EC 6.2.1.-, such as EC 6.2.1.5 or EC 6.2.1.15, or a CoA transferase classified under, for example, EC 2.8.3.-, such as EC 2.8.3.8 or EC 2.8.3.12 (e.g., a succinyl-CoA:acetate CoA-transferase from *Acetobacter aceti* (UniProtKB Accession No. B3EY95), the gene product of ANACAC_01149 from *Anaerostipes caccae* (UniProtKB Accession No. B0MC58), a butyryl-CoA:acetate CoA-transferase from *Butyrivibrio fibrisolvens* (UniProtKB Accession No. D2WEY7), a butyryl-CoA:acetate CoA-transferase from *Eubacterium hallii* (UniProtKB Accession No. D2WEY8), the gene product of FAEPRAA2165_01575 from *Faecalibacterium prausnitzii* (UniProtKB Accession No. C7H5K4), a butyryl-CoA:acetate CoA-transferase from *Faecalibacterium prausnitzii* (UniProtKB Accession No. D2WEZ2), the gene product of FAEPRAM212_02812 from *Faecalibacterium prausnitzii* (UniProtKB Accession No. A8SFP6), a butyryl-CoA transferase from *Roseburia hominis* (UniProtKB Accession No. Q2TME9), or a butyryl-CoA:acetate CoA-transferase from *Roseburia inulinivorans* (UniProtKB Accession No. D2WEY6)).

In some embodiments, pimeloyl-CoA is converted to pimelate semialdehyde by a polypeptide having the activity of an aldehyde dehydrogenase, such as an acetaldehyde dehydrogenase classified under, for example, EC 1.2.1.10, such as that encoded by pduB from *Salmonella typhimurium*.

Pimelate semialdehyde is then converted to pimelic acid by a polypeptide having the activity of an aldehyde dehydrogenase classified under, for example, EC 1.2.1.-, such as a 7-oxoheptanoate dehydrogenase (e.g., the gene product of thnG from *Sphingomonas macrogolitabida*), a 6-oxohexanoate dehydrogenase (e.g., the gene product of chnE from *Acinetobacter* sp.) classified, for example, under EC 1.2.1.63, a 5-oxopentanoate dehydrogenase classified, for example, under EC 1.2.1.20 (e.g., the gene product of cpnE from *Comamonas* sp), a succinate-semialdehyde dehydrogenase classified, for example, under EC 1.2.1.16, EC 1.2.1.24, or EC 1.2.1.79, or an aldehyde dehydrogenase classified under EC 1.2.1.3. See FIG. 3.

Pathways Using Pimeloyl-CoA as Central Precursor to 7-Aminoheptanoate

In some embodiments, pimeloyl-CoA is converted to pimelate semialdehyde using a polypeptide having the enzymatic activity of an aldehyde dehydrogenase classified under, for example, EC 1.2.1.10, such as an acetaldehyde dehydrogenase encoded by pduB from *Salmonella typhimurium* or pduP from *Klebsiella pneumoniae*. Pimelate semialdehyde is then converted to 7-aminoheptanoate using a polypeptide having the enzymatic activity of a ω-transaminase classified, for example, under EC 2.6.1.-, e.g., EC 2.6.1.18, EC 2.6.1.19, EC 2.6.1.29, EC 2.6.1.48, or EC 2.6.1.82, such as, for example, that obtained from *Chromobacterium violaceum* (GenBank Accession No. AAQ59697.1, SEQ ID NO: 7), *Pseudomonas aeruginosa* (GenBank Accession No. AAG08191.1, SEQ ID NO: 8), *Pseudomonas syringae* (GenBank Accession No. AAY39893.1, SEQ ID NO: 9), *Rhodobacter sphaeroides* (GenBank Accession No. ABA81135.1, SEQ ID NO: 10), *Vibrio fluvialis* (GenBank Accession No. AEA39183.1, SEQ ID NO: 12), *Streptomyces griseus*, or *Clostridium viride*.

In some embodiments, pimelate (see FIG. 3) is converted to pimelate semialdehyde using a polypeptide having the enzymatic activity of a carboxylate reductase classified, for example, under EC 1.2.99.6 such as, for example, the gene product of car in combination with a phosphopantetheine transferase enhancer (e.g., encoded by a sfp gene from *Bacillus subtilis* or npt gene from *Nocardia*) or the gene products of griC and griD from *Streptomyces griseus* (Suzuki et al., *J. Antibiot.*, 2007, 60(6), 380-387). The polypeptide having the activity of a carboxylate reductase can be obtained, for example, from *Mycobacterium marinum* (GenBank Accession No. ACC40567.1, SEQ ID NO: 1), *Mycobacterium smegmatis* (GenBank Accession No. ABK71854.1, SEQ ID NO: 2), *Segniliparus rugosus* (GenBank Accession No. EFV11917.1, SEQ ID NO: 3), *Mycobacterium smegmatis* (GenBank Accession No. ABK75684.1, SEQ ID NO: 4), *Mycobacterium* massiliense (GenBank Accession No. EIV11143.1, SEQ ID NO: 5), or *Segniliparus rotundus* (GenBank Accession No. ADG98140.1, SEQ ID NO: 6). Pimelate semialdehyde is then converted to 7-aminoheptanoate using a polypeptide having the enzymatic activity of a ω-transaminase classified, for example, under EC 2.6.1.-, e.g., EC 2.6.1.18, EC 2.6.1.19, EC 2.6.1.29, EC 2.6.1.48, or EC 2.6.1.82, such as that obtained from *Chromobacterium violaceum* (GenBank Accession No. AAQ59697.1, SEQ ID NO: 7), *Pseudomonas aeruginosa* (GenBank Accession No. AAG08191.1, SEQ ID NO: 8), *Pseudomonas syringae* (GenBank Accession No. AAY39893.1, SEQ ID NO: 9), *Rhodobacter sphaeroides* (GenBank Accession No. ABA81135.1, SEQ ID NO: 10), *Vibrio fluvialis* (GenBank Accession No. AEA39183.1, SEQ ID NO: 12), *Streptomyces griseus*, or *Clostridium viride*. See FIG. 4.

Pathways Using Pimeloyl-CoA as Central Precursor to 7-Hydroxyheptanoate

In some embodiments, 7-hydroxyheptanoate is synthesized from the central precursor, pimeloyl-CoA using a polypeptide having the enzymatic activity of an aldehyde dehydrogenase classified under, for example, EC 1.2.1.10, such as an acetaldehyde dehydrogenase encoded by pduB from *Salmonella typhimurium* or pduP from *Klebsiella pneumoniae*; followed by conversion of pimelate semialdehyde to 7-hydroxyheptanoate by a polypeptide having the activity of an alcohol dehydrogenase classified, for example, under EC 1.1.1.2 such as, for example, the gene product of YMR318C from *Saccharomyces cerevisiae*, a 6-hydroxyhexanoate dehydrogenase classified, for example, under EC 1.1.1.258, a 5-hydroxypentanoate dehydrogenase classified, for example, under EC 1.1.1.-, such as, for example, the gene product of cpnD from *Comamonas* sp. (Iwaki et al., *Appl. Environ. Microbiol.*, 1999, 65(11):5158-5162), or a 4-hydroxybutanoate dehydrogenase classified, for example, under EC 1.1.1.- such as, for example, the gene product of gbd. The alcohol dehydrogenase encoded by YMR318C has broad substrate specificity, including the oxidation of C7 alcohols. See FIG. 6.

Pathway Using 7-Aminoheptanoate, 7-Hydroxyheptanoate, Pimelate Semialdehyde, or 1,7-Heptanediol as a Central Precursor to Heptamethylenediamine In some embodiments, heptamethylenediamine is synthesized from the central precursor, 7-aminoheptanoate (which can be produced as described in FIG. 4), by conversion of 7-aminoheptanoate to 7-aminoheptanal by a polypeptide having the activity of a carboxylate reductase classified, for example, under EC 1.2.99.6, such as, for example, the gene product of car in combination with a phosphopantetheine transferase enhancer (e.g., encoded by a sfp gene from *Bacillus subtilis* or npt gene from *Nocardia*) or the gene products of griC and griD from *Streptomyces griseus* (Suzuki et al., *J. Antibiot.*, 2007, 60(6), 380-387); followed by conversion of 7-aminoheptanal to heptamethylenediamine by a polypeptide having the activity of a ω-transaminase such as a ω-transaminase classified under EC 2.6.1.- (e.g., EC 2.6.1.18, EC 2.6.1.19, EC 2.6.1.48, or EC 2.6.1.82, such as, for example, SEQ ID NOs: 7-12). The polypeptide having the activity of a carboxylate reductase can be obtained, for example, from *Mycobacterium marinum* (GenBank Accession No. ACC40567.1, SEQ ID NO: 1), *Mycobacterium smegmatis* (GenBank Accession No. ABK71854.1, SEQ ID NO: 2), *Segniliparus rugosus* (GenBank Accession No. EFV11917.1, SEQ ID NO: 3), *Mycobacterium smegmatis* (GenBank Accession No. ABK75684.1, SEQ ID NO: 4), *Mycobacterium* massiliense (GenBank Accession No. EIV11143.1, SEQ ID NO: 5), or *Segniliparus rotundus* (GenBank Accession No. ADG98140.1, SEQ ID NO: 6).

The carboxylate reductase encoded by the gene product of car and enhancer npt from *Nocardia* or sfp from *Bacillus subtilis* has broad substrate specificity, including terminal difunctional C4 and C5 carboxylic acids (Venkitasubramanian et al., *Enzyme and Microbial Technology*, 2008, 42, 130-137).

In some embodiments, heptamethylenediamine is synthesized from the central precursor, 7-hydroxyheptanoate (which can be produced as described in FIG. 6), by conversion of 7-hydroxyheptanoate to 7-hydroxyheptanal by a polypeptide having the activity of a carboxylate reductase classified, for example, under EC 1.2.99.6, such as, for example, the gene product of car in combination with a polypeptide having the activity of a phosphopantetheine transferase enhancer (e.g., encoded by a sfp gene from *Bacillus subtilis* or npt gene from *Nocardia*) or the gene product of griC & griD from *Streptomyces griseus* (Suzuki et al., *J. Antibiot.*, 2007, 60(6), 380-387); followed by conversion of 7-aminoheptanal to 7-aminoheptanol by a polypeptide having the activity of a ω-transaminase classified, for example, under EC 2.6.1.18, EC 2.6.1.19, EC 2.6.1.29, EC 2.6.1.48, or EC 2.6.1.82 such as, for example, SEQ ID NOs: 7-12, see above; followed by conversion to 7-aminoheptanal by a polypeptide having the activity of an alcohol dehydrogenase classified, for example, under EC 1.1.1.- (e.g., EC 1.1.1.1, EC 1.1.1.2, EC 1.1.1.21, or EC 1.1.1.184) such as, for example, the gene product of YMR318C from *Saccharomyces cerevisiae* or yqhD from *Escherichia coli* (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or a polypeptide represented by GenBank Accession No. CAA81612.1 (SEQ ID NO: 21); followed by conversion to heptamethylenediamine by a polypeptide having the activity of a ω-transaminase classified, for example, under EC 2.6.1.18, EC 2.6.1.19, EC 2.6.1.29, EC 2.6.1.48, or EC 2.6.1.82, such as, for example, SEQ ID NOs: 7-12, see above. See FIG. 5.

In some embodiments, heptamethylenediamine is synthesized from the central precursor, 7-aminoheptanoate (which can be produced as described in FIG. 4), by conversion of 7-aminoheptanoate to N7-acetyl-7-aminoheptanoate by a polypeptide having the activity of an N-acetyltransferase such as a lysine N-acetyltransferase classified, for example, under EC 2.3.1.32, such as, for example, the gene product of LYC1 from *Yarrowia lipolytica* (UniProtKB Accession No. P41929), the gene product of ablB from *Methanococcus maripaludis* (UniProtKB Accession No. Q6LYX3), or the gene product of ablB from *Methanosarcina mazei* (UniProtKB Accession No. Q8PYC8); followed by conversion to N7-acetyl-7-aminoheptanal by a polypeptide having the activity of a carboxylate reductase classified, for example, under EC 1.2.99.6 such as, for example, the gene product of car (see above, e.g., SEQ ID NOs: 1-6) in combination with a polypeptide having the activity of a phosphopantetheine transferase enhancer (e.g., encoded by a sfp gene from *Bacillus subtilis* or npt gene from *Nocardia*) or the gene product of griC & griD from *Streptomyces griseus* (Suzuki et al., *J. Antibiot.*, 2007, 60(6), 380-387; followed by conversion to N7-acetyl-1,7-diaminoheptane by a polypeptide having the activity of a ω-transaminase classified, for example, under EC 2.6.1.18, EC 2.6.1.19, EC 2.6.1.29, EC 2.6.1.48, or EC 2.6.1.82, such as SEQ ID NOs: 7-12, see above; followed by conversion to heptamethylenediamine by a polypeptide having the activity of a deacylase classified, for example, under EC 3.5.1.-, such as, for example, EC 3.5.1.62 or EC 3.5.1.82. See FIG. 6.

In some embodiments, heptamethylenediamine is synthesized from the central precursor, pimelate semialdehyde, by conversion of pimelate semialdehyde to heptanedial by a polypeptide having the activity of a carboxylate reductase classified, for example, under EC 1.2.99.6 such as, for example, the gene product of car (see above, e.g., SEQ ID NO: 5) in combination with a phosphopantetheine transferase enhancer (e.g., encoded by a sfp gene from *Bacillus subtilis* or npt gene from *Nocardia*) or the gene product of griC & griD from *Streptomyces griseus* (Suzuki et al., *J. Antibiot.*, 2007, 60(6), 380-387) followed by conversion to 7-aminoheptanal by a polypeptide having the activity of a ω-transaminase classified, for example, under EC 2.6.1.18, EC 2.6.1.19, EC 2.6.1.29, EC 2.6.1.48, or EC 2.6.1.82; followed by conversion to heptamethylenediamine by a polypeptide having the activity of a ω-transaminase classified, for example, under EC 2.6.1.18, EC 2.6.1.19, EC 2.6.1.29, EC 2.6.1.48, or EC 2.6.1.82, such as, for example, SEQ ID NOs: 7-12. See FIG. 5.

Pathways Using 7-Hydroxyheptanoate as Central Precursor to 1,7-Heptanediol

In some embodiments, 1,7 heptanediol is synthesized from the central precursor, 7-hydroxyheptanoate (which can be produced as described in FIG. 6), by conversion of 7-hydroxyheptanoate to 7-hydroxyheptanal by a polypeptide having the activity of a carboxylate reductase classified, for example, under EC 1.2.99.6 such as, for example, the gene product of car (see above, e.g., SEQ ID NOs: 1-6) in combination with a polypeptide having the activity of a phosphopantetheine transferase enhancer (e.g., encoded by a sfp gene from *Bacillus subtilis* or npt gene from *Nocardia*) or the gene products of griC and griD from *Streptomyces griseus* (Suzuki et al., *J. Antibiot.*, 2007, 60(6), 380-387); followed by conversion of 7-hydroxyheptanal to 1,7 heptanediol by a polypeptide having the activity of an alcohol dehydrogenase (classified, for example, under EC 1.1.1.- such as EC 1.1.1.1, EC 1.1.1.2, EC 1.1.1.21, or EC 1.1.1.184) such as, for example, the gene product of YMR318C from *Saccharomyces cerevisiae* or yqhD from *Escherichia coli* (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257), or a polypeptide represented by GenBank Accession No. CAA81612.1 (SEQ ID NO: 21) (from *Geobacillus stearothermophilus*). See FIG. 7.

Cultivation Strategy

In some embodiments, one or more C7 building blocks are biosynthesized in a recombinant microorganism using anaerobic, aerobic or micro-aerobic cultivation conditions. In some embodiments, the cultivation strategy entails nutrient limitation such as, for example, nitrogen, phosphate, or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, plant oils, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida*, and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus* necator and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida, Cupriavidus* necator (Bugg et al., *Current Opinion in Biotechnology*, 2011, 22, 394-400; Perez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn, and other agricultural sources has been demonstrated for several microorganism such as *Escherichia coli, Corynebacterium glutamicum, Lactobacillus delbrueckii,* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering,* 1999, 87(5):647-654).

The efficient utilization of furfural, derived from a variety of agricultural lignocellulosic sources, has been demonstrated for *Cupriavidus* necator (Li et al., *Biodegradation,* 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

The efficient catabolism of methanol has been demonstrated for the methylotrophic yeast *Pichia pastoris.*

The efficient catabolism of ethanol has been demonstrated for *Clostridium kluyveri* (Seedorf et al., *Proc. Natl. Acad. Sci. USA,* 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society,* 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology,* 2011, 77(15): 5467-5475).

The efficient catabolism of the non-volatile residue waste stream from cycloheptane processes has been demonstrated for numerous microorganisms, such as *Delftia acidovorans* and *Cupriavidus* necator (Ramsay et al., *Applied and Environmental Microbiology,* 1986, 52(1):152-156).

In some embodiments, the microorganism is a prokaryote. For example, the prokaryote can be a bacterium from the genus *Escherichia* such as *Escherichia coli*; from the genus Clostridia such as *Clostridium ljungdahlii, Clostridium autoethanogenum,* or *Clostridium kluyveri*; from the genus Corynebacteria such as *Corynebacterium glutamicum*; from the genus *Cupriavidus* such as *Cupriavidus* necator or *Cupriavidus metallidurans*; from the genus *Pseudomonas* such as *Pseudomonas fluorescens, Pseudomonas putida,* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis.* Such prokaryotes also can be a source of genes to construct recombinant microorganisms described herein that are capable of producing one or more C7 building blocks.

In some embodiments, the microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus Issatchenkia such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis.* Such eukaryotes also can be a source of genes to construct recombinant microorganisms described herein that are capable of producing one or more C7 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant microorganisms described herein can include any combination of the above enzymes such that one or more of the steps, e.g., one, two, three, four, five, six, seven, eight, nine, ten, or more of such steps, can be performed within a recombinant microorganism. This document provides cells of any of the genera and species listed and genetically engineered to express one or more (e.g., one, two, three, four, five, six, seven, eight, nine, 10, 11, 12 or more) recombinant forms of any of the enzymes recited in the document. Thus, for example, the cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described as accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing ω-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block.

Attenuation strategies include, but are not limited to; the use of transposons, homologous recombination (double cross-over approach), mutagenesis, enzyme inhibitors and RNAi interference.

Attenuation strategies have been employed to increase the yield of desired end products of engineered metabolic pathways. For example, genetic manipulations previously studied to make succinate the major fermentation product in *E. coli* include deletion of the fermentative lactate dehydrogenase (LDH) pathway (Mat-Jan et al., 1989), deletion of both the LDH and pyruvate formate lyase (PFL) pathways (Bunch et al., 1997), and deletion of multiple pathways including PFL and LDH pathways with an additional ptsG mutation (Donnelly et al., 1998; Chatterjee et al., 2001). Overexpression of phosphoenolpyruvate carboxylase (PEPC) (Millard et al., 1996), overexpression of the malic enzyme (Stols and Donnelly, 1997; Hong and Lee, 2000), overexpression of pyruvate carboxylase (PYC) (Gokarn et al., 1998; Gokarn et al., 2000; Vemuri et al., 2002a), and overexpression of the heterologous *Actinobacillus succinogenes* phosphoenolpyruvate carboxykinase in a PEPC *E. coli* mutant (Kim et al., 2004) have also been studied to improve succinate yield from recombinant *E. coli*.

In some embodiments, fluxomic, metabolomic and transcriptomal data can be utilized to inform or support genome-scale system biology techniques, thereby devising genome scale attenuation or knockout strategies in directing carbon flux to a C7 building block.

In some embodiments, the microorganism's tolerance to high concentrations of a C7 building block can be improved through continuous cultivation in a selective environment.

In some embodiments, the microorganism's endogenous biochemical network can be attenuated or augmented to (1) ensure the intracellular availability of acetyl-CoA or malonyl-CoA, (2) create an NADH or NADPH imbalance that may only be balanced via the formation of one or more C7 building blocks, (3) prevent degradation of central metabolites, central precursors leading to and including one or more C7 building blocks, and/or (4) ensure efficient efflux from the cell.

In some embodiments requiring intracellular availability of acetyl-CoA for C7 building block synthesis, endogenous enzymes catalyzing the hydrolysis of acetyl-CoA such as short-chain length thioesterases can be attenuated in the microorganism.

In some embodiments requiring the intracellular availability of acetyl-CoA for C7 building block synthesis, an endogenous gene encoding a phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for C7 building block synthesis, an endogenous gene in an acetate synthesis pathway encoding an acetate kinase, such as ack, can be attenuated.

In some embodiments requiring the intracellular availability of acetyl-CoA and NADH for C7 building block synthesis, an endogenous gene encoding an enzyme that catalyzes the degradation of pyruvate to lactate such as lactate dehydrogenase encoded by ldhA can be attenuated (Shen et al., 2011, supra).

In some embodiments, enzymes that catalyze anapleurotic reactions such as PEP carboxylase and/or pyruvate carboxylase can be overexpressed in the microorganism.

In some embodiments requiring the intracellular availability of acetyl-CoA and NADH for C7 building block synthesis, endogenous genes encoding enzymes, such as menaquinol-fumarate oxidoreductase, that catalyze the degradation of phosphoenolpyruvate to succinate such as frdBC can be attenuated (see, e.g., Shen et al., 2011, supra).

In some embodiments requiring the intracellular availability of acetyl-CoA and NADH for C7 building block synthesis, an endogenous gene encoding an enzyme that catalyzes the degradation of acetyl-CoA to ethanol such as, for example, the alcohol dehydrogenase encoded by adhE from *Clostridium acetobutylicum* can be attenuated (Shen et al., 2011, supra). In some embodiments, where pathways require excess NADH ω-factor for C7 building block synthesis, a recombinant formate dehydrogenase gene, e.g., fdh1 from *Candida boidinii*, can be overexpressed in the microorganism (Shen et al., 2011, supra).

In some embodiments, where pathways require excess NADH ω-factor for C7 building block synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for C7 building block synthesis, a recombinant acetyl-CoA synthetase such as, for example, the gene product of acsA from *Cupriavidus* necator can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449) from, for example, *Escherichia coli*.

In some embodiments, where pathways require excess NADPH ω-factor in the synthesis of a C7 building block, a gene such as udhA from *Escherichia coli* encoding a puridine nucleotide transhydrogenase can be overexpressed in the microorganisms (Brigham et al., *Advanced Biofuels and Bioproducts*, 2012, Chapter 39, 1065-1090).

In some embodiments, where pathways require excess NADPH ω-factor in the synthesis of a C7 Building Block, a recombinant glyceraldehyde-3-phosphate-dehydrogenase gene such as gapN from *Sulfolobus solfataricus* can be overexpressed in the microorganisms (Brigham et al., 2012, supra).

In some embodiments, where pathways require excess NADPH ω-factor in the synthesis of a C7 building block, a recombinant malic enzyme gene such as maeA or maeB from *Cupriavidus* necator can be overexpressed in the microorganisms (Brigham et al., 2012, supra).

In some embodiments, where pathways require excess NADPH ω-factor in the synthesis of a C7 building block, a recombinant glucose-6-phosphate dehydrogenase gene such as zwf from *Escherichia coli* can be overexpressed in the microorganisms (Lim et al., *J. Bioscience and Bioengineering*, 2002, 93(6), 543-549).

In some embodiments, where pathways require excess NADPH ω-factor in the synthesis of a C7 building block, a recombinant fructose 1,6 diphosphatase gene such as fbp from *Corynebacterium glutamicum* can be overexpressed in the microorganisms (Becker et al., *J. Biotechnol.*, 2007, 132:99-109).

In some embodiments, where pathways require excess NADPH ω-factor in the synthesis of a C7 building block, endogenous triose phosphate isomerase (EC 5.3.1.1) can be attenuated.

In some embodiments, where pathways require excess NADPH ω-factor in the synthesis of a C7 building block, a recombinant glucose dehydrogenase such as, for example, the gene product of gdh from *Bacillus subtilis* can be overexpressed in the microorganism (Satoh et al., *J. Bioscience and Bioengineering*, 2003, 95(4):335-341).

In some embodiments, endogenous enzymes facilitating the conversion of NADPH to NADH can be attenuated, such as, for example, the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as ω-factors can be attenuated.

In some embodiments, a membrane-bound cytochrome P450 such as CYP4F3B can be solubilized by only expressing the cytosolic domain and not the N-terminal region that anchors the P450 to the endoplasmic reticulum (Scheller et al., *J. Biol. Chem.*, 1994, 269(17):12779-12783).

In some embodiments, an enoyl-CoA reductase can be solubilized via expression as a fusion protein with a small soluble protein, for example, the maltose binding protein (Gloerich et al., *FEBS Letters*, 2006, 580, 2092-2096).

In some embodiments using microorganisms that naturally accumulate polyhydroxyalkanoates, the endogenous polymer synthase enzymes can be attenuated in the microorganism strain.

In some embodiments, a L-alanine dehydrogenase can be overexpressed in the microorganism to regenerate L-alanine from pyruvate as an amino donor for ω-transaminase catalyzed reactions. For example, the L-alanine dehydrogenase may be from *Escherichia coli*.

In some embodiments, an L-glutamate dehydrogenase, a L-glutamine synthetase, or an alpha-aminotransferase can be overexpressed in the microorganism to regenerate L-glutamate from 2-oxoglutarate as an amino donor for ω-transaminase catalyzed reactions. For example, the L-glutamate dehydrogenase, the L-glutamine synthetase, or the alpha-aminotransferase may be from *Escherichia coli*.

In some embodiments, enzymes such as a pimeloyl-CoA dehydrogenase classified, for example, under EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6 that degrade central metabolites and central precursors leading to and including C7 building blocks can be attenuated. Examples of polypeptides having the activity of an acyl-CoA dehydrogenase classified under EC 1.3.99.- include, but are not limited to, the gene product of atuD from *Pseudomonas aeruginosa* (UniProtKB Accession No. Q9HZV8), the gene product of scu from *Drosophila melanogaster* (UniProtKB Accession No. O18404), the gene product of fadE26 from *Mycobacterium tuberculosis* (UniProtKB Accession No. I6YCA3), the gene product of aidB from *Escherichia coli* (UniProtKB Accession No. P33224), the gene product of acdh-11 from *Caenorhabditis elegans* (UniProtKB Accession No. Q9XWZ2), and the gene product of Acad11 from *Mus musculus* (UniProtKB Accession No. Q80XL6).

In some embodiments, endogenous enzymes activating C7 building blocks via Coenzyme A esterification such as CoA-ligases (e.g., an adipyl-CoA synthetase) classified under, for example, EC 6.2.1.- can be attenuated.

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multi-drug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother,* 38(6), 1345-1355), or Bmr from *Bacillus subtilis* (Neyfakh, 1992, *Antimicrob Agents Chemother,* 36(2), 484-485).

The efflux of 7-aminoheptanoate and heptamethylenediamine can be enhanced or amplified by overexpressing the solute transporters such as, for example, the lysE transporter from *Corynebacterium glutamicum* (Bellmann et al., 2001, *Microbiology,* 147, 1765-1774).

The efflux of pimelic acid can be enhanced or amplified by overexpressing a dicarboxylate transporter such as, for example, the SucE transporter from *Corynebacterium glutamicum* (Huhn et al., *Appl. Microbiol. & Biotech.,* 89(2), 327-335).

Metabolically engineering recombinant hosts with various enzymes to produce final products has been successfully demonstrated by several groups. See, e.g., Blombach B et al., *Bioeng Bugs.,* 2011, 2(6):346-50 (teaching successful metabolic engineering of the last two steps of the Ehrlich pathway (by expression of genes encoding a broad range 2-ketoacid decarboxylase and an alcohol dehydrogenase) in recombinant hosts for the production of higher isobutanol); Adkins, J. et al., *Front Microbiol.,* 2012, 3:313 (summarizing numerous biomonomers (such as polyester building-blocks) that can be produced as a result of metabolic and pathway engineering in various recombinant hosts); Chan, S. et al., *Bioresour Technol.,* 2012, 103(1):329-36 (teaching production of succinic acid from sucrose and sugarcane molasses by metabolically engineering *E. coli* with sucrose-utilizing genes (cscKB and cscA)); Lee, S. et al., *Appl Biochem Biotechnol.,* 2012, 167(1):24-38 (teaching successful metabolic engineering of *P. aeruginosa* and *E. coli* for improving long-chain fatty acid production by ω-expressing essential enzymes that are involved in the fatty acid synthesis metabolic pathway (accA andfabD) as well as fatty acyl-acyl carrier protein thioesterase gene); Rathnasingh, C. et al., *Biotechnol Bioeng.,* 2009, 104(4):729-39 (teaching successful metabolic engineering of *E. coli* for producing 3-hydroxypropionic acid from glycerol by overexpression of glycerol dehydratase (DhaB) and aldehyde dehydrogenase (AldH) along with glycerol dehydratase reactivase (GDR)).

Producing C7 Building Blocks Using a Recombinant Microorganism

Typically, one or more C7 building blocks can be produced by providing a microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or greater than 500 gallon tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

The invention will be further described in the following examples, which do not limit the scope of the invention described in the claims.

EXAMPLES

Example 1

Enzyme Activity of ω-Transaminase Using Pimelate Semialdehyde as Substrate and Forming 7-Aminoheptanoate A nucleotide sequence encoding an N-terminal His-tag was added to the nucleic acid sequences from *Chromobacterium violaceum, Pseudomonas syringae, Rhodobacter sphaeroides*, and Vibriofluvialis encoding the ω-transaminases of SEQ ID NOs: 7, 9, 10, and 12, respectively (see FIGS. 8G-8J) such that N-terminal HIS tagged ω-transaminases could be produced. Each of the resulting modified genes was cloned into a pET21a expression vector under control of the T7 promoter and each expression vector was transformed into a BL21 [DE3] *E. coli* strain. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate, and 100 µM pyridoxyl 5' phosphate. Each enzyme activity assay reaction was initiated by adding cell free extract of the ω-transaminase gene product or the empty vector control to the assay buffer containing the 7-aminoheptanoate and incubated at 25° C. for 4 h, with shaking at 250 rpm. The formation of L-alanine from pyruvate was quantified via RP-HPLC.

Figure 14:
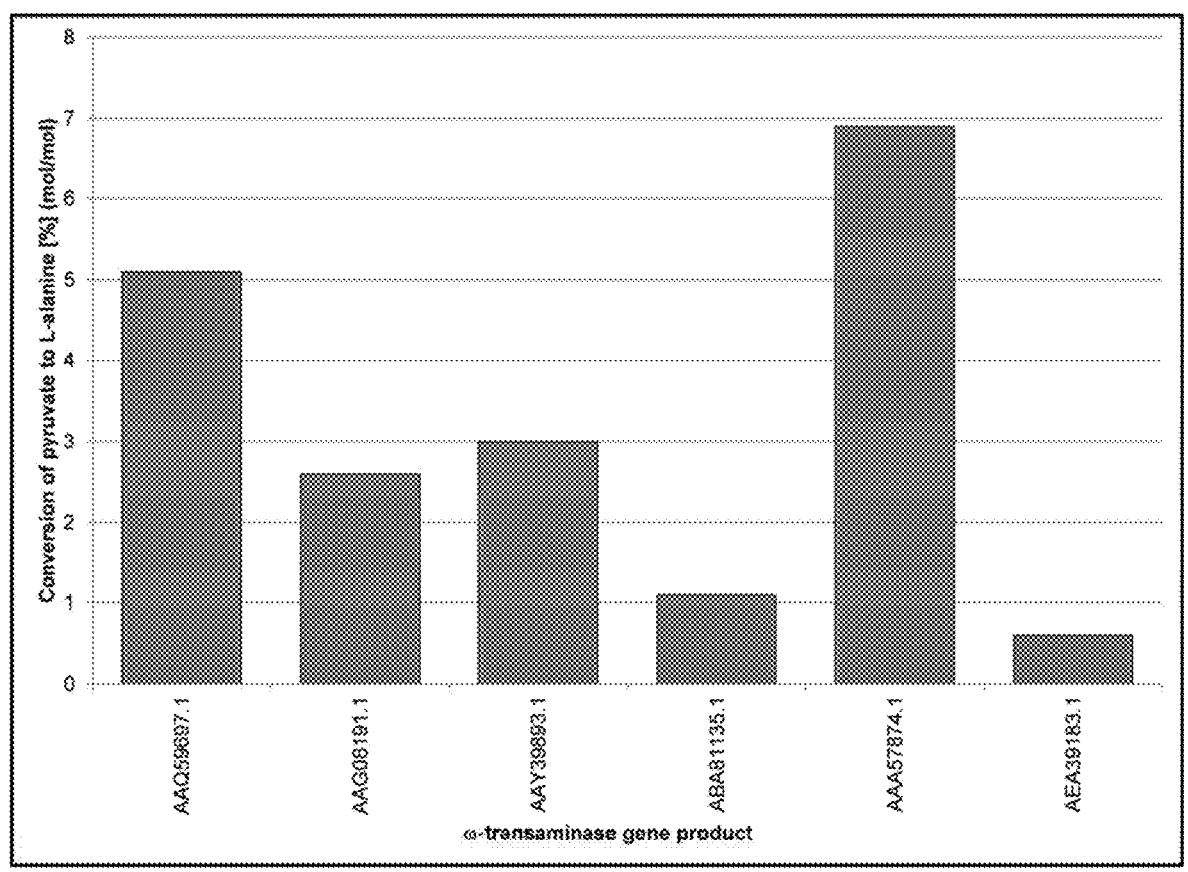
FIG. 14 is a bar graph summarizing the percent conversion of pyruvate to L-alanine (mol/mol) as a measure of the co-transaminase activity of the enzyme only controls (no substrate).
Figure 15:
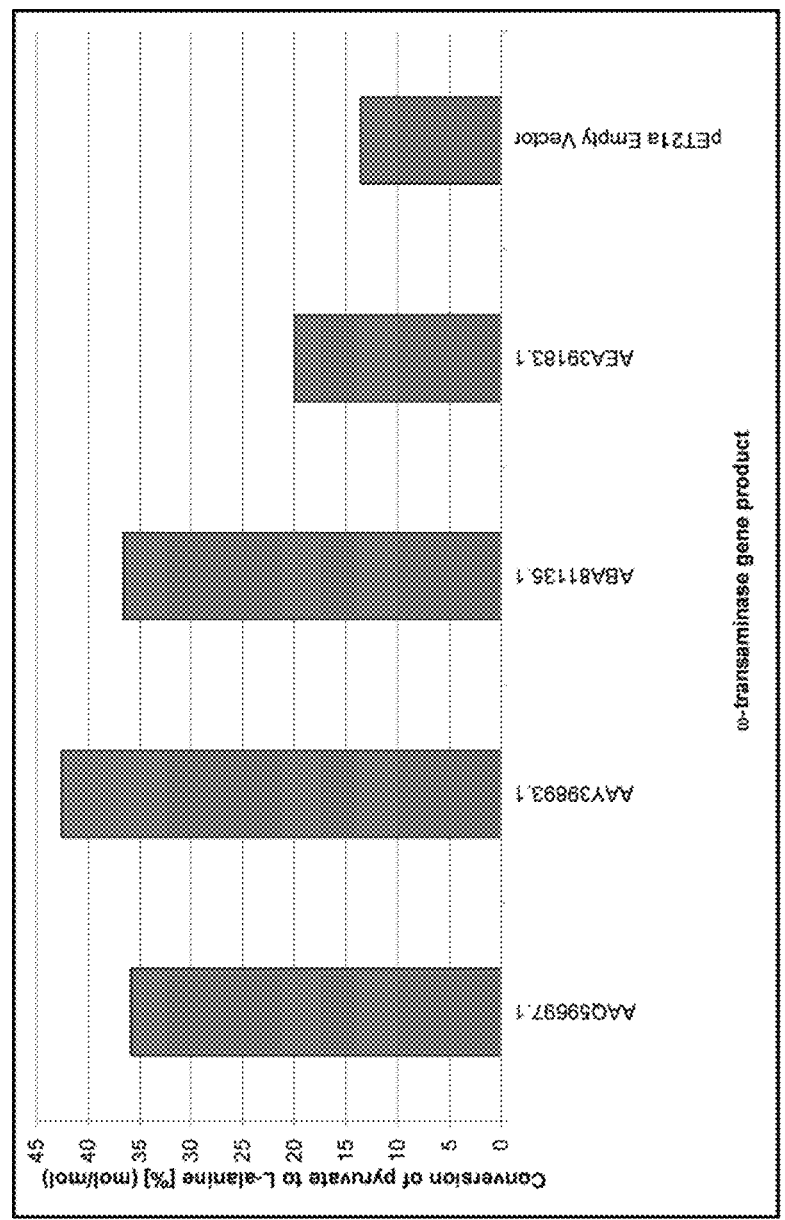
FIG. 15 is a bar graph of the percent conversion after 4 hours of pyruvate to L-alanine (mol/mol) as a measure of the co-transaminase activity of four co-transaminase preparations for converting 7-aminoheptanoate to pimelate semialdehyde relative to the empty vector control.

Each enzyme only control without 7-aminoheptanoate demonstrated low base line conversion of pyruvate to L-alanine. See FIG. 14. The gene product of SEQ ID NO: 7, SEQ ID NO: 9, SEQ ID NO: 10, and SEQ ID NO: 12 accepted 7-aminoheptanoate as a substrate as confirmed against the empty vector control. See FIG. 15.

Figure 16:
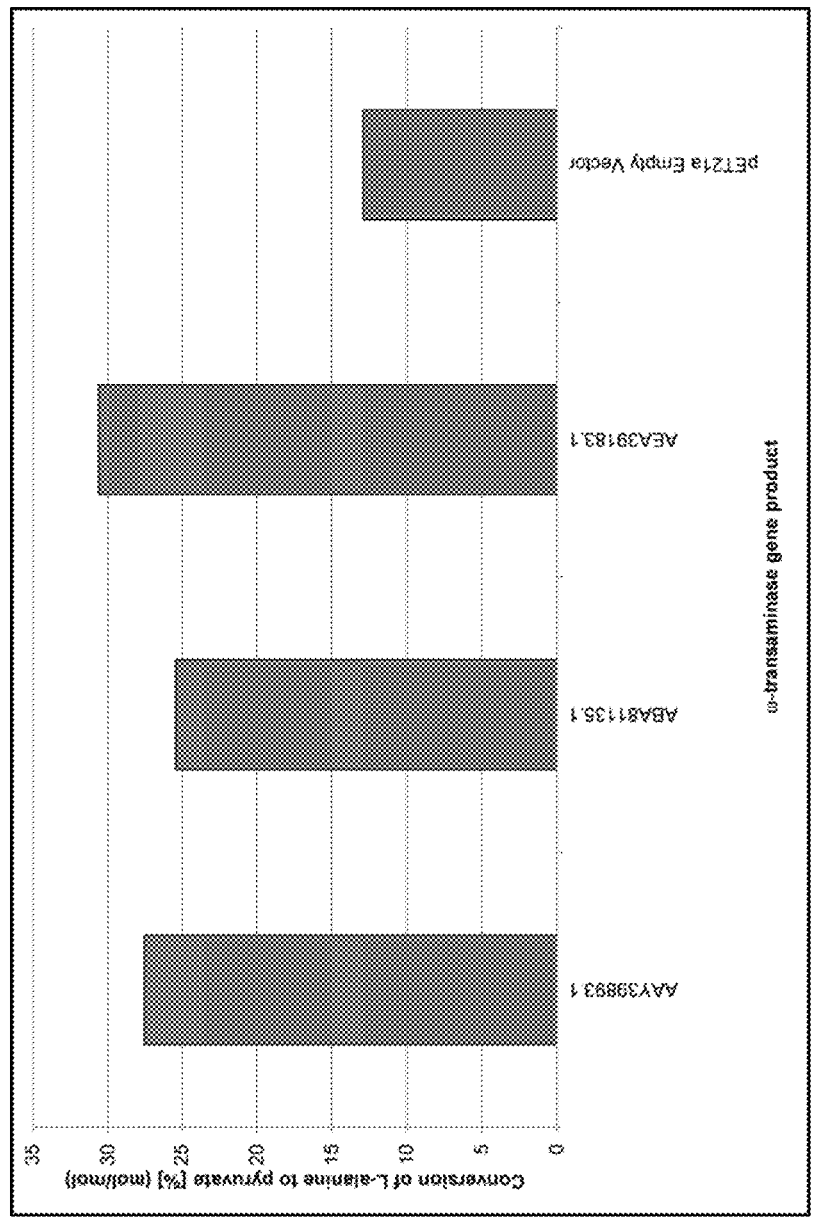
FIG. 16 is a bar graph of the percent conversion after 4 hours of L-alanine to pyruvate (mol/mol) as a measure of the co-transaminase activity of three co-transaminase preparations for converting pimelate semialdehyde to 7-aminoheptanoate relative to the empty vector control.

Enzyme activity in the forward direction (i.e., pimelate semialdehyde to 7-aminoheptanoate) was confirmed for the transaminases of SEQ ID NO: 9, SEQ ID NO: 10, and SEQ ID NO: 12. See FIG. 16. Enzyme activity assays were performed in a buffer composed of a final concentration of 50 mM HEPES buffer (pH=7.5), 10 mM pimelate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the pimelate semialdehyde and incubated at 25° C. for 4 h, with shaking at 250 rpm. The formation of pyruvate was quantified via RP-HPLC.

The gene products represented by SEQ ID NO: 9, SEQ ID NO: 10, and SEQ ID NO: 12 accepted pimelate semialdehyde as substrate as confirmed against the empty vector control. See FIG. 16. The reversibility of the ω-transaminase activity was confirmed, demonstrating that the ω-transaminases represented by SEQ ID NO: 7, SEQ ID NO: 9, SEQ ID NO: 10, and SEQ ID NO: 12 accepted 7-aminoheptanoate as substrate and synthesized pimelate semialdehyde as a reaction product. See FIG. 15.

Example 2

Enzyme Activity of Carboxylate Reductase Using Pimelate as Substrate and Forming Pimelate Semialdehyde A nucleotide sequence encoding a HIS-tag was added to the nucleic acid sequences from *Segniliparus rugosus* and *Segniliparus rotundus* that encode the carboxylate reductases of SEQ ID NOs: 3 (EFV11917.1) and 6 (ADG98140.1), respectively (see FIGS. 8C-8D, 8F-8G), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* strain, and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Enzyme activity assays (i.e., from pimelate to pimelate semialdehyde) were performed in triplicate in a buffer composed of a final concentration of 50 mM HEPES buffer (pH=7.5), 2 mM pimelate, 10 mM MgCl$_2$, 1 mM ATP, and 1 mM NADPH. Each enzyme activity assay reaction was initiated by adding purified carboxylate reductase and phosphopantetheine transferase gene products or the empty vector control to the assay buffer containing the pimelate and then incubated at room temperature for 20 min. The consumption of NADPH was monitored by absorbance at 340 nm. Each enzyme only control without pimelate demonstrated low base line consumption of NADPH. See bars for EFV11917.1 and ADG98140.1 in FIG. 9.

Figure 10:
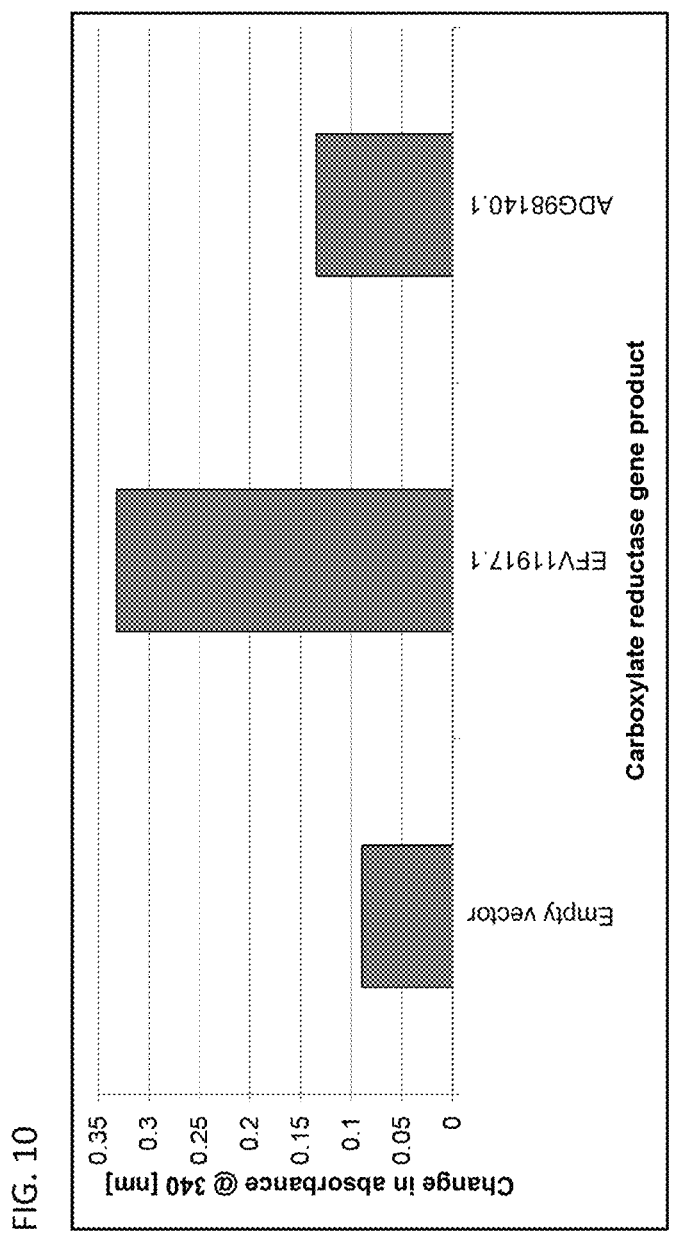
FIG. 10 is a bar graph of the change in absorbance at 340 nm after 20 minutes, which is a measure of the consumption of NADPH and the activity of two carboxylate reductase preparations for converting pimelate to pimelate semialdehyde relative to the empty vector control.

The gene products represented by SEQ ID NO: 3 (EFV11917.1) and SEQ ID NO: 6 (ADG98140.1), enhanced by the gene product of sfp from *Bacillus subtilis*, accepted pimelate as a substrate, as confirmed against the empty vector control (see FIG. 10), and synthesized pimelate semialdehyde.

Example 3

Enzyme Activity of Carboxylate Reductase Using 7-Hydroxyheptanoate as Substrate and Forming 7-Hydroxyheptanal A nucleotide sequence encoding a His-tag was added to the nucleic acids from *Mycobacterium marinum, Mycobacterium smegmatis, Segniliparus rugosus, Mycobacterium massiliense*, and *Segniliparus rotundus* that encode the carboxylate reductases of SEQ ID NOs: 1-6 respectively (see FIGS. 8A-8G) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* strain along with the expression vectors from Example 2. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme only control without 7-hydroxyheptanoate demonstrated low base line consumption of NADPH. See FIG. 9.

Figure 11:
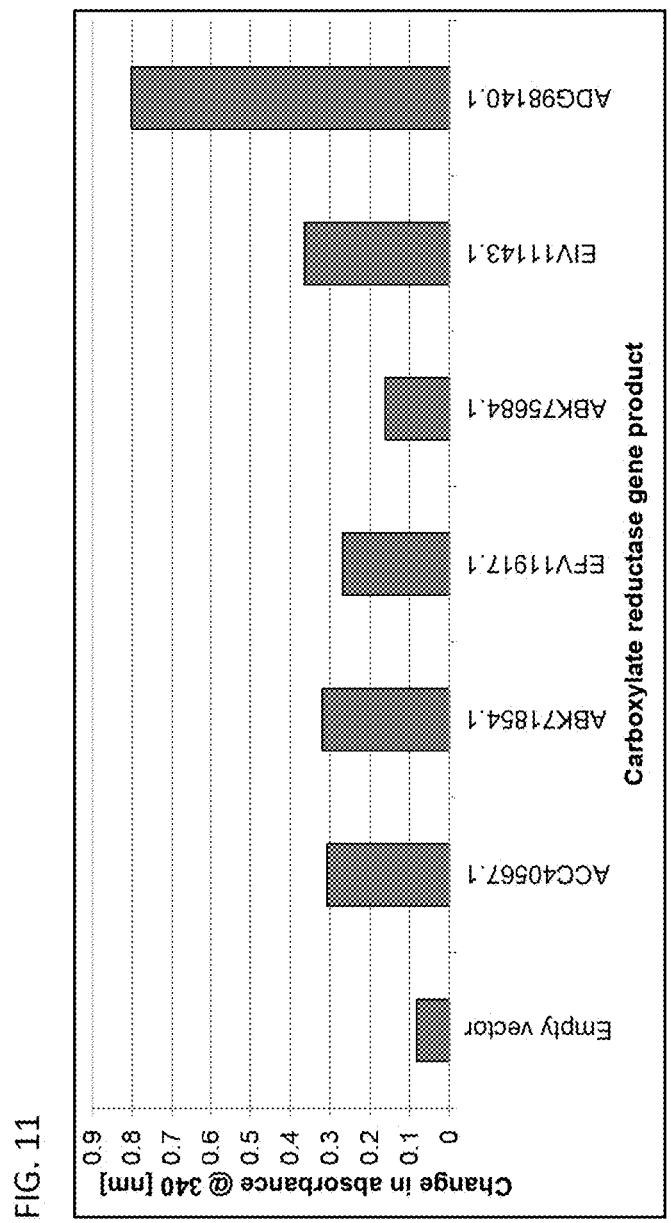
FIG. 11 is a bar graph of the change in absorbance at 340 nm after 20 minutes, which is a measure of the consumption of NADPH and the activity of six carboxylate reductase preparations for converting 7-hydroxyheptanoate to 7-hydroxyheptanal relative to the empty vector control.

The gene products represented by SEQ ID NO 1-6 enhanced by the gene product of sfp, accepted 7-hydroxyheptanoate as substrate as confirmed against the empty vector control (see FIG. 11), and synthesized 7-hydroxyheptanal.

Example 4

Enzyme Activity of ω-Transaminase for 7-Aminoheptanol, Forming 7-Oxoheptanol

A nucleotide sequence encoding an N-terminal His-tag was added to the *Chromobacterium violaceum, Pseudomonas syringae*, and *Rhodobacter sphaeroides* nucleic acids encoding the ω-transaminases of SEQ ID NOs: 7, 9, and 10, respectively (see FIGS. 8G-8I) such that N-terminal HIS tagged ω-transaminases could be produced. The modified genes were cloned into a pET21a expression vector under the T7 promoter. Each expression vector was transformed into a BL21[DE3] *E. coli* strain. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanol to 7-oxoheptanol) were performed in a buffer composed of a final concentration of 50 mM HEPES buffer (pH=7.5), 10 mM 7-aminoheptanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 7-aminoheptanol and then incubated at 25° C. for 4 h, with shaking at 250 rpm. The formation of L-alanine was quantified via RP-HPLC.

Each enzyme only control without 7-aminoheptanol had low base line conversion of pyruvate to L-alanine. See FIG. 14.

Figure 19:
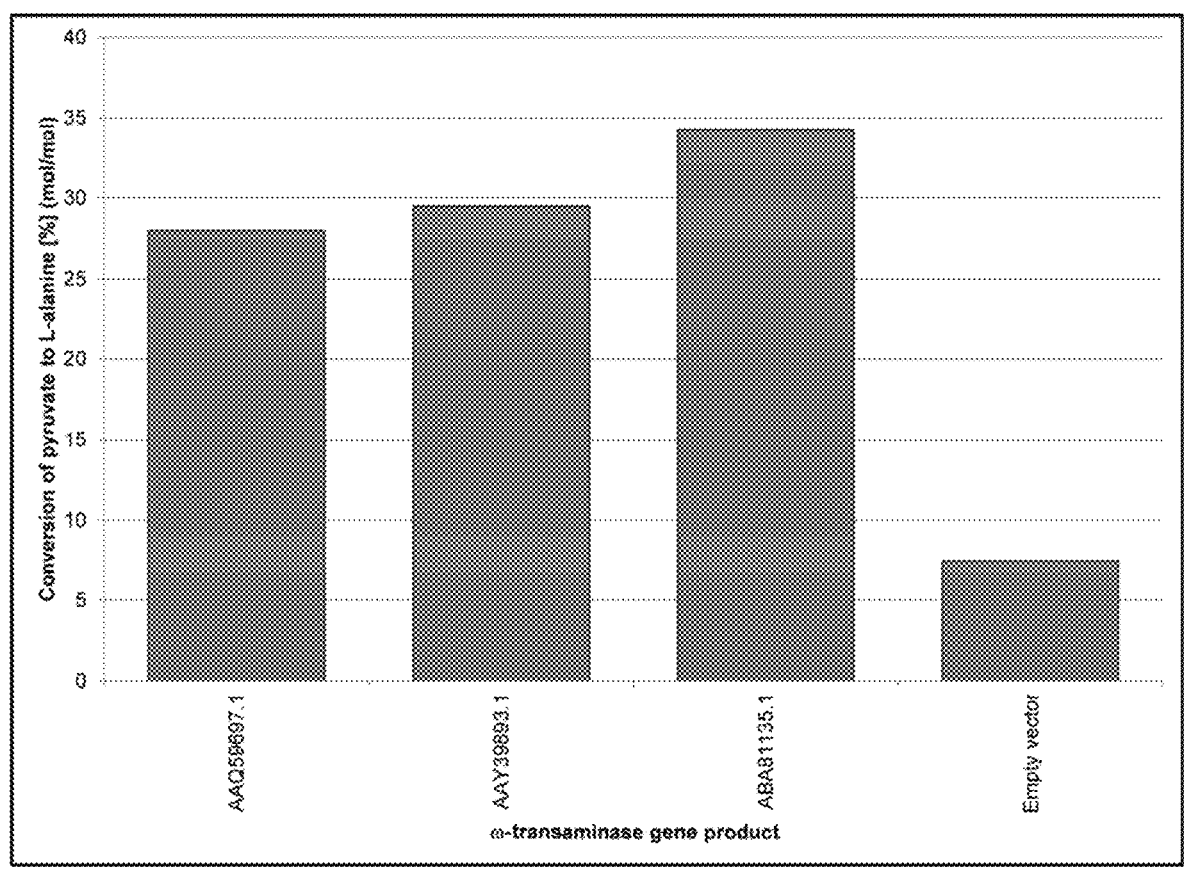
FIG. 19 is a bar graph of the percent conversion after 4 hours of pyruvate to L-alanine (mol/mol) as a measure of the co-transaminase activity of three co-transaminase preparations for converting 7-aminoheptanol to 7-oxoheptanol relative to the empty vector control.

The gene products represented by SEQ ID NOs: 7, 9, and 10 accepted 7-aminoheptanol as substrate as confirmed against the empty vector control (see FIG. 19) and synthesized 7-oxoheptanol as reaction product. Given the reversibility of the ω-transaminase activity (see Example 1), it can be concluded that the gene products of SEQ ID NOs: 7, 9, and 10 accept 7-oxoheptanol as substrate and form 7-aminoheptanol.

Example 5

Enzyme Activity of ω-Transaminase Using Heptamethylenediamine as Substrate and Forming 7-Aminoheptanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* nucleic acids encoding the ω-transaminases of SEQ ID NOs: 7-12, respectively (see FIGS. 8G-8J) such that N-terminal HIS tagged ω-transaminases could be produced. The modified genes were cloned into a pET21a expression vector under the T7 promoter. Each expression vector was transformed into a BL21[DE3] *E. coli* strain. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation, and the cell free extract was used immediately in enzyme activity assays.

Enzyme activity assays in the reverse direction (i.e., heptamethylenediamine to 7-aminoheptanal) were performed in a buffer composed of a final concentration of 50 mM HEPES buffer (pH=7.5), 10 mM heptamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the heptamethylenediamine and then incubated at 25° C. for 4 h, with shaking at 250 rpm. The formation of L-alanine was quantified via RP-HPLC.

Each enzyme only control without heptamethylenediamine had low base line conversion of pyruvate to L-alanine. See FIG. 14.

Figure 17:
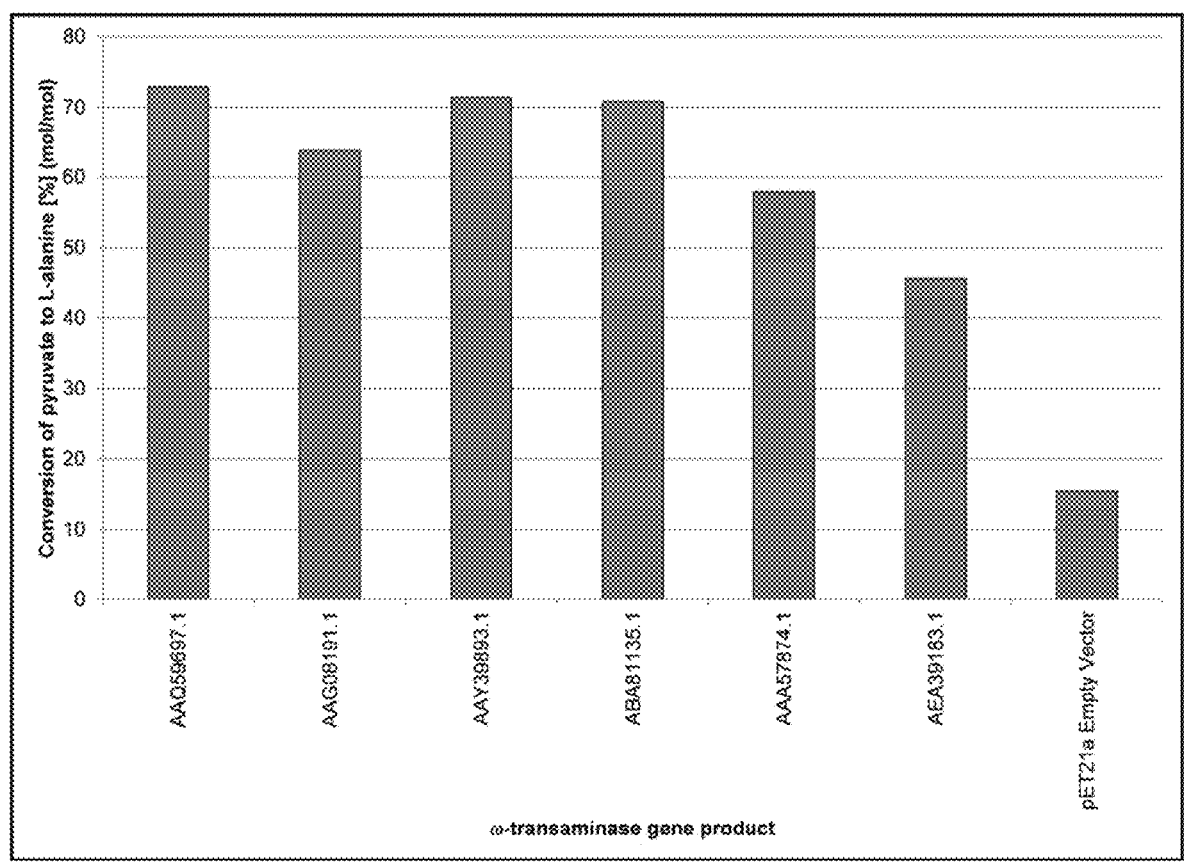
FIG. 17 is a bar graph of the percent conversion after 4 hours of pyruvate to L-alanine (mol/mol) as a measure of the co-transaminase activity of six co-transaminase preparations for converting heptamethylenediamine to 7-aminoheptanal relative to the empty vector control.

The gene products of SEQ ID NOs: 7-12 accepted heptamethylenediamine as substrate as confirmed against the empty vector control (see FIG. 17) and synthesized 7-aminoheptanal as reaction product. Given the reversibility of the ω-transaminase activity (see Example 1), it can be concluded that the gene products of SEQ ID NOs: 7-12 accept 7-aminoheptanal as substrate and form heptamethylenediamine.

Example 6

Enzyme Activity of Carboxylate Reductase for N7-Acetyl-7-Aminoheptanoate, Forming N7-Acetyl-7-Aminoheptanal The activity of each of the N-terminal His-tagged carboxylate reductases of SEQ ID NOs: 2, 5, and 6 (see Examples 2 and 3, and FIGS. 8B-8C, 8E-8G) for converting N7-acetyl-7-aminoheptanoate to N7-acetyl-7-aminoheptanal was assayed in triplicate in a buffer composed of a final concentration of 50 mM HEPES buffer (pH=7.5), 2 mM N7-acetyl-7-aminoheptanoate, 10 mM $MgCl_2$, 1 mM ATP, and 1 mM NADPH. The assays were initiated by adding purified carboxylate reductase and phosphopantetheine transferase or the empty vector control to the assay buffer containing the N7-acetyl-7-aminoheptanoate then incubated at room temperature for 20 min. The consumption of NADPH was monitored by absorbance at 340 nm. Each enzyme only control without N7-acetyl-7-aminoheptanoate demonstrated low base line consumption of NADPH. See FIG. 9.

Figure 12:
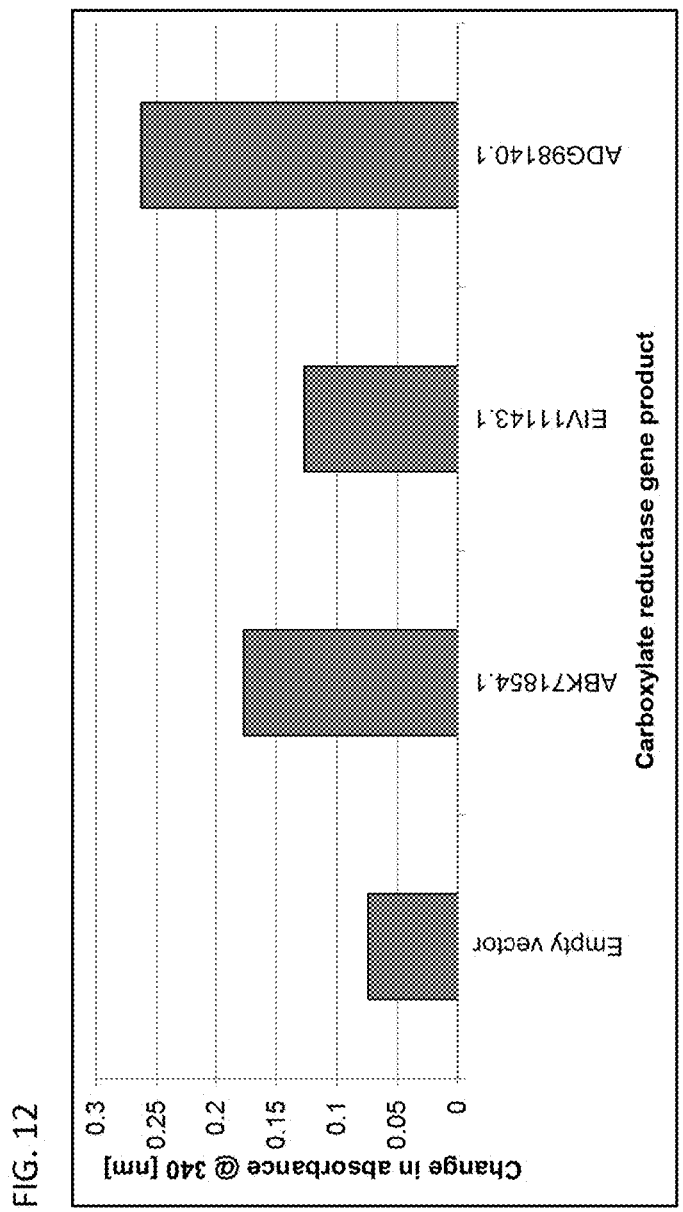
FIG. 12 is a bar graph of the change in absorbance at 340 nm after 20 minutes, which is a measure of the consumption of NADPH and the activity of three carboxylate reductase preparations for converting N7-acetyl-7-aminoheptanoate to N7-acetyl-7-aminoheptanal relative to the empty vector control.

The gene products of SEQ ID NOs: 2, 5, and 6, enhanced by the gene product of sfp, accepted N7-acetyl-7-aminoheptanoate as substrate as confirmed against the empty vector control (see FIG. 12), and synthesized N7-acetyl-7-aminoheptanal.

Example 7

Enzyme Activity of ω-Transaminase Using N7-Acetyl-1,7-Diaminoheptane, and Forming N7-Acetyl-7-Aminoheptanal The activity of the N-terminal His-tagged ω-transaminases of SEQ ID NOs: 7-12 (see Example 5, and FIGS. 8G-8J) for converting N7-acetyl-1,7-diaminoheptane to N7-acetyl-7-aminoheptanal was assayed using a buffer composed of a final concentration of 50 mM HEPES buffer (pH=7.5), 10 mM N7-acetyl-1,7-diaminoheptane, 10 mM pyruvate and 100 μM pyridoxyl 5' phosphate. Each enzyme activity assay reaction was initiated by adding a cell free extract of the ω-transaminase or the empty vector control to the assay buffer containing the N7-acetyl-1,7-diaminoheptane then incubated at 25° C. for 4 h, with shaking at 250 rpm. The formation of L-alanine was quantified via RP-HPLC.

Each enzyme only control without N7-acetyl-1,7-diaminoheptane demonstrated low base line conversion of pyruvate to L-alanine. See FIG. 14.

Figure 18:
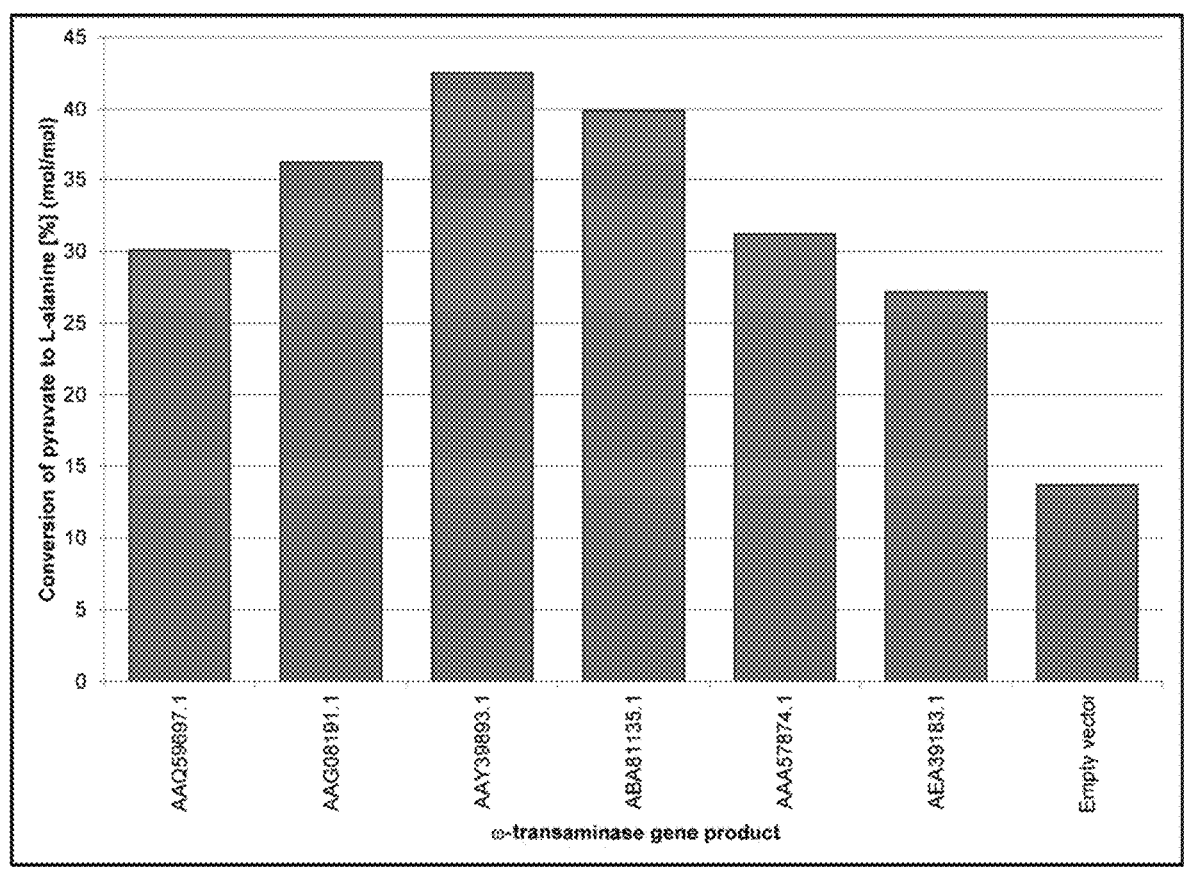
FIG. 18 is a bar graph of the percent conversion after 4 hours of pyruvate to L-alanine (mol/mol) as a measure of the co-transaminase activity of six co-transaminase preparations for converting N7-acetyl-1,7-diaminoheptane to N7-acetyl-7-aminoheptanal relative to the empty vector control.

The gene product of SEQ ID NOs: 7-12 accepted N7-acetyl-1,7-diaminoheptane as substrate as confirmed against the empty vector control (see FIG. 18) and synthesized N7-acetyl-7-aminoheptanal as reaction product.

Given the reversibility of the ω-transaminase activity (see Example 1), the gene products represented by SEQ ID NOs: 7-12 accept N7-acetyl-7-aminoheptanal as substrate forming N7-acetyl-1,7-diaminoheptane.

Example 8

Enzyme Activity of Carboxylate Reductase Using Pimelate Semialdehyde as Substrate and Forming Heptanedial The N-terminal His-tagged carboxylate reductase of SEQ ID NO: 6 (see Example 3 and FIGS. 8F-8G) was assayed using pimelate semialdehyde as substrate. The enzyme activity assay was performed in triplicate in a buffer composed of a final concentration of 50 mM HEPES buffer (pH=7.5), 2 mM pimelate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the pimelate semialdehyde and then incubated at room temperature for 20 min. The consumption of NADPH was monitored by absorbance at 340 nm. The enzyme only control without pimelate semialdehyde demonstrated low base line consumption of NADPH. See FIG. 9.

Figure 13:
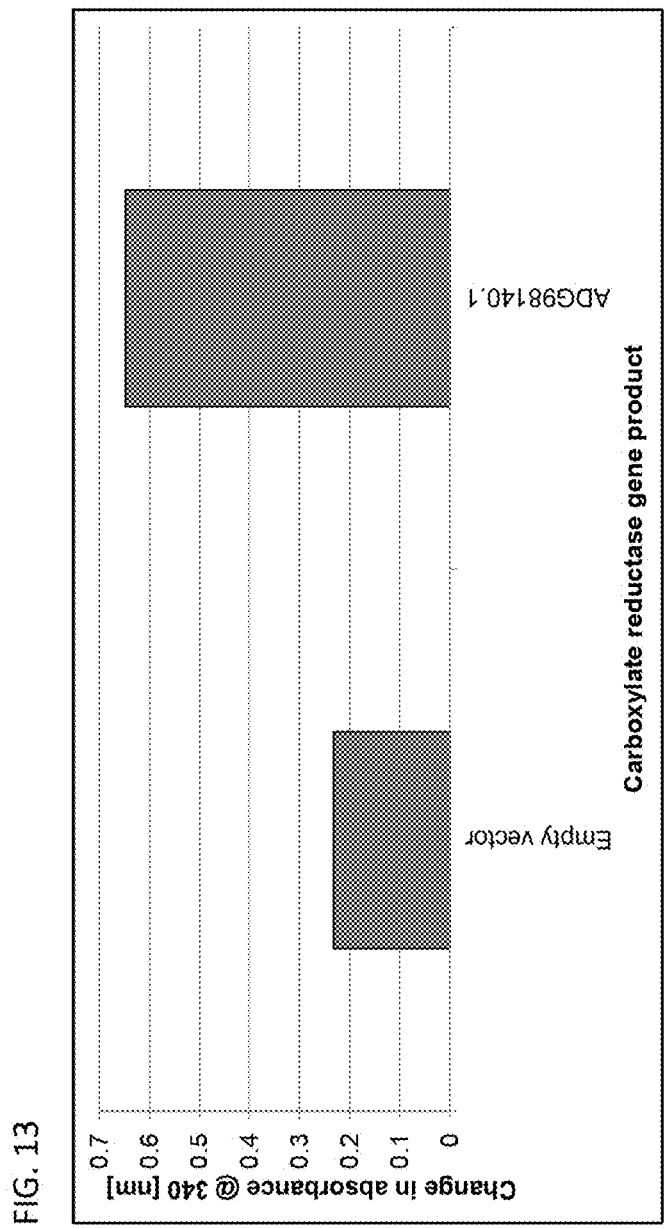
FIG. 13 is a bar graph of the change in absorbance at 340 nm after 20 minutes, which is a measure of the consumption of NADPH and activity of a carboxylate reductase preparation for converting pimelate semialdehyde to heptanedial relative to the empty vector control.

The gene product of SEQ ID NO: 6, enhanced by the gene product of sfp from *Bacillus subtilis*, accepted pimelate semialdehyde as substrate as confirmed against the empty vector control (see FIG. 13) and synthesized heptanedial.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing azelaic acid, said method comprising:

enzymatically converting a 9-hydroxyperoxyoctadec-10, 12-dienoate to non-3-enal and 9-oxononanoate in a recombinant *Escherichia coli* microorganism and in the presence of a carbon source, wherein the recombinant *Escherichia coli* microorganism has been transformed to express an exogenous polypeptide having the activity of a hydroperoxide lyase and at least 85% sequence identity to the polypeptide of SEQ ID NO: 13 or SEQ ID NO: 14; and enzymatically converting the non-3-enal to azelaic acid in the recombinant *Escherichia coli* microorganism and in the presence of a carbon source, wherein the recombinant *Escherichia coli* microorganism has been transformed to express one or more polypeptides comprising at least one polypeptide having the activity of a dodecenoyl-CoA isomerase and at least 85% sequence identity to the polypeptide of SEQ ID NO: 17 or at least one polypeptide having the activity of an enoate reductase and at least 85% sequence identity to the polypeptide of SEQ ID NO: 15 or SEQ ID NO: 16.

2. The method of claim 1, wherein enzymatically converting the non-3-enal to azelaic acid using one or more polypeptides comprises:
enzymatically converting nonanoic acid to 9-hydroxynonanoic acid using one or more polypeptides having the activity of a monooxygenase and comprising the gene products alkBGT from *Pseudomonas putida*, CYP153A from *Polaromonas* sp., or CYP52A3 from *Saccharomyces cerevisiae*.

3. The method of claim 1, wherein enzymatically converting the non-3-enal to azelaic acid using one or more polypeptides further comprises using at least one polypeptide having the enzymatic activity of:
a monooxygenase, wherein the polypeptide having the enzymatic activity of a monooxygenase comprises the gene products of any one of alkBGT from *Pseudomonas putida*, CYP153A from *Polaromonas* sp., or CYP52A3 from *Saccharomyces cerevisiae*;
an enal isomerase, wherein the polypeptide having the enzymatic activity of an enal isomerase has at least 85% sequence identity to the polypeptide of SEQ ID NO: 17;
an aldehyde dehydrogenase, wherein the polypeptide having the enzymatic activity of an aldehyde dehydrogenase comprises the polypeptide of any one of UniProtKB Accession No. Q9FAB1, UniProtKB Accession No. O34660, UniProtKB Accession No. A6ZR27, UniProtKB Accession No. Q56YU0, UniProtKB Accession No. Q840S9, UniProtKB Accession No. P12693, UniProtKB Accession No. Q9FDS1, or UniProtKB Accession No. P46368, or the gene products of any one of thnG from *Sphingomonas* macrogolitabida, chnE from *Acinetobacter* sp., or cpnE from *Comamonas* sp.;
a CoA ligase, wherein the polypeptide having the enzymatic activity of a CoA ligase comprises the polypeptide of any one of UniProtKB Accession No. Q9FNT6, UniProtKB Accession No. P38137, UniProtKB Accession No. Q00594, UniProtKB Accession No. Q6NUN0, or UniProtKB Accession No. Q9YF45;
a trans-2-enoyl-CoA reductase, wherein the polypeptide having the enzymatic activity of a trans-2-enoyl-CoA reductase comprises the gene product of ter from *Escherichia coli, Fibrobacter succinogenes*, or *Treponema denticola*, or the gene product of tdter from *Treponema denticola*;
a thioesterase, wherein the polypeptide having the enzymatic activity of a thioesterase has at least 85% sequence identity to the polypeptide of any one of SEQ ID NO: 18, SEQ ID NO: 20, SEQ ID NO: 22, or SEQ ID NO: 23; or
an alcohol dehydrogenase, wherein the polypeptide having the enzymatic activity of an alcohol dehydrogenase has at least 85% sequence identity to the polypeptide of SEQ ID NO: 21.

4. The method of claim 1, said method further comprising enzymatically converting 9-oxononanoate to azelaic acid using one or more polypeptides having the enzymatic activity of an aldehyde dehydrogenase and comprises the gene products of any one of thnG from *Sphingomonas* macrogolitabida, chnE from *Acinetobacter* sp., or cpnE from *Comamonas* sp.

5. The method of claim 1, said method further comprising enzymatically converting the azelaic acid to pimeloyl-CoA using one or more polypeptides comprising at least one polypeptide having the enzymatic activity of:
a CoA ligase, wherein the polypeptide having the enzymatic activity of a CoA ligase comprises the polypeptide of any one of UniProtKB Accession No. Q9FNT6, UniProtKB Accession No. P38137, UniProtKB Accession No. Q00594, UniProtKB Accession No. Q6NUN0, or UniProtKB Accession No. Q9YF45;
an enoyl-CoA hydratase, wherein the polypeptide having the enzymatic activity of an enoyl-CoA hydratase comprises the gene product of crt from *Clostridium acetobutylicum* or the gene product of phaJ from *Pseudomonas aeruginosa*;
a 3-hydroxyacyl-CoA dehydrogenase, wherein the polypeptide having the enzymatic activity of a 3-hydroxyacyl-CoA dehydrogenase comprises the gene products of any one of fadB from *Escherichia coli*, phaB from *Cupriavidus* necator, or hbd from *Clostridium acetobutylicum*;
a 3-oxoacyl-ACP reductase, wherein the polypeptide having the enzymatic activity of a 3-oxoacyl-ACP reductase comprises the gene product of fabG from *Escherichia coli*; or
a β-ketothiolase, wherein the polypeptide having the enzymatic activity of a β-ketothiolase comprises the gene product of bktB from *Cupriavidus* necator or the gene product of paaJ from *Escherichia coli*.

6. The method of claim 5, said method further comprising enzymatically converting the pimeloyl-CoA to one or more of pimelate semialdehyde, pimelic acid, 7-aminoheptanoate, 7-hydroxyheptanoate, heptamethylenediamine, or 1,7-heptanediol, or corresponding salts thereof, in one or more steps.

7. The method of claim 5, wherein said method comprises enzymatically converting the pimeloyl-CoA to pimelic acid using one or more polypeptides comprising at least one polypeptide having the enzymatic activity of:
a CoA ligase, wherein the polypeptide having the enzymatic activity of a CoA ligase comprises the polypeptide of any one of UniProtKB Accession No. Q9FNT6, UniProtKB Accession No. P38137, UniProtKB Accession No. Q00594, UniProtKB Accession No. Q6NUN0, or UniProtKB Accession No. Q9YF45;
a CoA transferase, wherein the polypeptide having the enzymatic activity of a CoA transferase comprises the polypeptide of any one of UniProtKB Accession No. B3EY95, UniProtKB Accession No. B0MC58, UniProtKB Accession No. D2WEY7, UniProtKB Accession No. D2WEY8, UniProtKB Accession No. C7H5K4, UniProtKB Accession No. D2WEZ2, UniProtKB Accession No. A8SFP6, UniProtKB Accession No. Q2TME9, or UniProtKB Accession No. D2WEY6; or
a thioesterase, wherein the polypeptide having the enzymatic activity of a thioesterase has at least 85% sequence identity to the polypeptide of any one of SEQ ID NO: 18, SEQ ID NO: 20, SEQ ID NO: 22, or SEQ ID NO: 23.

8. The method of claim 6, wherein said method comprises enzymatically converting the pimeloyl-CoA to pimelate semialdehyde using one or more polypeptides having the activity of an acetylating aldehyde dehydrogenase and comprising the gene product of pduB from *Salmonella typhimurium* or pduP from *Klebsiella pneumoniae.*

9. The method of claim 8, said method further comprising: enzymatically converting pimelate semialdehyde to 7-hydroxyheptanoate using one or more polypeptides having the activity of an alcohol dehydrogenase and at least 85% sequence identity to the polypeptide of SEQ ID NO: 21;
enzymatically converting 7-hydroxyheptanoate to 7-hydroxyheptanal using one or more polypeptides having the activity of a carboxylate reductase and at least 85% sequence identity to the polypeptide of any one of SEQ ID NO: 1, SEQ ID NO: 2, SEQ ID NO: 3, SEQ ID NO: 4, SEQ ID NO: 5, or SEQ ID NO: 6;
enzymatically converting 7-hydroxyheptanal to 7-aminoheptanol using one or more polypeptides having the activity of a co-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12;
enzymatically converting 7-aminoheptanol to 7-aminoheptanal using one or more polypeptides having the activity of an alcohol dehydrogenase and at least 85% sequence identity to the polypeptide of SEQ ID NO: 21; and
enzymatically converting 7-aminoheptanal to heptamethylenediamine using one or more polypeptides having the activity of a co-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12; or
enzymatically converting 7-hydroxyheptanoate to 7-hydroxyheptanal using a carboxylate reductase and at least 85% sequence identity to the polypeptide of any one of SEQ ID NO: 1, SEQ ID NO: 2, SEQ ID NO: 3, SEQ ID NO: 4, SEQ ID NO: 5, or SEQ ID NO: 6; and
enzymatically converting 7-hydroxyheptanal to 1,7 heptanediol using one or more polypeptides having the activity of an alcohol dehydrogenase and at least 85% sequence identity to the polypeptide of SEQ ID NO: 21.

10. The method of claim 1, wherein said 9-hydroxyperoxyoctadec-10,12-dienoate is enzymatically produced from an octadecanoyl-CoA using one or more polypeptides comprising at least one polypeptide having the enzymatic activity of:
a delta9-desaturase, wherein the polypeptide having the enzymatic activity of a delta9-saturase comprises the polypeptide of any one of UniProtKB Accession No. Q76C19, UniProtKB Accession No. A7LCI9, UniProtKB Accession No. B7SB75, UniProtKB Accession No. P07308, UniProtKB Accession No. Q8I0W9, or UniProtKB Accession No. A5CKEI;
a delta12-desaturase, wherein the polypeptide having the enzymatic activity of a delta12-saturase comprises the polypeptide of any one of UniProtKB Accession No. B7SB91, UniProtKB Accession No. Q8W2B9, UniProtKB Accession No. D3U658, UniProtKB Accession No. A5J295, UniProtKB Accession No. D4Q8H2, UniProtKB Accession No. D4Q8S6, or UniProtKB Accession No. Q5BEJ3;
a thioesterase, wherein the polypeptide having the enzymatic activity of a thioesterase has at least 85% sequence identity to the polypeptide of any one of SEQ ID NO: 18, SEQ ID NO: 20, SEQ ID NO: 22, or SEQ ID NO: 23; and/or
a 9-lipoxygenase, wherein the polypeptide having the enzymatic activity of a 9-lipoxygenase comprises the polypeptide of any one of UniProtKB Accession No. 016025, UniProtKB Accession No. Q6RET3, UniProtKB Accession No. C1KH66, or UniProtKB Accession No. Q9UUS2.

11. The method of claim 1, wherein:
said recombinant *Escherichia coli* microorganism is cultured under aerobic, anaerobic, or micro-aerobic conditions; and/or
said recombinant *Escherichia coli* microorganism is cultured under conditions of nutrient limitation.

12. The method of claim 1, wherein the carbon source is from a biological feedstock.

13. The method of claim 12, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, plant oils, or municipal waste.

14. The method of claim 1, wherein the carbon source is from a non-biological feedstock.

15. The method of claim 14, wherein the non-biological feedstock is, or derives from, natural gas, syngas, $CO_2/H_2$, methanol, ethanol, benzoate, non-volatile residue (NVR) caustic wash waste stream from cycloheptane oxidation processes, or terephthalic acid/isophthalic acid mixture waste streams.

16. The method of claim 8, said method further comprising: enzymatically converting the pimelate semialdehyde to 7-aminoheptanoate using one or more polypeptides having the activity of a w-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12.

17. The method of claim 16, said method further comprising: enzymatically converting the 7-aminoheptanoate to N7-acetyl-7-aminoheptanoate using one or more polypeptides having the activity of an N-acetyltransferase and comprising the polypeptide of any one of UniProtKB Accession No. P41929, UniProtKB Accession No. Q6LYX3, or UniProtKB Accession No. Q8PYC8;
enzymatically converting the N7-acetyl-7-aminoheptanoate to N7-acetyl-7-aminoheptanal using one or more polypeptides having the activity of a carboxylate reductase and at least 85% sequence identity to the polypeptide of any one of SEQ ID NO: 1, SEQ ID NO: 2, SEQ ID NO: 3, SEQ ID NO: 4, SEQ ID NO: 5, or SEQ ID NO: 6;
enzymatically converting the N7-acetyl-7-aminoheptanal to N7-acetyl-1,7-diaminoheptane using one or more polypeptides having the activity of w-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12; and
converting the N7-acetyl-1,7-diaminoheptane to heptamethylenediamine using one or more polypeptides having the activity of a deacylase and at least 85% sequence identity to the polypeptide of UniProtKB Accession No. P94211.

18. The method of claim 8, said method further comprising: enzymatically converting the pimelate semialdehyde to 7-hydroxyheptanoate using one or more polypeptides having the activity of an alcohol dehydrogenase and at least 85% sequence identity to the polypeptide of SEQ ID NO: 21.

19. The method of claim 8, said method further comprising: enzymatically converting the pimelate semialdehyde to heptanedial using one or more polypeptides having the activity of a carboxylate reductase and at least 85% sequence identity to the polypeptide of any one of SEQ ID NO: 1, SEQ ID NO: 2, SEQ ID NO: 3, SEQ ID NO: 4, SEQ ID NO: 5, or SEQ ID NO: 6;

enzymatically converting the heptanedial to 7-aminoheptanal using one or more polypeptides having the activity of w-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12; and enzymatically converting the 7-aminoheptanal to heptamethylenediamine using one or more polypeptides having the activity of w-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12.

20. The method of claim 16, said method further comprising: enzymatically converting the 7-aminoheptanoate to 7-aminoheptanal using one or more polypeptides having the activity of a carboxylate reductase and at least 85% sequence identity to the polypeptide of any one of SEQ ID NO: 1, SEQ ID NO: 2, SEQ ID NO: 3, SEQ ID NO: 4, SEQ ID NO: 5, or SEQ ID NO: 6; and enzymatically converting the 7-aminoheptanal to heptamethylenediamine using one or more polypeptides having the activity of a co-transaminase and at least 85% sequence identity to the polypeptide of any one of SEQ ID NO: 7, SEQ ID NO: 8, SEQ ID NO: 9, SEQ ID NO: 10, SEQ ID NO: 11, or SEQ ID NO: 12.

21. The method of claim 1, wherein the recombinant *Escherichia coli* is a BL21[DE3] strain.

\* \* \* \* \*